United States Patent
Babich et al.

(10) Patent No.: US 11,285,227 B2
(45) Date of Patent: Mar. 29, 2022

(54) TRIFUNCTIONAL CONSTRUCTS WITH TUNABLE PHARMACOKINETICS USEFUL IN IMAGING AND ANTI-TUMOR THERAPIES

(71) Applicant: CORNELL UNIVERSITY, Ithaca, NY (US)

(72) Inventors: John W. Babich, New York, NY (US); James M. Kelly, New York, NY (US); Alejandro Amor-Coarasa, New York, NY (US); Shashikanth Ponnala, New York, NY (US)

(73) Assignee: Cornell University, Ithaca, NY (US)

( * ) Notice: Subject to any disclaimer, the term of this patent is extended or adjusted under 35 U.S.C. 154(b) by 36 days.

(21) Appl. No.: 16/500,380

(22) PCT Filed: Apr. 5, 2018

(86) PCT No.: PCT/US2018/026340
§ 371 (c)(1),
(2) Date: Oct. 2, 2019

(87) PCT Pub. No.: WO2018/187631
PCT Pub. Date: Oct. 11, 2018

(65) Prior Publication Data
US 2021/0128757 A1 May 6, 2021

Related U.S. Application Data

(60) Provisional application No. 62/482,038, filed on Apr. 5, 2017, provisional application No. 62/574,720, filed on Oct. 19, 2017.

(51) Int. Cl.
| | | |
|---|---|---|
| A61P 35/00 | (2006.01) |
| A61K 51/04 | (2006.01) |
| A61K 51/06 | (2006.01) |
| A61P 35/04 | (2006.01) |
| A61K 9/00 | (2006.01) |
| C07B 59/00 | (2006.01) |

(52) U.S. Cl.
CPC ........ A61K 51/065 (2013.01); A61K 9/0019 (2013.01); A61K 51/0402 (2013.01); A61K 51/0497 (2013.01); A61P 35/04 (2018.01); C07B 59/00 (2013.01)

(58) Field of Classification Search
CPC ........ A61K 51/065; A61K 51/04; A61K 9/00; A61P 35/04
See application file for complete search history.

(56) References Cited

U.S. PATENT DOCUMENTS

| | | |
|---|---|---|
| 8,778,305 B2 | 7/2014 | Pomper et al. |
| 9,226,981 B2 | 1/2016 | Pomper et al. |
| 2006/0252107 A1 | 11/2006 | Kubota et al. |
| 2010/0178246 A1 | 7/2010 | Babich et al. |
| 2015/0064185 A1 | 3/2015 | Holt et al. |
| 2015/0139905 A1 | 5/2015 | Chimmanamada et al. |
| 2016/0222036 A1 | 8/2016 | Babich et al. |
| 2017/0070482 A1 | 3/2017 | Mandyam |

FOREIGN PATENT DOCUMENTS

| | | |
|---|---|---|
| JP | 2010-509358 A | 3/2010 |
| JP | 2011-529919 A | 12/2011 |
| WO | WO-2008/058192 A2 | 5/2008 |
| WO | WO-2010/014933 A2 | 2/2010 |
| WO | WO 2010/032248 A2 | 3/2010 |
| WO | WO2015/055318 A1 | 4/2015 |
| WO | WO-2017/070482 A2 | 4/2017 |
| WO | WO 2017/070482 A2 | 4/2017 |

OTHER PUBLICATIONS

Cristina Muller et el., DOTA Conjugate with an Albumin-Binding Entity Enables the First Folic Acid-Targeted 177Lu-Radionuclide Tumor Therapy in Mice, J Nucl Med 54, 124-131. (Year: 2013).*
Notice of Allowance in U.S. Appl. No. 16/246,422 dated Mar. 5, 2020.
Official Action issued in co-pending European Patent Application No. 17816235.0, dated Jan. 24, 2020.
Non-Final Office Action issued in co-pending U.S. Appl. No. 17/016,189, dated Sep. 1, 2021.
Third Party Submission under 37 C.F.R §1.290 issued in co-pending U.S. Appl. No. 17/016,189, dated Jun. 30, 2021, received by Applicant on Sep. 29, 2021.
Dvořáková, et al., "Inhibitor-Decorated Polymer Conjugates Targeting Fibroblast Activation Protein," *Journ. of Medicinal Chemistry*, vol. 60, pp. 8385-8393 (2017).
Huang, et al., "Evaluation of the Tumor Targeting of a FAP α-based Doxorubicin Prodrug," *Journ. of Drug Targeting*, vol. 19, No. 7, pp. 487-496 (2011).

(Continued)

*Primary Examiner* — Michael G. Hartley
*Assistant Examiner* — Jagadishwar R Samala
(74) *Attorney, Agent, or Firm* — Foley & Lardner LLP

(57) ABSTRACT

The present technology provides compounds, as well as compositions including such compounds, useful for imaging and/or treatment of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and/or a prostate cancer. The compounds are represented by the following formula: (I) or a pharmaceutically acceptable salt thereof.

(I)

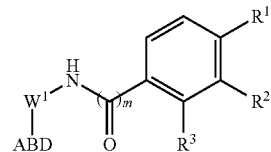

19 Claims, 20 Drawing Sheets

(56) References Cited

OTHER PUBLICATIONS

Müller, et al., "DOTA Conjugate with an Albumin-Binding Entity Enables the First Folic Acid-Targeted [177]Lu-Radionuclide Tumor Therapy in Mice," *The Journ. of Nuclear Medicine*, vol. 54, No. 1, pp. 124-131 (2013).
Baccala, et al., "Expression of Prostate-Specific Membrane Antigen in Tumor-Associated Neovasculature of Renal Neoplasms," Urology, 70 (2), 2007, pp. 385-390.
Cancer [online], [retrieved on Jul. 6, 2007]. Retrieved from the Internet,URL: http://www.nlm.nih.gov/medlineplus/cancer.html.
Chang, et al., "Five Different Anti-Prostate-specific Membrane Antigen (PSMA) Antibodies Confirm PSMA Expression in Tumor-associated Neovasculature," Cancer Research 59, Jul. 1, 1999, pp. 3192-3198.
Chen, et al., "Quantitative Studies of Allosteric Effects by Biointeraction Chromatography: Analysis of Protein Binding for Low-Solubility Drugs," Analytical Chemistry, vol. 78, No. 8, Apr. 15, 2006, pp. 2672-2683.
Chen, et al., "Radiohalogenated Prostate-Specific Membrane Antigen (PSMA)-Based Ureas as Imagine Agents for Prostate Cancer," J. Med. Chem., 51, 2008, pp. 7933-7943.
Dennis et al., "Imaging Tumors with an Albumin-Binding Fab, a Novel Tumor-Targeting Agent," Cancer Research, vol. 67, Jan. 1, 2007, pp. 254-261.
Fendler, et al., "Preliminary experience with dosimetry, response and patient reported outcome after 177Lu-PSMA-617 therapy for metastatic castration-resistant prostate cancer," Oncotarget, vol. 8, No. 2, 2017, pp. 3581-3590.
Golub, et al., "Molecular Classification of Cancer: Class Discovery and Class Prediction by Gene Expression Monitoring", Science 286: 531-537 (1999).
Haffner, et al., "Prostate-specific membrane antigen expression in the neovasculature of gastric and colorectal cancers," Human Pathology, 40, 2009, pp. 1754-1761.
Hillier et al, "Preclinical Evaluation of Novel Glutamate-Urea-Lysine Analogues That Target Prostate-Specific Membrane Antigen as Molecular Imaging Pharmaceuticals for Prostate Cancer," Cancer Research, vol. 69, pp. 6932-6240, 2009.
Joseph, et al., "The effects of glycation on the binding of human serum albumin to warfarin and L-tryptophan," Journal of Pharmaceutical and Biomedical Analysis, 53, 2010, pp. 811-818.
Kelly et al., "Double Targeting Ligands with Modulated Pharmacokinetics for Endoradiotherapy of Prostate Cancer," J. Nucl. Med, Apr. 27, 2017, 36 pages.
Kelly, et al., "Synthesis and pre-clinical evaluation of a new class of high-affinity 18F-labeled PSMA ligands for detection of prostate cancer by PET imaging," Eur J Nucl Med Mol Imaging, 44, 2017, pp. 647-661.
Kiess et al. "(2S)-2-(3-1Carboxy-5-(4-211AT-Astatobenzamido)Pentyl)Ureido)-Pentanedioc Acid for PSMA-Targeted alpha-Particle Radiopharmaceutical Therapy," J Nucl Med., 2016, vol. 57, pp. 1569-1575.
Kratochwil, et al., "225Ac-PSMA-617 for PSMA-Targeted FFD3B1-Radiation Therapy of Metastatic Castration-Resistant Prostate Cancer," The Journal of Nuclear Medicine, vol. 57, No. 12, Dec. 2016, pp. 1941-1944.
Kratochwil, et al., "PSMA-Targeted Radionuclide Therapy of Metastatic Castration-Resistant Prostate Cancer with 177Lu-Labeled PSMA-617," The Journal of Nuclear Medicine, vol. 57, No. 8, Aug. 2016, pp. 1170-1176.
Lala, et al., "Role of nitric oxide in tumor progression: Lessons from experimental tumors," Cancer and Metastasis Reviews, (1998), 17(1):91-106.
Maresca, et al., "A Series of Halogenated Heterodimeric Inhibitors of Prostate Specific Membrane Antigen (PSMA) as Radiolabeled Probes for Targeting Prostate Cancer," J. Med. Chem., 52, 2009, pp. 347-367.
Matsuda, "Analysis of Drug-Protein Interactions by High-Performance Affinity Chromatography: Interactions of Sulfonylurea Drugs with Normal and Glycated Human Serum Albumin," Methods in Molecular Biology, vol. 1286, 2015, pp. 255-277.
Non-Final Office Action on U.S. Appl. No. 16/134,789 dated Sep. 20, 2019.
Non-Final Office Action on U.S. Appl. No. 16/246,422 dated Jul. 11, 2019.
Notice of Allowance on U.S. Appl. No. 15/630,808 dated Sep. 6, 2018.
O'Keefe, et al., "Comparative Analysis of Prostate-Specific Membrane Antigen )PSMA) Versus a Prostate-Specific Membrane Antigen-Like Gene," The Prostate 58, 2004, pp. 200-210.
Samplaski, et al., "Folate hydrolase (prostate-specific antigen) 1 expression in bladder cancer subtypes and associated tumor neovasculature," Modern Pathology, 2011, pp. 1521-1529.
Wang, et al., "Expression of Prostate-Specific Membrane Antigen in Lung Cancer Cells and Tumor Neovasculature Endothelial Cells and Its Clinical Significance," PLOS ONE, May 15, 2015, pp. 1-8.
Wernicke, et al., "Prostate-specific Membrane Antigen (PSMA) Expression in the Neovasculature of Gynecological Malignancies: Implications for PSMA-targeted Therapy," Appl Immunohistochem Mol Morphol, vol. 25, No. 4, Apr. 2017, pp. 271-276.
Wustemann, et al., "protecting salivary glands: Displacement of off-target bound prostate-specific membrane antigen ligands," 2016, p. S15.
Zechmann, et al., "Radiation dosimetry and first therapy results with a 124I/131 I-labeled small molecule (MIP-1095) targeting PSMA for prostate cancer therapy," Eur J Nucl Med Mol Imaging, 41, 2014, pp. 1280-1292.
Zheng, et al., "Development of enhanced capacity affinity microcolumns by using a hybrid of protein cross-linking/modification and immobilization," Journal of Chromatography A, 1400, 2015, pp. 82-90.
Notice of Reasons for Rejection issued in co-pending Japanese Patent Application No. 2018-567684, dated May 18, 2021.
Non-Final Office Action issued in co-pending U.S. Appl. No. 16/906,956, dated Jun. 9, 2021.
C. Muller et al., "DOTA Conjugate with an Albumin-Binding Entity Enables the First Folic Acid-Targeted 177Lu-Radionuclide Tumor Therapy in Mice", The Journal of Nuclear Medicine, vol. 54, No. 1, pp. 124-131 (Jan. 1, 2013).
Renata Farkas, et al. "64 Cu- and 68 Ga-Based PET Imaging of Folate Receptor-Positive Tumors: Development and Evaluation of an Albumin-Binding N0DAGA-Folate", Molecular Pharmaceutics, vol. 13, No. 6, pp. 1979-1987 (Jun. 6, 2016).
Foreign Search Report on EP 18780348.1, dated Dec. 7, 2020.
Fischer, et al., "Radioimmunotherapy of Fibroblast Activation Protein Positive Tumors by Rapidly Internalizing Antibodies," Clinical Cancer Research, 18(22):6208-6218 (2012) (12 pages).
Third-Party Submission Under 37 CFR 1.290 issued in U.S. Appl. No. 17/132,552, filed Sep. 29, 2021 (19 pages).
Kelly, et al., "Dual-Target Binding Ligands with Modulated Pharmacokinetics for Endoradiotherapy of Prostate Cancer," *The Journ. of Nuclear Medicine*, vol. 58, No. 9, pp. 1442-1449 (Sep. 2017).
Office Action issued in Chinese Patent Application No. 201780046339.7, dated Apr. 23, 2021.
Non-Final Office Action issued in co-pending U.S. Appl. No. 17/016,189, dated Oct. 21, 2021.
Guo, et al., "Receptor-Targeted Gene Delivery ViaFolate-Conjugated Polyethylenimine," *AAPS Pharmsci.*, 1(4) Article 19, pp. 1-7 (1999).
Non-Final Office Action issued in co-pending U.S. Appl. No. 17/132,552, dated Dec. 13, 2021.

* cited by examiner

TRIFUNCTIONAL CONSTRUCTS WITH TUNABLE PHARMACOKINETICS USEFUL IN IMAGING AND ANTI-TUMOR THERAPIES

CROSS-REFERENCE TO RELATED APPLICATIONS

This application is a U.S. national phase application under 35 U.S.C. § 371 of International Application No. PCT/US2018/026340, filed on Apr. 5, 2018, which claims the benefit of and priority to U.S. Provisional Patent Application No. 62/482,038, filed on Apr. 5, 2017, and U.S. Provisional Patent Application No. 62/574,720, filed on Oct. 19, 2017, the entire disclosures of each of which is incorporated herein by reference for any and all purposes.

U.S. GOVERNMENT LICENSE RIGHTS

This invention was made with Government support under grant number UL1TR00457 awarded by the National Institutes of Health. The Government has certain rights in the invention.

FIELD

The present technology generally relates to trifunctional constructs that include (1) an antigen-binding domain, (2) cytotoxin-containing and/or imaging agent-containing domain; and (3) an albumin-binding moiety. The present technology also provides compositions including such compounds as well as methods of use in imaging and/or anti-tumor therapy. For example, the compounds and compositions of the present technology are useful theranostic compounds.

SUMMARY

In an aspect, a compound of Formula I is provided:

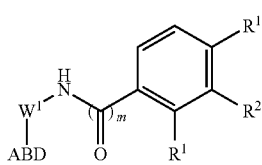

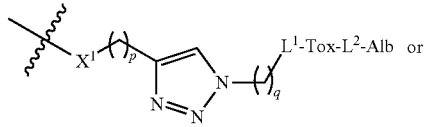

or a pharmaceutically acceptable salt and/or solvate thereof, wherein
ABD is an antigen-binding domain;
$W^1$ is —C(O)—, —(CH$_2$)$_n$—, or —(CH$_2$)$_o$—NH—C(O)—;
one of $R^1$, $R^2$, and $R^3$ is

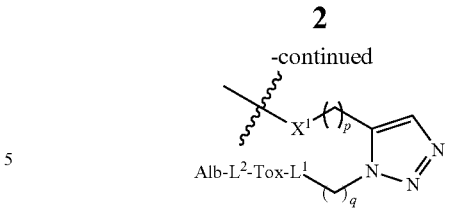

and the remaining two of $R^1$, $R^2$, and $R^3$ are each H;
$X^1$ is absent, O, S, or NH;
$L^1$ is absent, —C(O)—, —C(O)—NR$^4$—, —C(O)—NR$^5$—C$_1$-C$_{12}$ alkylene-, —C$_1$-C$_{12}$ alkylene-C(O)—, —C(O)—NR$^6$—C$_1$-C$_{12}$ alkylene-C(O)—, -arylene-, —O(CH$_2$CH$_2$O)$_r$—CH$_2$CH$_2$C(O)—, an amino acid, a peptide of 2, 3, 4, 5, 6, 7, 8, 9, or 10 amino acids, or a combination of any two or more thereof, where r is 0, 1, 2, 3, 4, 5, 6, 7, 8, or 9, and where R$^4$, R$^5$, and R$^6$ are each independently H, alkyl, or aryl;
Tox is a cytotoxin-containing and/or imaging agent-containing domain;
$L^2$ is absent, —C(O)—, —(CH$_2$CH$_2$O)$_s$—CH$_2$CH$_2$C(O)—, a peptide of 2, 3, 4, 5, 6, 7, 8, 9, 10, 11, 12, 13, 14, 15, 16, 17, 18, 19, or 20 amino acids, or a combination of any two or more thereof, where s is 0, 1, 2, 3, 4, 5, 6, 7, 8, 9, 10, 11, 12, 13, 14, 15, 16, 17, 18, or 19;
Alb is an albumin-binding moiety;
m is 0 or 1; n is 1 or 2; o is 1 or 2; p is 0, 1, 2, or 3, provided that when p is 0 then $X^1$ is absent;
and q is 1 or 2.

In any embodiment herein the compound of Formula I may be a compound of Formula II

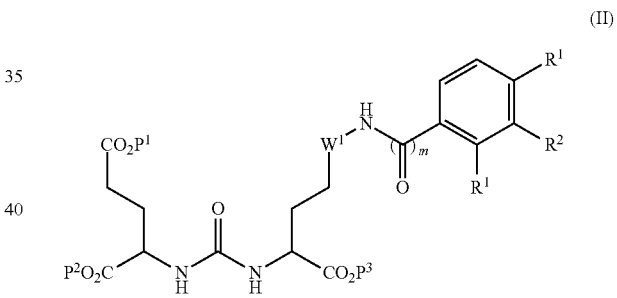

or a pharmaceutically acceptable salt and/or solvate thereof, wherein
$P^1$, $P^2$, and $P^3$ are each independently H, methyl, benzyl, 4-methoxybenzyl, or tert-butyl; one of $R^1$, $R^2$, and $R^3$ is

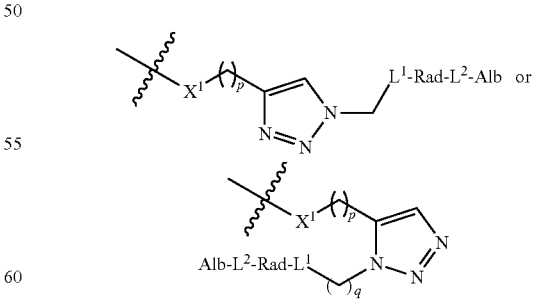

and the remaining two of $R^1$, $R^2$, and $R^3$ are each H;
Rad is a moiety capable of including a metal ion, optionally further including a metal ion; p is 0, 1, 2, or 3, provided that when p is 0 then $X^1$ is absent; and q is 1 or 2.

In another aspect, the present technology provides compositions (e.g., pharmaceutical compositions) and medicaments comprising any of one of the embodiments of the compounds of Formula I (or a pharmaceutically acceptable salt thereof) disclosed herein and a pharmaceutically acceptable carrier or one or more excipients or fillers.

In another aspect, the present technology provides methods of treatment and/or methods of imaging by administering an effective amount of the comprising any of one of the embodiments of the compounds of Formula I (or a pharmaceutically acceptable salt thereof) disclosed herein to a subject in need of treatment and/or imaging.

In another aspect, the present technology provides a method of achieving an in vivo tissue distribution of a radiotherapeutic in a mammalian subject in which a ratio of tumor activity to kidney activity of 1 or greater is observed within about 4 hours to about 24 hours of administration of the radiotherapeutic to the mammalian subject, wherein the method comprises administering to the mammalian subject the radiotherapeutic; and the radiotherapeutic comprises a first moiety that targets prostate specific membrane antigen ("PSMA"), a second moiety that bears a radionuclide, and a third moiety that has an affinity for serum albumin, the first moiety being separated from the second moiety by a first covalent linker and the third moiety being separated from the second moiety by a second covalent linker, wherein the separation between the first and second moieties (on the basis of a contiguous atom count associated with the first covalent linker) is from about 8 atoms to about 40 atoms, and the separation between the third moiety and the first and second moieties (on the basis of a contiguous atom count associated with the second covalent linker) is from about 10 atoms to about 100 atoms.

DETAILED DESCRIPTION

Figure 1:
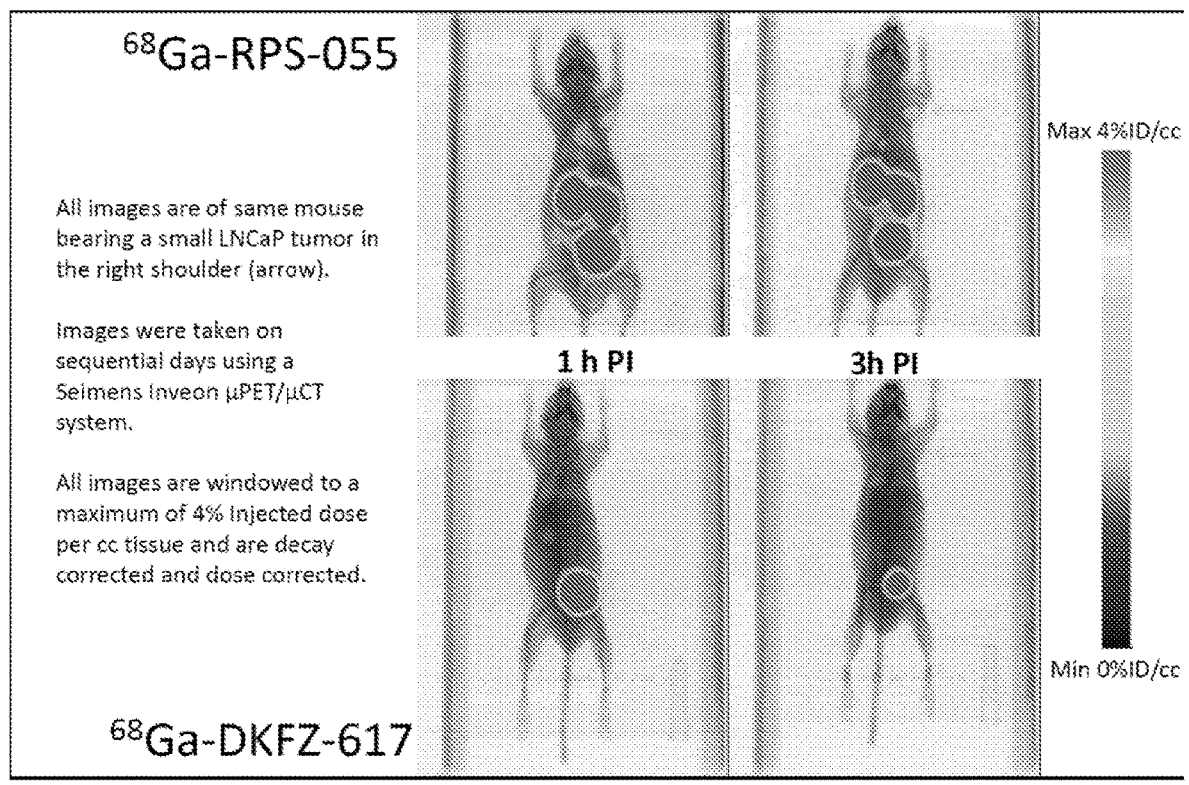
FIG. 1 provides PET images of mice injected with $^{68}$Ga-RPS-055 (top) or $^{68}$Ga-DKFZ-617 (bottom) both 1 h and 3 h post injection. All images are of the same mouse bearing a small LNCaP tumor in the right shoulder (arrow). Images were taken on sequential days using a Siemens Inveon μPET/μCT system (Siemens Corp., Munich, Germany). All images were windowed to a maximum of 4% injected dose per cc tissue and are decay corrected and dose corrected.
Figure 2:
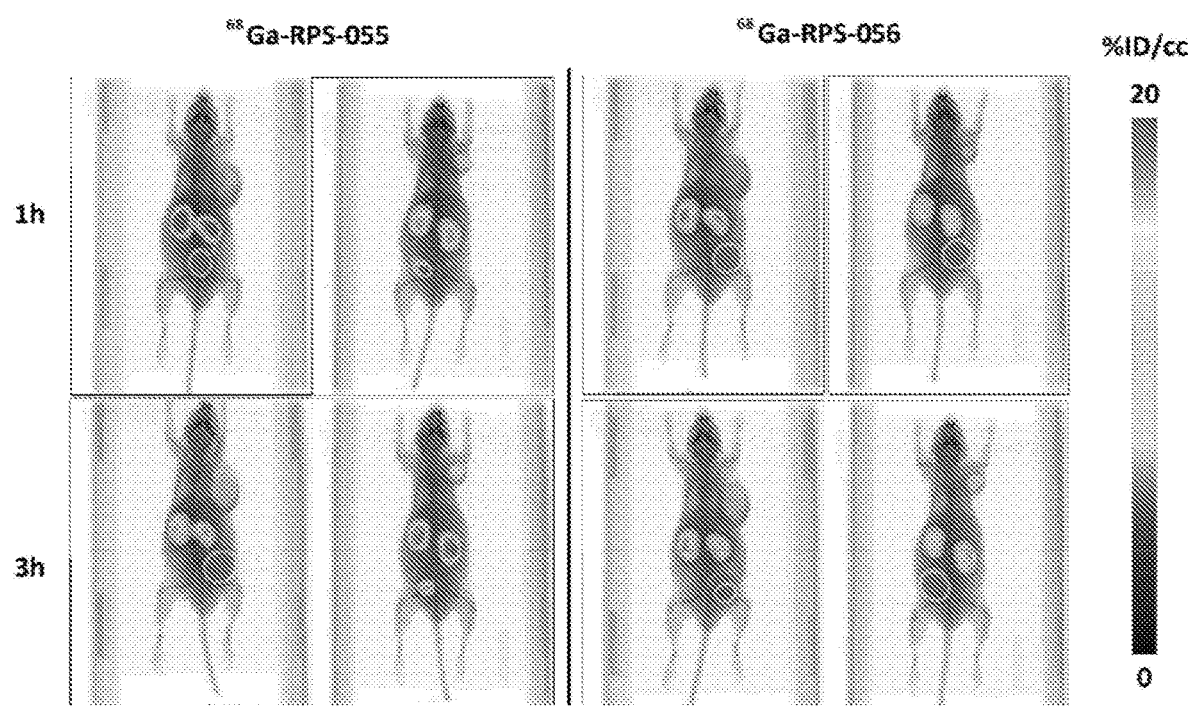
FIG. 2 provides PET images of mice injected with $^{68}$Ga-RPS-055 (left panels) or $^{68}$Ga-RPS-056 (right panels) both 1 h (top) and 3 h (bottom) post injection. All images are of the same mice bearing small LNCaP tumors in their right shoulders. Images were taken on sequential days usings a Siemens Inveon μPET/μCT system (Siemens Corp., Munich, Germany). All images were windowed to a maximum of 20% injected dose per cc tissue and are decay corrected and dose corrected.
Figure 3:
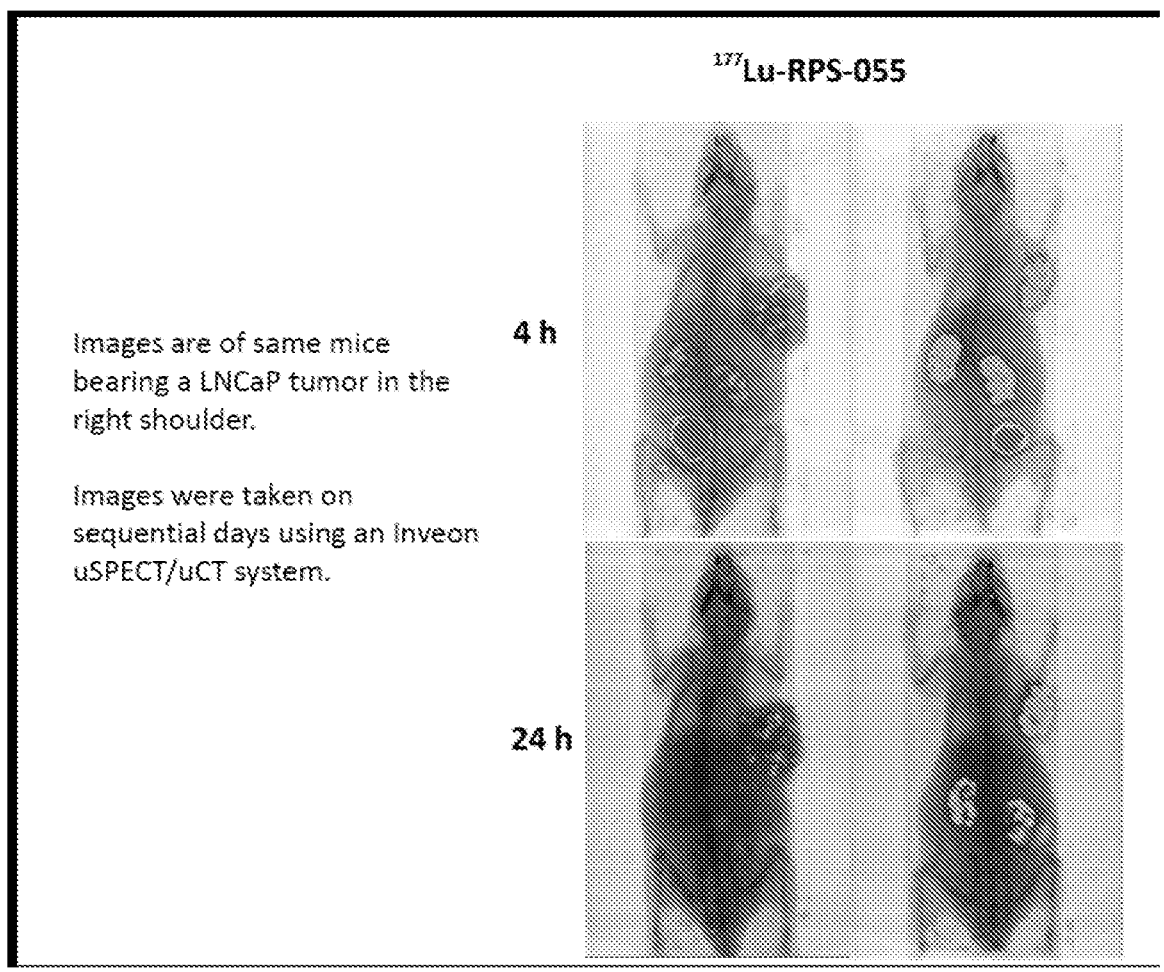
FIG. 3 provides SPECT images of mice injected with $^{177}$Lu-RPS-055 both 4 h (top) and 3 h (bottom) post injection. All images are of the same mice bearing small LNCaP tumors in their right shoulders (left panels and right panels). Images were taken on the same day using a Siemens Inveon μSPECT/μCT system (Siemens Corp., Munich, Germany).
Figure 4:
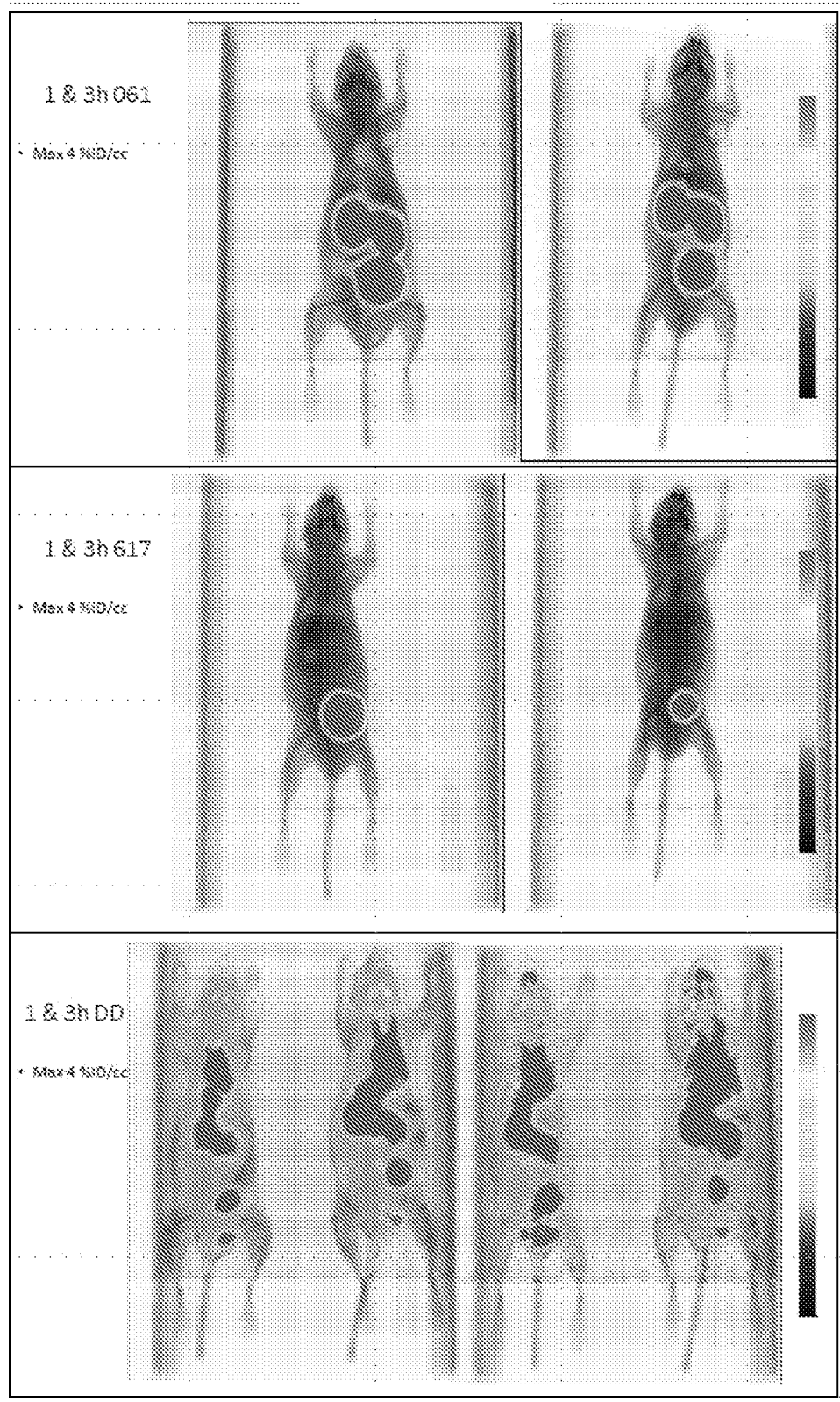
FIG. 4 shows PET images of BALB/C nu/nu mice bearing LNCaP tumor xenografts and injected intravenously with either $^{68}$Ga-RPS-061, $^{68}$Ga-PSMA-617 or $^{68}$Ga-RPS-030. The mice were imaged on sequential days at 1 h (left) and 3 h (right) post injection using a Siemens Inveon μSPECT/μCT system (Siemens Corp., Munich, Germany).

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH($CH_3$), —CH=C($CH_3$)$_2$, —C($CH_3$)$CH_2$, —C($CH_3$)CH($CH_3$), —C($CH_2CH_3$)=$CH_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O— group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)═C(R$^{95}$)NR$^{96}$R$^{97}$ and —NR$^{94}$C(R$^{95}$)═C(R$^{6}$)R$^{97}$, wherein R$^{94}$, R$^{95}$, R$^{6}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

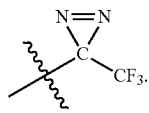

The term "isocyano" refers to —NC.
The term "isothiocyano" refers to —NCS.
The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

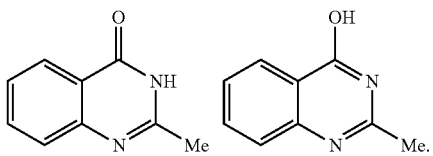

As another example, guanidines may exhibit the following isomeric forms in protic organic solution, also referred to as tautomers of each other:

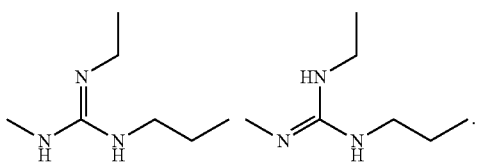

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided in sections within the Examples. The disclosures of these publications, patents and published patent specifications are hereby incorporated by reference into the present disclosure to more fully describe the present technology.

The Present Technology

In general, there is a need for radiotherapeutic compounds that accumulate to a greater degree in tumors without unacceptable uptake in normal organs, as absorbed dose is a function of the integral of cumulative activity. Furthermore, although targeted radiotherapy has been practiced for some time using macrocyclic complexes of radionuclides, the macrocycles currently in use (e.g., DOTA) generally form complexes of insufficient stability with radionuclides, particularly for radionuclides of larger size, such as actinium, radium, bismuth, and lead isotopes. These larger radionuclides are generally alpha-emitting radionuclides, i.e., radionuclides of much higher energy, and thus substantially more potent, than beta-emitting radionuclides. The instability of currently known macrocyclic-containing compounds results in dissociation of the radionuclide from the macrocycle, and this results in a lack of selectivity to targeted tissue, which also results in toxicity to non-targeted tissue.

The present technology provides new trifunctional compounds that overcome these problems, particularly accumulating to a greater degree in tumors without unacceptable uptake in normal organs. The present technology also includes macrocyclic complexes that are substantially more stable than those of the conventional art, providing for the use of alpha-emitting radionuclides instead of beta radionuclides. Thus, the compounds of the present technology advantageously target cancer cells more effectively, with substantially less toxicity to non-targeted tissue than complexes of the art. Moreover, the new complexes can advantageously be produced at room temperature, in contrast to DOTA-type complexes, which generally require elevated temperatures (e.g., at least 80° C.) for complexation with the radionuclide.

Thus, in one aspect of the present technology, a compound of Formula I is provided:

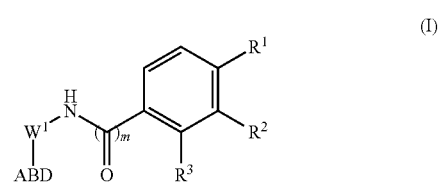

or a pharmaceutically acceptable salt and/or solvate thereof, wherein
ABD is an antigen-binding domain;
$W^1$ is —C(O)—, —(CH$_2$)$_n$—, or —(CH$_2$)$_o$—NH—C(O)—;
one of $R^1$, $R^2$, and $R^3$ is

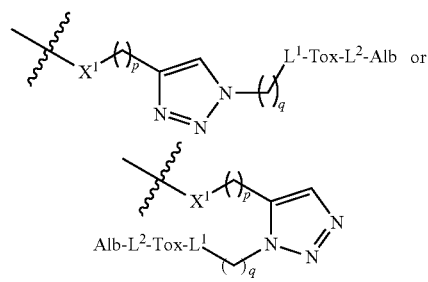

and the remaining two of $R^1$, $R^2$, and $R^3$ are each H;
$X^1$ is absent, O, S, or NH;
$L^1$ is absent, —C(O)—, —C(O)—NR$^4$—, —C(O)—NR$^5$—C$_1$-C$_{12}$ alkylene-, —C$_1$-C$_{12}$ alkylene-C(O)—, —C(O)—NR$^6$—C$_1$-C$_{12}$ alkylene-C(O)—, -arylene-, —O(CH$_2$CH$_2$O)$_r$—CH$_2$CH$_2$C(O)—, an amino acid, a peptide of 2, 3, 4, 5, 6, 7, 8, 9, or 10 amino acids, or a combination of any two or more thereof, where r is 0, 1, 2, 3, 4, 5, 6, 7, 8, or 9, and where $R^4$, $R^5$, and $R^6$ are each independently H, alkyl, or aryl;
Tox is a cytotoxin-containing and/or imaging agent-containing domain;
$L^2$ is absent, —C(O)—, —(CH$_2$CH$_2$O)$_s$—CH$_2$CH$_2$C(O)—, a peptide of 2, 3, 4, 5, 6, 7, 8, 9, 10, 11, 12, 13, 14, 15, 16, 17, 18, 19, or 20 amino acids, or a combination of any two or more thereof, where s is 0, 1, 2, 3, 4, 5, 6, 7, 8, 9, 10, 11, 12, 13, 14, 15, 16, 17, 18, or 19;
Alb is an albumin-binding moiety;
m is 0 or 1; n is 1 or 2; o is 1 or 2; p is 0, 1, 2, or 3, provided that when p is 0 then $X^1$ is absent; and q is 1 or 2.

For the sake of clarity, in the compounds of the present technology the term "absent" in reference to a divalent group such as $X^1$, $L^1$, and $L^2$ means that instead of the divalent group there is a bond. For example, when L is "absent" one of R¹, R² and R³ is

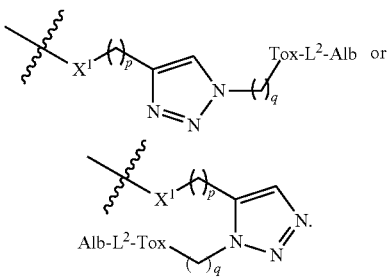

The antigen-binding domain includes a moiety capable of recognizing or interacting with molecular targets on the surface of cells. These molecular targets include cell surface proteins such as receptors, enzymes, and antigens. For example, the molecular target may be a receptor, an enzyme, and/or an antigens expressed on a tumor cell surface (such as a tumor-specific cell surface protein) capable of interacting with the antigen-binding domain. An example of such a tumor targeting moiety is the glutamate-urea-lysine motif recognized by prostate specific membrane antigen (PSMA) which is expressed on the surface of most prostate cancer cells. Another example is edotreotide, recognized by somatostatin receptors expressed on the surface of many neuroendocrine cancers. Thus, the antigen-binding domain of any embodiment herein may include a moiety capable of binding to one or more of PSMA, somatostatin peptide receptor-2 (SSTR2), somatostatin peptide receptor-5 (SSTR5), an integrin (e.g., alphavbeta6, alphavbeta3, and/or alphavbeta5), a gastrin-releasing peptide receptor, a seprase, fibroblast activation protein alpha (FAP-alpha), an incretin receptor, a glucose-dependent insulinotropic polypeptide receptor, VIP-1, NPY, a folate receptor, LHRH, a neuronal transporter (e.g., noradrenaline transporter (NET)), EGFR, HER-2, VGFR, MUC-1, CEA, MUC-4, ED2, TF-antigen, an endothelial specific marker, neuropeptide Y, uPAR, TAG-72, a CCK analog, VIP, bombesin, VEGFR, GLP-1, CXCR4, hepsin, TMPRSS2, a caspace, and cMET.

The albumin-binding moiety plays a role in modulating the rate of blood plasma clearance of the compounds in a subject, thereby increasing circulation time and compartmentalizing the cytotoxic action of cytotoxin-containing domain and/or imaging capability of the imaging agent-containing domain in the plasma space instead of normal organs and tissues that may express antigen. Without being bound by theory, this component of the structure is believed to interact reversibly with serum proteins, such as albumin and/or cellular elements. The affinity of this albumin-binding moiety for plasma or cellular components of the blood may be configured to affect the residence time of the compounds in the blood pool of a subject. In any embodiment herein, the albumin binding-moiety may be configured so that it binds reversibly or non-reversibly with albumin when in blood plasma. In any embodiment herein, the albumin binding-moiety may be selected such that the binding affinity of the compound with human serum albumin is about 5 µM to about 15 µM.

By way of example, the albumin-binding moiety of any embodiment herein may include a short-chain fatty acid, medium-chain chain fatty acid, a long-chain fatty acid, myristic acid, a substituted or unsubstituted indole-2-carboxylic acid, a substituted or unsubstituted 4-oxo-4-(5,6,7, 8-tetrahydronaphthalen-2-yl)butanoic acid, a substituted or unsubstituted naphthalene acylsulfonamide, a substituted or unsubstituted diphenylcyclohexanol phosphate ester, a substituted or unsubstituted 2-(4-iodophenyl)acetic acid, a substituted or unsubstituted 3-(4-iodophenyl)propionic acid, or a substituted or unsubstituted 4-(4-iodophenyl)butanoic acid. Certain representative examples of albumin-binding moieties that may be included in any embodiment herein include one or more of the following:

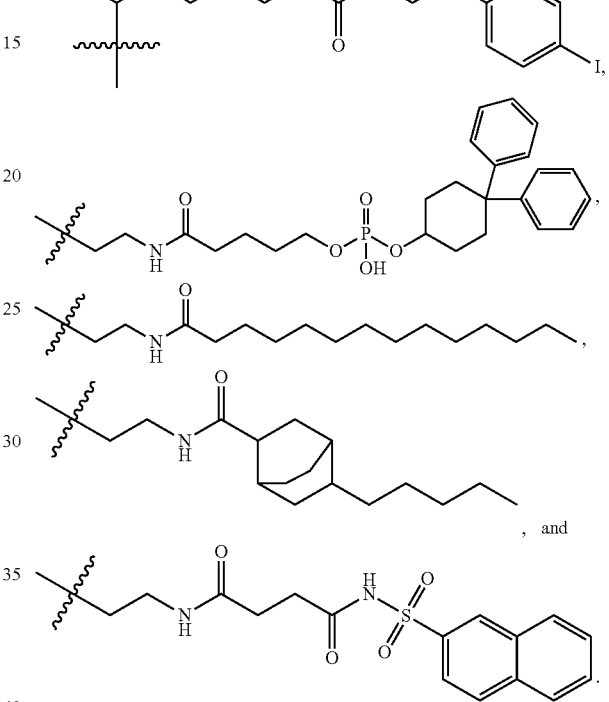

In any embodiment herein, the compounds may include an albumin-binding moiety that is

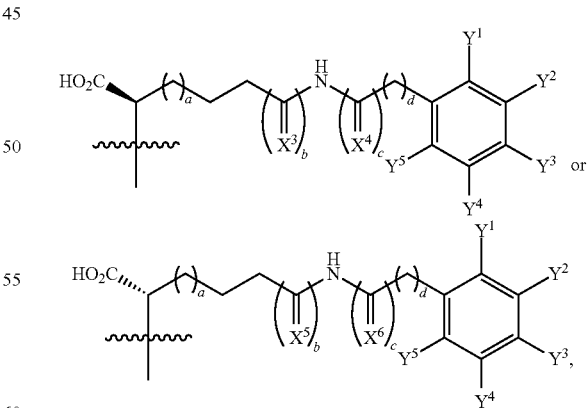

where Y¹, Y², Y³, Y⁴, and Y⁵ are independently H, halo, or alkyl, X³, X⁴, X⁵, and X⁶ are each independently O or S, a is independently at each occurrence 0, 1, or 2, b is independently at each occurrence 0 or 1, c is independently at each occurrence 0 or 1, and d is independently at each occurrence 0, 1, 2, 3, or 4. In any embodiment herein, it may be that b and c cannot be the same value. In any embodiment herein, it may be that $Y^3$ is I and each of $Y^1$, $Y^2$, $Y^4$, and $Y^5$ are independently H.

As discussed above, the Tox group of Formula I is a cytotoxin-containing and/or imaging agent-containing domain, such as a cytotoxic chemical moiety, a moiety capable of including a metal ion, a chelator, a metal ion-bearing moiety, or a combination of any two or more thereof. By way of example of compounds that include a moiety capable of including a metal ion (such as by chelation of the metal ion and/or via a covalent bond with the metal ion), in any embodiment herein the compound of Formula I may be a compound of Formula II:

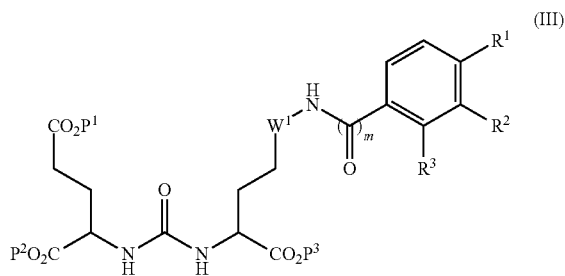

(III)

or a pharmaceutically acceptable salt and/or solvate thereof, wherein
 $W^1$, $X^1$, $L^1$, $L^2$, r, s, m, n, and o (and any other variable) are as provided for any embodiment herein of Formula I;
 $P^1$, $P^2$, and $P^3$ are each independently H., methyl, benzyl, 4-methoxybenzyl, or tert-butyl; one of $R^1$, $R^2$, and $R^3$ is

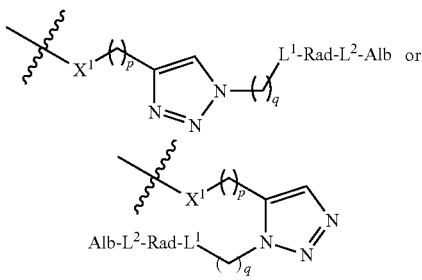

and the remaining two of R, R, and $R^3$ are each H;
 Rad is a moiety capable of including a metal ion, optionally further including a metal ion; p is 0, 1, 2, or 3, provided that when p is 0 then $X^1$ is absent; and q is 1 or 2.

In any embodiment herein, it may be $P^1$, $P^2$, and $P^3$ are each independently H.

Rad in the compound of Formula II may or may not include a metal ion, where compounds that do not include a metal ion. In any embodiment herein, Tox and/or Rad may include a chelator; in any embodiment herein, Tox and/or Rad may include a chelator that chelates a metal ion. Such chelated metal ions may provide the compounds of the present technology may be used in, e.g., magnetic resonance imaging, luminescence imaging, radiotherapy, or a combination of any two or more thereof. The metal ion of any embodiment herein for Tox and/or Rad may be a radionuclide, such as $^{177}Lu^{3+}$, $^{175}Lu^{3+}$, $^{45}Sc^{3+}$, $^{66}Ga^{3+}$, $^{67}Ga^{3+}$, $^{68}Ga^{3+}$, $^{69}Ga^{3+}$, $^{71}Ga^{3+}$, $^{89}Y^{3+}$, $^{86}Y^{3+}$, $^{89}Zr^{4+}$, $^{90}Y^{3+}$, $^{99m}Tc^{+1}$, $^{111}In^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{152}Dy^{3+}$, $^{149}Tb^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, $^{160}Gd^{3+}$, $^{188}Re^{+1}$, $^{186}Re^{+1}$, $^{213}Bi^{3+}$, $^{211}At^{+}$, $^{217}At^{+}$, $^{227}Th^{4+}$, $^{226}Th^{4+}$, $^{225}Ac^{3+}$, $^{233}Ra^{2+}$, $^{152}Dy^{3+}$, $^{213}Bi^{3+}$, $^{212}Bi^{3+}$, $^{211}Bi^{3+}$, $^{212}Pb^{2+}$, $^{212}Pb^{4+}$, $^{255}Fm^{3+}$, or uranium-230. For example, the metal ion may be an alpha-emitting radionuclide selected from $^{213}Bi^{3+}$, $^{211}At^{+}$, $^{225}Ac^{3+}$, $^{152}Dy^{3+}$, $^{212}Bi^{3+}$, $^{211}Bi^{3+}$, $^{217}At^{+}$, $^{227}Th^{4+}$, $^{226}Th^{4+}$, $^{233}Ra^{2+}$, $^{212}Pb^{2+}$, and $^{212}Pb^{4+}$.

Chelators useful in any embodiment of the present technology include, but are not limited to, a covalently conjugated substituted or unsubstituted chelator of the following group:
 1,4,7-triazacyclononane-1,4,7-triacetic acid (NOTA),
 1,4,7,10-tetraazacyclododecane-1,4,7,10-tetraacetic acid (DOTA),
 p-SCN-Bn-DOTA (also known as 2B-DOTA-NCS),
 PIP-DOTA,
 diethylenetriaminepentaacetic acid (DTPA),
 PIP-DTPA,
 AZEP-DTPA,
 ethylenediamine tetraacetic acid (EDTA),
 triethylenetetraamine-N,N,N',N'',N''',N''''-hexa-acetic acid (TTHA),
 7-[2-(bis-carboxymethylamino)-ethyl]-4,10-bis-carboxymethyl-1,4,7,10-tetraaza-cyclododec-1-yl-acetic acid (DEPA),
 2,2',2''-(10-(2-(bis(carboxymethyl)amino)-5-(4-isothiocyanatophenyl) pentyl)-1,4,7,10-tetraazacyclododecane-1,4,7-triyl)triacetic acid (3p-C-DEPA-NCS),
 NETA,
 {4-carboxymethyl-7-[2-(carboxymethylamino)-ethyl]-perhydro-1,4,7-triazonin-1-yl}-acetic acid (NPTA),
 diacetylpyridinebis(benzoylhydrazone),
 1,4,7,10,13,16-hexaazacyclooctadecane-N,N',N'',N''', N'''',N'''''-hexaaceticacid (HEHA),
 octadentate terephthalamide ligands,
 siderophores,
 2,2'-(4-(2-(bis(carboxymethyl)amino)-5-(4-isothiocyanatophenyl)pentyl)-10-(2-(bis(carboxymethyl)amino) ethyl)-1,4,7,10-tetraazacyclododecane-1,7-diyl)diacetic acid,
 N,N-bis[(6-carboxy-2-pyridyl)methyl]-4,13-diaza-18-crown-6 ($H_2$ macropa),
 6-((16-((6-carboxypyridin-2-yl)methyl)-1,4,10,13-tetraoxa-7,16-diazacyclooctadecan-7-yl)methyl)-4-isothiocyanatopicolinic acid (macropa-NCS), and
 3,9-carboxymethyl-6-(2-methoxy-5-isothiocyanatophenyl)carboxymethyl-3,6,9,15-tetraazabicyclo-[9.3.1] pentadeca-1(15),11,13-triene.
Certain members of this exemplary group are illustrated below.

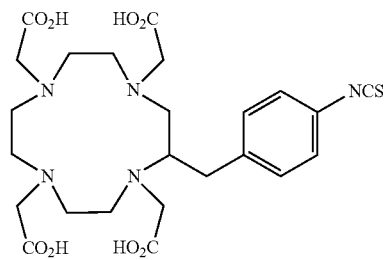

-continued

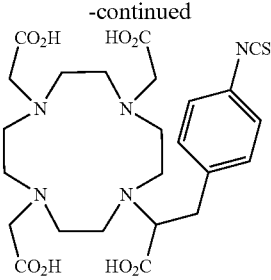

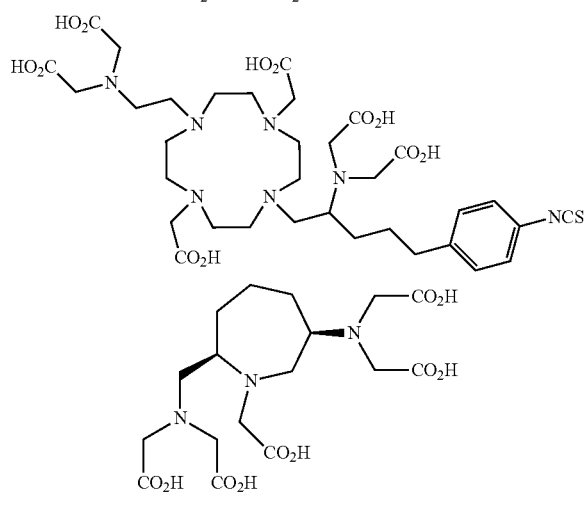

AZEP-DTPA

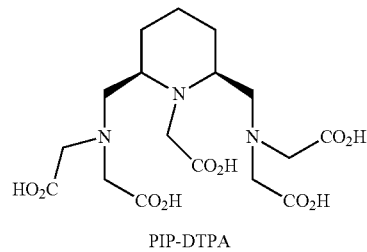

PIP-DTPA

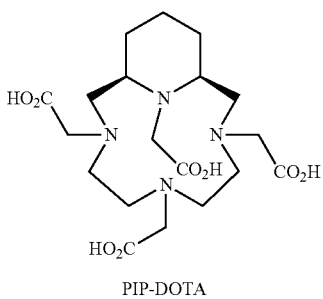

PIP-DOTA

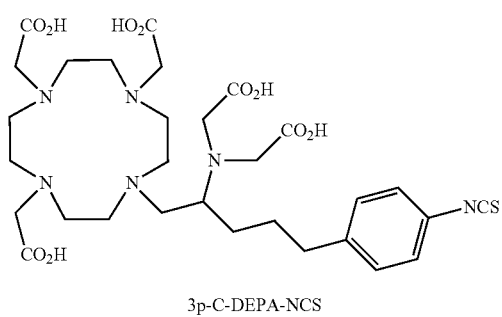

3p-C-DEPA-NCS

-continued

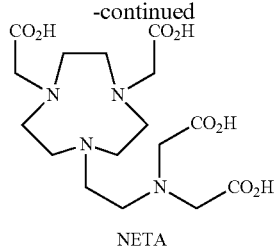

NETA

It is to be understood that a "covalently conjugated" chelator means a chelator (such as those listed above) wherein one or more bonds to a hydrogen atom contained therein are replaced by a bond to an atom of the remainder of the TOX and/or RAD moiety, to $L^1$, and/or to $L^2$, or a pi bond between two atoms is replaced by a bond from one of the two atoms to an atom of the remainder of the TOX and/or RAD moiety, to $L^1$, and/or to $L^2$, and the other of the two atoms includes a new bond, e.g. to a hydrogen (such as reaction of an —NCS group in the chelator to provide the covalently conjugated chelator).

A Tox and/or Rad group that includes a covalently conjugated chelator may, in any embodiment herein, be represented by

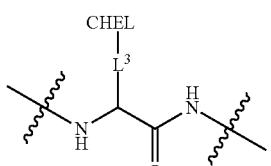

where $L^3$ is absent, —C(O)—, —$C_1$-$C_{12}$ alkylene-, —$C_1$-$C_{12}$ alkylene-C(O)—, —$C_1$-$C_{12}$ alkylene-$NR^{10}$—, or -arylene-; $R^{10}$ is H, alkyl, or aryl, and CHEL is a covalently conjugated chelator that may or may not include a chelated metal ion of any embodiment described herein. For example, compound of Formula I with such a Tox group or a compound of Formula II with such a Rad group may be a compound where one of $R^1$, $R^2$, and $R^3$ is

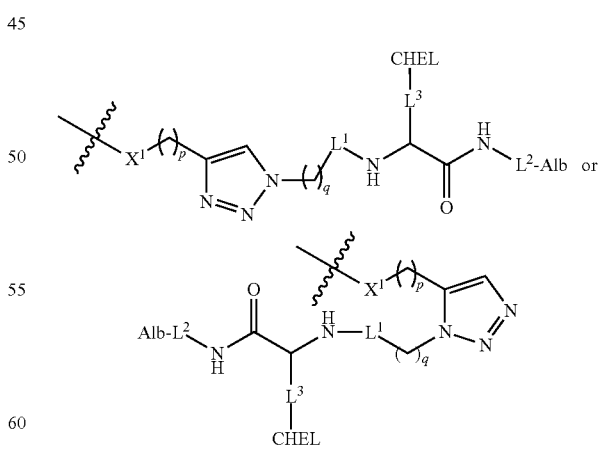

and the remaining two of $R^1$, $R^2$, and $R^3$ are each H; $L^3$ is absent, —C(O)—, —$C_1$-$C_{12}$ alkylene-, —$C_1$-$C_{12}$ alkylene-C(O)—, —$C_1$-$C_{12}$ alkylene-$NR^{10}$—, or -arylene-; $R^{10}$ is H, alkyl, or aryl; and CHEL is a covalently conjugated chelator that optionally includes a chelated metal ion.

As another example, compound of Formula II with such a Rad group may be a compound of Formula III

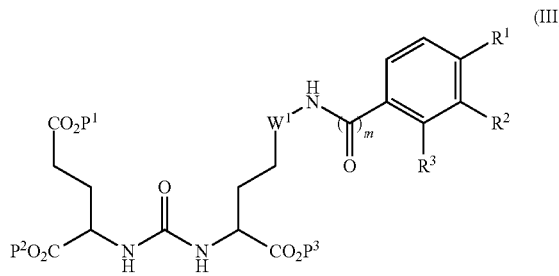

(III)

or a pharmaceutically acceptable salt and/or solvate thereof, wherein $W^1$, $X^1$, $L^1$, $L^2$, $P^1$, $P^2$, $P^3$, r, s, m, n, o, p, q (and any other variables) are as provided for any embodiment herein of Formulas I and II;

one of $R^1$, $R^2$, and $R^3$ is

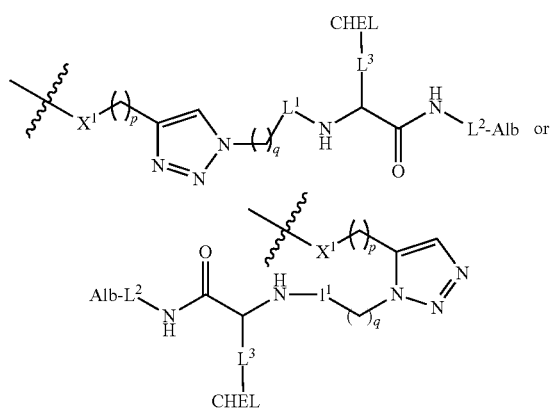

and the remaining two of $R^1$, $R^2$, and $R^3$ are each H; $L^3$ is absent, —C(O)—, —$C_1$-$C_{12}$ alkylene-, —$C_1$-$C_{12}$ alkylene-C(O)—, —$C_1$-$C_{12}$ alkylene-$NR^{10}$—, or -arylene-; $R^{10}$ is H, alkyl, or aryl; and CHEL is a covalently conjugated chelator that optionally includes a chelated metal ion.

In any embodiment herein, $L^1$ may be —O($CH_2CH_2$O)$_r$—$CH_2CH_2$C(O)—, an amino acid, a peptide of 2, 3, 4, 5, 6, 7, 8, 9, or 10 amino acids, or a combination of any two or more thereof. In any embodiment herein, $L^1$ may be —O($CH_2CH_2$O)$_r$—$CH_2CH_2$C(O)—, glycine, a polyglycine composed of 2, 3, 4, 5, 6, 7, 8, 9, or 10 glycine residues, or a combination of any two or more thereof.

In any embodiment herein, $L^2$ may be —C(O)—, —($CH_2CH_2$O)$_s$—$CH_2CH_2$C(O)—, a peptide of 2, 3, 4, 5, 6, 7, 8, 9, 10, 11, 12, 13, 14, 15, 16, 17, 18, 19, or 20 amino acids, or a combination of any two or more thereof. In any embodiment herein, $L^2$ may be —C(O)—, —($CH_2CH_2$O)$_s$—$CH_2CH_2$C(O)—, a polyglycine composed of 2, 3, 4, 5, 6, 7, 8, 9, 10, 11, 12, 13, 14, 15, 16, 17, 18, 19, or 20 amino acids, or a combination of any two or more thereof.

The present technology also provides compositions and medicaments comprising any of one of the embodiments of the compounds of Formulas I, II, and III (or a pharmaceutically acceptable salt thereof) disclosed herein and a pharmaceutically acceptable carrier or one or more excipients or fillers (collectively referred to as "pharmaceutically acceptable carrier" unless otherwise specified). The compositions may be used in the methods and treatments described herein. The present technology also provides pharmaceutical compositions including a pharmaceutically acceptable carrier and an effective amount of a compound of any one of the aspects and embodiments of compounds of Formulas I-III for imaging and/or treating a condition; and where the condition may include a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and/or a prostate cancer. For example, such conditions may include a mammalian tissue overexpressing PSMA, such as a cancer expressing PSMA (including cancer tissues, cancer related neo-vasculature, or a combination thereof), Crohn's disease, or IBD.

In a further related aspect, an imaging method is provided that includes administering a compound of any one of the aspects and embodiments of compounds of Formulas I-III (e.g., such as administering an effective amount) or administering a pharmaceutical composition comprising an effective amount of a compound of any one of the aspects and embodiments of compounds of Formulas I-III to a subject and, subsequent to the administering, detecting positron emission, detecting gamma rays from positron emission and annihilation (such as by positron emission tomography), and/or detecting Cerenkov radiation due to positron emission (such as by Cerenkov luminescene imaging). In any embodiment of the imaging method, the subject may be suspected of suffering from a condition that includes a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, a prostate cancer, a mammalian tissue overexpressing PSMA, such as a cancer expressing PSMA (including cancer tissues, cancer related neo-vasculature, or a combination thereof), Crohn's disease, or IBD. The detecting step may occur during a surgical procedure on a subject, e.g., to remove a mammalian tissue overexpressing PSMA. The detecting step may include use of a handheld device to perform the detecting step. For example, Cerenkov luminescene images may be acquired by detecting the Cerenkov light using ultra-high-sensitivity optical cameras such as electron-multiplying charge-coupled device (EMCCD) cameras.

In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer. Another example of an effective amount includes amounts or dosages that are capable of reducing symptoms associated with e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, or a prostate cancer, such as, for example, reduction in proliferation and/or metastasis. An effective amount of a compound of the present technology may include an amount sufficient to enable detection of binding of the compound to a target of interest including, but not limited to, one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, or a prostate cancer (such as castration resistant prostate cancer). Another example of an effective amount includes amounts or dosages that are capable of providing a detectable gamma ray emission from positron emission and annihilation (above background) in a subject with a tissue overexpressing PSMA, such as, for example, statistically significant emission above background. Another example of an effective amount includes amounts or dosages that are capable of providing a detectable Cerenkov radiation emission due to positron emission above background) in a subject with a tissue overexpressing PSMA, such as, for example, statistically significant emission above background. The effective amount may be from about 0.01 µg to about 1 mg of the compound per gram of the composition, and preferably from about 0.1 µg to about 500 µg of the compound per gram of the composition.

As used herein, a "subject" or "patient" is a mammal, such as a cat, dog, rodent or primate. Typically the subject is a human, and, preferably, a human suffering from or suspected of suffering from a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, or a prostate cancer. The term "subject" and "patient" can be used interchangeably.

In particular, the effective amount of a compound of any embodiment herein for treating a cancer and/or a mammalian tissue overexpressing PSMA may be from about 0.1 µg to about 50 µg per kilogram of the mass of the subject. Thus, for treating a cancer (e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, a prostate cancer, and/or a castration resistant prostate cancer) and/or a mammalian tissue overexpressing PSMA; the effective amount of a compound of any embodiment described herein may be about 0.1 µg/kg, about 0.2 µg/kg, about 0.3 µg/kg, about 0.4 µg/kg, about 0.5 µg/kg, about 0.6 µg/kg, about 0.7 µg/kg, about 0.8 µg/kg, about 0.9 µg/kg, about 1 µg/kg, about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 11 µg/kg, about 12 µg/kg, about 13 µg/kg, about 14 µg/kg, about 15 µg/kg, about 16 µg/kg, about 17 µg/kg, about 18 µg/kg, about 19 µg/kg, about 20 µg/kg, about 22 µg/kg, about 24 µg/kg, about 26 µg/kg, about 28 µg/kg, about 30 µg/kg, about 32 µg/kg, about 34 µg/kg, about 36 µg/kg, about 38 µg/kg, about 40 µg/kg, about 42 µg/kg, about 44 µg/kg, about 46 µg/kg, about 48 µg/kg, about 50 µg/kg, or any range including and/or in between any two of these values.

In particular, the effective amount of a compound of any embodiment herein for imaging a cancer and/or a mammalian tissue overexpressing PSMA may be from about 0.1 µg to about 50 µg per kilogram of the mass of the subject. Thus, for treating a cancer (e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, a prostate cancer, and/or a castration resistant prostate cancer) and/or a mammalian tissue overexpressing PSMA; the effective amount of a compound of any embodiment described herein may be about 0.1 µg/kg, about 0.2 µg/kg, about 0.3 µg/kg, about 0.4 µg/kg, about 0.5 µg/kg, about 0.6 µg/kg, about 0.7 µg/kg, about 0.8 µg/kg, about 0.9 µg/kg, about 1 µg/kg, about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 11 µg/kg, about 12 µg/kg, about 13 µg/kg, about 14 µg/kg, about 15 µg/kg, about 16 µg/kg, about 17 µg/kg, about 18 µg/kg, about 19 µg/kg, about 20 µg/kg, about 22 µg/kg, about 24 µg/kg, about 26 µg/kg, about 28 µg/kg, about 30 µg/kg, about 32 µg/kg, about 34 µg/kg, about 36 µg/kg, about 38 µg/kg, about 40 µg/kg, about 42 µg/kg, about 44 µg/kg, about 46 µg/kg, about 48 µg/kg, about 50 µg/kg, or any range including and/or in between any two of these values.

The compounds of the present technology may also be administered to a patient along with other conventional imaging agents that may be useful in the imaging and/or treatment of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, a prostate cancer, or a mammalian tissue overexpressing PSMA. Such mammalian tissues include, but are not limited to, a cancer expressing PSMA (including cancer tissues, cancer related neovasculature, or a combination thereof), Crohn's disease, or IBD. Thus, a pharmaceutical composition and/or method of the present technology may further include an imaging agent different than the compounds of Formulas I-III; a pharmaceutical composition and/or method of the present technology may include an treatment agent different than the compounds of Formulas I-III; a pharmaceutical composition and/or method of the present technology may further include an imaging agent according to any embodiment of a compound of Formulas I-III and therapeutic agent that is also according to any embodiment of a compound of Formulas I-III. It may be that the compound according to any embodiment of a compound of Formula I, II, and/or III is both a therapeutic agent and an imaging agent. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology may also include administering, either sequentially or in combination with one or more compounds of the present technology, a conventional imaging agent in an amount that can potentially or synergistically be effective for the imaging of a mammalian tissue overexpressing PSMA.

In any of the embodiments of the present technology described herein, the pharmaceutical composition may be packaged in unit dosage form. The unit dosage form is effective in treating a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and/or a prostate cancer. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges. suppositories. patches. nasal sprays, injectables, implantable sustained-release formulations, rnucoadherent films, topical varnishes, lipid complexes, etc.

The pharmaceutical compositions may be prepared by mixing one or more compounds of Formulas I, II, and III, pharmaceutically acceptable salts thereof, stereoisomers thereof, tautomers thereof, or solvates thereof, with pharmaceutically acceptable carriers, excipients, binders, diluents or the like to prevent and treat disorders associated with cancer (e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer). The compounds and compositions described herein may be used to prepare formulations and medicaments that treat e.g., a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. The instant compositions may also include, for example, micelles or liposomes, or some other encapsulated form.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For the indicated condition, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The present technology further provides a method of achieving an in vivo tissue distribution of a radiotherapeutic in a mammalian subject in which a ratio of tumor activity to kidney activity of 1 or greater is observed within about 4 hours to about 24 hours of administration of the radiotherapeutic to the mammalian subject. Such a method includes administering to the mammalian subject the radiotherapeutic, where the radiotherapeutic comprises a first moiety that targets prostate specific membrane antigen ("PSMA"), a second moiety that bears a radionuclide, and a third moiety that has an affinity for serum albumin, the first moiety being separated from the second moiety by a first covalent linker and the third moiety being separated from the second moiety by a second covalent linker. The separation between the first and second moieties (on the basis of a contiguous atom count associated with the first covalent linker) is from about 8 atoms to about 40 atoms, and the separation between the third moiety and the first and second moieties (on the basis of a contiguous atom count associated with the second covalent linker) is from about 10 atoms to about 100 atoms.

The method may include obtaining an image of the mammalian subject about 4 hours to about 24 hours after administration of the radiotherapeutic; thus, obtaining an image after administration of the radiotherapeutic may occur after about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or any range including and/or in between any two of these values. The ratio of tumor activity to kidney activity of 1 or greater may persist up to about 24 hours after administration of the radiotherapeutic. In any embodiment herein of the method, it may be that substantially no radionuclide activity is observed in salivary glands of the mammalian subject about 24 hours to about 48 hours after administration of the radiotherapeutic. In any embodiment herein of the method, it may be that the contiguous atom count associated with the first covalent linker ranges from about 10 atoms to about 30 atoms. In any embodiment herein of the method, it may be that the contiguous atom count associated with the second covalent linker ranges from about 15 atoms to about 40 atoms. In any embodiment herein of the method, it may be that the administration comprises intravenous administration.

The examples herein are provided to illustrate advantages of the present technology and to further assist a person of ordinary skill in the art with preparing or using the compounds of the present technology or salts, pharmaceutical compositions, derivatives, prodrugs, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Examples

Section 1.1

Materials and Instrumentation. All solvents and reagents, unless otherwise noted, were purchased from commercial sources and used as received without further purification. Solvents noted as "dry" were obtained following storage over 3 Å molecular sieves. Reactions were monitored by thin-layer chromatography (TLC, Whatman UV254 aluminum-backed silica gel). The HPLC system used for analysis and purification of compounds consisted of a CBM-20A communications bus module, an LC-20AP (preparative) pump, and an SPD-20AV UV/Vis detector monitoring at 270 nm (Shimadzu, Japan). Purification was performed with an Epic Polar preparative column, 120 Å, 10 μm, 25 cm×20 mm (ES Industries, West Berlin, N.J.) at a flow rate of 14 mL/min, unless otherwise noted. Gradient HPLC methods were employed using a binary mobile phase that contained $H_2O$ (A) and either MeOH (B) or ACN (C). HPLC Method A: 10% B (0-5 min), 10-100% B (5-25 min). Method B: 10% C (0-5 min), 10-100% C (5-25 min). Method C: 10% C (0-5 min), 10-100% C (5-40 min). Method D: 10% C (0-5 min), 10-100% C (5-20 min). The solvent systems contained 0.2% trifluoroacetic acid (TFA). NMR spectra were recorded at ambient temperature on Varian Inova 300 MHz, 400 MHz, 500 MHz or 600 MHz spectrometers, or on a Bruker AV III HD 500 MHz spectrometer equipped with a broadband Prodigy cryoprobe. Chemical shifts are reported in ppm. $^1$H and $^{13}$C NMR spectra were referenced to the TMS internal standard (0 ppm), to the residual solvent peak, or to an acetonitrile internal standard (2.06 ppm in $D_2O$ spectra). $^{19}$F NMR spectra were referenced to a monofluorobenzene internal standard (−113.15 ppm). The splitting of proton resonances in the reported $^1$H spectra is defined as:

s=singlet, d=doublet, t=triplet, q=quartet, m=multiplet, dt=doublet of triplets, td=triplet of doublets, and br=broad. IR spectroscopy was performed on a KBr pellet of sample using a Nicolet Avatar 370 DTGS (ThermoFisher Scientific, Waltham, Mass.). High-resolution mass spectra (HRMS) were recorded on an Exactive Orbitrap mass spectrometer in positive ESI mode (ThermoFisher Scientific, Waltham, Mass.). UV/visible spectra were recorded on a Cary 8454 UV-Vis (Agilent Technologies, Santa Clara, Calif.) using 1-cm quartz cuvettes, unless otherwise noted. Elemental analysis (EA) was performed by Atlantic Microlab, Inc. (Norcross, Ga.).

Preparation of di-tert-butyl ((1-(tert-butoxy)-6-(3-(3-ethynylphenyl)ureido)-1-oxohexan-2-yl)carbamoyl)glutamate (5)

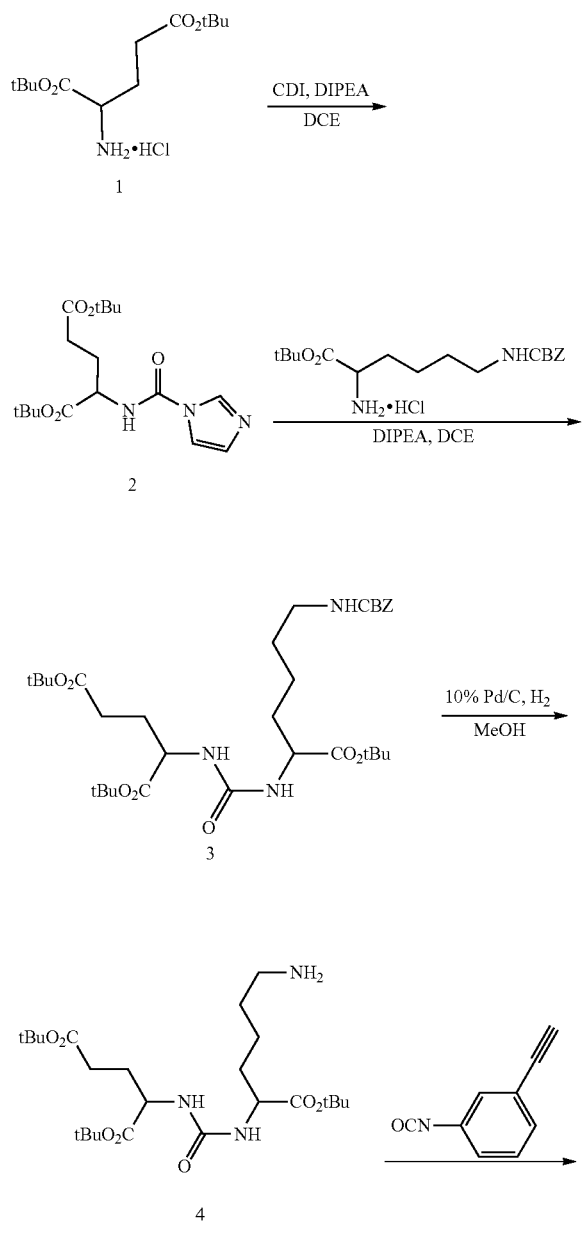

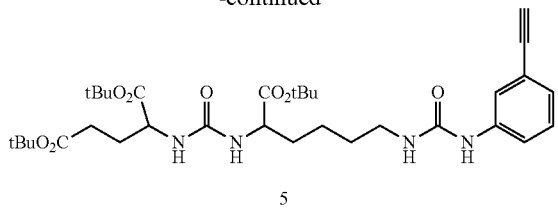

(S)-2-[(Imidazole-1-carbonyl)amino]pentanedioic acid di-tertbutyl Ester (2): To a suspension of L-di-tert-butyl glutamate hydrochloride (15.0 g, 51 mmol) in DCM (150 mL) cooled to 0° C. was added TEA (18 mL) and DMAP (250 mg). After the mixture was stirred for 5 min, CDI (9.0 g, 56 mmol) was added and the mixture was stirred overnight with warming to room temperature. The mixture was diluted with DCM (150 mL) and washed with saturated sodium bicarbonate (60 mL), water (2×100 mL), and brine (100 mL). The organic layer was dried over sodium sulfate and concentrated to afford the crude product as a semi-solid, which slowly solidified upon standing. The crude material was triturated with hexane/ethyl acetate to afford a white solid which was filtered, washed with hexane (100 mL), and dried to afford 2 (15.9 g, 45 mmol, 88%) as a white solid.

(S)-2-[3((S)-(5-Benzyloxycarbonylamino)-1-tert-butoxycarbonylpentylureido]pentanedioic acid di-tert-butyl Ester (3): To a solution of 2 (1 g, 2.82 mmol) in DCE (10 mL) at 0° C. was added MeOTf (0.47 g, 2.85 mmol) and TEA (0.57 g, 5.65 mmol). After the solution was stirred for 30 min, Cbz-L-Lys-Ot-Bu (1.06 g, 2.82 mmol) was added in one portion and allowed to stir for 1 h at 40° C. The mixture was concentrated to dryness and purified by column chromatography (SiO$_2$) to afford 3 as a white solid (1.37 g, 79%).

2-[3-(5-Amino-1-tert-butoxycarbonylpentyl)ureido]pentanedioic acid di-tert-butyl ester (4): To a solution of 3 (630 mg, 1.0 mmol) in ethanol (20 mL) under a hydrogen atmosphere was added ammonium formate (630 mg, 10 eq) followed by 10% Pd—C. The suspension was allowed to stand with occasional agitation overnight until complete. The mixture was filtered through Celite and concentrated to afford the desired product (479 mg, 98%) as a waxy solid.

Di-tert-butyl ((1-(tert-butoxy)-6-(3-(3-ethynylphenyl) ureido)-1-oxohexan-2-yl)carbamoyl)glutamate (5): To a solution of 4 (0.488, 1 mmol) in DCM (10 mL) was added 1-ethynyl-3-isocyanatobenzene (185 mg, 1.3 mmol) in DCM (5 mL) at r.t under N$_2$. The resulting reaction mixture was stirred for 12 h at the same temperature and transferred to a separating funnel and washed with water (2×50 mL) and brine (30 mL). The organic layer was dried over sodium sulfate and concentrated to afford the crude product as a semisolid which was purified by column chromatography (SiO$_2$) to afford 5 as a white foam (84%).

Preparation of tert-butyl-N2-(N2-(((9H-fluoren-9-yl)methoxy)carbonyl) glycylglycylglycyl-N6-(tert-butoxycarbonyl)lysyl)-N6-((benzyloxy)carbonyl)-L-lysinate (10)
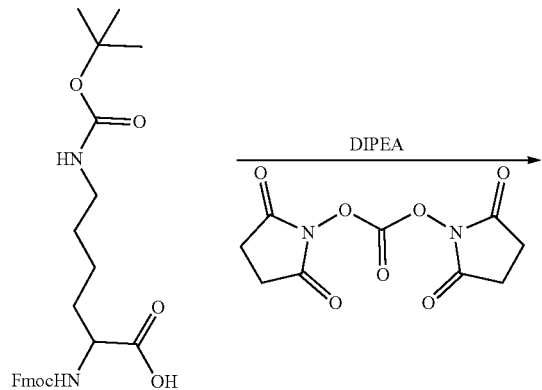
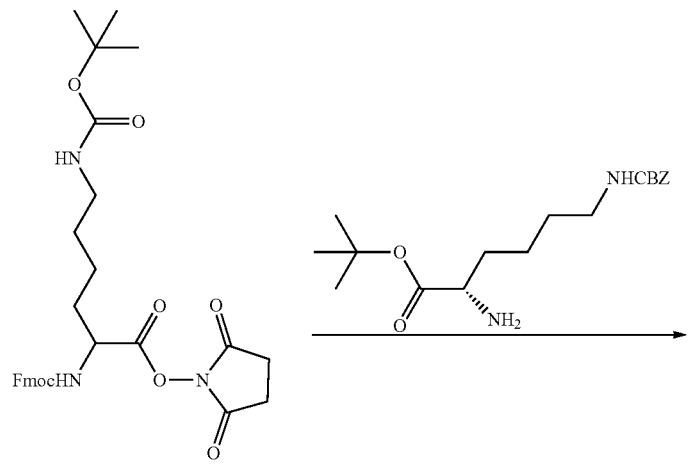
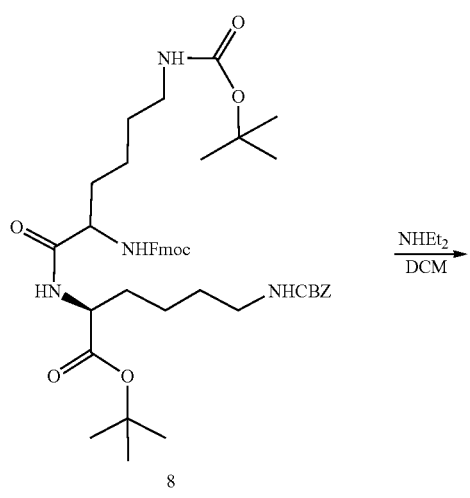

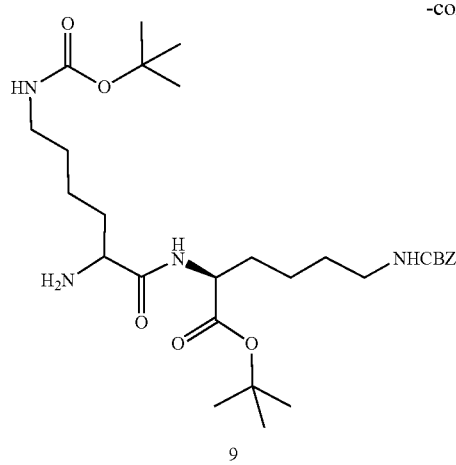 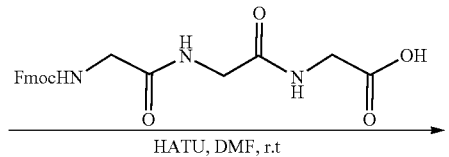

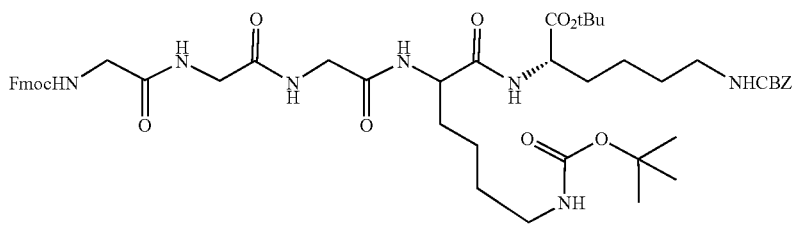

2,5-dioxopyrrolidin-1-yl N2-(((9H-fluoren-9-yl)methoxy)carbonyl)-N6-(tert-butoxycarbonyl)-L-lysinate (7): N2-(((9H-fluoren-9-yl)methoxy)carbonyl)-N6-(tert-butoxycarbonyl)-L-lysine 6 (4.68 g, 10 mmol) was dissolved in dry DCM (20 mL) and DIPEA (1.74 mL, 10 mmol) was added. The reaction mixture was stirred at r.t. for 10 min and solid di(N-succinimidyl) carbonate (3.84 g, 15 mmol) was added in one portion. The resulting reaction mixture was stirred for 3-4 h and diluted with DCM, transferred to a separating funnel and washed with an excess of water. The organic layer was collected, dried on MgSO₄ and evaporated to dryness to afford a semi-solid. The crude product was recrystallized from ethanol and diethyl ether to give 7 as a cream colored solid (3.44 g, 61%).

tert-butyl N2-(N2-(((9H-fluoren-9-yl)oxy)carbonyl)-N6-(tert-butoxycarbonyl)-L-lysyl)-N6-((benzyloxy)carbonyl)-L-lysinate (8): To a suspension of H-Lys(Z)-OtBu HCl (3.72 g, 10 mmol) in DCM (25 mL) was added DIPEA (1.74 mL, 10 mmol) at 0° C. followed by dropwise addition of compound 7 (5.65 g, 10 mmol) in DCM (20 mL). The resulting clear solution was stirred overnight at r.t. The solvent was evaporated and the crude compound was purified by column chromatography (SiO₂) to afford 8 as a white solid (76%).

tert-butyl N6-((benzyloxy)carbonyl)-N2-(N6-(tert-butoxycarbonyl)-L-lysyl)-L-lysinate (9): To a solution of compound 8 (1.156 g, 2 mmol) in DCM was added diethylamine (6 mL) dropwise and the resulting reaction mixture was stirred at r.t for 4-5 h. Solvents were evaporated under reduced pressure and the crude product was re-dissolved in DCM and washed with water (2×100 mL), and brine (100 mL). The organic layer was dried over sodium sulfate and concentrated to afford the crude product as a semisolid, which was used as such without any further purification.

tert-butyl-N2-(N2-(((9H-fluoren-9-yl)methoxy)carbonyl)glycylglycylglycyl-N6-(tert-butoxycarbonyl)-L-lysyl)-N6-((benzyloxy)carbonyl)-L-lysinate (10): To a solid mixture of (((9H-fluoren-9-yl)methoxy)carbonyl)glycylglycylglycine (246 mg, 0.6 mmol) and HATU (230 mg, 0.6 mmol) under N2 was added dry DMF, and the mixture was stirred for 5 min at r.t. DIPEA (0.12 mL, 0.7 mmol) was added to the reaction mixture and stirring was continued for 10 min at r.t. A solution of compound 9 (282 mg, 0.5 mmol) in DMF was added dropwise at r.t and stirred at the same temperature for 12 h. DMF was evaporated under reduced pressure to give a suspension, which was dissolved in DCM (10 mL), transferred to a separating funnel and washed with water (2×20 mL) and brine (15 mL). The organic layer was collected, dried on MgSO₄ and evaporated to dryness to afford a semi-solid. The crude compound was purified by column chromatography (SiO₂) to afford the desired product 10 as a brown solid (41%).

tert-butyl N2-(N2-(2-azidoacetyl)
glycylglycylglycyl-N6-(tert-butoxycarbonyl) lysyl)-
N6-((benzyloxy)carbonyl)-L-lysinate (12)

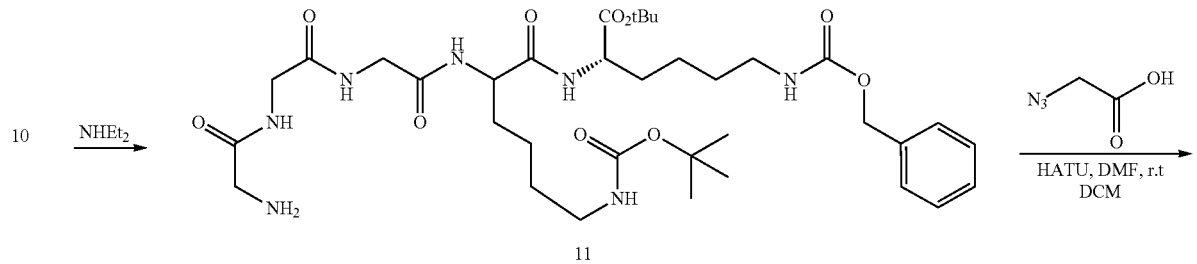

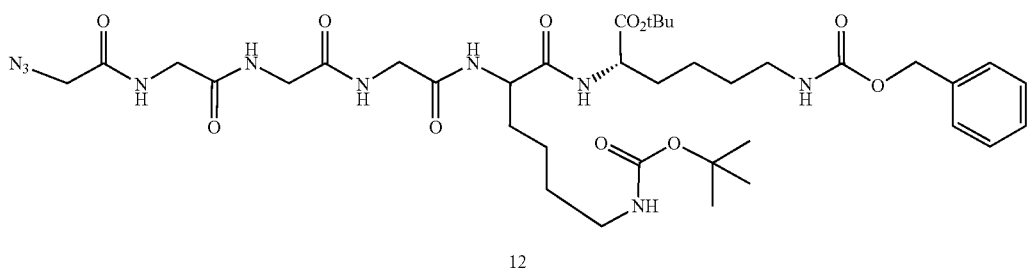

tert-butyl N6-((benzyloxy)carbonyl)-N2-(N6-(tert-butoxycarbonyl)-N2-glycylglycylglycyl-L-lysyl)-L-lysinate (11): To a solution of compound 10 (0.478 g, 0.5 mmol) in DCM (10 mL) was added diethylamine (2 mL) dropwise and the resulting reaction mixture was stirred at r.t for 3 h. Solvents were evaporated under reduced pressure and re-dissolved in DCM and washed with water (2×20 mL) and brine (20 mL). The organic layer was dried over sodium sulfate and concentrated to afford the crude product 11 as a semisolid, which was used without any further purification.

tert-butyl N2-(N2-(2-azidoacetyl)glycylglycylglycyl-N6-(tert-butoxycarbonyl)-L-lysyl)-N6-((benzyloxy)carbonyl)-L-lysinate (12): To a solid mixture of azidoacetic acid (101 mg, 1 mmol) and HATU (383 mg, 1 mmol) under N2 was added dry DMF (5 mL), and the mixture was stirred for 5 min at r.t. DIPEA (0.17 mL, 1 mmol) was added to the reaction mixture and stirring was continued for 10 min at r.t. A solution of compound 11 (367 mg, 0.5 mmol) in DMF (5 mL) was added dropwise at r.t and stirred at the same temperature for 12 h. DMF was evaporated under reduced pressure to give a suspension, which was dissolved in DCM (10 mL) and washed with water (2×20 mL), and brine (15 mL). The crude compound was used without any further purification.

Preparation of 10-(6-alkamido-1-(tert-butoxy)-1-oxohexan-2-yl)-24,28,30-tri-tert-butyl-2,2-dimethyl-4,12,21,26-tetraoxo-3-oxa-5,11,20,25,27-pentaaza-triacontane-10,24,28,30-tetracarboxylate (14)

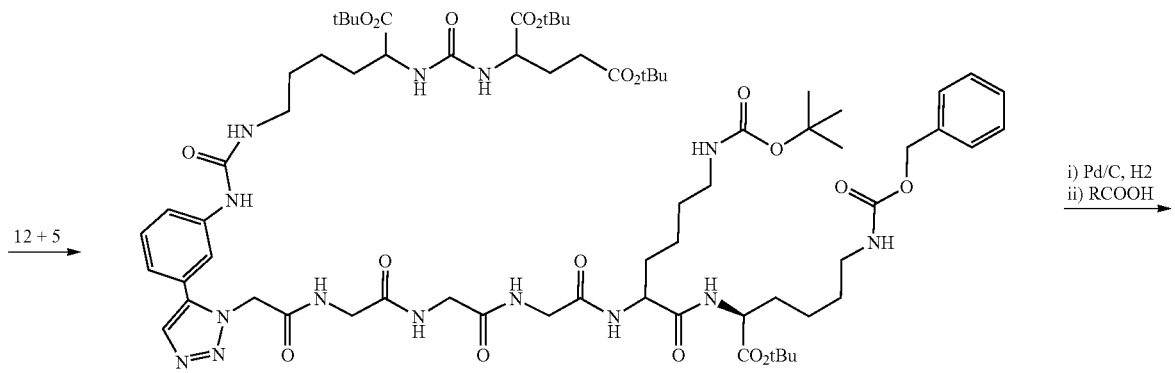

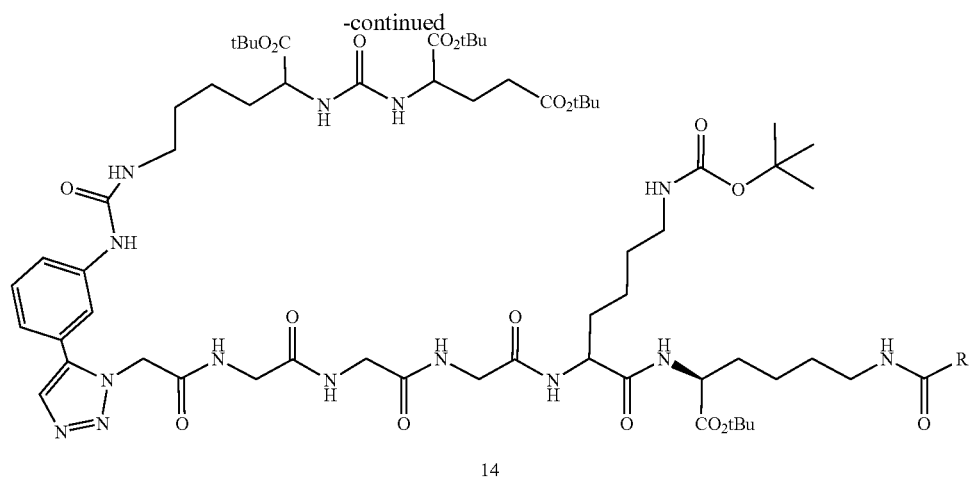

14 di-tert-butyl(((S)-1-(tert-butoxy)-6-(3-(3-(1-((9S,12S)-9-(tert-butoxycarbonyl)-12-(4-((tert-butoxycarbonyl)amino)butyl)-3,11,14,17,20,23-hexaoxo-1-phenyl-2-oxa-4,10,13,16,19,22-hexaazatetracosan-24-yl)-1H-1,2,3-triazol-5-yl)phenyl)ureido)-1-oxohexan-2-yl)carbamoyl)-L-glutamate (13): Compound 12 (140 mg, 0.1 mmol) and compound 5 (63 mg, 0.1 mmol) were dissolved in DMF (2 mL) and aqueous solutions of 0.5M $CuSO_4$ and 0.5M sodium ascorbate were added subsequently. The resulting reaction was stirred for 3 h at r.t. DMF was evaporated and the crude compound 13 was used without any further purification.

10-(6-alkamido-1-(tert-butoxy)-1-oxohexan-2-yl)-24,28,30-tri-tert-butyl-2,2-dimethyl-4,12,21,26-tetraoxo-3-oxa-5,11,20,25,27-pentaazatriacontane-10,24,28,30-tetracarboxylate (14): Compound 13 (144 mg, 0.1 mmol) was dissolved in a mixture of methanol:THF (1:1, 10 mL) and 10% Pd—C was added. The resulting suspension was stirred under $H_2$ (balloon pressure) atmosphere for 3 h. The mixture was filtered through Celite and concentrated to afford the corresponding amine (not shown) as semi solid, which was used immediately to the next step. To a solid mixture of acid RCOOH (0.1 mmol) and HATU (38 mg, 0.1 mmol) under $N_2$ was added dry DMF (3 mL) and the mixture was stirred for at r.t. for 5 min. DIPEA (0.017 mL, 0.1 mmol) was added to the reaction mixture and stirring was continued for 10 min at r.t. A solution of amine (0.1 mmol) in DMF (2 mL) was added dropwise at r.t and stirred at the same temperature for 12 h. DMF was evaporated under reduced pressure to give a suspension, which was dissolved in DCM (5 mL) and washed with water (2×10 mL) and brine (10 mL). The organic layer was dried over sodium sulfate and concentrated to afford the crude product which was purified by column chromatography ($SiO_2$), and product 14 was isolated as a semi-solid.

Preparation of 15

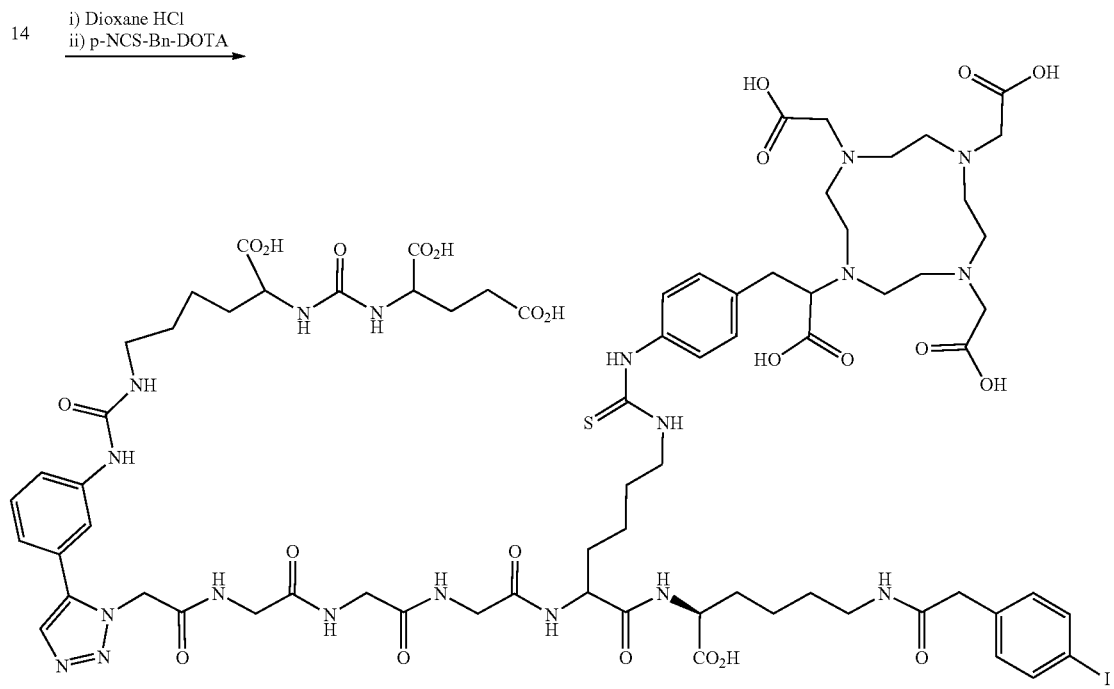

15

To a solution of compound 14 (1 eq; R=(4-iodophenyl)CH₂—) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts formed were dissolved in DMF (1.5 mL) and DIPEA (0.5 mmol, 20 eq) was added. The resulting reaction mixture was stirred for 10 min before adding p-NCS-Bn-DOTA (2 eq) and distilled water (0.5 mL). Stirring was continued for 3 h at r.t. The reaction mixture was directly subjected to LCMS purification using 0.1% formic acid in ACN and water. The product was collected and lyophilized. $^1$H NMR (500 MHz, DMSO-d₆): δ 12.25 (bs, 7H), 9.40 (bs, 1H), 8.64-8.62 (m, 1H, N—H), 8.54-8.52 (m, 1H, N—H), 8.42 (s, 1H), 8.34-8.31 (m, 1H, N—H), 8.15-8.11 (m, 3H), 8.04-8.02 (m, 1H, N—H), 7.94-7.91 (m, 2H, N—H), 7.64-7.63 (m, 3H), 7.37-7.31 (m, 5H), 7.28-7.25 (m, 1H), 7.17-7.16 (m, 2H), 7.05-7.04 (m, 3H), 6.34-6.30 (m, 2H), 6.17 (bs, 1H), 5.21 (s, 2H), 4.34-4.30 (m, 1H), 4.13-4.04 (m, 4H), 3.84-3.83 (m, 2H), 3.75-3.74 (m, 4H), 3.63-3.60 (m, 3H), 3.16-3.13 (m, 4H), 3.12-3.05 (m, 4H), 3.02-2.98 (m, 6H), 2.30-2.18 (m, 3H), 1.95-1.88 (m, 1H), 1.71-1.65 (m, 5H), 1.58-1.49 (m, 6H), 1.45-1.22 (m, 12H). $^{13}$C NMR (500 MHz, DMSO-d₄): δ 174.3, 174.0, 173.5, 173.2, 171.4, 169.3, 168.9, 168.7, 168.2, 165.6, 157.1, 154.9, 146.1, 140.9, 136.7, 136.1, 131.2, 130.8, 129.0, 122.6, 118.4, 117.8, 116.9, 116.0, 113.9, 53.4, 52.1, 51.9, 51.6, 51.4, 41.9, 41.8, 41.6, 41.5, 38.2, 31.8, 31.7, 30.3, 29.7, 29.3, 28.5, 28.0, 27.3, 22.7, 22.5, 22.4, 17.9, 16.5, 12.3. HRMS calculated for $C_{73}H_{102}IN_{19}O_{24}S$ ([M+2H]⁺), 1787.6110, found 1787.6048.

Preparation of 2-[3-(5-Amino-1-tert-butoxycarbonylpentyl)ureido]pentanedioic Acid di-tert-butyl Ester (17)

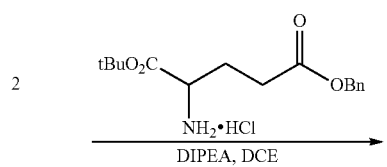

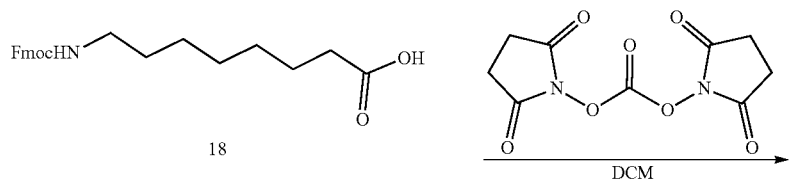

5-benzyl 1-(tert-butyl) (((S)-1,5-di-tert-butoxy-1,5-dioxopentan-2-yl)carbamoyl)-L-glutamate (16): To a solution of 2 (1 g, 2.82 mmol) in DCE (10 mL) at 0° C. was added MeOTf (0.47 g, 2.85 mmol) and TEA (0.57 g, 5.65 mmol). After the solution was stirred for 30 min, H-L-Glu(Bzl)-OtBu hydrochloride (0.927 g, 2.82 mmol) was added in one portion and allowed to stir for 1 h at 40° C. The mixture was concentrated to dryness and purified by column chromatography (SiO₂) to afford the desired product as a white solid (79%).

(S)-5-(tert-butoxy)-4-(3-((S)-1,5-di-tert-butoxy-1,5-dioxopentan-2-yl)ureido)-5-oxopentanoic acid (17): To a solution of 16 in ethanol (20 mL) under a hydrogen atmosphere was added ammonium formate (630 mg, 10 eqv) followed by 10% Pd—C, and the suspension was allowed to stand with occasional agitation overnight until complete. The mixture was filtered through Celite and concentrated to afford 17, the desired product (479 mg, 98%) as a waxy solid.

Preparation of 2,5-dioxopyrrolidin-1-yl 8-(((9H-fluoren-9-yl)methoxy)carbonyl) amino)octanoate (19)

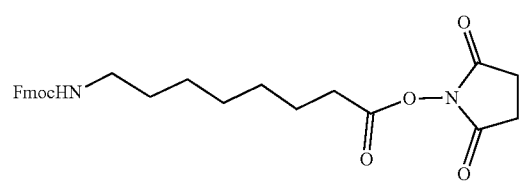

8-((((9H-fluoren-9-yl)methoxy)carbonyl)amino)octanoic acid, 18 (1.43 g, 3 mmol) was dissolved in anhydrous DCM (20 mL) and DIPEA (0.522 mL, 3 mmol) was added. The reaction mixture was stirred at r.t for 10 min and solid di(N-succinimidyl) carbonate (1.152 g, 4.5 mmol) was added in one portion. The resulting reaction mixture was stirred for 3 h and diluted with DCM and transferred in to a separating funnel and washed with excess of water. The organic layer was collected, dried on MgSO$_4$ and evaporated to dryness to afford a semi-solid, which was recrystallized from ethanol and diethyl ether to give the desired product as an off-white solid (0.932 g, 65.08%).

Preparation of tetra-tert-butyl (3S,7S,21S,24S)-28-amino-21-(4-((tert-butoxycarbonyl)amino)butyl)-5,10,19,22-tetraoxo-4,6,11,20,23-pentaazaoctacosane-1,3,7,24-tetracarboxylate (23)

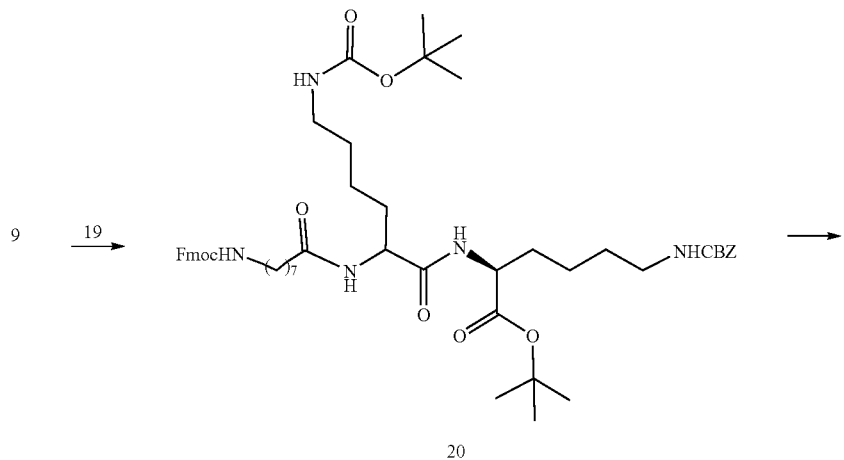

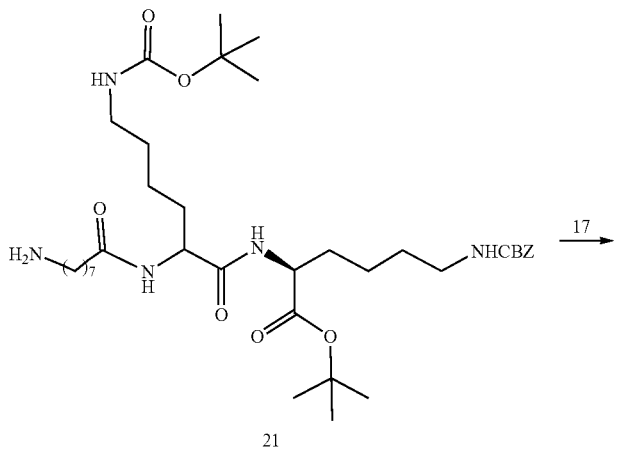

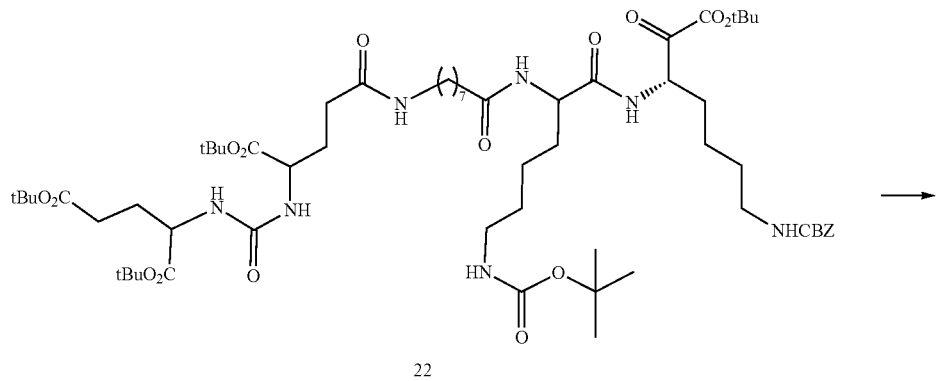

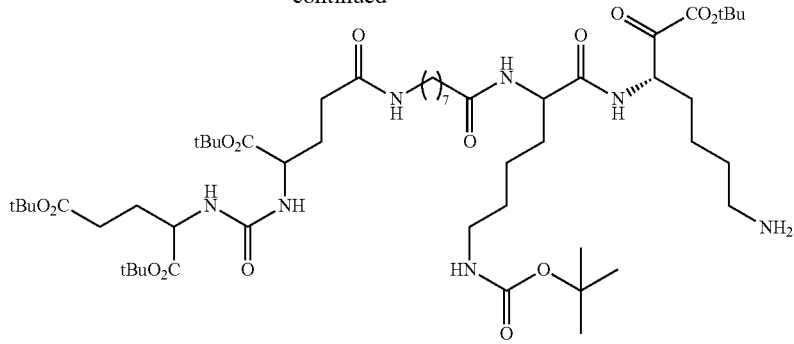

23 tert-butyl N2-(N2-(8-((((9H-fluoren-9-yl)methoxy)carbonyl)amino)octanoyl)-N6-(tert-butoxycarbonyl)-L-lysyl)-N6-((benzyloxy)carbonyl)-L-lysinate (20): Compound 9 (0.551 g, 1 mmol) and compound 19 (0.573, 1.2 mmol) were dissolved in DCM (10 mL) and stirred for 12 h at r.t. Progress of the reaction was monitored by TLC. The mixture was concentrated to dryness and purified by column chromatography ($SiO_2$) to afford the desired product 20 as a brown solid (41%).

tert-butyl N2-(N2-(8-aminooctanoyl)-N6-(tert-butoxycarbonyl)-L-lysyl)-N6-((benzyloxy)carbonyl)-L-lysinate (21): To a solution of compound 20 (0.457 g, 0.5 mmol) in DCM (10 mL) was added diethylamine (3 mL) dropwise and the resulting reaction mixture was stirred at r.t for 3 h. Solvents were evaporated under reduced pressure and re-dissolved in DCM and washed with water (2×20 mL) and brine (20 mL). The organic layer was dried over sodium sulfate and concentrated to afford the crude product 21 as a semisolid, which was used without any further purification.

tetra-tert-butyl (9S,12S,26S,30S)-12-(4-((tert-butoxycarbonyl)amino)butyl)-3,11,14,23,28-pentaoxo-1-phenyl-2-oxa-4,10,13,22,27,29-hexaazadotriacontane-9,26,30,32-tetracarboxylate (22): To a solid mixture of compound 17 (0.114, 0.24 mmol) and HATU (0.092 g, 0.24 mmol) under $N_2$ was added dry DMF, and the mixture was stirred for 5 min at r.t. DIPEA (0.041 mL, 0.24 mmol) was added to the reaction mixture and stirring was continued for 10 min at r.t. A solution of compound 21 (0.141, 0.2 mmol) in DMF was added dropwise at r.t and stirred at the same temperature for 12 h. DMF was evaporated under reduced pressure to give a suspension, which was dissolved in DCM (10 mL) and washed with water (2×20 mL), and brine (15 mL). The organic layer was dried over sodium sulfate and concentrated to afford the crude product which was purified by column chromatography ($SiO_2$) to afford the product 22 as a semi-solid (28%).

tetra-tert-butyl (3S,7S,21S,24S)-28-amino-21-(4-((tert-butoxycarbonyl)amino)butyl)-5,10,19,22-tetraoxo-4,6,11,20,23-pentaazaoctacosane-1,3,7,24-tetracarboxylate (23): Compound 22 (0.1 g, 0.085 mmol) was dissolved in a mixture of methanol:THF (1:1, 10 mL) and 10% Pd—C was added. The resulting suspension was stirred under $H_2$ (balloon pressure) atmosphere for 3 h. The mixture was filtered through Celite and concentrated to afford the desired product 23 (91%) as a waxy solid.

Preparation of 24 (a-g) and 25 (a-h)

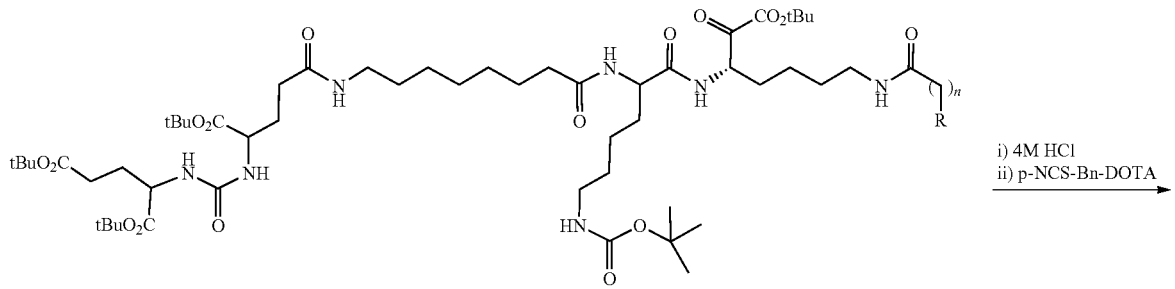

24 (a-g) or 22

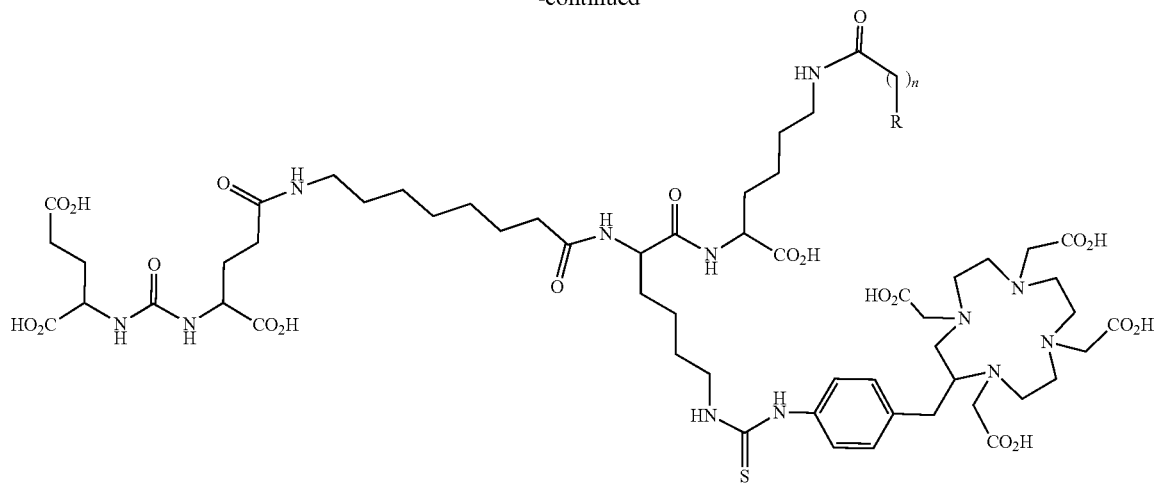

25 (a-h)

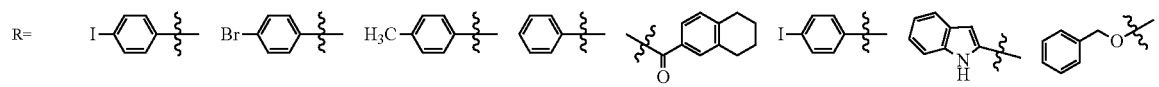

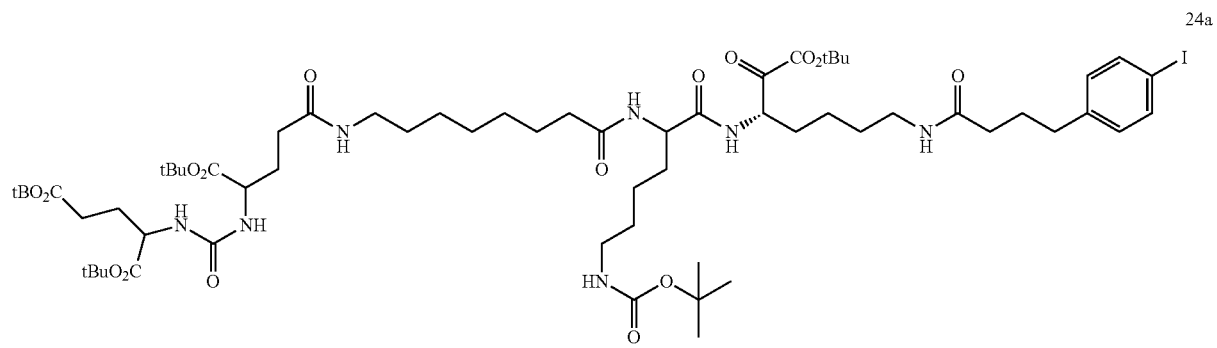

24a tetra-tert-butyl (2S)-5-(4-((tert-butoxycarbonyl)amino)butyl)-2-(4-(4-(4-iodophenyl)butanamido)butyl)-1,4,7,16,21-pentaoxo-3,6,15,20,22-pentaazapentacosane-1,19,23,25-tetracarboxylate (24a): To a solid mixture of 4-(4-iodophenyl)butanoic acid (0.029 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL) and brine (10 mL). The organic layer was dried over sodium sulfate and concentrated to afford the crude product which was purified by column chromatography (SiO$_2$), and product 24a was isolated as a semi-solid (18%).

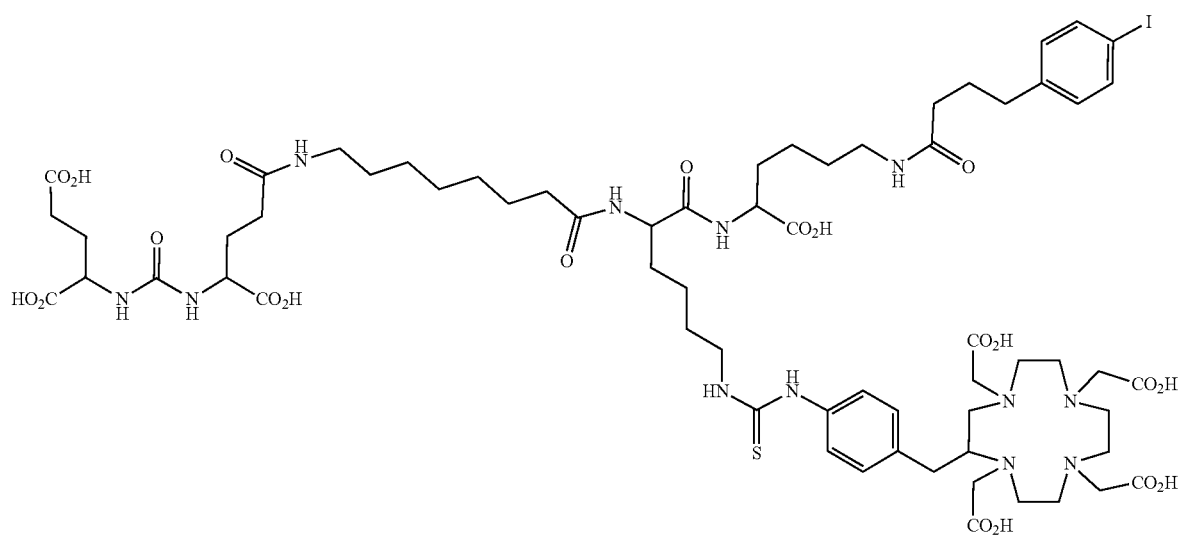

33-(4-iodophenyl)-5,10,19,22,30-pentaoxo-21-(4-(3-(4-((1,4,7,10-tetrakis(carboxymethyl)-1,4,7,10-tetraazacyclododecan-2-yl)methyl)phenyl) thioureido)butyl)-4,6,11,20,23,29-hexaazatritriacontane-1,3,7,24-tetracarboxylic acid (25a): definted, but the a solution of compound 24a (0.025 mmol, 1 eq) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.050 mmol, 2 eq) and distilled water (0.5 mL). Stirring was continued for 3 h at r.t. The reaction mixture was directly subjected to LCMS purification using 0.1% formic acid in ACN and water.

tetra-tert-butyl (2S)-2-(4-(4-(4-bromophenyl)butanamido)butyl)-5-(4-((tert-butoxycarbonyl)amino)butyl)-1,4,7,16,21-pentaoxo-3,6,15,20,22-pentaazapentacosane-1,19,23,25-tetracarboxylate (24b): To a solid mixture of 4-(4-bromophenyl)butanoic acid (0.024 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO$_2$), and product 24b was isolated as a semi-solid (6%).

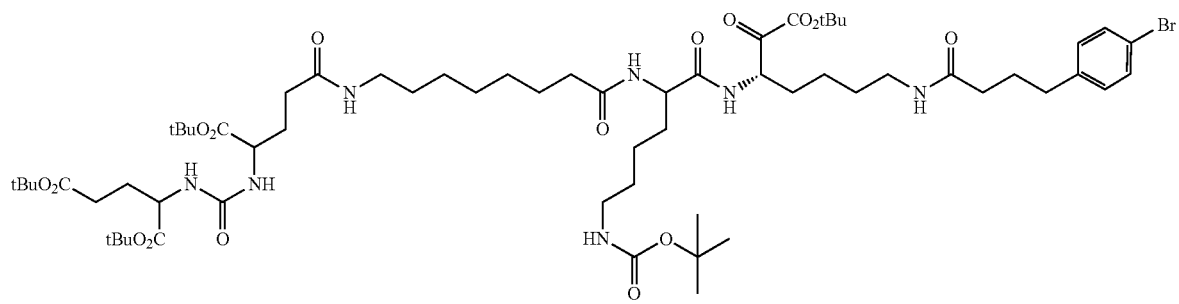

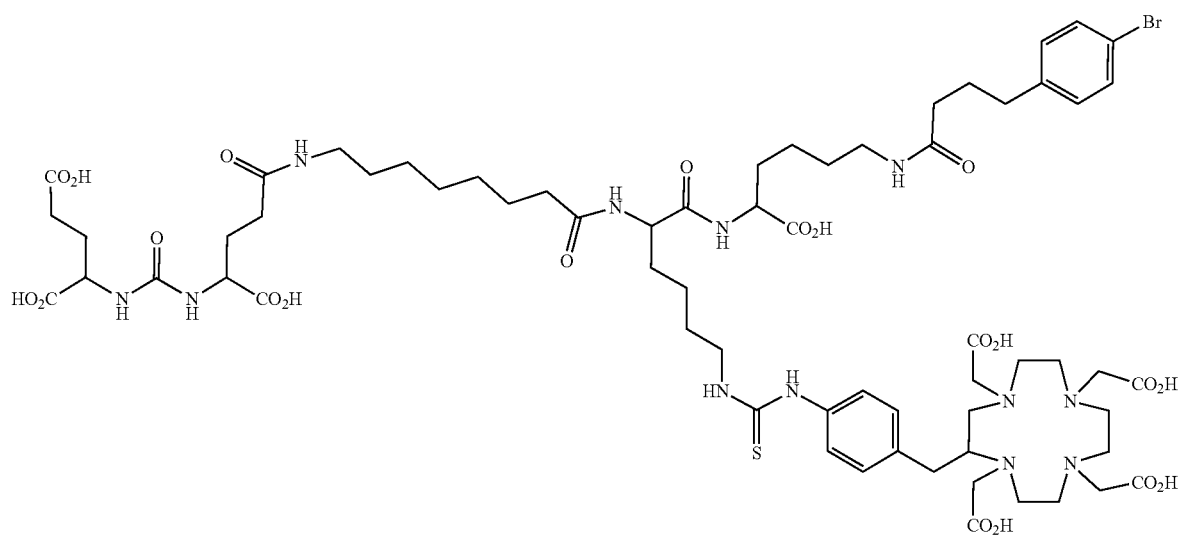

33-(4-bromophenyl)-5,10,19,22,30-pentaoxo-21-(4-(3-(4-((1,4,7,10-tetrakis(carboxymethyl)-1,4,7,10-tetraazacyclododecan-2-yl)methyl)phenyl)thioureido) butyl)-4,6,11,20,23,29-hexaazatritriacontane-1,3,7,24-tetracarboxylic acid (25b): To a solution of compound 24b (0.020 mmol, 1 eq) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.050 mmol, 2 eq) and distilled water (0.5 mL). Stirring was continued for 3 h at r.t. The reaction mixture was directly subjected to LCMS purification using 0.1% formic acid in ACN and water to afford 25b.

tetra-tert-butyl (2S,5S,19S,23S)-5-(4-((tert-butoxycarbonyl)amino)butyl)-2-(4-(4-(4-iodophenyl)butanamido) butyl)-1,4,7,16,21-pentaoxo-3,6,15,20,22-pentaazapentacosane-1,19,23,25-tetracarboxylate (24a): To a solid mixture of 4-(4-iodophenyl)butanoic acid (0.029 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL) and brine (10 mL). The organic layer was dried over sodium sulfate and concentrated to afford the crude product which was purified by column chromatography (SiO2), and product 24a was isolated as a semi-solid (18%).

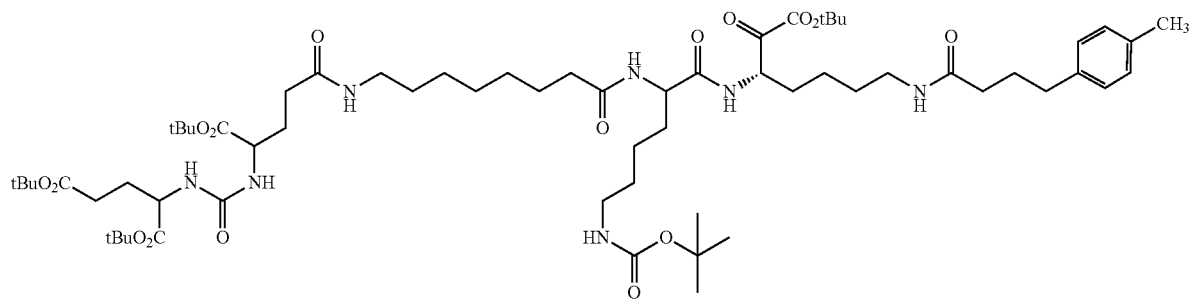

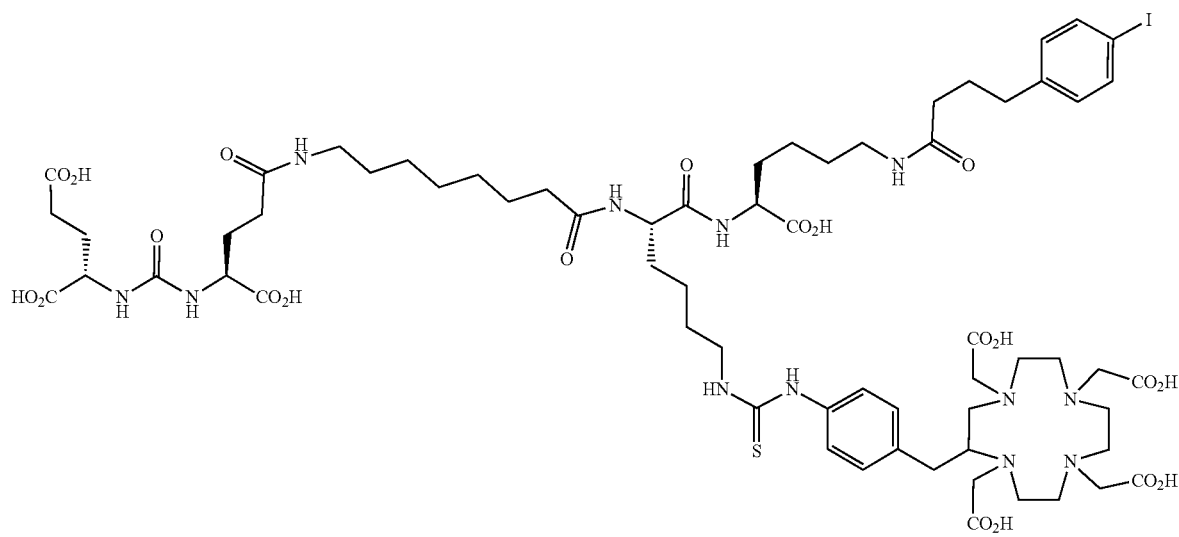

(3S,7S,21S,24S)-33-(4-iodophenyl)-5,10,19,22,30-pentaoxo-21-(4-(3-(4-((1,4,7,10-tetrakis(carboxymethyl)-1,4,7,10-tetraazacyclododecan-2-yl)methyl)phenyl) thioureido)butyl)-4,6,11,20,23,29-hexaazatritriacontane-1,3,7,24-tetracarboxylic acid (25a): definted, but the a solution of compound 24a (0.025 mmol, 1 eq) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.050 mmol, 2 eq) and distilled water (0.5 mL). Stirring was continued for 3 h at r.t. The reaction mixture was directly subjected to LCMS purification using 0.1% formic acid in ACN and water.

tetra-tert-butyl (2S,5S,19S,23S)-2-(4-(4-(4-bromophenyl)butanamido)butyl)-5-(4-((tert-butoxycarbonyl)amino)butyl)-1,4,7,16,21-pentaoxo-3,6,15,20,22-pentaazapentacosane-1,19,23,25-tetracarboxylate (24b): To a solid mixture of 4-(4-bromophenyl)butanoic acid (0.024 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO2), and product 24b was isolated as a semi-solid (6%).

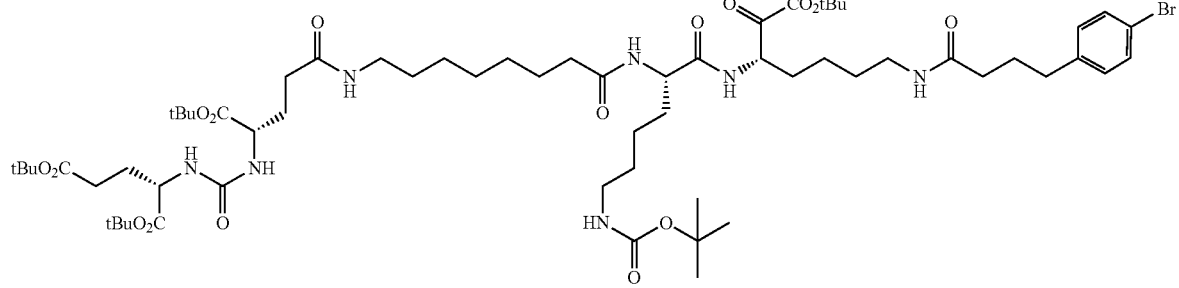

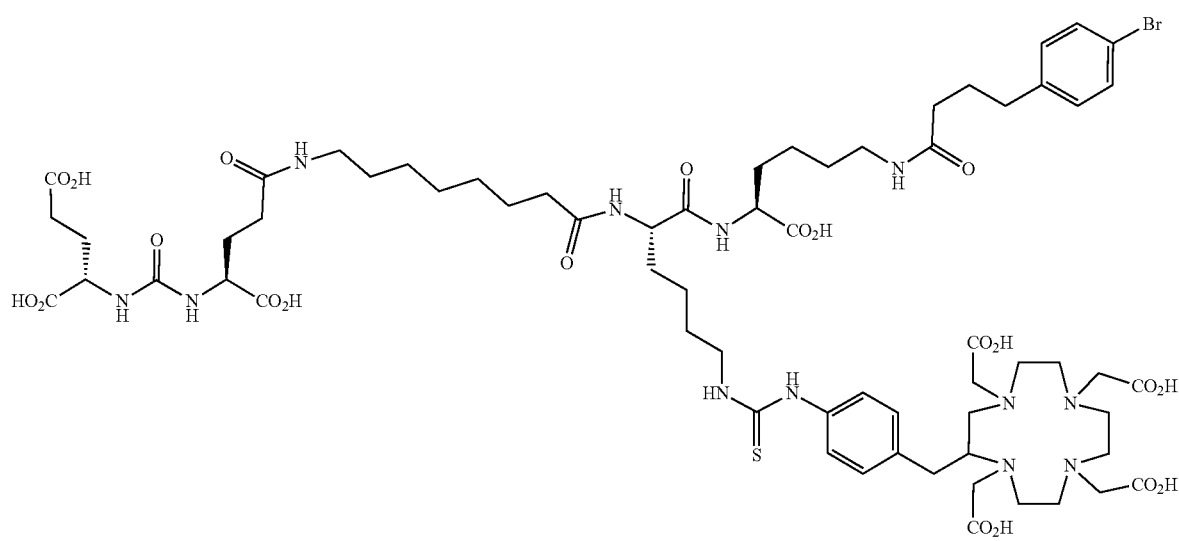

(3S,7S,21S,24S)-33-(4-bromophenyl)-5,10,19,22,30-pentaoxo-21-(4-(3-(4-(((1,4,7,10-tetrakis(carboxymethyl)-1,4,7,10-tetraazacyclododecan-2-yl)methyl)phenyl)thioureido) butyl)-4,6,11,20,23,29-hexaazatritriacontane-1,3,7,24-tetracarboxylic acid (25b): To a solution of compound 24b (0.020 mmol, 1 eq) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.050 mmol, 2 eq) and distilled water (0.5 mL). Stirring was continued for 3 h at r.t. The reaction mixture was directly subjected to LCMS purification using 0.1% formic acid in ACN and water to afford 25b.

tetra-tert-butyl (2S,5S,19S,23S)-5-(4-(((tert-butoxycarbonyl)amino)butyl)-1,4,7,16,21-pentaoxo-2-(4-(4-(p-tolyl)butanamido)butyl)-3,6,15,20,22-pentaazapentacosane-1,19,23,25-tetracarboxylate (24c): To a solid mixture of 4-(p-tolyl)butanoic acid (0.0178 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO₂), and product 24c was isolated as a semi-solid (18%).

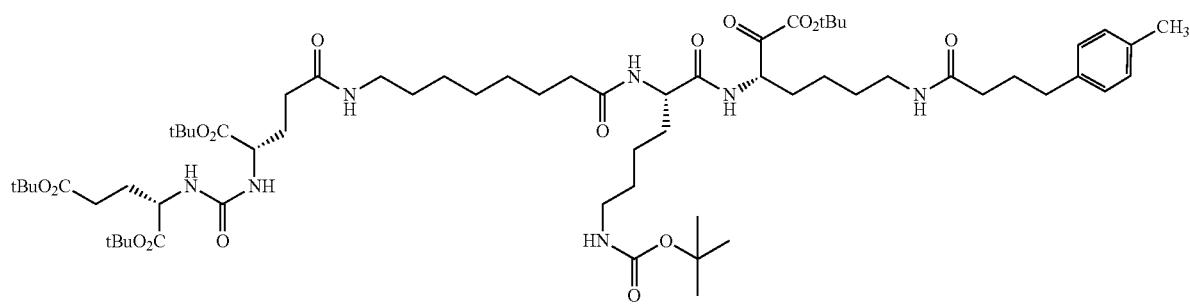

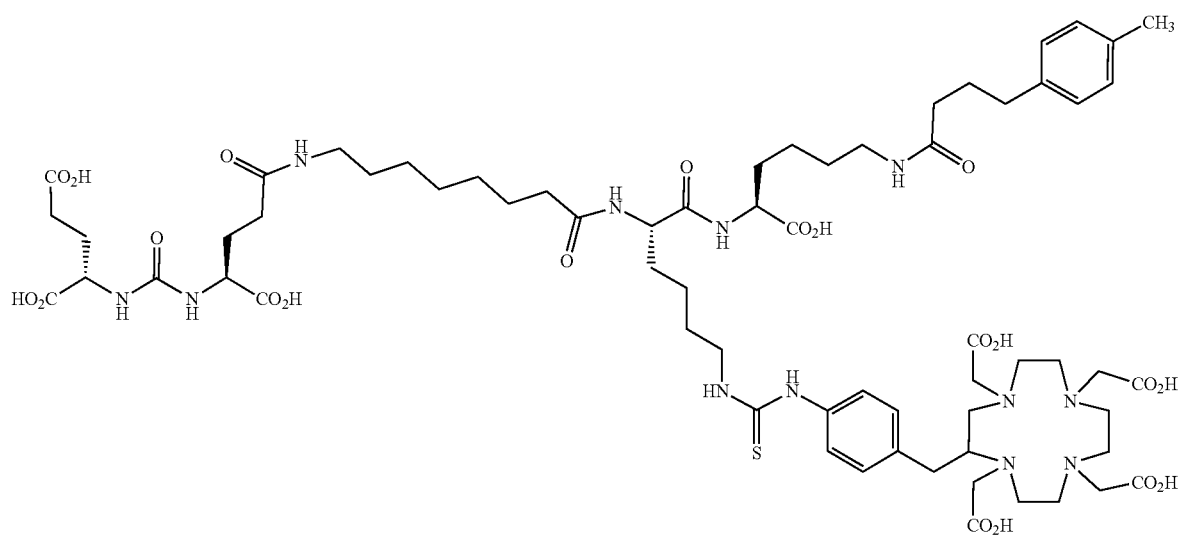

(3S,7S,21S,24S)-5,10,19,22,30-pentaoxo-21-(4-(3-(4-((1,4,7,10-tetrakis(carboxymethyl)-1,4,7,10-tetraazacyclododecan-2-yl)methyl)phenyl)thioureido)butyl)-33-(p-tolyl)-4,6,11,20,23,29-hexaazatritriacontane-1,3,7,24-tetracarboxylic acid (25c): To a solution of compound 24c (0.03 mmol, 1 eq) in dioxane (2 mL) was added 4M HCl in dioxane (2 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.050 mmol, 2 eq) and distilled water (0.5 mL). Stirring was continued for 3 h at r.t. The reaction mixture was directly subjected to LCMS purification using 0.1% formic acid in ACN and water.

tetra-tert-butyl (2S,5S,19S,23S)-5-(4-((tert-butoxycarbonyl)amino)butyl)-1,4,7,16,21-pentaoxo-2-(4-(4-phenylbutanamido)butyl)-3,6,15,20,22-pentaazapentacosane-1,19,23,25-tetracarboxylate (24d): To a solid mixture of 4-phenylbutanoic acid (0.0164 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography ($SiO_2$), and product 24d was isolated as a semi-solid (21%).

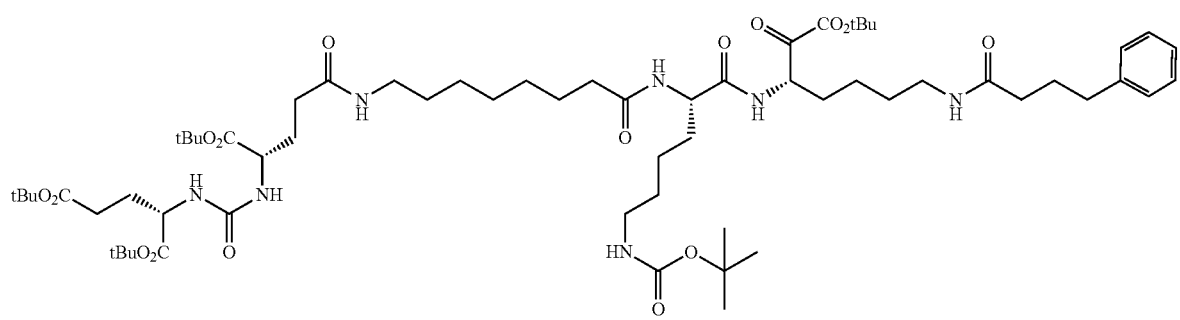

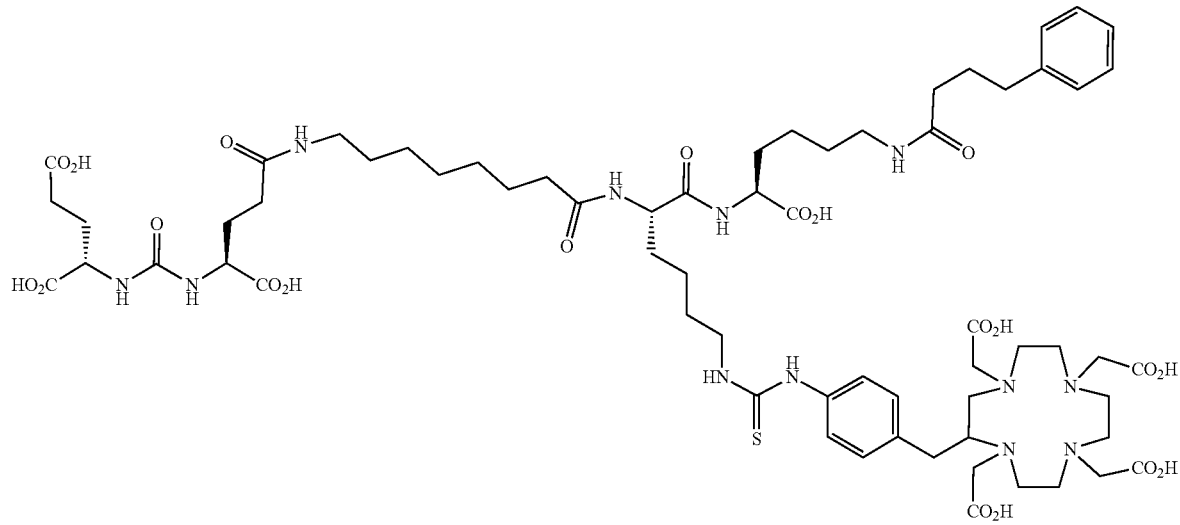

25d (3S,7S,21S,24S)-5,10,19,22,30-pentaoxo-33-phenyl-21-(4-(3-(4-((1,4,7,10-tetrakis(carboxymethyl)-1,4,7,10-tetraazacyclododecan-2-yl)methyl)phenyl) thioureido)butyl)-4,6,11,20,23,29-hexaazatritriacontane-1,3,7,24-tetracarboxylic acid (25d): To a solution of compound 24d (0.04 mmol, 1 eq) in dioxane (3 mL) was added 4M HCl in dioxane (3 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.080 mmol, 2 eq) and distilled water (0.5 mL). Stirring was continued for 3 h at r.t. The reaction mixture was directly subjected to LCMS purification using 0.1% formic acid in ACN and water to afford 25d.

tetra-tert-butyl (2S,5S,19S,23S)-5-(4-((tert-butoxycarbonyl)amino)butyl)-1,4,7,16,21-pentaoxo-2-(4-(4-phenylbutanamido)butyl)-3,6,15,20,22-pentaazapentacosane-1,19,23,25-tetracarboxylate (24e): To a solid mixture of 4-oxo-4-(5,6,7,8-tetrahydronaphthalen-2-yl)butanoic acid (0.023 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO2), and product 24e was isolated as a semi-solid (17%).

24e

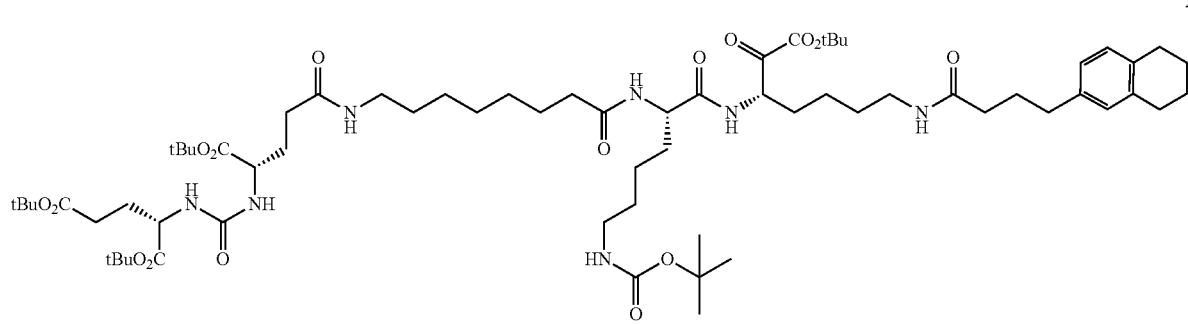

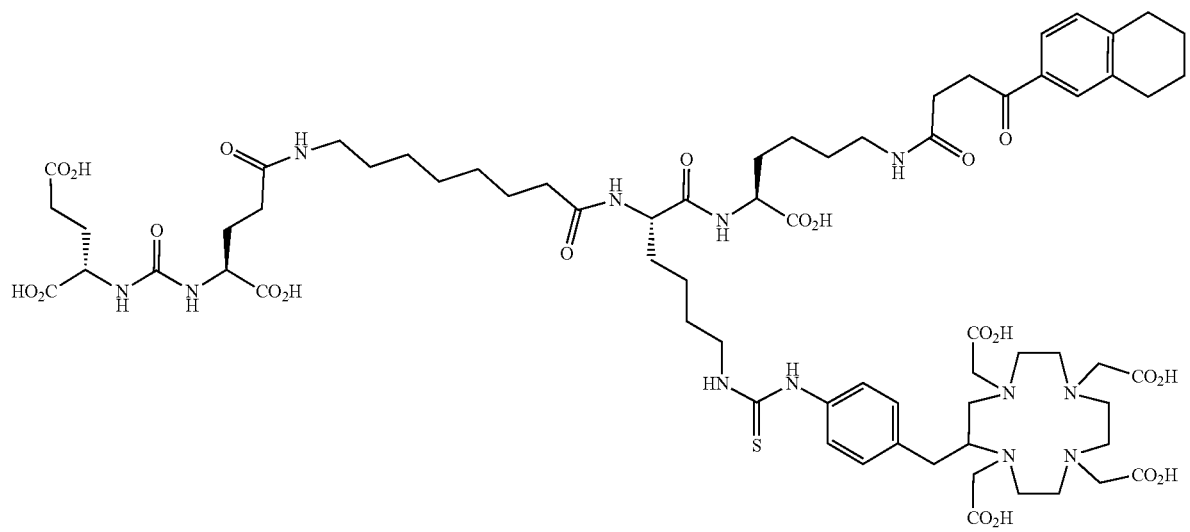

25e (3S,7S,21S,24S)-5,10,19,22,30,33-hexaoxo-33-(5,6,7,8-tetrahydronaphthalen-2-yl)-21-(4-(3-(4-(((1,4,7,10-tetrakis(carboxymethyl)-1,4,7,10-tetraazacyclododecan-2-yl)methyl)phenyl)thioureido)butyl)-4,6,11,20,23,29-hexaazatritriacontane-1,3,7,24-tetracarboxylic acid (25e): To a solution of compound 24e (0.02 mmol, 1 eq) in dioxane (3 mL) was added 4M HCl in dioxane (3 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.080 mmol, 2 eq) and distilled water (0.5 mL). Stirring was continued for 3 h at r.t. The reaction mixture was directly subjected to LCMS purification using 0.1% formic acid in ACN and water to afford 25e.

tetra-tert-butyl (2S,5S,19S,23S)-5-(4-((tert-butoxycarbonyl)amino)butyl)-2-(4-(2-(4-iodophenyl)acetamido)butyl)-1,4,7,16,21-pentaoxo-3,6,15,20,22-pentaazapentacosane-1,19,23,25-tetracarboxylate (24f): To a solid mixture of 2-(4-Idophenyl)acetic acid (0.026 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO₂), and product 24f was isolated as a semi-solid (10%).

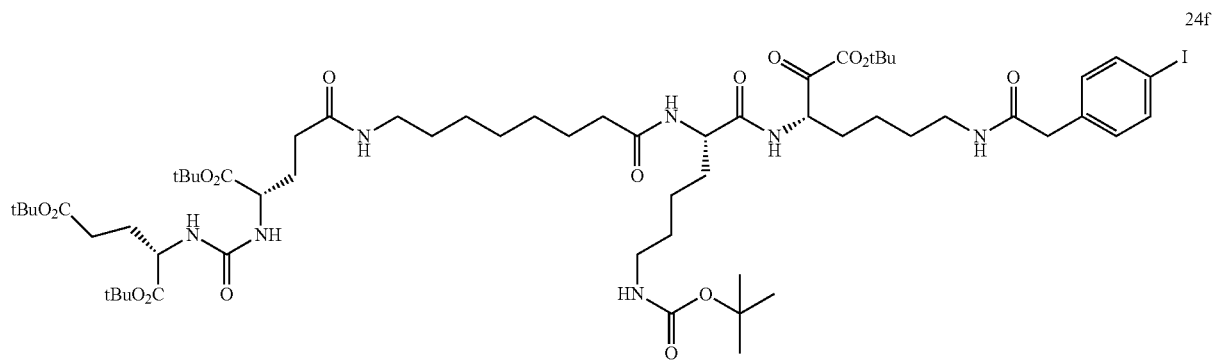 [SMILES: CC(C)(C)OC(=O)CC[C@H](NC(=O)N[C@@H](CCC(=O)NCCCCCCCC(=O)N[C@@H](CCCCNC(=O)OC(C)(C)C)C(=O)N[C@@H](CCCCNC(=O)Cc1ccc(I)cc1)C(=O)C(=O)OC(C)(C)C)C(=O)OC(C)(C)C)C(=O)OC(C)(C)C]

24f

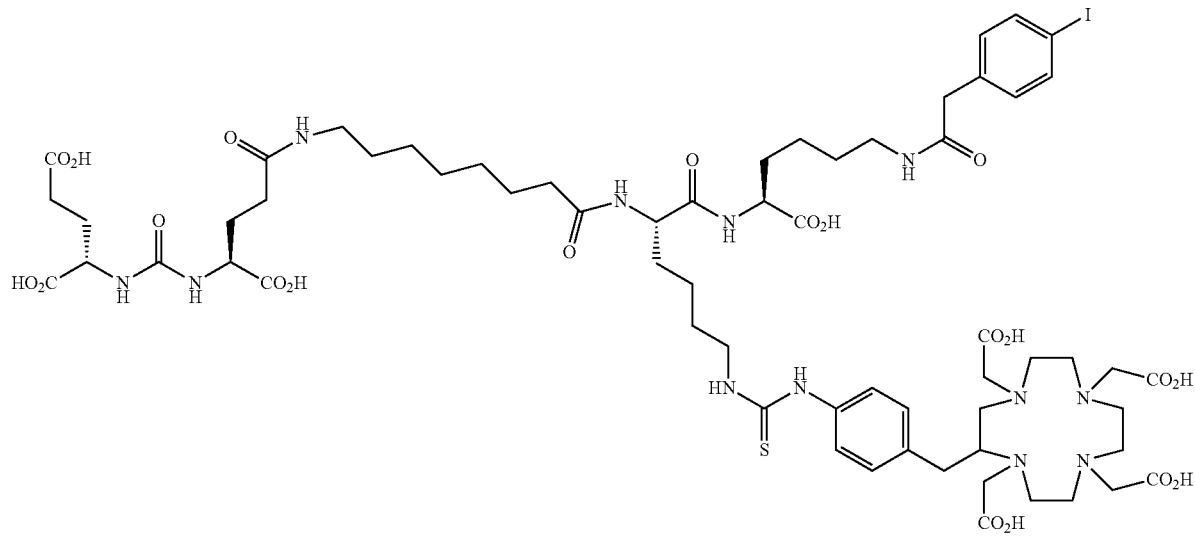

25f (8S,11S,25S,29S)-1-(4-iodophenyl)-2,10,13,22,27-pentaoxo-11-(4-(3-(4-((1,4,7,10-tetrakis(carboxymethyl)-1,4,7,10-tetraazacyclododecan-2-yl)methyl)phenyl) thioureido) butyl)-3,9,12,21,26,28-hexaazahentriacontane-8,25,29,31-tetracarboxylic acid (25f): To a solution of compound 24f (0.02 mmol, 1 eq) in dioxane (3 mL) was added 4M HCl in dioxane (3 mL). The resulting reaction mixture was stirred for 3 h at r.t. Completion of the reaction was monitored by TLC. Solvents was removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.080 mmol, 2 eq) and distilled water (0.5 mL). Stirring was continued for 3 h at r.t. The reaction mixture was directly subjected to LCMS purification using 0.1% formic acid in ACN and water to afford 25f.

tetra-tert-butyl (2S,5S,19S,23S)-2-(4-(1H-indole-2-carboxamido)butyl)-5-(4-((tert-butoxycarbonyl)amino)butyl)-1,4,7,16,21-pentaoxo-3,6,15,20,22-pentaazapentacosane-1,19,23,25-tetracarboxylate (24 g): To a solid mixture of indole-2-acetic acid (0.016 g, 0.1 mmol) and HATU (0.038 g, 0.1 mmol) under N2 was added dry DMF (2 mL) and the mixture was stirred for at r.t. for 5 min. DIPEA (0.017 mL, 0.1 mmol) was added to the reaction mixture and stirring was continued for 10 min at r.t. A solution of compound 23 (0.052, 0.05 mmol) in DMF (1 mL) was added dropwise at r.t and stirred at the same temperature for 12 h. DMF was evaporated under reduced pressure to give a suspension, which was dissolved in DCM (5 mL) and washed with water (2×10 mL), and brine (10 mL). The organic layer was dried over sodium sulfate and concentrated to afford the crude product which was purified by column chromatography (SiO$_2$), and product 24 g was isolated as a semi-solid (15%).

24g

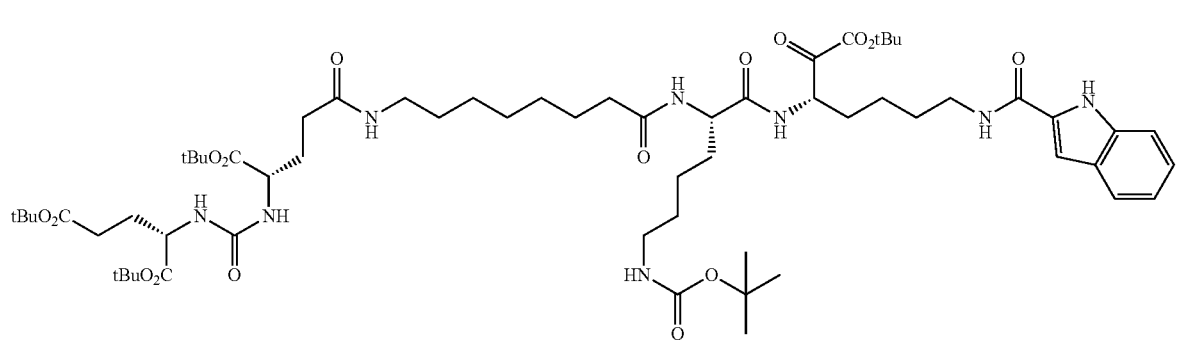

25g

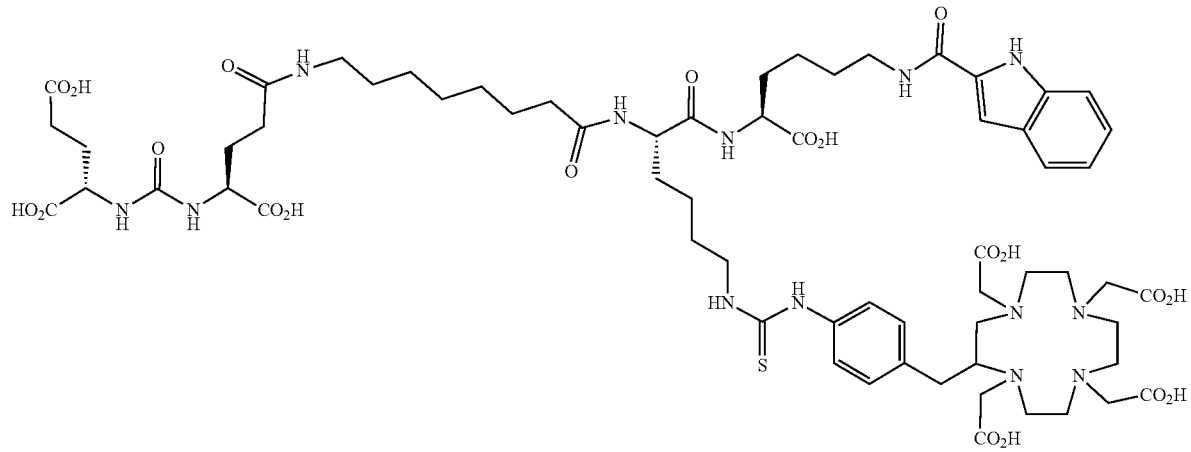

(7S,10S,24S,28S)-1-(1H-indol-2-yl)-1,9,12,21,26-pentaoxo-10-(4-(3-(4-((1,4,7,10-tetrakis(carboxymethyl)-1,4,7,10-tetraazacyclododecan-2-yl)methyl)phenyl) thioureido)butyl)-2,8,11,20,25,27-hexaazatriacontane-7,24,28,30-tetracarboxylic acid (25 g): To a solution of compound 24g (0.02 mmol, 1 eq) in dioxane (3 mL) was added 4M HCl in dioxane (3 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.080 mmol, 2 eq) and distilled water (0.5 mL). Stirring was continued for 3 h at r.t. The reaction mixture was directly subjected to LCMS purification using 0.1% formic acid in ACN and water to afford 25 g.

(9S,12S,26S,30S)-3,11,14,23,28-pentaoxo-1-phenyl-12-(4-(3-(4-((1,4,7,10-tetrakis(carboxymethyl)-1,4,7,10-tetraazacyclododecan-2-yl)methyl)phenyl)thioureido)butyl)-2-oxa-4,10,13,22,27,29-hexaazadotriacontane-9,26,30,32-tetracarboxylic acid (25h): To a solution of compound 22 (produced as defined herein) (0.02 mmol, 1 eq) in dioxane (3 mL) was added 4M HCl in dioxane (3 mL). The resulting reaction mixture was stirred for 3 h at r.t. Completion of the reaction was monitored by TLC. Solvents were removed under reduced pressure and co-distilled with toluene (2×5 mL). The amine HCl salts were dissolved in DMF (1.5 mL) and DIPEA (0.5 mmol, 20 eq) was added. The resulting reaction mixture was stirred for 10 min before adding p-NCS-Bn-DOTA (0.080 mmol, 2 eq) and distilled water (0.5 mL). Stirring was continued for 3 h at r.t. The reaction mixture was directly subjected to LCMS purification using 0.1% formic acid in ACN and water to afford 25h.

25h

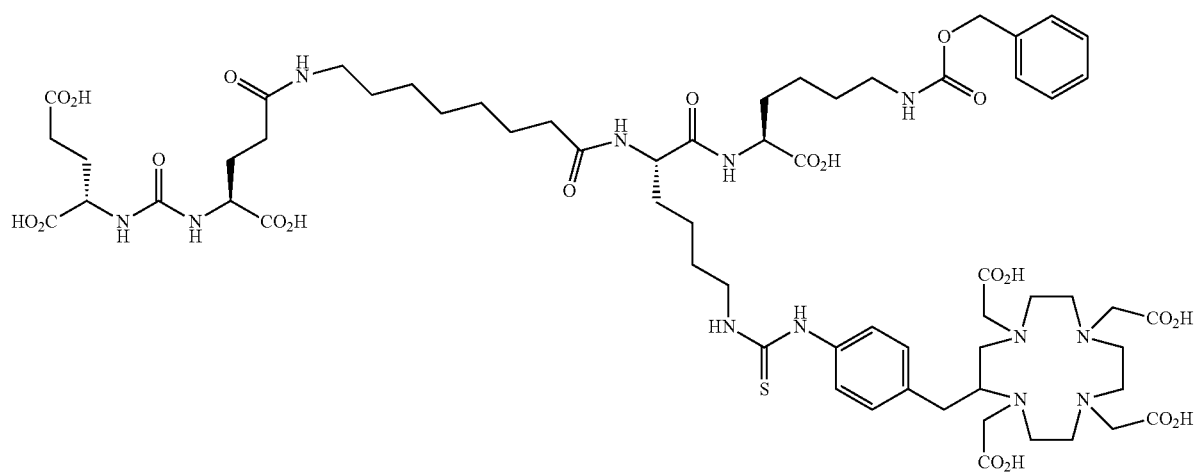

Section 1.2.

Preparation of dimethyl
4-aminopyridine-2,6-dicarboxylate (204)

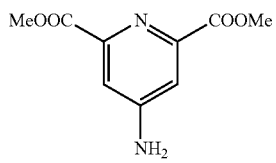

Dimethyl 4-azidopyridine-2,6-dicarboxylate[245] (0.9445 g, 4.0 mmol), 10% Pd/C (0.1419 g), and DCM:MeOH (1:1, 18 mL) were combined in a round-bottom flask. After purging the flask with a balloon of $H_2$, the reaction was stirred vigorously at room temperature under an $H_2$ atmosphere for 46 h. The gray mixture was diluted with DMF (450 mL) and filtered through a bed of Celite. Following a subsequent filtration through a 0.22 μm nylon membrane, the filtrate was concentrated at 60° C. under reduced pressure and further dried in vacuo to obtain 204 as a pale-tan solid (0.824 g, 98% yield). $^1$H NMR (500 MHz, DMSO-$d_6$): δ=7.36 (s, 2H), 6.72 (s, 2H), 3.84 (s, 6H). $^{13}$C{$^1$H} APT NMR (126 MHz, DMSO-$d_6$): δ=165.51, 156.24, 148.05, 111.99, 52.29. IR (cm$^{-1}$): 3409, 3339, 3230, 1726, 1639, 1591, 1443, 1265, 996, 939, 787, 630, 543. HPLC $t_R$=9.369 min (Method B). HRMS (m/z): 211.07213 [M+H]$^+$; Calc: 211.07133.

Preparation of Ethyl
4-amino-6-(hydroxymethyl)picolinate (205)

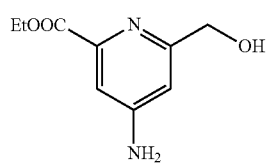

To a refluxing suspension of 204 (0.677 g, 3.22 mmol) in absolute EtOH (27 mL) was added NaBH$_4$ (0.1745 g, 4.61 mmol) portionwise over 1 h to give a pale-yellow suspension. The reaction was then quenched with acetone (32 mL) and concentrated at 60° C. under reduced pressure to a tan solid. The crude product was dissolved in H$_2$O (60 mL) and washed with ethyl acetate (4×150 mL). The combined organics were dried over sodium sulfate and concentrated at 40° C. under reduced pressure. Further drying in vacuo yielded 205 as a pale-yellow solid (0.310 g, 49% yield). $^1$H NMR (300 MHz, DMSO-$d_6$): δ=7.07 (d, J=2.1 Hz, 1H), 6.78 (m, 1H), 6.32 (s, 2H), 5.30 (t, J=5.8 Hz, 1H), 4.39 (d, J=5.6 Hz, 2H), 4.26 (q, J=7.1 Hz, 2H), 1.28 (t, J=7.1 Hz, 3H). $^{13}$C APT NMR (126 MHz, DMSO-$d_6$) δ=165.57, 162.38, 155.68, 147.25, 108.50, 107.01, 63.95, 60.61, 14.24. IR (cm$^1$): 3439, 3217, 2974, 2917, 1717, 1643, 1600, 1465, 1396, 1378, 1239, 1135, 1022, 974, 865, 783. HPLC $t_R$=8.461 min (Method B). HRMS (m/z): 197.09288 [M+H]$^+$; Calc: 197.09207.

Preparation of Ethyl
4-amino-6-(chloromethyl)picolinate (206)

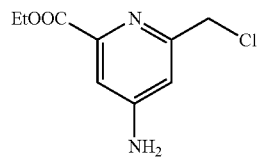

A mixture of thionyl chloride (2.5 mL) and 205 (0.301 g, 1.53 mmol) was stirred in an ice bath for 1 h, and then at RT for 30 min. The yellow-orange emulsion was concentrated at 40° C. under reduced pressure to an oily residue. The residue was neutralized with sat. aq. NaHCO$_3$ (12 mL) and then extracted with ethyl acetate (75 mL). The organic extract was washed with H$_2$O (2 mL), dried over sodium sulfate, and concentrated at 40° C. under reduced pressure. Further drying in vacuo gave 206 as an amber wax (0.287 g, 80% yield, corrected for residual ethyl acetate). $^1$H NMR (500 MHz, DMSO-$d_6$) δ=7.18 (d, J=2.1 Hz, 1H), 6.78 (d, J=2.1 Hz, 1H), 6.62 (br s, 2H), 4.62 (s, 2H), 4.29 (q, J=7.1 Hz, 2H), 1.30 (t, J=7.1 Hz, 3H). $^{13}$C{$^1$H}APT NMR (126 MHz, DMSO-$d_6$) δ=164.75, 156.42, 156.19, 147.17, 109.79, 109.50, 60.97, 46.47, 14.15. IR (cm$^{-1}$): 3452, 3322, 3209, 2978, 2922, 1726, 1639, 1604, 1513, 1465, 1378, 1248, 1126, 1026, 983, 861, 783, 752, 700. HPLC $t_R$=12.364 min (Method B). HRMS (m/z): 215.05903 [M+H]$^+$; Calc: 215.05818.

Preparation of Methyl 6-((1,4,10,13-tetraoxa-7,16-diazacyclooctadecan-7-yl)methyl)picolinate (209.2TFA.1H$_2$O)

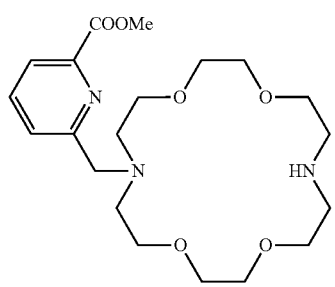

To a clear and colorless solution of 1,7,10,16-tetraoxa-4,13-diazacyclooctadecane (7, 1.9688 g, 7.5 mmol) and diisopropylethylamine (0.8354 g, 6.5 mmol) in dry ACN (1.075 L) at 75° C. was added dropwise a solution of 206 (0.9255 g, 5.0 mmol) in dry ACN (125 mL) over 2 h 40 min. The flask was then equipped with a condenser and drying tube, and the slightly-yellow solution was heated at reflux for 42 h. Subsequently, the dark-gold solution containing fine, white precipitate was concentrated at 60° C. under reduced pressure to an amber oil. To the crude oil was added 10% MeOH/H$_2$O containing 0.1% TFA (10 mL). The slight suspension was filtered, and the filtrate was purified by preparative HPLC (Method A). Pure fractions were combined, concentrated at 60° C. under reduced pressure, and then lyophilized to give 209 (1.6350 g, 50% yield) as a pale-orange solid. $^1$H NMR (500 MHz, DMSO-d$_6$) δ=8.75 (br s, 2H), 8.17-8.06 (m, 2H), 7.83 (dd, J=7.4, 1.5 Hz, 1H), 4.68 (br s, 2H), 3.91 (s, 3H), 3.85 (br t, J=5.1 Hz, 4H), 3.69 (t, J=5.1 Hz, 4H), 3.59 (br s, 8H), 3.50 (br s, 4H), 3.23 (br t, J=5.1 Hz, 4H). $^{13}$C{$^1$H} APT NMR (126 MHz, DMSO-d$_6$) δ 164.68, 158.78-157.98 (q, TFA), 151.44, 147.13, 139.01, 128.63, 124.87, 120.08-113.01 (q, TFA), 69.33, 69.00, 65.31, 64.60, 56.43, 53.29, 52.67, 46.32. $^{19}$F NMR (470 MHz, DMSO-d$_6$) δ=−73.84. EA Found: C, 43.88; H, 5.29; N, 6.28. Calc. for C$_{20}$H$_{33}$N$_3$O$_6$·2CF$_3$COOH·1H$_2$O: C, 43.84; H., 5.67; N, 6.39. HPLC t$_R$=12.372 min (Method B). HRMS (m/z): 412.24568 [M+H]$^+$; Calc: 412.24421.

Preparation of Ethyl 4-amino-6-((16-((6-(methoxy-carbonyl)pyridin-2-yl)methyl)-1,4,10,13-tetraoxa-7,16-diazacyclooctadecan-7-yl)methyl)picolinate (210)

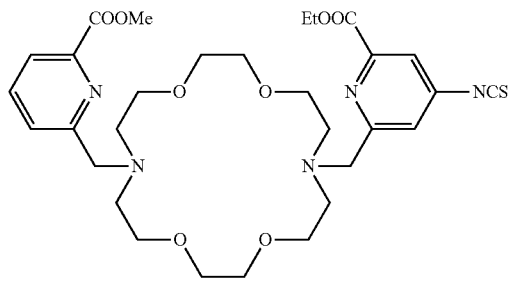

Into a round-bottom flask equipped with a condenser and drying tube were added 209 (0.4210 g, 0.64 mmol), Na$_2$CO$_3$ (0.3400 g, 3.2 mmol), and dry ACN (10 mL). The pale-yellow suspension was heated to reflux over 15 min, after which 206 (0.1508 g, 0.70 mmol, corrected for residual ethyl acetate) was added as a slight suspension in dry ACN (3.5 mL). The mixture was heated at reflux for 44 h and then filtered. The orange filtrate was concentrated at 60° C. under reduced pressure to an orange-brown oil (0.612 g), which was used in the next step without further purification. HRMS (m/z): 590.32021 [M+H]$^+$; Calc: 590.31844.

Preparation of 4-Amino-6-((16-((6-carboxypyridin-2-yl)methyl)-1,4,10,13-tetraoxa-7,16-diazacyclooctadecan-7-yl)methyl)picolinic acid (211·4TFA)

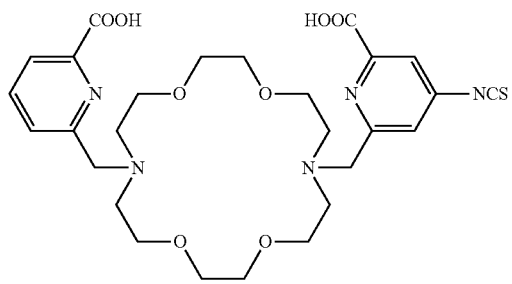

Compound 210 (0.612 g) was dissolved in 6 M HCl (7 mL) and heated at 90° C. for 17 h. The orange-brown solution containing slight precipitate was concentrated at 60° C. under reduced pressure to a pale-tan solid. To this solid was added 10% MeOH/H$_2$O containing 0.1% TFA (3 mL). The slight suspension was filtered and the filtrate was purified by preparative HPLC using Method A. Pure fractions were combined, concentrated at 60° C. under reduced pressure, and then lyophilized to give 211 as an off-white solid (0.2974 g, 46% yield over 2 steps). $^1$H NMR (500 MHz, DMSO-d$_6$) δ=8.13-8.08 (m, 2H), 7.80 (dd, J=7.3, 1.6 Hz, 1H), 7.64 (br s), 7.24 (d, J=2.3 Hz, 1H), 6.76 (d, J=2.3 Hz, 1H), 4.74 (s, 2H), 4.15 (s, 2H), 3.85 (t, J=5.0 Hz, 4H), 3.63 (t, J=5.1 Hz, 4H), 3.57-3.50 (m, 12H), 3.09 (br t, J=5.2 Hz, 4H). $^{13}$C {$^1$H} NMR (126 MHz, DMSO-d$_6$) δ 165.96, 163.37, 159.47, 158.78-157.98 (q, TFA), 151.93, 151.64, 148.25, 144.68, 139.59, 128.43, 124.96, 120.79-113.68 (q, TFA), 109.40, 108.96, 70.03, 69.89, 67.09, 65.16, 57.28, 55.85, 54.47, 53.81. $^{19}$F NMR (470 MHz, DMSO-d$_6$) δ=−74.03. EA Found: C, 40.60; H, 4.29; N, 7.04. Calc. for C$_{26}$H$_{37}$N$_5$O$_8$·4CF$_3$COOH: C, 40.69; H, 4.12; N, 6.98. IR (cm$^{-1}$): 3387, 3161, 1735, 1670, 1204, 1130, 791, 722. HPLC t$_R$=11.974 min (Method B); 11.546 min (Method D). HRMS (m/z): 548.26883 [M+H]$^+$; Calc: 548.27149.

Preparation of 6-((16-((6-carboxypyridin-2-yl)methyl)-1,4,10,13-tetraoxa-7,16-diazacyclooctadecan-7-yl)methyl)-4-isothiocyanatopicolinic acid (212, macropa-NCS)

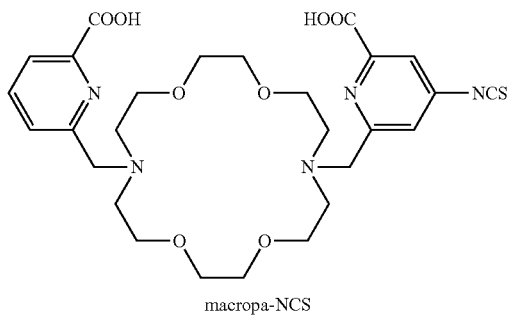

A white suspension of 211 (0.1598 g, 0.16 mmol) and Na$_2$CO$_3$ (0.2540 g, 2.4 mmol) was heated at reflux in acetone (10 mL) for 30 min before the slow addition of CSCl$_2$ (305 μL of CSCl$_2$, 85%, Acros Organics). The resulting orange suspension was heated at reflux for 3 h and then concentrated at 30° C. under reduced pressure to a pale-orange solid. The solid was dissolved portionwise in 10% ACN/H$_2$O containing 0.2% TFA (8 mL total), filtered, and immediately purified by preparative HPLC using Method C.[246] Pure fractions were combined, concentrated at RT under reduced pressure to remove the organic solvent, and then lyophilized. Fractions that were not able to be concentrated immediately were frozen at −80° C. Isothiocyanate 212 was obtained as a mixture of white and pale-yellow solid (0.0547 g) and was stored at −80° C. in a jar of Drierite. Calculations from $^1$H NMR and $^{19}$F NMR spectra of a sample of 212 spiked with a known concentration of fluorobenzene estimated that 212 was isolated as a tetra-TFA salt. $^1$H NMR (400 MHz, DMSO-d$_6$) δ=8.17-8.06 (m, 2H), 8.00 (s w/fine splitting, 1H), 7.84 (d, J=1.5 Hz, 1H), 7.81-7.75 (d w/fine splitting, J=7.16 Hz, 1H), 4.71 (s, 2H), 4.64 (s, 2H), 3.89-3.79 (m, 8H), 3.62-3.46 (m, 16H). $^{19}$F NMR (470 MHz, DMSO-d$_6$) δ=−74.17. IR (cm$^{-1}$): ~3500-2800, 2083, 2026, 1735, 1670, 1591, 1448, 1183, 1130, 796, 717.

HPLC $t_R$=15.053 min (Method B); 13.885 min (Method D). HRMS (m/z): 590.22600 [M+H]⁺; Calc: 590.22791.

Preparation of Di-tert-butyl (((S)-1-(tert-butoxy)-6-(3-(3-ethynylphenyl)ureido)-1-oxohexan-2-yl)carbamoyl)-L-glutamate (214)

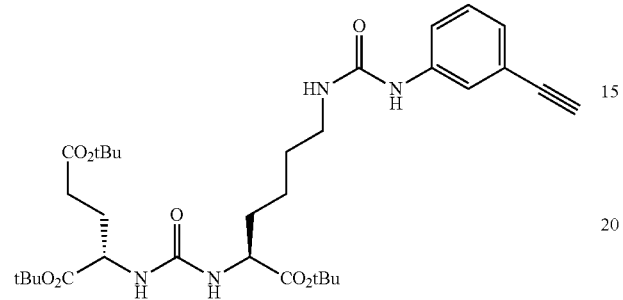

Alkyne 214 was prepared according to published methods [247] and isolated as an off-white powder. ¹H NMR (500 MHz, CDCl₃) &=7.90 (s, 1H), 7.58 (t, 1H, J=1.7 Hz), 7.51 (dd, 1H, J₁=8.2 Hz, J₂=1.3 Hz), 7.18 (t, 1H, J=7.9 Hz), 7.05 (d, 1H, J=7.7 Hz), 6.38 (d, 1H, J=7.9 Hz), 6.28 (br s, 1H), 5.77 (d, 1H, J=6.9 Hz), 4.32 (m, 1H), 4.02 (m, 1H), 3.53 (m, 1H), 3.05 (m, 1H), 3.00 (s, 1H), 2.39 (m, 2H), 2.07 (m, 1H), 1.88 (m, 1H), 1.74 (m, 1H), 1.62 (m, 1H), 1.49-1.37 (m, 4H), 1.41 (s, 18H), 1.37 (s, 9H).

Preparation of 2,5-Dioxopyrrolidin-1-yl N²-(((9H-fluoren-9-yl)methoxy)carbonyl)-N⁶-(tert-butoxycarbonyl)-L-lysinate (215)

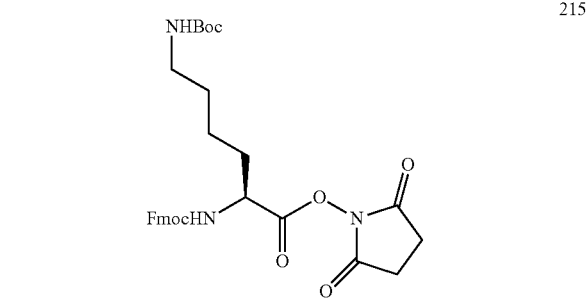

A suspension of Fmoc-L-Lys(Boc)-OH (5.0 g, 10.7 mmol) and N,N'-disuccinimidyl carbonate (2.74 g, 10.7 mmol) in CH₂Cl₂ (50 mL) was stirred at room temperature under argon. Then DIPEA (1.86 mL, 10.7 mmol) was added, and the suspension was stirred overnight. The solvent was evaporated under reduced pressure and the crude product was purified by flash chromatography (0-100% EtOAc in hexane). Lysine 215 was isolated as a white powder (2.5 g, 41%). ¹H NMR (500 MHz, CDCl₃) δ=7.76 (d, 2H, J=7.6 Hz), 7.59 (d, 2H, J=7.3 Hz), 7.40 (t, 2H, J=7.4 Hz), 7.32 (t, 2H, J=7.3 Hz), 5.46 (br s, 1H), 4.71 (m, 2H), 4.45 (m, 2H), 4.23 (t, 1H, J=6.6 Hz), 3.14 (br s, 2H), 2.85 (s, 4H), 2.02 (m, 1H), 1.92 (m, 1H), 1.58 (m, 4H), 1.44 (s, 9H).

Preparation of tert-Butyl N²—(N²-(((9H-fluoren-9-yl)methoxy)carbonyl)-N⁶-(tert-butoxycarbonyl)-L-lysyl)-N⁶-((benzyloxy)carbonyl)-L-lysinate (216)

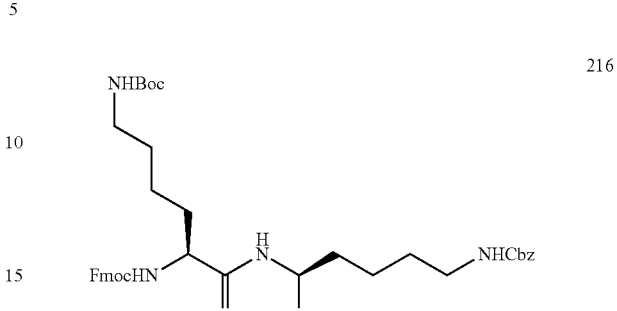

A suspension of L-Lys(Z)-OtBu HCl (1.49 g, 4.0 mmol) in CH₂Cl₂ (15 mL) was treated with DIPEA (0.87 mL, 5.0 mmol). To the resulting mixture was added a solution of lysine 215 (2.2 g, 3.9 mmol) in CH₂Cl₂ (10 mL), and the reaction was stirred overnight at room temperature under argon. It was then washed with saturated NaCl solution, and the organic layer was dried over MgSO₄, filtered and concentrated under reduced pressure. The crude product was purified by flash chromatography (0-100% EtOAc in hexane), and di-lysine 216 was isolated as a white powder (2.2 g, 72%). ¹H NMR (500 MHz, CDCl₃) δ=7.76 (d, 2H, J=7.5 Hz), 7.59 (d, 2H, J=7.3 Hz), 7.40 (t, 2H, J=7.5 Hz), 7.32 (m, 8H), 6.69 (br s, 1H), 5.60 (br s, 1H), 5.06 (m, 4H), 4.72 (br s, 1H), 4.43 (m, 1H), 4.38 (m, 1H), 4.21 (m, 1H), 3.14 (m, 4H), 1.85 (m, 2H), 1.73 (m, 2H), 1.50 (m, 4H), 1.46 (s, 9H), 1.44 (s, 9H), 1.39 (m, 4H).

Preparation of 2,5-Dioxopyrrolidin-1-yl 2-(4-iodophenyl)acetate (217)

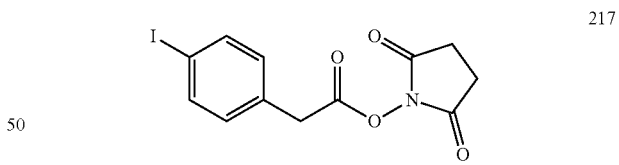

A solution of 2-(4-iodophenyl)acetic acid (786 mg, 3.0 mmol) and EDC HCl (671 mg, 3.5 mmol) in CH₂Cl₂ (20 mL) was stirred for 15 min at room temperature under argon. Then N-hydroxysuccinimide (368 mg, 3.2 mmol) and NEt₃ (0.56 mL, 4.0 mmol) were added and the reaction was stirred for 7 h. It was then washed with saturated NaCl solution, and the organic layer was dried over MgSO₄, filtered and concentrated under reduced pressure. The crude residue was purified by flash chromatography (0-100% EtOAc in hexane), and the NHS ester 217 was isolated as a white solid (760 mg, 70%). ¹H NMR (500 MHz, CDCl₃) δ=7.69 (d, 2H, J=7.9 Hz), 7.09 (d, 2H, J=7.9 Hz), 3.88 (s, 2H), 2.83 (s, 4H).

Preparation of tert-Butyl $N^2$—($N^2$-(1-azido-3,6,9,12,15,18-hexaoxahenicosan-21-oyl)-$N^6$-(tert-butoxycarbonyl)-L-lysyl)-$N^6$-((benzyloxy)carbonyl)-L-lysinate (218)

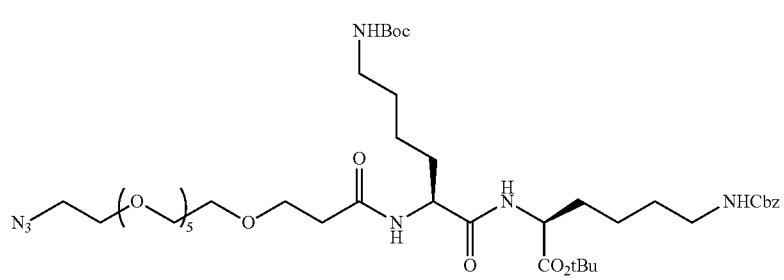

To a solution of Fmoc-protected di-lysine 216 (768 mg, 0.97 mmol) in $CH_2Cl_2$ (4 mL) was added $NHEt_2$ (2.07 mL, 20 mmol). The solution was stirred overnight at room temperature. The solvents were removed under reduced pressure, and the crude product, a yellow oil, was used without further purification. To a solution of this oil (183 mg, 0.32 mmol) in $CH_2Cl_2$ (3 mL) were added successively solutions of $NEt_3$ (57 μL, 0.41 mmol) in $CH_2Cl_2$ (1 mL) and azido-$PEG_6$-NHS ester (100 mg, 0.21 mmol; Broadpharm, USA) in $CH_2Cl_2$ (1 mL), and the reaction was stirred overnight at room temperature. It was then diluted with $CH_2Cl_2$ and washed successively with $H_2O$ and saturated NaCl solution. The organic layer was dried over $MgSO_4$, filtered and concentrated under reduced pressure to give azide 218 as a colorless oil (184 mg; 95%) without need for further purification. Mass (ESI+): 926.4 $[M+H]^+$. Calc. Mass=925.54.

Preparation of Di-tert-butyl (((S)-1-(tert-butoxy)-6-(3-(3-(1-((9S,12S)-9-(tert-butoxycarbonyl)-12-(4-((tert-butoxycarbonyl)amino)butyl)-3,11,14-trioxo-1-phenyl-2,17,20,23,26,29,32-heptaoxa-4,10,13-triazatetratriacontan-34-yl)-1H-1,2,3-triazol-4-yl)phenyl)ureido)-1-oxohexan-2-yl)carbamoyl)-L-glutamate (219)

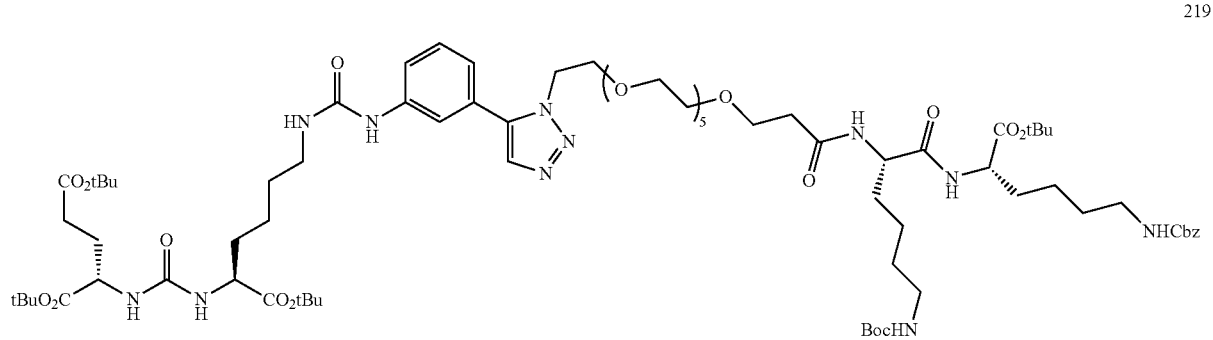

A solution of 100 μL of 0.5 M $CuSO_4$ and 100 μL of 1.5 M sodium ascorbate in DMF (0.5 mL) was mixed for 5 min and was then added to a solution of 218 (184 mg, 0.20 mmol) and 214 (132 mg, 0.21 mmol) in DMF (2.5 mL). The resulting mixture was stirred at room temperature for 45 min. It was then concentrated under reduced pressure and the crude residue was purified by flash chromatography (0-30% MeOH in EtOAc) to give triazole 219 as an orange oil (285 mg; 87%). Mass (ESI+): 1557.2 $[M+H]^+$. Calc. Mass=1555.90.

Preparation of Di-tert-butyl (((S)-1-(tert-butoxy)-6-(3-(3-(1-((23S,26S)-26-(tert-butoxycarbonyl)-23-(4-((tert-butoxycarbonyl)amino)butyl)-33-(4-iodophenyl)-21,24,32-trioxo-3,6,9,12,15,18-hexaoxa-22,25,31-triazatritriacontyl)-1H-1,2,3-triazol-4-yl)phenyl)ureido)-1-oxohexan-2-yl)carbamoyl)-L-glutamate (220)

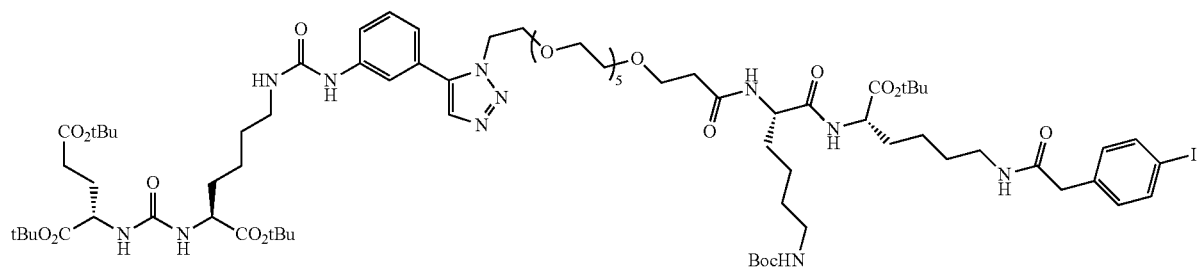

Cbz-Protected triazole 219 (285 mg, 0.18 mmol) was dissolved in MeOH (15 mL) in a two-neck flask. To the solution was added 10% Pd/C (20 mg), and the suspension was shaken and the flask evacuated. The suspension was then placed under an $H_2$ atmosphere and stirred overnight. It was filtered through celite, and the filter cake was washed three times with MeOH. The combined filtrate was concentrated under reduced pressure to give the free amine as a colorless oil (117 mg; 45%) that was used without further purification. Mass (ESI+): 1423.8 [M+H]$^+$. Calc. Mass=1422.77. To a solution of the amine (117 mg, 82 μmol) in $CH_2Cl_2$ (4 mL) was added a solution of DIPEA (23 μL, 131 mmol) in $CH_2Cl_2$ (1 mL), and the mixture was stirred at room temperature under argon. Then a solution of 217 (37 mg, 103 μmol) in $CH_2Cl_2$ (2 mL) was added, and the reaction was stirred at room temperature for 2 h. It was then poured into $H_2O$ (10 mL) and the layers were separated. The organic layer was dried over $MgSO_4$, filtered and concentrated under reduced pressure to give the crude product as a colorless semi-solid. The crude product was purified by prep TLC (10% MeOH in EtOAc) to give phenyl iodide 220 as a colorless oil (34 mg; 25%). Mass (ESI+): 1666.6 [M+H]$^+$. Calc. Mass=1665.80.

Preparation of (((S)-1-Carboxy-5-(3-(3-(1-((23S, 26S)-26-carboxy-23-(4-(3-(2-carboxy-6-((16-((6-carboxypyridin-2-yl)methyl)-1,4,10,13-tetraoxa-7, 16-diazacyclooctadecan-7-yl)methyl)pyridin-4-yl) thioureido)butyl)-33-(4-iodophenyl)-21,24,32-trioxo-3,6,9,12,15,18-hexaoxa-22,25,31-triazatritriacontyl)-1H-1,2,3-triazol-4-yl)phenyl) ureido)pentyl)carbamoyl)-L-glutamic acid (221, macropa-RPS-070)

Preparation of Radiosynthesis of 225Ac-macropa-RPS-070

General. All reagents were purchased from Sigma Aldrich unless otherwise noted, and were reagent grade. Hydrochloric acid (HCl) was traceSELECT® (>99.999%) for trace analysis quality. Aluminum-backed silica thin layer chromatography (TLC) plates were purchased from Sigma

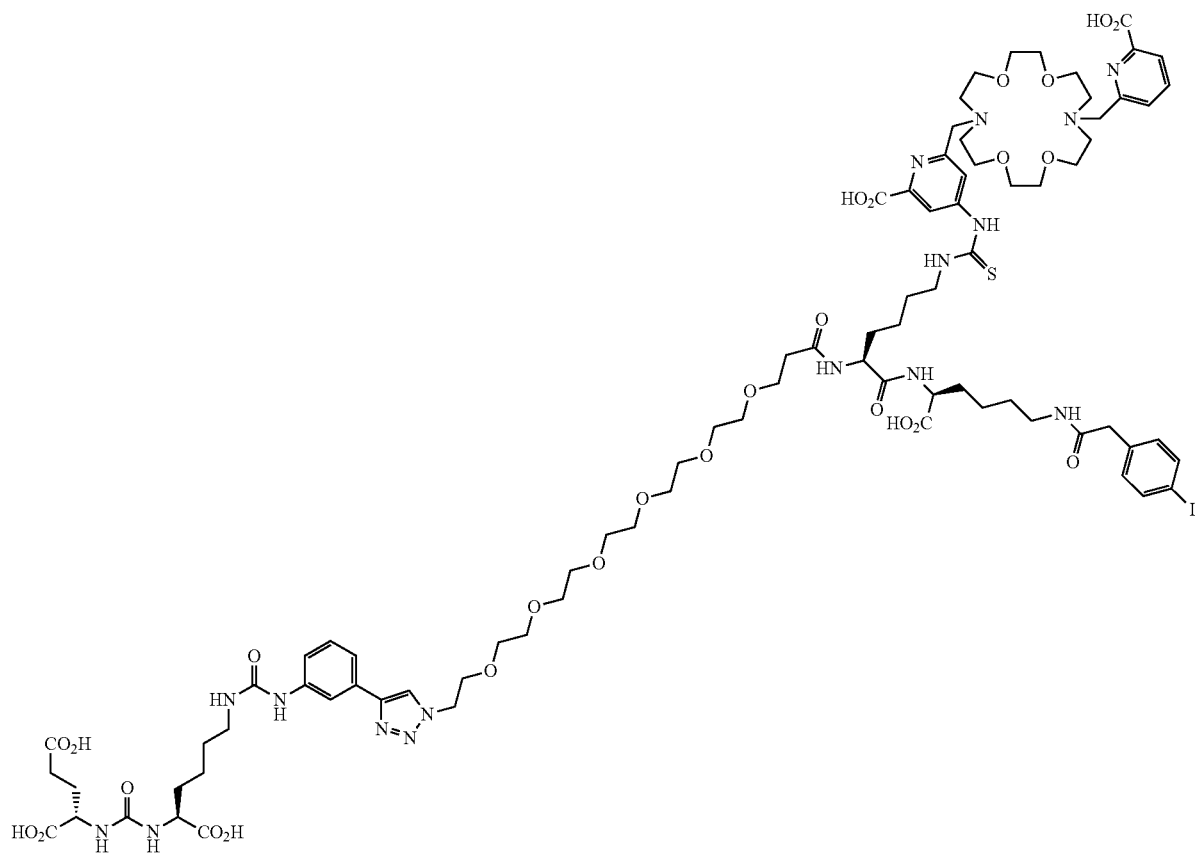

macropa-RPS-070

To a solution of 220 (34 mg, 20 µmol) in CH$_2$Cl$_2$ (2 mL) was added TFA (0.5 mL), and the reaction was stirred at room temperature for 5 h. It was then concentrated under reduced pressure, and the crude product was diluted with H$_2$O and lyophilized to give the free amine as a TFA salt. Mass (ESI+): 1342.5 [M+H]$^+$. Mass (ESI−): 1340.6 [M−H]$^−$. Calc. Mass=1341.50. To a solution of the amine (9 mg, 6.7 µmol) in DMF (0.5 mL) was added a solution of macropa-NCS 212 (15 mg, 25.4 µmol) in DMF (0.5 mL). Then DIPEA (300 µL, 1.72 mmol) was added and the reaction was stirred at room temperature for 2 h. The volatiles were removed under reduced pressure and the crude product was purified by prep HPLC to give macropa-RPS-070 (221) as a white powder (5.4 mg; 42%). Mass (ESI+): 1932.76 [M+H]$^+$. 1931.09 [M+H]$^−$. Calc. Mass=1931.91.

Aldrich. Stock solutions of 0.05 M HCl and 1 M NH$_4$OAc were prepared by dilution in Milli-Q® water.

Radiolabeling Procedure. To a solution of $^{225}$Ac(NO$_3$)$_3$ (Oak Ridge National Laboratory, USA) in 0.05 M HCl (17.9 MBq in 970 µL) was added 20 µL of a 1 mg/mL solution of macropa-RPS-070 in DMSO. The pH was raised to 5-5.5 by addition of 90 µL 1 M NH$_4$OAc. The reaction was allowed to stand at room temperature for 20 min with periodic shaking. Then, 200 µL of the reaction solution was removed and diluted with 3.8 mL of normal saline (0.9% NaCl in deionized H$_2$O; VWR) to give a solution with a concentration of 910 kBq/mL. An aliquot was removed from the final solution and spotted onto an aluminum-backed silica TLC plate to determine radiochemical yield. An aliquot of the $^{225}$Ac(NO$_3$)$_3$ solution in 0.05M HCl was spotted in a parallel lane as a control. The plate was immediately run in a 10% v/v MeOH/10 mM EDTA mobile phase, and then allowed to stand for 8 h to enable radiochemical equilibrium to be reached. The plate was visualized on a Cyclone Plus Storage Phosphor System (Perkin Elmer) following a 3-min exposure on the phosphor screen. The radiochemical yield was expressed as a ratio of $^{225}$Ac-macropa-RPS-070 to total activity and was determined to be 98.1%.

Biodistribution Studies with $^{225}$Ac-Macropa-RPS-070.

Cell Culture. The PSMA-expressing human prostate cancer cell line, LNCaP, was obtained from the American Type Culture Collection. Cell culture supplies were from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 µg/mL gentamicin in a humidified incubator at 37° C./5% $CO_2$. Cells were removed from flasks for passage or for transfer to 12-well assay plates by incubating them with 0.25% trypsin/ethylenediaminetetraacetic acid (EDTA).

Inoculation of Mice with Xenografts. All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Hairless male nu/nu mice were purchased from the Jackson Laboratory. For inoculation in mice, LNCaP cells were suspended at $4\times10^7$ cells/mL in a 1:1 mixture of PBS: Matrigel (BD Biosciences). Each mouse was injected in the left flank with 0.25 mL of the cell suspension. Biodistributions were conducted when tumors were in the range 100-400 $mm^3$.

Biodistribution of $^{225}$Ac-macropa-RPS-070 in LNCaP xenograft mice. Fifteen LNCaP xenograft tumor-bearing mice (5 per time point) were injected intravenously with a bolus injection of 85-95 kBq and 100 ng (50 pmol) of each ligand. The mice were sacrificed by cervical dislocation at 4, 24 and 96 h post injection. A blood sample was removed, and a full biodistribution study was conducted on the following organs (with contents): heart, lungs, liver, small intestine, large intestine, stomach, spleen, pancreas, kidneys, muscle, bone, and tumor. Tissues were weighed and counted on a 2470 Wizard Automatic Gamma Counter (Perkin Elmer). 1% ID/mL samples were counted prior to and following each set of tissue samples to enable decay correction to be undertaken. Counts were corrected for decay and for activity injected, and tissue uptake was expressed as percent injected dose per gram (% ID/g). Standard error measurement was calculated for each data point.

TABLE 1

Organ distribution of $^{225}$Ac-macropa-RPS-070 at t = 4 h, 24 h, and 96 h following intravenous injection in LNCaP xenograft mice (n = 5 per time point). Values are expressed as % ID/g.

| | 1 | 2 | 3 | 4 | 5 | Mean | SEM |
|---|---|---|---|---|---|---|---|
| | | | | 4 h | | | |
| Blood | 0.90654 | 0.55246 | 1.11808 | 0.8276 | 0.65638 | 0.81221 | 0.0986 |
| Heart | 0.75759 | 0.65317 | 0.77395 | 0.75148 | 0.6585 | 0.71894 | 0.02604 |
| Lungs | 0.99558 | 0.60669 | 1.25979 | 0.98587 | 0.88664 | 0.94691 | 0.10516 |
| Liver | 1.62187 | 1.34632 | 1.74207 | 1.68077 | 1.3957 | 1.55735 | 0.0788 |
| Small Intestine | 0.1998 | 0.16282 | 0.3104 | 0.24413 | 0.17094 | 0.21762 | 0.02721 |
| Large Intestine | 1.38298 | 0.65162 | 1.27419 | 0.91656 | 0.81901 | 1.00487 | 0.13563 |
| Stomach | 0.33963 | 0.2471 | 0.30417 | 0.4109 | 0.21221 | 0.3028 | 0.03489 |
| Spleen | 1.40902 | 0.70804 | 1.61264 | 1.10815 | 0.8756 | 1.14269 | 0.16632 |
| Pancreas | 0.55487 | 0.41637 | 0.55317 | 0.4675 | 0.6604 | 0.53047 | 0.04182 |
| Kidneys | 65.5884 | 20.5274 | 108.233 | 33.654 | 33.0707 | 52.2146 | 15.8618 |
| Muscle | 0.68006 | 0.80579 | 0.72817 | 0.67666 | 0.65617 | 0.70937 | 0.02684 |
| Bone | 1.14861 | 1.12335 | 1.48731 | 0.92036 | 1.15463 | 1.16685 | 0.09106 |
| Tumor | 6.73177 | 10.7309 | 23.8367 | 15.3682 | 7.50352 | 12.8342 | 3.1429 |
| | | | | 24 h | | | |
| Blood | 0.34825 | 0.31324 | 0.22083 | 0.29453 | 0.27697 | 0.29076 | 0.0211 |
| Heart | 0.52256 | 0.56334 | 0.4521 | 0.47914 | 0.46483 | 0.49639 | 0.02052 |
| Lungs | 0.53778 | 0.45077 | 0.46083 | 0.4286 | 0.44831 | 0.46526 | 0.01887 |
| Liver | 1.57844 | 1.47552 | 1.13776 | 1.14264 | 1.48473 | 1.36382 | 0.09305 |
| Small Intestine | 0.08784 | 0.09914 | 0.08822 | 0.09466 | 0.10376 | 0.09473 | 0.00309 |
| Large Intestine | 0.13296 | 0.1259 | 0.13252 | 0.13425 | 0.13176 | 0.13148 | 0.00145 |
| Stomach | 0.1296 | 0.12119 | 0.1119 | 0.14675 | 0.15329 | 0.13255 | 0.00773 |
| Spleen | 0.62075 | 0.65764 | 0.62013 | 0.57685 | 0.58554 | 0.61218 | 0.01443 |
| Pancreas | 0.39847 | 0.39119 | 0.50347 | 0.33315 | 0.31944 | 0.38914 | 0.03252 |
| Kidneys | 4.98792 | 4.25707 | 3.94586 | 3.66457 | 4.10348 | 4.19178 | 0.22185 |
| Muscle | 0.61193 | 0.5149 | 0.44832 | 0.78028 | 0.44579 | 0.56025 | 0.06276 |
| Bone | 1.27255 | 1.06645 | 0.83943 | 1.00576 | 0.69755 | 0.97635 | 0.09828 |
| Tumor | 11.6163 | 9.26927 | 7.50158 | 4.41446 | 8.04683 | 8.16969 | 1.17583 |
| | | | | 96 h | | | |
| Blood | 0.19042 | 0.19188 | 0.15206 | 0.16528 | 0.23822 | 0.18757 | 0.01475 |
| Heart | 0.39939 | 0.42398 | 0.42861 | 0.45863 | 0.45595 | 0.43331 | 0.01098 |
| Lungs | 0.30165 | 0.50912 | 0.46944 | 0.37811 | 0.36979 | 0.40562 | 0.03717 |
| Liver | 0.79406 | 0.8144 | 0.73301 | 0.7917 | 0.79415 | 0.78546 | 0.01374 |
| Small Intestine | 0.04372 | 0.0577 | 0.03752 | 0.04431 | 0.04136 | 0.04492 | 0.00341 |

TABLE 1-continued

Organ distribution of $^{225}$Ac-macropa-RPS-070 at t = 4 h,
24 h, and 96 h following intravenous injection in LNCaP xenograft
mice (n = 5 per time point). Values are expressed as % ID/g.

|  | 1 | 2 | 3 | 4 | 5 | Mean | SEM |
|---|---|---|---|---|---|---|---|
| Large Intestine | 0.04349 | 0.09663 | 0.04522 | 0.04198 | 0.03927 | 0.05332 | 0.01087 |
| Stomach | 0.03442 | 0.04708 | 0.03448 | 0.02845 | 0.02366 | 0.03362 | 0.00393 |
| Spleen | 0.48373 | 0.394 | 0.44261 | 0.43481 | 0.53966 | 0.45896 | 0.02469 |
| Pancreas | 0.09848 | 0.37696 | 0.30549 | 0.31625 | 0.33352 | 0.28614 | 0.04847 |
| Kidneys | 1.30286 | 1.3239 | 2.00405 | 1.39886 | 1.45955 | 1.4978 | 0.12958 |
| Muscle | 0.3022 | 0.52492 | 0.25089 | 0.29815 | 0.2528 | 0.32579 | 0.05095 |
| Bone | 0.86391 | 0.86874 | 0.83831 | 1.12223 | 0.82042 | 0.90272 | 0.05557 |
| Tumor | 4.04259 | 4.07799 | 6.73954 | 4.58107 | 4.84503 | 4.85724 | 0.49449 |

Figure 5A:
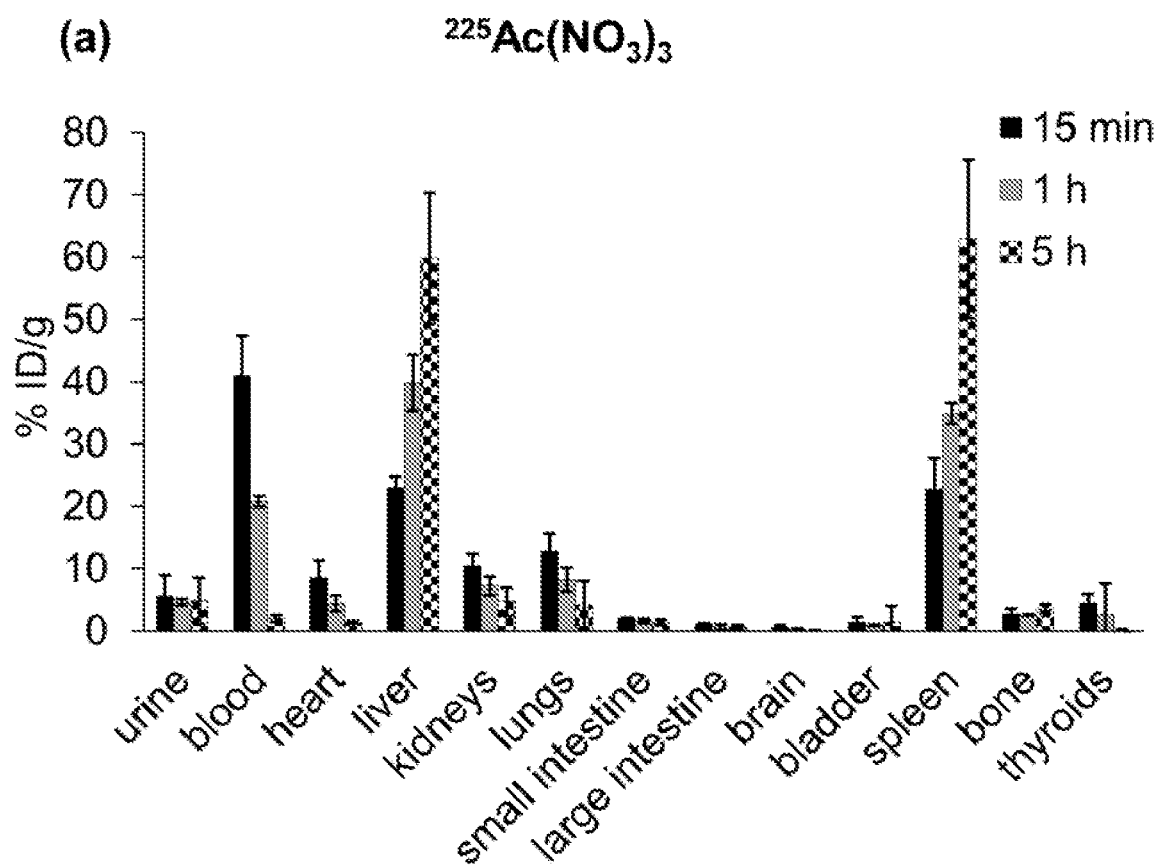
FIGS. 5A-C provide histograms illustrating the biodistribution of $^{255}$Ac(NO$_3$)$_3$ (FIG. 5A), [$^{225}$Ac(macropa)]$^+$ (FIG. 5B), and [$^{225}$Ac(DOTA)]$^-$ (FIG. 5C) for select organs following intravenous injection in mice. Adult C57BL/6 mice were sacrificed 15 min, 1 h, or 5 h post injection. Values for each time point are given as mean % ID/g 1 SD.
Figure 5B:
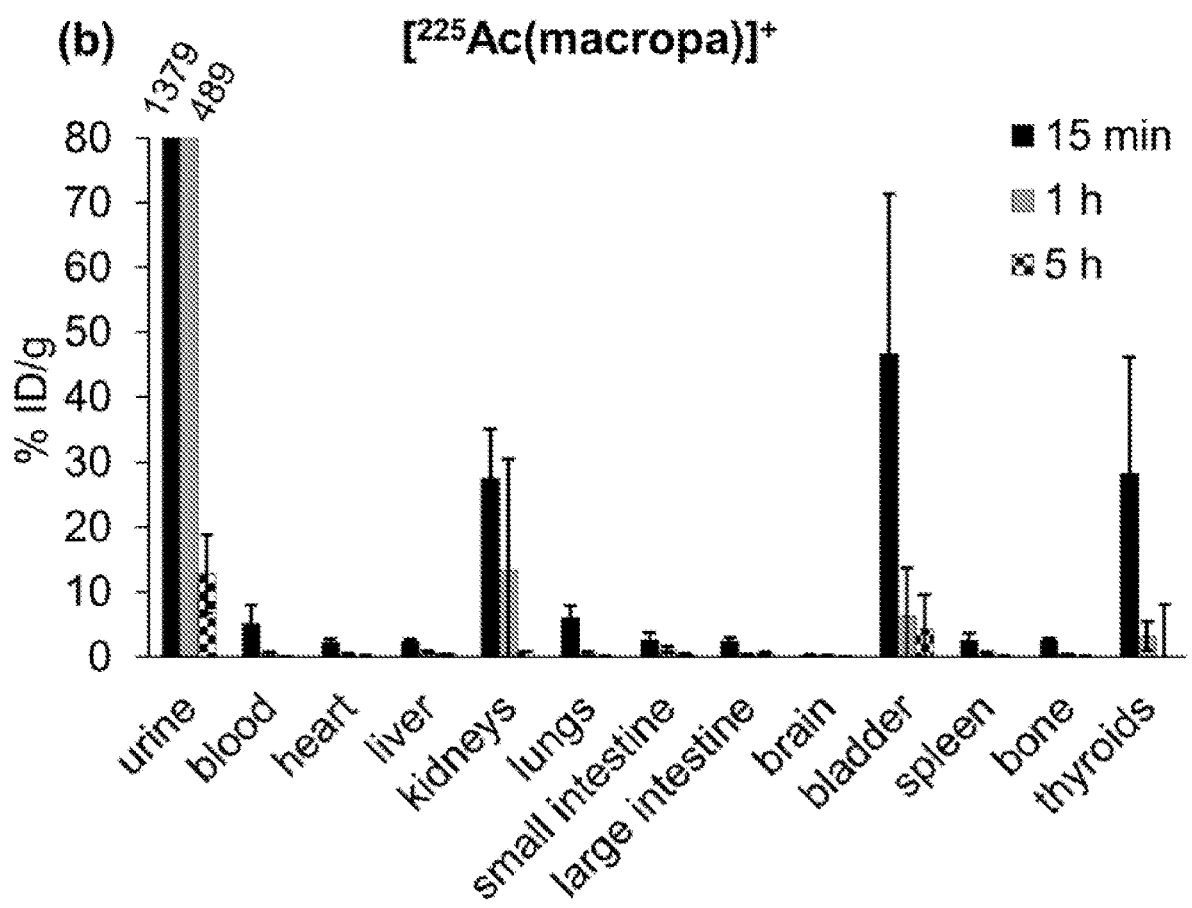
Figure 5C:
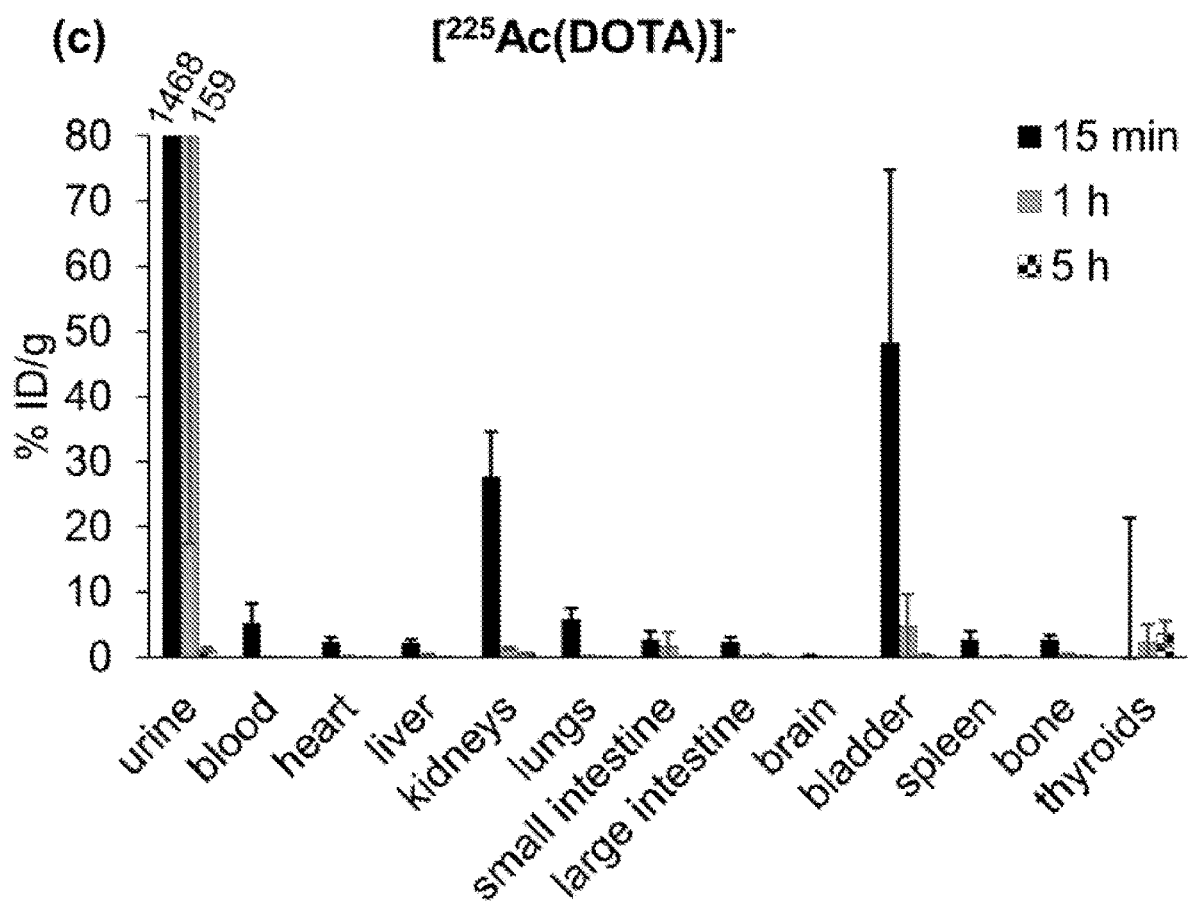

Discussion of Results for Above-Described of [$^{225}$Ac(Macropa)]$^+$ Complexes The in vivo stability of [$^{225}$Ac(macropa)]$^+$ was assessed by comparing its biodistribution to those of $^{225}$Ac(NO$_3$)$_3$ and [$^{225}$Ac(DOTA)]$^-$. C57BL/6 mice were injected via tail vein with 10-50 kBq of each radiometal complex and were sacrificed after 15 min, 1 h, or 5 h. The amount of $^{225}$Ac retained in each organ was quantified by gamma counting and reported as the percent of injected dose per gram of tissue (% ID/g). Inadequate stability of an $^{225}$Ac complex leading to the loss of radioisotope in vivo is manifested by the accumulation of $^{225}$Ac in the liver, spleen, and bone of mice.[11,12,31] The biodistribution profile of uncomplexed $^{225}$Ac(NO$_3$)$_3$ (FIG. 5A) reveals slow blood clearance and excretion, coupled to large accumulation in the liver and spleen. The biodistribution profile of [$^{225}$Ac(macropa)]$^+$ (FIG. 5B) differs markedly from that of $^{225}$Ac(NO$_3$)$_3$. [$^{225}$Ac(macropa)]$^+$ was rapidly cleared from mice, with very little activity measured in blood by 1 h post injection. Most of the injected dose was renally excreted and subsequently detected in the urine, which explains the moderate kidney and bladder uptake of [$^{225}$Ac(macropa)]$^+$ observed in mice at 15 min and 1 h post injection. Of significance, [$^{225}$Ac(macropa)]$^+$ did not accumulate in any organ over the time course of the study, indicating that the complex does not release free $^{225}$Ac$^{3+}$ in vivo. Its biodistribution profile was similar to that of [$^{225}$Ac(DOTA)]$^-$ (FIG. 5C), which has been previously shown to retain $^{225}$Ac$^{3+}$ in-vivo.[7] Notably, [$^{225}$Ac(DOTA)]$^-$ appeared to clear more rapidly through the urine and was taken up to a lesser extent in the thyroid. These differences may arise in part due to the opposite charges of the complexes. Collectively, the results of these biodistribution studies demonstrate that [$^{225}$Ac(macropa)]$^+$ is highly stable in vivo.

Figure 6:
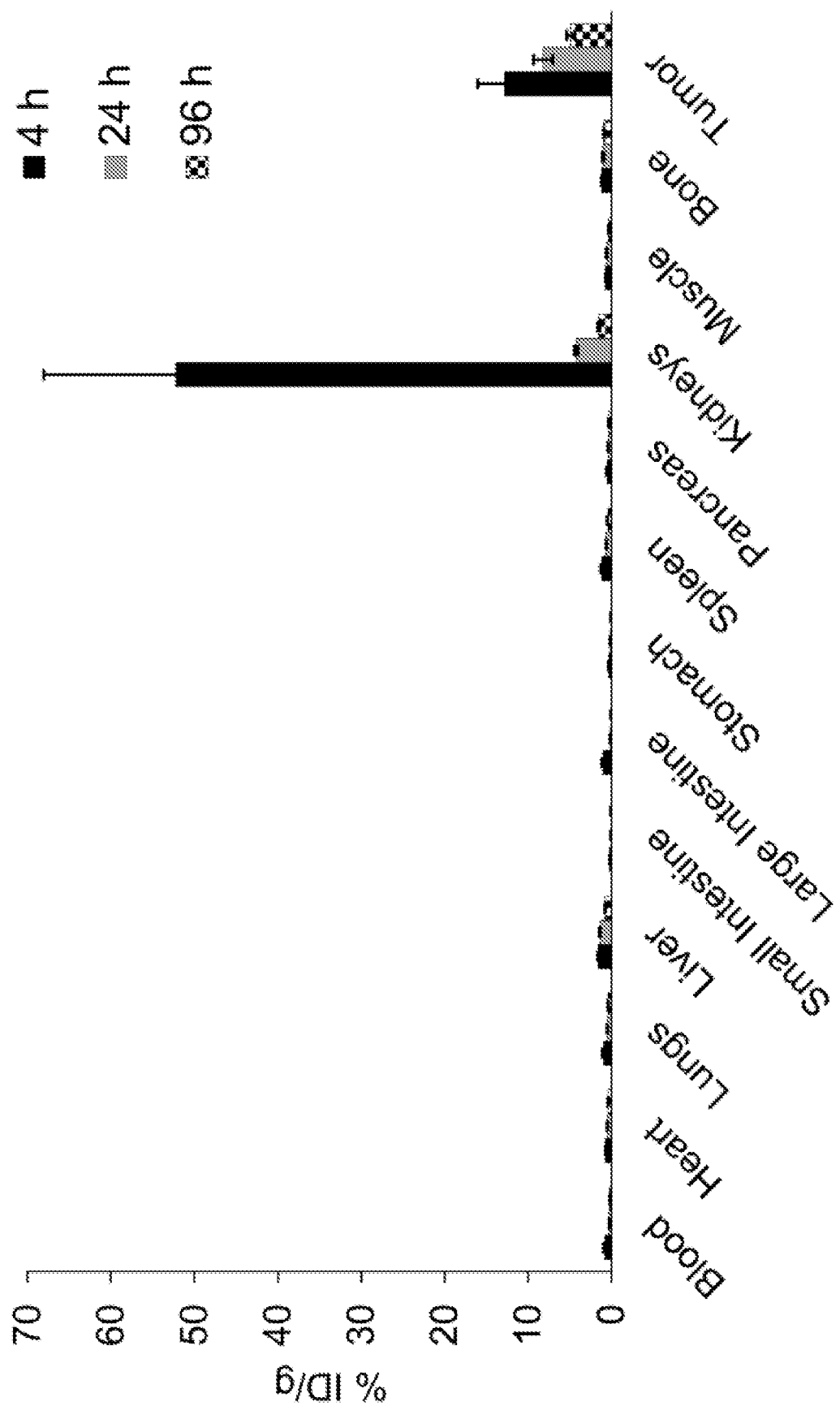
FIG. 6 illustrates the biodistribution of $^{225}$Ac-macropa-RPS-070 following intravenous injection in LNCaP tumor xenograft mice. Mice were sacrificed 4, 24, or 96 h post injection. Values for each time point are given as mean % ID/g±1 SEM.

RPS-070 was conjugated to macropa-NCS, where this construct bears a glutamate-urea-lysine moiety that inhibits the prostate-specific membrane antigen (PSMA),[237-241] a membrane-bound glycoprotein that is overexpressed in prostate cancer cells.[242] An albumin-binding functional group, in this case the group including iodophenyl, is also a critical component of these compounds that prolongs their circulation half-life.[243,244] Radiolabeling of macropa-RPS-070 with $^{225}$Ac proceeded in 20 min at RT and pH 5-5.5 to give a RCY of 98%. $^{225}$Ac-macropa-RPS-070 (85-95 kBq) was then injected into LNCaP (prostate cancer) tumor xenograft-bearing mice, and the biodistribution of the complex was determined at 4, 24, and 96 h post injection (Table 1 supra, FIG. 6). $^{225}$Ac-macropa-RPS-070 was rapidly cleared from the blood and primarily distributed to the kidneys and tumor (52±16% ID/g and 13±3% ID/g, respectively, at 4 h post injection). After 4 h, most of the activity cleared from the kidneys and gradual tumor washout was observed. Importantly, the complex exhibited negligible uptake by other organs (<1% ID/g at 96 h post injection) and did not amass in any organ over time. The activity that cleared from the tumor from 4-96 h remained chelated by macropa-RPS-070, as evidenced by the lack of accumulation of $^{225}$Ac in the liver, spleen, and bone of mice during this time. These results are significant because they demonstrate that macropa-RPS-070 can stably retain $^{225}$Ac in vivo over several days and that the construct can be selectively targeted to tumors.

SECTION 1.2 REFERENCES

[1] M. R. Harrison, T. Z. Wong, A. J. Armstrong, D. George, Cancer Manag. Res. 2013, 5, 1.
[2] R. Coleman, Semin. Nucl. Med. 2016, 46, 99.
[3] Y.-S. Kim, M. W. Brechbiel, Tumor Biol. 2012, 33, 573.
[4] Y. Dekempeneer, M. Keyaerts, A. Krasniqi, J. Puttemans, S. Muyldermans, T. Lahoutte, M. D'huyvetter, N. Devoogdt, Expert Opin. Biol. Ther. 2016, 16, 1035.
[5] E. W. Price, C. Orvig, Chem. Soc. Rev. 2014, 43, 260.
[6] M. W. Geerlings, F. M. Kaspersen, C. Apostolidis, R. van der Hout, Nucl. Med. Commun. 1993, 14, 121.
[7] M. R. McDevitt, D. Ma, L. T. Lai, J. Simon, P. Borchardt, R. K. Frank, K. Wu, V. Pellegrini, M. J. Curcio, M. Miederer, et al., Science 2001, 294, 1537.
[8] M. Miederer, D. A. Scheinberg, M. R. McDevitt, Adv. Drug Deliv. Rev. 2008, 60, 1371.
[9] D. A. Scheinberg, M. R. McDevitt, Curr. Radiopharm. 2011, 4, 306.
[10] Memorial Sloan Kettering Cancer Center, Targeted Atomic Nano-Generators (Actinium-225-Labeled Humanized Anti-CD33 Monoclonal Antibody HuM195) in Patients With Advanced Myeloid Malignancies. ClinicalTrials.gov [website], Bethesda, Md.: US National Library of Medicine. https://clinicaltrials.gov/ct2/show/NCT00672165. NLM identifier NCT00672165. Accessed Apr. 20, 2017.
[11] I. A. Davis, K. A. Glowienka, R. A. Boll, K. A. Deal, M. W. Brechbiel, M. Stabin, P. N. Bochsler, S. Mirzadeh, S. J. Kennel, Nucl. Med. Biol. 1999, 26, 581.
[12] K. A. Deal, I. A. Davis, S. Mirzadeh, S. J. Kennel, M. W. Brechbiel, J. Med. Chem. 1999, 42, 2988.
[13] L. L. Chappell, K. A. Deal, E. Dadachova, M. W. Brechbiel, Bioconjug. Chem. 2000, 11, 510.
[14] S. J. Kennel, L. L. Chappell, K. Dadachova, M. W. Brechbiel, T. K. Lankford, I. A. Davis, M. Stabin, S. Mirzadeh, Cancer Biother. Radiopharm. 2000, 15, 235.

[15] P. Comba, U. Jermilova, C. Orvig, B. O. Patrick, C. F. Ramogida, K. Ruck, C. Schneider, M. Starke, Chem.—A Eur. J. 2017, DOI 10.1002/chem.201702284.

[16] M. R. McDevitt, D. Ma, J. Simon, R. K. Frank, D. A. Scheinberg, Appl. Radiat. Isot. 2002, 57, 841.

[17] A. E. Martell, R. M. Smith, in Crit. Stab. Constants Second Suppl., Springer, Boston, Mass., 1989, pp. 1-66.

[18] S. L. Wu, W. D. Horrocks, J. Chem. Soc., Dalton Trans. 1997, 1497.

[19] R. D. Shannon, Acta Crystallogr. Sect. A 1976, 32, 751.

[20] M. Miederer, G. Henriksen, A. Alke, I. Mossbrugger, L. Quintanilla-Martínez, R. Senekowitsch-Schmidtke, M. Essler, Clin. Cancer Res. 2008, 14, 3555.

[21] M. Essler, F. C. Gärtner, F. Neff, B. Blechert, R. Senekowitsch-Schmidtke, F. Bruchertseifer, A. Morgenstern, C. Seidl, Eur. J. Nucl. Med. Mol. Imaging 2012, 39, 602.

[22] W. F. Maguire, M. R. McDevitt, P. M. Smith-Jones, D. A. Scheinberg, J. Nucl. Med. 2014, 55, 1492.

[23] M. Mato-Iglesias, A. Roca-Sabio, Z. Pálinkás, D. Esteban-Gómez, C. Platas-Iglesias, É. Tóth, A. de Blas, T. Rodríguez-Blas, Inorg. Chem. 2008, 47, 7840.

[24] A. Roca-Sabio, M. Mato-Iglesias, D. Esteban-Gómez, É. Tóth, A. de Blas, C. Platas-Iglesias, T. Rodríguez-Blas, J. Am. Chem. Soc. 2009, 131, 3331.

[25] R. Ferreirós-Martínez, D. Esteban-Gómez, É. Tóth, A. de Blas, C. Platas-Iglesias, T. Rodríguez-Blas, Inorg. Chem. 2011, 50, 3772.

[26] M. P. Jensen, R. Chiarizia, I. A. Shkrob, J. S. Ulicki, B. D. Spindler, D. J. Murphy, M. Hossain, A. Roca-Sabio, C. Platas-Iglesias, A. de Blas, et al., Inorg. Chem. 2014, 53, 6003.

[27] A. E. Martell, R. M. Smith, Critical Stability Constants: Vol. 1, Plenum Press, New York; London, 1974.

[28] M. Regueiro-Figueroa, J. L. Barriada, A. Pallier, D. Esteban-Gómez, A. de Blas, T. Rodríguez-Blas, É. Tóth, C. Platas-Iglesias, Inorg. Chem. 2015, 54, 4940.

[29] M. G. Ferrier, E. R. Batista, J. M. Berg, E. R. Birnbaum, J. N. Cross, J. W. Engle, H. S. La Pierre, S. A. Kozimor, J. S. Lezama Pacheco, B. W. Stein, et al., Nat. Commun. 2016, 7, 12312.

[30] M. G. Ferrier, B. W. Stein, E. R. Batista, J. M. Berg, E. R. Birnbaum, J. W. Engle, K. D. John, S. A. Kozimor, J. S. Lezama Pacheco, L. N. Redman, ACS Cent. Sci. 2017, 3, 176.

[31] R. Ferreirós-Martínez, D. Esteban-Gómez, A. De Blas, C. Platas-Iglesias, T. Rodriguez-Blas, Inorg. Chem. 2009, 48, 11821.

[32] G. J. Beyer, R. Bergmann, K. Schomäcker, F. Rösch, G. Schäfer, E. V Kulikov, A. F. Novgorodov, Isot. Isot. Environ. Heal. Stud. 1990, 26, 111.

[33] M. M. Moasser, Oncogene 2007, 26, 6469.

[34] B. Leyland-Jones, K. Gelmon, J.-P. Ayoub, A. Arnold, S. Verma, R. Dias, P. Ghahramani, J. Clin. Oncol. 2003, 21, 3965.

[35] D. Leveque, L. Gigou, J. P. Bergerat, Curr. Clin. Pharmacol. 2008, 3, 51.

[36] J. M. Kelly, A. Amor-Coarasa, A. Nikolopoulou, T. Wüstemann, P. Barelli, D. Kim, C. Williams Jr., X. Zheng, C. Bi, B. Hu, et al., J. Nucl. Med. 2017, 58, 1442.

[37] A. P. Kozikowski, F. Nan, P. Conti, J. Zhang, E. Ramadan, T. Bzdega, B. Wroblewska, J. H. Neale, S. Pshenichkin, J. T. Wroblewski, J. Med. Chem. 2001, 44, 298.

[38] K. P. Maresca, S. M. Hillier, F. J. Femia, D. Keith, C. Barone, J. L. Joyal, C. N. Zimmerman, A. P. Kozikowski, J. A. Barrett, W. C. Eckelman, et al., J. Med. Chem. 2009, 52, 347.

[39] S. M. Hillier, K. P. Maresca, F. J. Femia, J. C. Marquis, C. A. Foss, N. Nguyen, C. N. Zimmerman, J. A. Barrett, W. C. Eckelman, M. G. Pomper, et al., Cancer Res. 2009, 69, 6932.

[40] J. A. Barrett, R. E. Coleman, S. J. Goldsmith, S. Vallabhajosula, N. A. Petry, S. Cho, T. Armor, J. B. Stubbs, K. P. Maresca, M. G. Stabin, et al., J. Nucl. Med. 2013, 54, 380.

[41] J. Kelly, A. Amor-Coarasa, A. Nikolopoulou, D. Kim, C. Williams Jr., S. Ponnala, J. W. Babich, Eur. J. Nucl. Med. Mol. Imaging 2017, 44, 647.

[42] A. Ghosh, W. D. W. Heston, J. Cell. Biochem. 2004, 91, 528.

[43] M. S. Dennis, M. Zhang, Y. Gloria Meng, M. Kadkhodayan, D. Kirchhofer, D. Combs, L. A. Damico, J. Biol. Chem. 2002, 277, 35035.

[44] C. E. Dumelin, S. Trüssel, F. Buller, E. Trachsel, F. Bootz, Y. Zhang, L. Mannocci, S. C. Beck, M. Drumea-Mirancea, M. W. Seeliger, et al., Angew. Chem. Int. Ed. 2008, 47, 3196.

[237] A. P. Kozikowski, F. Nan, P. Conti, J. Zhang, E. Ramadan, T. Bzdega, B. Wroblewska, J. H. Neale, S. Pshenichkin, J. T. Wroblewski, J. Med Chem. 2001, 44, 298.

[238] K. P. Maresca, S. M. Hillier, F. J. Femia, D. Keith, C. Barone, J. L. Joyal, C. N. Zimmerman, A. P. Kozikowski, J. A. Barrett, W. C. Eckelman, et al., J. Med Chem. 2009, 52, 347.

[239] S. M. Hillier, K. P. Maresca, F. J. Femia, J. C. Marquis, C. A. Foss, N. Nguyen, C. N. Zimmerman, J. A. Barrett, W. C. Eckelman, M. G. Pomper, et al., Cancer Res. 2009, 69, 6932.

[240] J. A. Barrett, R. E. Coleman, S. J. Goldsmith, S. Vallabhajosula, N. A. Petry, S. Cho, T. Armor, J. B. Stubbs, K. P. Maresca, M. G. Stabin, et al., J. Nucl. Med 2013, 54, 380.

[241] J. Kelly, A. Amor-Coarasa, A. Nikolopoulou, D. Kim, C. Williams Jr., S. Ponnala, J. W. Babich, Eur. J. Nucl. Med Mol. Imaging 2017, 44, 647.

[242] A. Ghosh, W. D. W. Heston, J. Cell. Biochem. 2004, 91, 528.

[243] M. S. Dennis, M. Zhang, Y. Gloria Meng, M. Kadkhodayan, D. Kirchhofer, D. Combs, L. A. Damico, J. Biol. Chem. 2002, 277, 35035.

[244] C. E. Dumelin, S. Trüssel, F. Buller, E. Trachsel, F. Bootz, Y. Zhang, L. Mannocci, S. C. Beck, M. Drumea-Mirancea, M. W. Seeliger, et al., Angew. Chem. Int. Ed. 2008, 47, 3196.

[245] Z. E. A. Chamas, X. Guo, J.-L. Canet, A. Gautier, D. Boyer, R. Mahiou, Dalton Trans. 2010, 39, 7091-7097.

[246] D. T. Corson, C. F. Meares, Bioconjug. Chem. 2000, 11, 292-299.

[247] G. M. Sheldrick, Acta Crystallogr. Sect. A 2015, 71, 3-8.

Section 1.3

General Methods. All solvents were purchased from Sigma Aldrich and were of reagent grade quality unless otherwise indicated. Solvents were dried either by distillation over an activated stainless steel column (Pure Process Technology, LLC) column or by drying over activated molecular sieves. Reagents were purchased from Sigma Aldrich, except for 2-azidoacetic acid-NHS ester and the azido-PEGn-NHS ester compounds, which were purchased from BroadPharm. The reagents were all of reagent grade and were used without any further purification.

All reactions described below were carried out in dried glassware. Purifications were performed using silica chromatography on VWR® High Purity Silica Gel 60 Å, preparative TLC on silica-coated glass plates (Analtech) and by flash chromatography using a CombiFlash Rf+ (Teledyne Isco) system. Preparative HPLC was performed using an XBridge™ Prep C18 5 µm OBD™ 19×100 mm column (Waters) on a dual pump Agilent ProStar HPLC fitted with an Agilent ProStar 325 Dual Wavelength UV-Vis Detector. UV absorption was monitored at 220 nm and 280 nm. A binary solvent system was used, with solvent A comprising $H_2O+0.01\%$ TFA and solvent B consisting of 90% v/v $MeCN/H_2O+0.01\%$ TFA. Purification was achieved using the following gradient HPLC method: 0% B 0-1 min., 0-100% B 1-28 mins., 100-0% B 28-30 mins.

Final products were identified and characterized using thin layer chromatography, analytical HPLC and mass spectrometry. NMR spectroscopy was used to confirm the structure of compounds 7a, 8a, 26 and 28. Analytical HPLC was performed using an XSelect™ CSH™ C18 5 µm 4.6×50 mm column (Waters). Mass determinations were performed by LCMS analysis using a Waters ACQUITY UPLC® coupled to a Waters SQ Detector 2. NMR analyses were performed using a Bruker Avance III 500 MHz spectrometer. Spectra are reported as ppm and are referenced to the solvent resonances in chloroform-d (Sigma Aldrich). The purity of all compounds evaluated in the biological assay was >95% as judged by analytical HPLC.

di-tert-butyl (((S)-1-(tert-butoxy)-6-(3-(3-ethynylphenyl)ureido)-1-oxohexan-2-yl)carbamoyl)-L-glutamate (26)

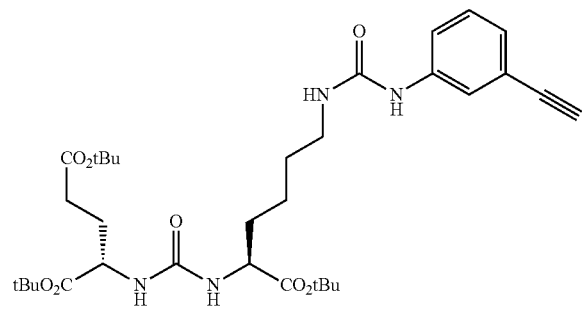

26

Alkyne 26 was prepared according to the protocols described in Kelly J, Amor-Coarasa A, Nikolopoulou A, Kim D, Williams C., Jr, Ponnala S, Babich J W. Synthesis and pre-clinical evaluation of a new class of high-affinity $^{18}$F-labeled PSMA ligands for detection of prostate cancer by PET imaging. *Eur J Nucl Med Mol Imaging* 2017; 44:647-61 and isolated as an off-white powder. $^1$H NMR (500 MHz, $CDCl_3$) δ 7.90 (s, 1H), 7.58 (t, 1H, J=1.7 Hz), 7.51 (dd, 1H, J=8.2 Hz, $J_2$=1.3 Hz), 7.18 (t, 1H, J=7.9 Hz), 7.05 (d, 1H, J=7.7 Hz), 6.38 (d, 1H, J=7.9 Hz), 6.28 (br s, 1H), 5.77 (d, 1H, J=6.9 Hz), 4.32 (m, 1H), 4.02 (m, 1H), 3.53 (m, 1H), 3.05 (m, 1H), 3.00 (s, 1H), 2.39 (m, 2H), 2.07 (m, 1H), 1.88 (m, 1H), 1.74 (m, 1H), 1.62 (m, 1H), 1.49-1.37 (m, 4H), 1.41 (s, 18H), 1.37 (s, 9H).

Synthetic Procedure to that in Section 1.1 for tert-butyl $N^2$—($N^2$-(((9H-fluoren-9-yl)methoxy)carbonyl)-$N^6$-(tert-butoxycarbonyl)-L-lysyl)-$N^6$-((benzyloxy)carbonyl)-L-lysinate (8a)

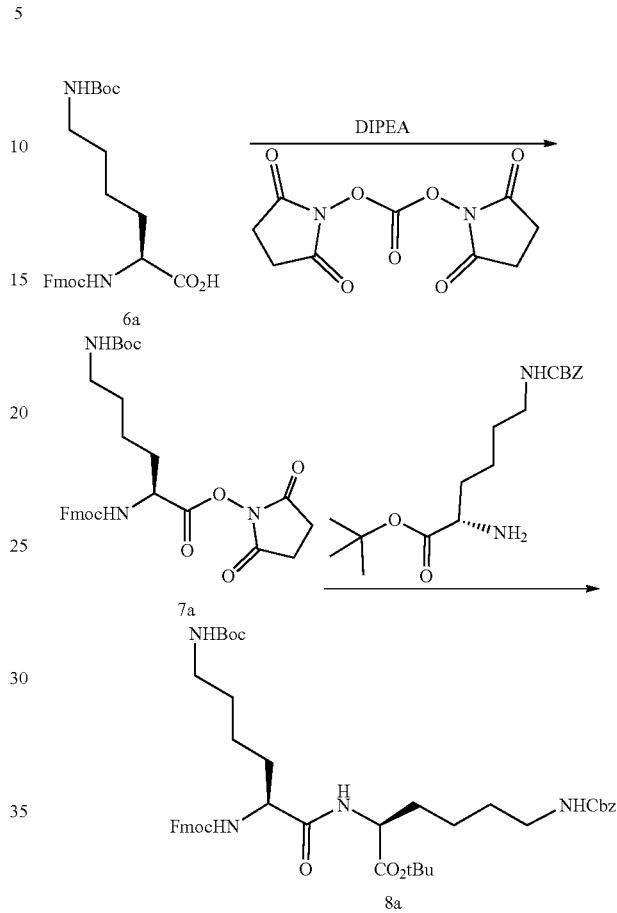

2,5-dioxopyrrolidin-1-yl $N^2$-(((9H-fluoren-9-yl)methoxy)carbonyl)-$N^6$-(tert-butoxycarbonyl)-L-lysinate (7a): A suspension of Fmoc-L-Lys(Boc)-OH 6a (5.0 g, 10.7 mmol) and N,N'-disuccinimidyl carbonate (2.74 g, 10.7 mmol) in $CH_2Cl_2$ (50 mL) was stirred at room temperature under argon. Then DIPEA (1.86 mL, 10.7 mmol) was added, and the suspension was stirred overnight. The solvent was evaporated under reduced pressure and the crude product was purified by flash chromatography (0-100% EtOAc in hexane). The NHS ester 7a was isolated as a white powder (2.5 g, 41%). $^1$H NMR (500 MHz, $CDCl_3$) δ 7.76 (d, 2H, J=7.6 Hz), 7.59 (d, 2H, J=7.3 Hz), 7.40 (t, 2H, J=7.4 Hz), 7.32 (t, 2H, J=7.3 Hz), 5.46 (br s, 1H), 4.71 (m, 2H), 4.45 (m, 2H), 4.23 (t, 1H, J=6.6 Hz), 3.14 (br s, 2H), 2.85 (s, 4H), 2.02 (m, 1H), 1.92 (m, 1H), 1.58 (m, 4H), 1.44 (s, 9H).

tert-butyl $N^2$—($N^2$-(((9H-fluoren-9-yl)methoxy)carbonyl)-$N^6$-(tert-butoxycarbonyl)-L-lysyl)-$N^6$-((benzyloxy)carbonyl)-L-lysinate (8a): A suspension of L-Lys(Z)-Ot-Bu.HCl (1.49 g, 4.0 mmol) in $CH_2Cl_2$ (15 mL) was treated with DIPEA (0.87 mL, 5.0 mmol). To the resulting mixture was added a solution of compound 7a (2.2 g, 3.9 mmol) in $CH_2Cl_2$ (10 mL), and the reaction was stirred overnight at room temperature under argon. It was then washed with saturated NaCl solution, and the organic layer was dried over $MgSO_4$, filtered and concentrated under reduced pressure. The crude product was purified by flash chromatography (0-100% EtOAc in hexane), and di-lysine 8a was isolated as a white powder (2.2 g, 72%). ¹H NMR (500 MHz, CDCl₃) δ 7.76 (d, 2H, J=7.5 Hz), 7.59 (d, 2H, J=7.3 Hz), 7.40 (t, 2H, J=7.5 Hz), 7.32 (m, 8H), 6.69 (br s, 1H), 5.60 (br s, 1H), 5.06 (m, 4H), 4.72 (br s, 1H), 4.43 (m, 1H), 4.38 (m, 1H), 4.21 (m, 1H), 3.14 (m, 4H), 1.85 (m, 2H), 1.73 (m, 2H), 1.50 (m, 4H), 1.46 (s, 9H), 1.44 (s, 9H), 1.39 (m, 4H).

2,5-dioxopyrrolidin-1-yl 2-(4-iodophenyl)acetate (28)

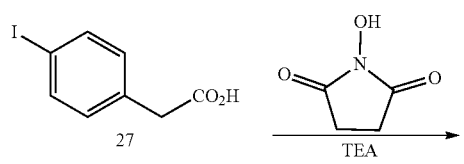

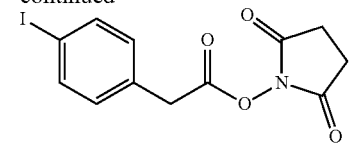

A solution of 2-(4-iodophenyl)acetic acid 27 (786 mg, 3.0 mmol) and EDC.HCl (671 mg, 3.5 mmol) in CH₂Cl₂ (20 mL) was stirred for 15 min at room temperature under argon. Then N-hydroxysuccinimide (368 mg, 3.2 mmol) and TEA (0.56 mL, 4.0 mmol) were added and the reaction was stirred for 7 h. It was then washed with saturated NaCl solution, and the organic layer was dried over MgSO₄, filtered and concentrated under reduced pressure. The crude residue was purified by flash chromatography (0-100% EtOAc in hexane), and the NHS ester 28 was isolated as a white solid (760 mg, 70%). ¹H NMR (500 MHz, CDCl₃) δ 7.69 (d, 2H, J=7.9 Hz), 7.09 (d, 2H, J=7.9 Hz), 3.88 (s, 2H), 2.83 (s, 4H).

Synthesis of Trifunctional Ligands (RPS-061, RPS-063, RPS-066, RPS-067, RPS-068, RPS-069) with Representative Procedure for Synthesis of RPS-069

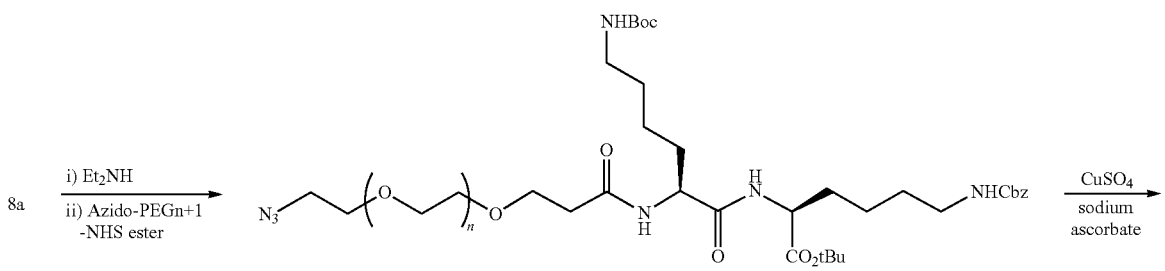

29a: n = 3
29b: n = 2
29c: n = 7
29d: n = 11
29e: n = 5

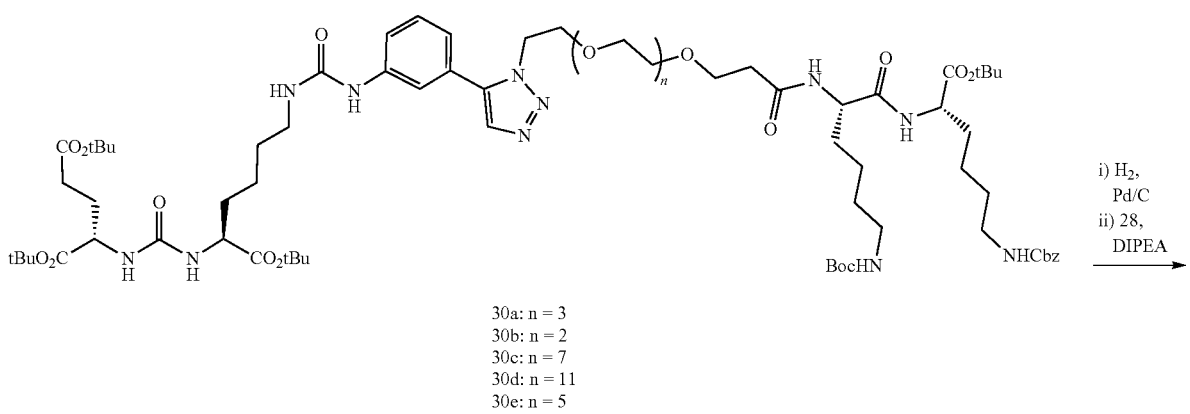

30a: n = 3
30b: n = 2
30c: n = 7
30d: n = 11
30e: n = 5

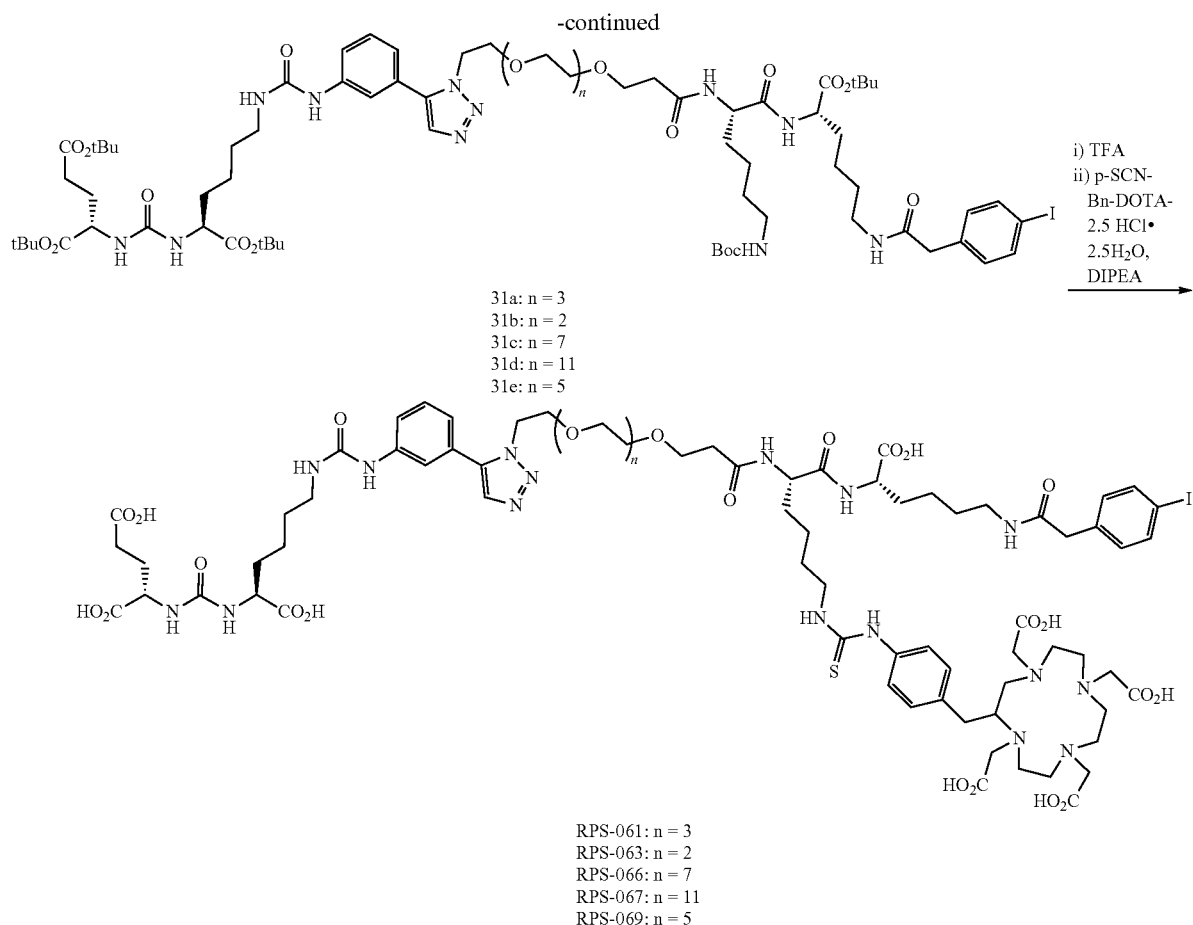

31a: n = 3
31b: n = 2
31c: n = 7
31d: n = 11
31e: n = 5

RPS-061: n = 3
RPS-063: n = 2
RPS-066: n = 7
RPS-067: n = 11
RPS-069: n = 5 tert-butyl $N^2$—($N^2$-(1-azido-3,6,9,12,15,18-hexaoxahenicosan-21-oyl)-$N^6$-(tert-butoxycarbonyl)-L-lysyl)-$N^6$-((benzyloxy)carbonyl)-L-lysinate (29e): To a solution of Fmoc-protected compound 8a (768 mg, 0.97 mmol) in $CH_2Cl_2$ (4 mL) was added diethylamine (2.07 mL, 20 mmol). The solution was stirred overnight at room temperature. The solvents were removed under reduced pressure, and the crude product, a yellow oil, was used without further purification. To a solution of this yellow oil (183 mg, 0.32 mmol) in $CH_2Cl_2$ (3 mL) were added solutions of TEA (57 µL, 0.41 mmol) in $CH_2Cl_2$ (1 mL) and azido-$PEG_6$-NHS ester (100 mg, 0.21 mmol) in $CH_2Cl_2$ (1 mL), and the reaction was stirred overnight at room temperature. It was then diluted with $CH_2Cl_2$ and washed successively with $H_2O$ and saturated NaCl solution. The organic layer was dried over $MgSO_4$, filtered and concentrated under reduced pressure to give azide 29e as a colorless oil (184 mg; 95%) without need for further purification. Mass (ESI+): 926.4 $[M+H]^+$. Calc. Mass=925.54.

di-tert-butyl (((S)-1-(tert-butoxy)-6-(3-(3-(1-((9S,12S)-9-(tert-butoxycarbonyl)-12-(4-((tert-butoxycarbonyl)amino)butyl)-3,11,14-trioxo-1-phenyl-2,17,20,23,26,29,32-heptaoxa-4,10,13-triazatetratriacontan-34-yl)-1H-1,2,3-triazol-4-yl)phenyl)ureido)-1-oxohexan-2-yl)carbamoyl)-L-glutamate (30e): A solution of 100 µL 0.5M $CuSO_4$ and 100 µL 1.5 M sodium ascorbate in DMF (0.5 mL) was mixed for 5 min and was then added to a solution of 29e (184 mg, 0.20 mmol) and 26 (132 mg, 0.21 mmol) in DMF (2.5 mL). The resulting mixture was stirred at room temperature for 45 min. It was then concentrated under reduced pressure and the crude residue was purified by flash chromatography (0-30% MeOH in EtOAc) to give triazole 30e as an orange oil (285 mg; 87%). Mass (ESI+): 1557.2 $[M+H]^+$. Calc. Mass=1555.90.

di-tert-butyl (((S)-1-(tert-butoxy)-6-(3-(3-(1-((23S,26S)-26-(tert-butoxycarbonyl)-23-(4-((tert-butoxycarbonyl)amino)butyl)-33-(4-iodophenyl)-21,24,32-trioxo-3,6,9,12,15,18-hexaoxa-22,25,31-triazatritriacontyl)-1H-1,2,3-triazol-4-yl)phenyl)ureido)-1-oxohexan-2-yl)carbamoyl)-L-glutamate (31e): Cbz-Protected triazole 30e (285 mg, 0.18 mmol) was dissolved in MeOH (15 mL) in a two-neck flask. To the solution was added 10% Pd/C (20 mg), and the suspension was shaken and the flask evacuated. The suspension was then placed under $H_2$ atmosphere and stirred overnight. It was filtered through celite, and the filter cake was washed three times with MeOH. The combined filtrate was concentrated under reduced pressure to give the free amine as a colorless oil (117 mg; 45%) that was used without further purification. Mass (ESI+): 1423.8 $[M+H]^+$. Calc. Mass=1422.77. To a solution of the free amine (117 mg, 82 µmol) in $CH_2Cl_2$ (4 mL) was added a solution of DIPEA (23 µL, 131 mmol) in $CH_2Cl_2$ (1 mL), and the mixture was stirred at room temperature under argon. Then a solution of 28 (37 mg, 103 µmol) in $CH_2Cl_2$ (2 mL) was added, and the reaction was stirred at room temperature for 2 h. It was then poured into $H_2O$ (10 mL) and the layers were separated. The organic layer was dried over $MgSO_4$, filtered and concentrated under reduced pressure to give the crude product as a colorless semi-solid. The crude product was purified by prep TLC (10% MeOH in EtOAc) to give phenyl iodide 31e as a colorless oil (34 mg; 25%). Mass (ESI+): 1666.6 [M+H]+. Calc. Mass=1665.80.

(((1S)-1-carboxy-5-(3-(3-(1-((23S,26S)-26-carboxy-33-(4-iodophenyl)-21,24,32-trioxo-23-(4-(3-(4-((1,4,7,10-tetrakis(carboxymethyl)-1,4,7,10-tetraazacyclododecan-2-yl)methyl)phenyl)thioureido)butyl)-3,6,9,12,15,18-hexaoxa-22,25,31-triazatritriacontyl)-1H-1,2,3-triazol-4-yl)phenyl)ureido)pentyl)carbamoyl)-L-glutamic acid (RPS-069): To a solution of 31e (34 mg, 20 µmol) in $CH_2Cl_2$ (2 mL) was added TFA (0.5 mL), and the reaction was stirred at room temperature for 5 h. It was then concentrated under reduced pressure and the crude product was diluted in $H_2O$ and lyophilized to give the free amine as a TFA salt. Mass (ESI+): 1342.5 [M+H]+. Mass (ESI−): 1340.6 [M−H]−. Calc. Mass=1341.50. To a solution of p-SCN-Bn-DOTA-2.5HCl.2.5$H_2O$ (Macrocyclics, Inc.) (13 mg, 19 µmol) in $H_2O$ (0.5 mL) was added a solution of the free amine (18 mg, 13 µmol) in DMF (1 mL). DIPEA was added until the reaction was pH≈9). The reaction was stirred at room temperature for 3 h, at which point the reaction mixture was then purified by prep HPLC. The peak corresponding to the desired product was collected and lyophilized to give RPS-069 as a white powder (8 mg; 32%). Mass (ESI+): 1893.3 [M+H]+, 947.6 [(M+2H)/2]+. Mass (ESI−): 1891.4 [M−H]−, 945.5 [(M−2H)/2]−. Calc. Mass=1892.70.

(((1S)-1-carboxy-5-(3-(3-(1-((17S,20S)-20-carboxy-27-(4-iodophenyl)-15,18,26-trioxo-17-(4-(3-(4-((1,4,7,10-tetrakis(carboxymethyl)-1,4,7,10-tetraazacyclododecan-2-yl)methyl)phenyl)thioureido)butyl)-3,6,9,12-tetraoxa-16,19,25-triazaheptacosyl)-1H-1,2,3-triazol-4-yl)phenyl)ureido)pentyl)carbamoyl)-L-glutamic acid (RPS-061): RPS-061 was synthesized from the common building blocks 26, 8a and 28 and azido-$PEG_4$-NHS ester according to the procedure described for RPS-069. Mass (ESI+): 1805.6664 [M+H]+. Calc. Mass=1804.6594.

(((1S)-1-carboxy-5-(3-(3-(1-((14S,17S)-17-carboxy-24-(4-iodophenyl)-12,15,23-trioxo-14-(4-(3-(4-((1,4,7,10-tetrakis(carboxymethyl)-1,4,7,10-tetraazacyclododecan-2-yl)methyl)phenyl)thioureido)butyl)-3,6,9-trioxa-13,16,22-triazatetracosyl)-1H-1,2,3-triazol-4-yl)phenyl)ureido)pentyl)carbamoyl)-L-glutamic acid (RPS-063): RPS-063 was synthesized from the common building blocks 26, 8a and 28 and azido-$PEG_3$-NHS ester according to the procedure described for RPS-069. Mass (ESI+): 1762.4 [M+H]+. Mass (ESI−): 1760.5 [M−H]−. Calc. Mass=1761.71.

(((1S)-1-carboxy-5-(3-(3-(1-((29S,32S)-32-carboxy-39-(4-iodophenyl)-27,30,38-trioxo-29-(4-(3-(4-((1,4,7,10-tetrakis(carboxymethyl)-1,4,7,10-tetraazacyclododecan-2-yl)methyl)phenyl)thioureido)butyl)-3,6,9,12,15,18,21,24-octaoxa-28,31,37-triazanonatriacontyl)-1H-1,2,3-triazol-4-yl)phenyl)ureido)pentyl)carbamoyl)-L-glutamic acid (RPS-066): RPS-066 was synthesized from the common building blocks 26, 8a and 28 and azido-$PEG_8$-NHS ester according to the procedure described for RPS-069. Mass (ESI+): 1982.3 [M+H]+, 991.5 [(M+2H)/2]−. Calc. Mass=1980.76.

(((1S)-1-carboxy-5-(3-(3-(1-((41S,44S)-44-carboxy-51-(4-iodophenyl)-39,42,50-trioxo-41-(4-(3-(4-((1,4,7,10-tetrakis(carboxymethyl)-1,4,7,10-tetraazacyclododecan-2-yl)methyl)phenyl)thioureido)butyl)-3,6,9,12,15,18,21,24,27,30,33,36-dodecaoxa-40,43,49-triazahenpentacontyl)-1H-1,2,3-triazol-5-yl)phenyl)ureido)pentyl)carbamoyl)-L-glutamic acid (RPS-067): RPS-067 was synthesized from the common building blocks 26, 8a and 28 and azido-$PEG_{12}$-NHS ester according to the procedure described for RPS-069. Mass (ESI+): 1079.7 [(M+2H)/2]+. Mass (ESI−): 2155.6 (M−H)−, 1077.7 [(M−2H)/2]−. Calc. Mass=2156.86.

Synthesis of RPS-068

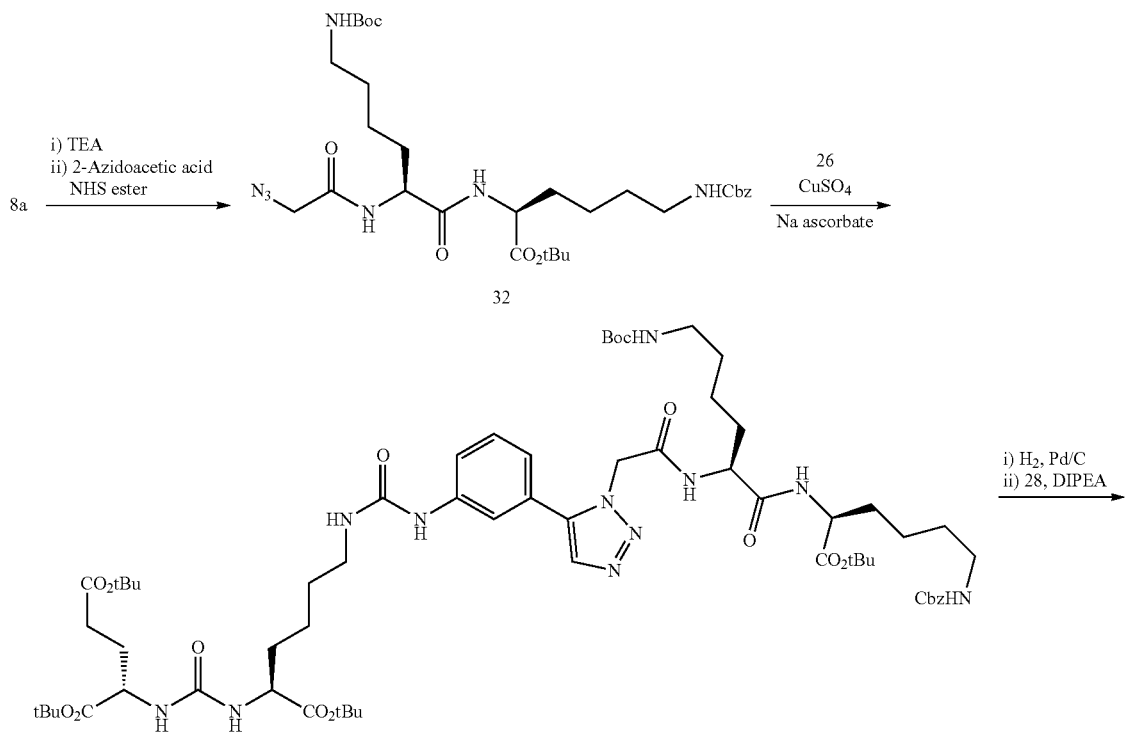

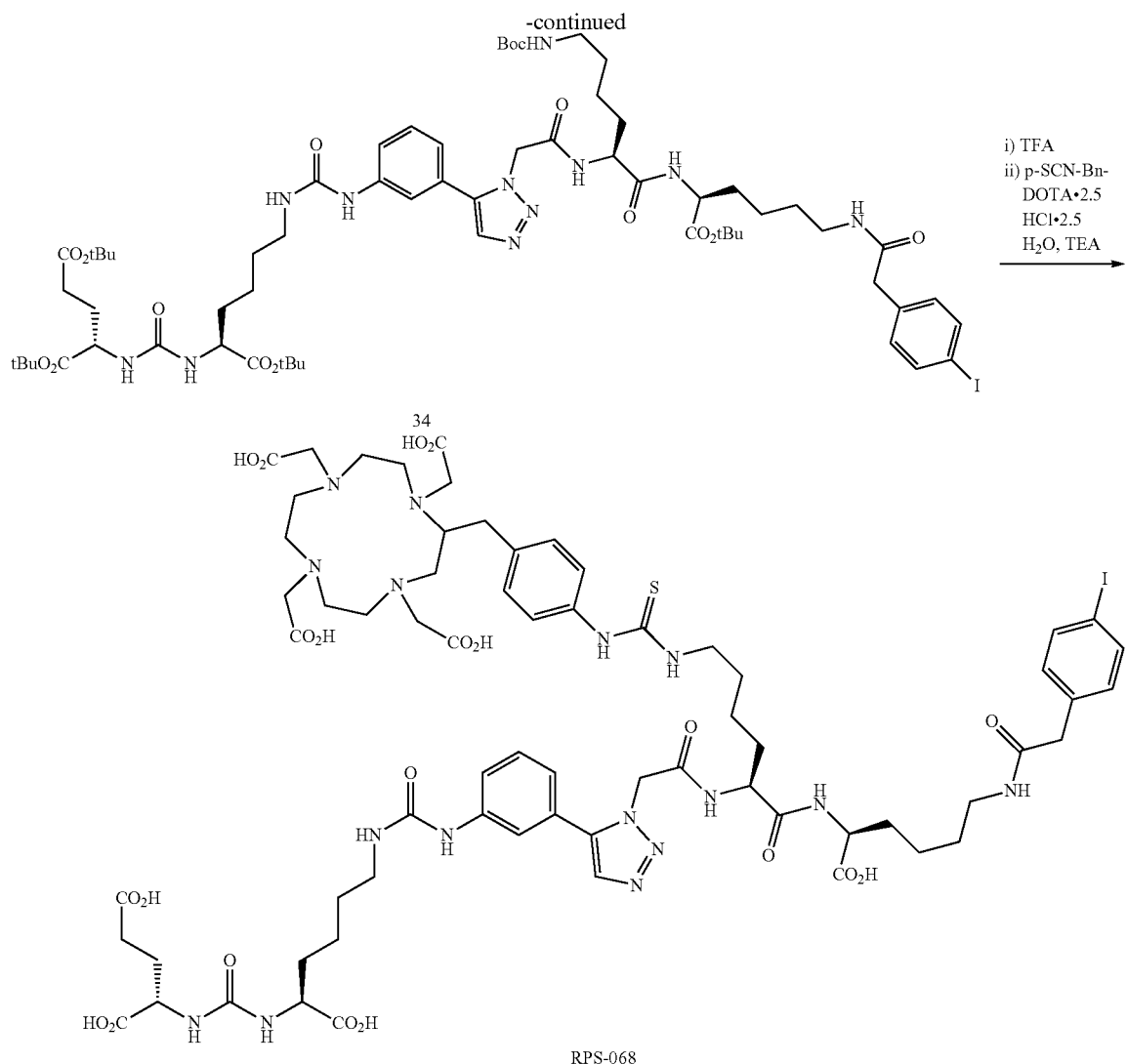

RPS-068 tert-butyl $N^2$—($N^2$-(2-azidoacetyl)-$N^6$-(tert-butoxycarbonyl)-L-lysyl)-$N^6$-((benzyloxy)carbonyl)-L-lysinate (32): To a solution of Fmoc-protected 8a (768 mg, 0.97 mmol) in $CH_2Cl_2$ (4 mL) was added diethylamine (2.07 mL, 20 mmol). The solution was stirred overnight at room temperature. The solvents were removed under reduced pressure, and the crude product, the free amine as a yellow oil, was used without further purification. To a solution of free amine (356 mg, 0.63 mmol) in $CH_2Cl_2$ (6 mL) was added a solution of TEA (175 µL, 1.26 mmol) in $CH_2Cl_2$ (1 mL), and the resulting mixture was stirred at room temperature. Then a solution of 2-azidoacetic acid NHS ester (138 mg, 0.69 mmol) in $CH_2Cl_2$ (3 mL) was added, and the reaction was stirred at room temperature. After 3 h, it was diluted with $CH_2Cl_2$ and washed successively with $H_2O$ and saturated NaCl solution. The organic layer was dried over $MgSO_4$, filtered and concentrated under reduced pressure to give pale yellow azide 32 (374 mg, 92%) that was used without further purification. Mass (ESI+): 648.1 [M+H]$^+$. Calc. Mass=647.36.

di-tert-butyl (((S)-1-(tert-butoxy)-6-(3-(3-(1-((9S,12S)-9-(tert-butoxycarbonyl)-12-(4-((tert-butoxycarbonyl)amino)butyl)-3,11,14-trioxo-1-phenyl-2-oxa-4,10,13-triazapentadecan-15-yl)-1H-1,2,3-triazol-5-yl)phenyl)ureido)-1-oxohexan-2-yl)carbamoyl)-L-glutamate (33): A solution of 150 µL 0.5M $CuSO_4$ and 150 µL 1.5M sodium ascorbate in DMF (0.2 mL) was mixed for 5 min and was then added to a solution of azide 32 (374 mg, 0.54 mmol) and alkyne 26 (358 mg, 0.54 mmol) in DMF (2 mL). The mixture was stirred at room temperature for 2 h before the solvent was removed under reduced pressure. The resulting residue was dissolved in $CH_2Cl_2$ and washed with $H_2O$. The organic layer was dried over $MgSO_4$, filtered and concentrated under reduced pressure. The crude product was purified by flash chromatography (0-10% MeOH in EtOAc), but a small impurity remained. Therefore a second purification was performed by prep TLC (100% EtOAc), and the product was isolated as a colorless oil (146 mg; 21%). Mass (ESI+): 1278.6 [M+H]$^+$. Calc. Mass=1277.73.

di-tert-butyl (((S)-1-(tert-butoxy)-6-(3-(3-(1-(2-(((10S,13S)-13-(tert-butoxycarbonyl)-20-(4-iodophenyl)-2,2-dimethyl-4,11,19-trioxo-3-oxa-5,12,18-triazaicosan-10-yl)amino)-2-oxoethyl)-1H-1,2,3-triazol-5-yl)phenyl)ureido)-1-oxohexan-2-yl)carbamoyl)-L-glutamate (34): Triazole 33 (146 mg, 0.11 mmol) was dissolved in MeOH (10 mL) in a two-neck flask. To the solution was added 10% Pd/C (10 mg), and the suspension was shaken while the flask was evacuated. Then the suspension was stirred under $H_2$ atmosphere for 2 h before the mixture was filtered through celite. The filter cake was washed three times with McOH and the filtrates were combined and concentrated under reduced pressure to give the free amine as a black residue (91 mg; 72%) that contained traces of minor impurities. The crude product was used without further purification. Mass (ESI+): 1144.6 [M+H]$^+$. Calc. Mass=1143.69. To a solution of free amine (90 mg, 79 μmol) and NEt$_3$ (14 μL, 150 μmol) in $CH_2Cl_2$ (4 mL) was added a solution of 28 (36 mg, 100 μmol) in $CH_2Cl_2$ (1 mL). The resulting mixture was stirred overnight at room temperature, then it was diluted with $CH_2Cl_2$ and washed successively with $H_2O$ and saturated NaCl solution. The organic layer was dried over $MgSO_4$, filtered and concentrated under reduced pressure to give a black residue. The residue was dissolved in EtOAc, and a black precipitate was removed by filtration. The resulting crude product was purified by prep TLC (5% MeOH in EtOAc), and phenyl iodide 34 was isolated as a white solid (21 mg; 19%). Mass (ESI+): 1388.4 [M+H]$^+$. Calc. Mass=1387.63.

(((1S)-1-carboxy-5-(3-(3-(1-(2-(((2S)-1-(((S)-1-carboxy-5-(2-(4-iodophenyl)acetamido)pentyl)amino)-1-oxo-6-(3-(4-((1,4,7,10-tetrakis(carboxymethyl)-1,4,7,10-tetraazacyclododecan-2-yl)methyl)phenyl)thioureido)hexan-2-yl)amino)-2-oxoethyl)-1H-1,2,3-triazol-5-yl)phenyl)ureido)pentyl)carbamoyl)-L-glutamic acid (RPS-068): To a solution of 34 (20 mg, 15 μmol) in $CH_2Cl_2$ (3.5 mL) was added TFA (0.5 mL). The reaction was stirred at room temperature for 4 h, then it was concentrated under reduced pressure. The crude residue was dissolved in $H_2O$ and lyophilized to give the free amine as a TFA salt. Mass (ESI+): 1064.1 [M+H]$^+$. Calc. Mass=1063.33. To a solution of p-SCN-Bn-DOTA·2.5HCl·2.5H$_2$O (Macrocyclics, Inc.) (10 mg, 15 μmol) in 1 mL 50% DMF in $H_2O$ was added a solution of free amine (16 mg, 15 μmol) in DMF (0.7 mL). NEt$_3$ was added (110 μL) until the pH of the reaction was approximately 9. The reaction was stirred for 1 h, then the reaction mixture was purified by prep HPLC. The peak corresponding to the product was collected and lyophilized to give RPS-068 as a white powder (2.4 mg; 10%). Mass (ESI+): 1615.2 [M+H]$^+$. Mass (ESI-): 1613.3 [M-H]$^-$, 806.4 [(M-2H)/2]$^-$. Calc. Mass=1614.53.

Radiochemistry

General Methods: All reagents were purchased from Sigma Aldrich unless otherwise noted, and were reagent grade. Hydrochloric acid (HCl) and sodium acetate (NaOAc) were of traceSELECT® (>99.999%) quality. All water ($H_2O$) used was highly pure (18 mΩ). Analytical HPLC was performed on a dual-pump Varian Dynamax HPLC (Agilent Technologies) fitted with a dual UV-Vis detector, and radiochemical purity was determined using a NaI(Tl) flow count detector (Bioscan). UV absorption was monitored at 220 nm and 280 nm. Solvent A was 0.01% trifluoroacetic acid (TFA) in $H_2O$ and solvent B was 0.01% TFA in 90% v/v acetonitrile (MeCN):$H_2O$. Analyses were performed on a Symmetry C18 4.6×50 mm, 100-Å column (Waters) at a flow rate of 2 mL/min and a gradient of 0% B to 100% B over 10 minutes.

Production of Ga-66: Gallium-66 ($t_{1/2}$=9.4 h) was produced from the irradiation of a natural zinc target (Alfa Aesar; 0.5 g, 100 μm thickness, 99.999%) by a (p,n) reaction over 2 h using a 15 MeV beam and a 17.5 mA current. The irradiation of natural zinc produces Ga-66, Ga-67 and Ga-68. The target was left overnight to allow Ga-68 ($t_{1/2}$=68 min) to decay before processing. The principal radionuclidic impurity during processing was Ga-67 ($t_{1/2}$=78.3 h), at approximately 3%. The target was dissolved in conc. HCl (5 mL) and the Ga$^{3+}$ ions were separated from Zn$^{2+}$ ions by 20 mg UTEVA anion exchange (Eichrom) according to previously published methods [20]. The column was later washed twice with 3 ml of a 5M HCl solution to eliminate the excess Zn$^{2+}$. Finally, the purified $^{66}$Ga$^{3+}$ ions were eluted with $H_2O$ (0.5 mL), leading to a final solution containing 2.14-2.36 GBq/mL (58-64 mCi/mL) and approximately 0.1 M HCl.

Radiolabeling of RPS series: $^{66}$Ga-Labeled ligands were prepared according to the following procedure. 100 μL of the Ga-66 stock solution containing 167-205 MBq (4.5-5.5 mCi) was diluted with 1 mL 0.05M HCl. To this solution was added 40-80 μL of a 1 mg/mL solution of precursor in DMSO. The reaction was initiated by addition of 40 μL 3N NaOAc, and the solution was mixed at 95° C. on an Eppendorf ThermoMixer® C (VWR) for 25 min. The mixture was then diluted with $H_2O$ and passed through a pre-activated Sep-Pak C18 Plus Light cartridge (Waters). The cartridge was washed with $H_2O$ and the product was eluted with 100 μL EtOH (300 proof, VWR) followed by 900 μL saline (0.9% NaCl solution; VWR). Final radioactivity concentrations were in the range 7.4-85 MBq/mL (0.2-2.3 mCi/mL), and radiochemical purity was greater than 90%.

Labeling with Lu-177: No-carrier-added Lu-177 (EndolucinBeta®) was purchased from iTG (Garching, Germany) as the chloride salt, with an activity at calibration of 1.5-3.0 GBq (40-80 mCi). An aliquot containing 0.52-0.93 GBq (14-25 mCi) of the Lu-177 stock solution was diluted to 1 mL with 0.05M HCl. To this solution was added 20 μg of precursor as a 1 mg/mL solution in DMSO. The reaction was initiated by raising the pH to 4-5 using 3N NaOAc (20-30 μL). The buffered solution was heated for 10 min at 95° C. on an analog heating block (VWR). After the solution had cooled to room temperature, it was diluted with $H_2O$ (9 mL) and passed through a pre-activated Sep-Pak C18 Plus Light cartridge (Waters). The cartridge was washed with $H_2O$ (5 mL) and the product was eluted with 500 μL EtOH (200 proof, VWR) followed by 500 μL saline (0.9% NaCl solution; VWR). An aliquot (40-98 μL) was removed from this solution and diluted to 4 mL with saline. The final concentration of each ligand in the injected solution was 0.23-0.28 μM, with a range of activity of 3.5-8.8 MBq/mL (93-240 μCi/mL). The specific activity of the $^{177}$Lu-labeled compounds ranged from 15.8-48.8 GBq/pmol. Radiochemical yields were 33-80% after purification and reformulation, and radiochemical purity was greater than 98%.

Cell Culture: The PSMA expressing human prostate cancer cell line, LNCaP, was obtained from the American Type Culture Collection. Cell culture supplies were obtained from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 μg/mL gentamicin in a humidified incubator at 37° C./5% $CO_2$. Cells were removed from flasks for passage or for transfer to 12-well assay plates by incubating them with 0.25% trypsin/ethylenediaminetetraacetic acid (EDTA).

In vitro determination of IC$_{50}$: IC$_{50}$ values of the non-labeled, metal-free ligands were determined by screening in a multi-concentration competitive binding assay against $^{99m}$Tc-((7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid technetium tricarbonyl complex) ($^{99m}$Tc-MIP- 1427) for binding to PSMA on LNCaP cells, according to previously described methods [18,19] with small modifications. Briefly, LNCaP cells were plated 48 h prior to the experiment to achieve a density of approximately $5 \times 10^5$ cells/well (in triplicate) in RPMI-1640 medium supplemented with 0.25% bovine serum albumin. The cells were incubated for 2 h with 1 nM $^{99m}$Tc-MIP-1427 in serum-free RPMI-1640 medium in the presence of 0.001-10,000 nM test compounds. Radioactive incubation media was then removed by pipette and the cells were washed twice using 1 mL ice-cold PBS 1× solution. Cells were harvested from the plates following treatment with 1 mL 1M NaOH and transferred to tubes for radioactive counting using a 2470 Wizard$^2$ Automatic Gamma Counter (Perkin Elmer). Standard solutions (10% of activity added to each well) were prepared to enable decay correction. IC$_{50}$ values were determined by fitting the data points to a sigmoidal Hills1 curve in Origin software.

Inoculation of mice with xenografts: All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Hairless male nu/nu mice were purchased from the Jackson Laboratory. For inoculation in mice, LNCaP cells were suspended at $4 \times 10^7$ cells/mL in a 1:1 mixture of PBS:Matrigel (BD Biosciences). Each mouse was injected in the left flank with 0.25 mL of the cell suspension. The mice were imaged when the tumors reached approximately 200-400 mm$^3$, while biodistributions were conducted when tumors were in the range 100-400 mm$^3$.

Imaging of $^{66}$Ga-RPS ligands in LNCaP xenograft mice: LNCaP xenograft tumor-bearing mice (2-3 per compound) injected intravenously with a bolus injection of 0.56-5.4 MBq (15-145 µCi) of the $^{66}$Ga-labeled ligand. The specific activity of the tracers was in the range 14.8-47 MBq/pmol (0.4-1.27 mCi/pmol). The mice were imaged using µPET/CT (Inveon™; Siemens Medical Solutions, Inc.) at 1, 3, 6 and 24 h post-injection following inhalation anesthetization with isoflurane. Total acquisition time was 30 min for the 1 h, 3 h and 6 h images, and 60 min for 24 h time point. A CT scan was obtained immediately before the acquisition for both anatomical co-registration and attenuation correction. Images were reconstructed using the Inveon™ software supplied by the vendor. Image-derived tumor and kidney uptake was estimated by comparison to a 10% injected dose per cubic mm (% ID/mm$^3$) standard introduced into the imaging field of view. The standard was prepared by dilution of 10% of the injected activity to 1 mL with saline. Volumes of interest (VOIs) were drawn with the aid of the CT and confirmed by PET. The contents of the VOIs were integrated and the calculated counts were converted to % ID/mm$^3$ by direct comparison to the aforementioned standard following correction for activity injected.

Biodistribution studies of $^{177}$Lu-labeled ligands in LNCaP xenograft mice: LNCaP xenograft tumor-bearing mice (5 per time point per compound) were injected intravenously with a bolus injection of 348-851 kBq (9.4-23 µCi) and 37-50 ng (23-25 pmol) of each ligand. The mice were sacrificed at 4, 24 and 96 h post injection. A blood sample was removed, and a full biodistribution study was conducted on the following organs (with contents): heart, lungs, liver, small intestine, large intestine, stomach, spleen, pancreas, kidneys, muscle, bone and tumor. Tissues were weighed and counted on a 2470 Wizard$^2$ Automatic Gamma Counter (Perkin Elmer). Counts were corrected for decay and for activity injected, and tissue uptake was expressed as percent injected dose per gram (% ID/g). Standard error measurement was calculated for each data point.

Dosimetry: The dosimetry was calculated assuming a linear interpolation between the three time points. The average injected dose per organ was calculated by using the average of the activity and organ weights of the mice at that time point. Intermediate time points at every 4 hours were generated using the linear approximation and all time points were corrected for decay during the time interval between points. These curves were integrated using a trapezoidal approximation and the sum used to determine the residence time.

Statistical Analysis: A comprehensive statistical analysis was performed to compare the tissue uptake of each compound across time. The normality assumption was visually checked by a quantile-quantile (QQ) plot, and a log transformation was applied to the data to remove the skew effect. Under each organ and each compound, a one-way ANOVA (Analysis of Variance) with Tukey's honestly significant difference (HSD) post-hoc test was used to evaluate the difference in measurement across three time points. An overall P-value under an F-test and pairwise ones under t-test was determined. Furthermore, a two-way ANOVA was used to assess the influence of time, compound and their interaction in each organ. The P-values are reported. A confidence interval of 95% was used to determine statistical significance.

Section 1.3 Results and Discussion

The three moieties were linked by an azide-derivatized polyethyleneglycol (PEG) spacer incorporating 0 (RPS-068), 3 (RPS-063), 4 (RPS-061), 6 (RPS-069), 8 (RPS-066) or 12 (RPS-067) PEG subunits (see Table 2). No degradation or decomposition of the ligands was observed over the course of three months during storage at 4° C. as determined by analytical HPLC. In contrast, similar analogues in which a Gly-Gly-Gly linker or a $C_7H_{14}$ linker was used in place of the PEG spacer were found to decompose over the course of a few weeks under the same storage conditions.

In an effort to minimize the use of animals, an initial screening of the compounds was performed using µPET/CT imaging to avoid unnecessary testing. For this purpose, Ga-66 was selected in preference to other PET radionuclides such as Ga-68 or Sc-44 due to its longer half-life ($t_{1/2}$=9.4 h) and the possibility of producing larger quantities (>1.85 GBq/50 mCi) in the cyclotron. Greater than 99% of the Ga-66 was recovered in the purification process, but labeling yields remained consistently low (46.4±20.5%, n=7). The variable and low labeling yields were likely due to the presence of $Zn^{2+}$ ions in the labeling reaction due to incomplete separation of the $^{66}Ga^{3+}$ ions from the dissolved target material.

The $^{177}$Lu-labeled constructs were prepared in 67±17% (n=20) radiochemical yield following purification and reformulation. Variation in final product yield was largely due to differences in trapping efficiency by the C18 cartridge, with $^{177}$Lu-RPS-067 and $^{177}$Lu-RPS-068 showing the lowest trapping (approximately 40%). Labeling yields prior to purification were typically >75% for all ligands as determined by radioHPLC. There was no apparent correlation between PEG length and labeling yield. The Lu-177 labeled ligands were stable to radiolysis for 24 h when stored at 4° C. Radiochemical stability was not determined at room temperature.

The total amount of ligand injected was 22-24 pmol per mouse in order to remain proportional to clinical mass doses of $^{177}$Lu-PSMA-617 administered to human subjects [4]. The specific activity of the preparations ranged from 15.8-48.8 GBq/pmol, consistent with the values reported for the preclinical evaluation of $^{177}$Lu-PSMA-617 [21]. The mass of $^{68}$Ga-labeled ligands injected was 4 μg per mouse, corresponding to 1.8-2.5 nmol. This greater mass was required to account for the poorer labeling yields with this radionuclide.

All compounds were evaluated for PSMA binding in vitro using a cell-based competitive binding assay. All compounds were highly potent ($IC_{50}$<10 nM), validating our selection of the 3-ethynylphenylurea derivative of Glu-urea-Lys as the PSMA-targeting pharmacophore. The range of affinities was defined by RPS-063 ($IC_{50}$=1.5±0.3 nM) and RPS-067 ($IC_{50}$=9.5±1.1 nM) (Table 2). Potency generally decreased with increasing PEG linker length, although RPS-068 (PEG$_0$; $IC_{50}$=2.1±0.1 nM) was slightly less potent than RPS-063. In the same assay the $IC_{50}$ of PSMA-617 was determined to be 6.6±0.7 nM (Table 2), consistent with the previously reported value [21].

TABLE 2

Summary of compound structures and key in vitro and in vivo characteristics. $IC_{50}$ values were determined by a competitive binding assay in LNCaP cells. Tumor uptake was determined by biodistribution studies with the corresponding $^{177}$Lu-labeled compound in LNCaP xenograft tumor-bearing mice. (a = 4 h p.i.; b = 24 h p.i.)

| Cpd. | PEG | Structure | Mol. Wt. (g/mol) | $IC_{50}$ (nM) | Max. Tumor Uptake$^a$ (% ID/g) |
|---|---|---|---|---|---|
| PSMA-617 | n.a. | (structure) | 1042.15 | 6.6 ± 0.7 | 14.4 ± 2.5 |
| RPS-068 | 0 | (structure) | 1615.52 | 2.1 ± 0.1 | 26.9 ± 2.0$^b$ |

TABLE 2-continued

Summary of compound structures and key in vitro and in vivo characteristics. $IC_{50}$ values were determined by a competitive binding assay in LNCaP cells. Tumor uptake was determined by biodistribution studies with the corresponding $^{177}$Lu-labeled compound in LNCaP xenograft tumor-bearing mice. (a = 4 h p.i.; b = 24 h p.i.)

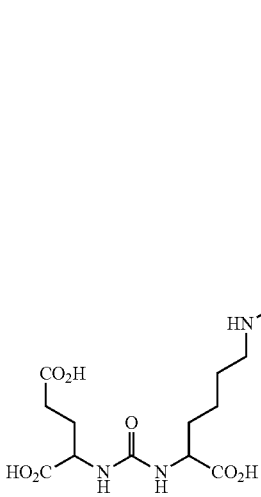

| Cpd. | PEG | Structure | Mol. Wt. (g/mol) | $IC_{50}$ (nM) | Max. Tumor Uptake[a] (% ID/g) |
|---|---|---|---|---|---|
| RPS-063 | 3 | n = 2 | 1761.71 | 1.5 ± 0.3 | 30.0 ± 6.9 |
| RPS-061 | 4 | n = 3 | 1805.76 | 4.1 ± 0.9 | 20.4 ± 3.1 |
| RPS-069 | 6 | n = 5 | 1893.87 | 3.8 ± 0.4 | 17.0 ± 2.1 |
| RPS-066 | 8 | n = 7 | 1981.97 | 5.2 ± 0.4 | 18.7 ± 1.1 |
| RPS-067 | 12 | n = 11 | 2158.18 | 9.5 ± 1.1 | 7.6 ± 1.2 |

Figure 7:
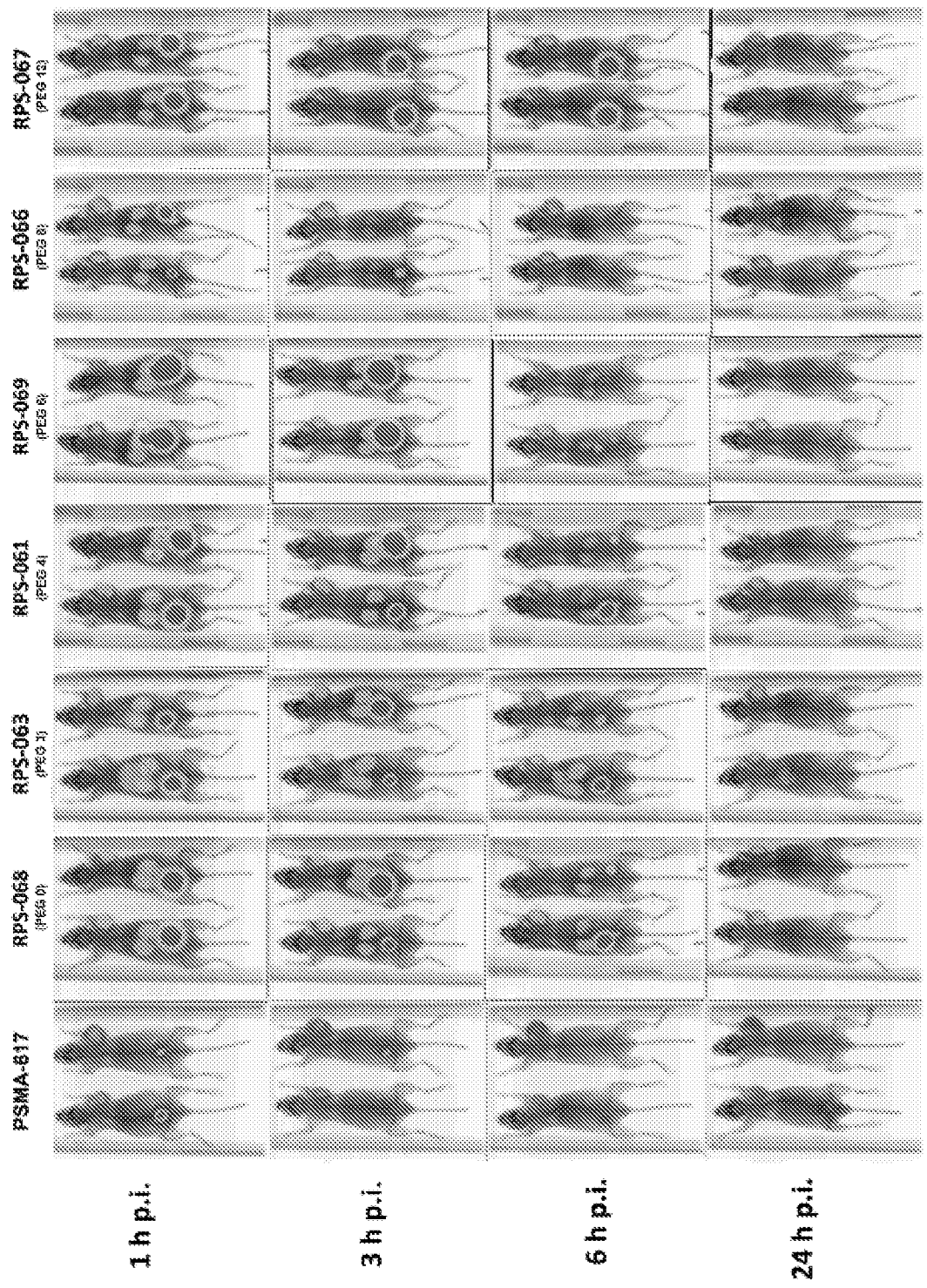
FIG. 7 provides PET images of LNCaP xenograft mice with $^{66}$Ga-labeled tracers at 1 h, 3 h, 6 h and 24 h post injection. Mice were injected intravenously with a bolus injection of 0.56-5.4 MBq (15-145 μCi) of the tracer. The total mass of ligand injected was 4 μg. Prior to imaging, the mice were anesthetized with isoflurane and then imaged for 30 min. The images were corrected for decay and for activity injected.

Preliminary screening of the compounds in mice was performed by μPET/CT imaging using $^{66}$Ga (FIG. 7) with the intention of avoiding full biodistribution studies on compounds that showed poor targeting. Images were analyzed to determine quantitative uptake in the tumor and kidneys at 1, 3, 6 and 24 h post injection. In the tumor, uptake was high but decreased with increasing PEG length. $^{66}$Ga-RPS-068 (PEG0; maximum uptake of 9.7±2.0% ID/cm³ (3 h); 8.3 f 2.8% ID/cm³ at 24 h) and $^{68}$Ga-RPS-063 (PEG3; maximum uptake of 9.5±2.4% ID/cm³ (6 h); 7.9±3.0% ID/cm³ at 24 h) showed the greatest uptake, with $^{66}$Ga-RPS-061 (PEG4; 6.1±1.1% ID/cm³) and $^{66}$Ga-RPS-069 (PEG6; 7.0±3.9% ID/cm³) demonstrating comparable uptake at 24 h post injection. $^{66}$Ga-RPS-066 (PEG8; maximum uptake of 7.8±0.7% ID/cm³ (3 h); 5.5 f 0.4% ID/cm³ at 24 h) and $^{66}$Ga-RPS-067 (PEG12; maximum uptake of 6.6±3.2% ID/cm³ (1 h); 3.1±1.7% ID/cm³ at 24 h) showed lower uptake at all time points, but still exceeded $^{66}$Ga-PSMA-617 (maximum uptake of 3.1±0.4% ID/cm³ (1 h); 1.1±0.4% ID/cm³ at 24 h. Kidney uptake was generally on the same order as tumor uptake and was greatest at 1 h post injection. Uptake ranged from 10.5±2.1% ID/cm³ ($^{66}$Ga-RPS-061) to 3.7±0.5% ID/cm³ ($^{68}$Ga-RPS-067) at 1 h post injection, and from 1.9±0.3% ID/cm³ ($^{66}$Ga-RPS-068) to 0.2±0.1% ID/cm³ ($^{66}$Ga-RPS-066 and $^{66}$Ga-RPS-067) at 24 h post injection. In comparison, the maximum kidney uptake of $^{68}$Ga-PSMA-617 was 0.4±0.1% ID/cm³, while uptake at 24 h was 0.1±0.1% ID/cm³.

Figure 8:
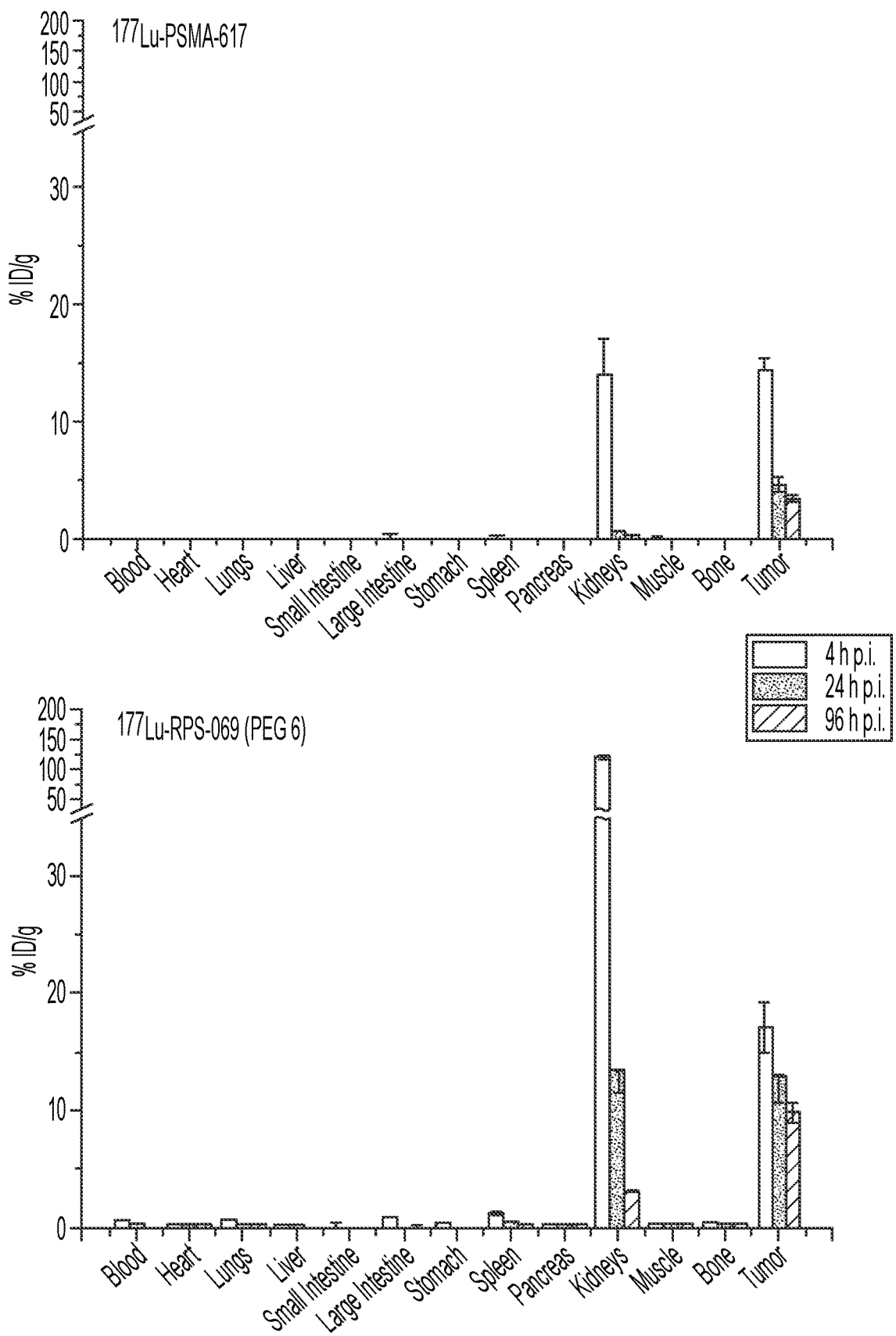
FIG. 8 provides the biodistribution of $^{177}$Lu-RPS-068, $^{177}$Lu-RPS-063, $^{177}$Lu-RPS-061, $^{177}$Lu-RPS-069, $^{177}$Lu-RPS-066, $^{177}$Lu-RPS-067 and $^{177}$Lu-PSMA-617. Male athymic nude mice bearing LNCaP xenograft tumors (n=5 per time point) were injected intravenously with 348-851 kBq (9.4-23 μCi) of the labeled compound and sacrificed at 4 h, 24 h and 96 h p.i. The total mass of ligand injected was 37-50 ng (23-25 pmol).
Figure 8:
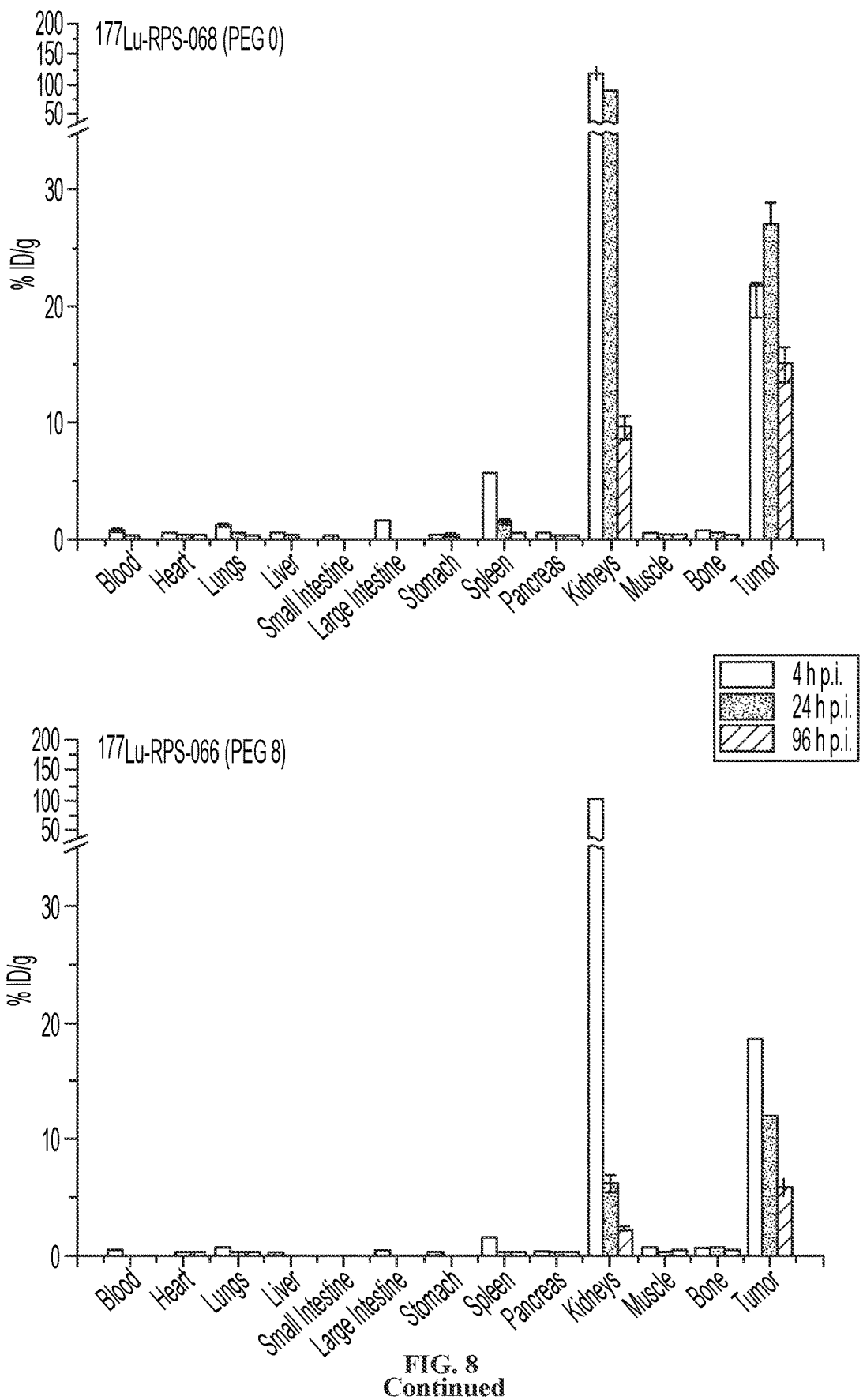
Figure 8:
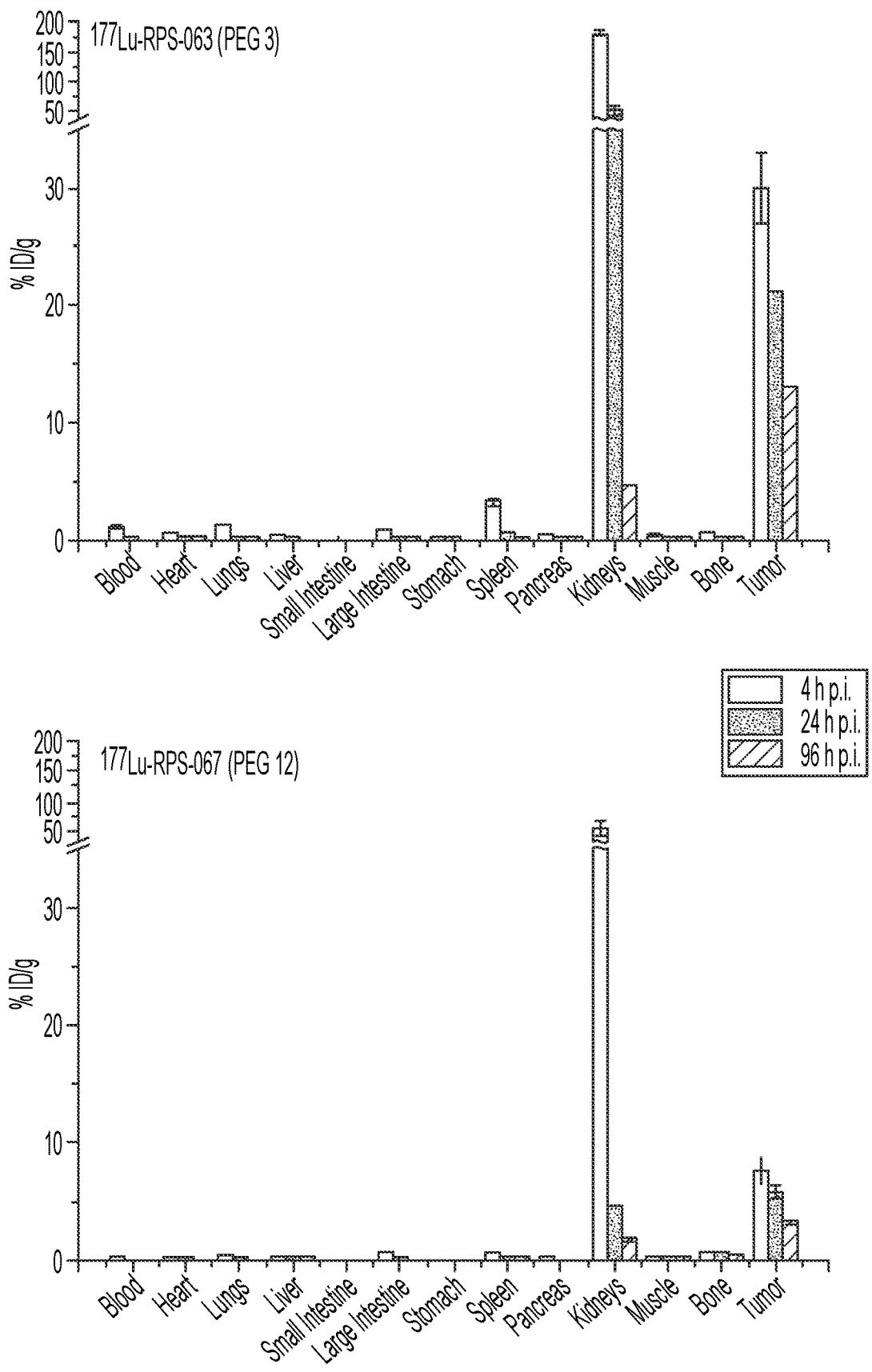
Figure 8:
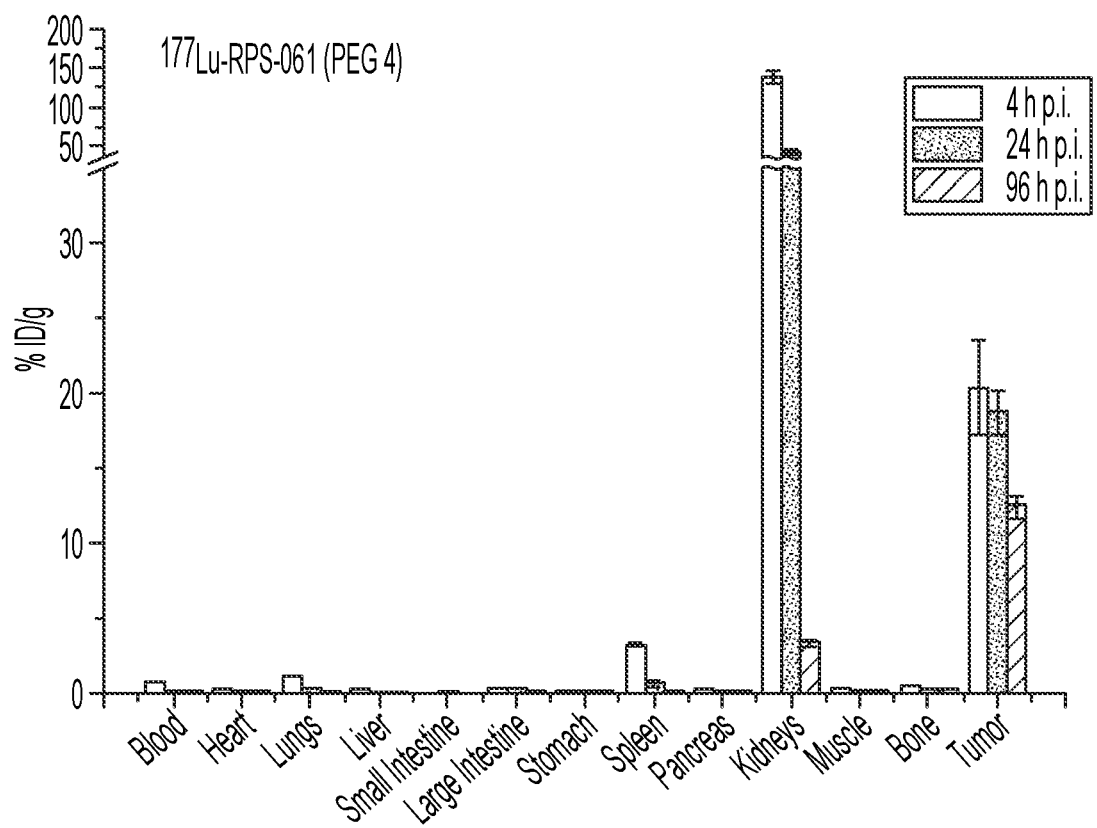

Following the promising imaging studies, biodistribution studies of the $^{177}$Lu-labeled ligands confirmed the trends evident in the PET images. Although the affinity of the compounds for PSMA is clustered within one order of magnitude, the tissue distribution of the ligands showed considerable variation. This was most evident in the tissues that are known to express PSMA, including the tumor and the kidney (FIG. 8). Tumor uptake was high and remained high for $^{177}$Lu-RPS-068 (PEG$_0$), $^{177}$Lu-RPS-063 (PEG$_3$), $^{177}$Lu-RPS-061 (PEG$_4$), $^{177}$Lu-RPS-069 (PEG$_6$) and $^{177}$Lu-RPS-066 (PEG$_8$). For the higher affinity compounds $^{177}$Lu-RPS-068 and $^{177}$Lu-RPS-063, uptake at 4 h p.i. was 21.8±2.8% ID/g and 30.0±3.1% ID/g, respectively, with 14.9±1.5% ID/g and 12.9±0.5% ID/g still remaining at 96 h p.i. Clearance was not statistically significant by 24 h (p>0.13). Uptake of $^{177}$Lu-RPS-069 and $^{177}$Lu-RPS-066 was 17.0±2.1% ID/g and 18.7±1.1% ID/g respectively at 4 h p.i. and decreased to 9.8±0.8% ID/g and 5.9 f 0.7% ID/g at 96 h p.i. Nevertheless, these uptake values are significantly greater after 24 h p.i. than those observed for $^{177}$Lu-PSMA-617 (14.4±1.1% ID/g and 3.5±0.3% ID/g at 4 h and 96 h p.i., p<0.001). $^{177}$Lu-RPS-067 (PEG$_{12}$), the lowest affinity ligand, accumulated at only 7.6±1.2% ID/g at 4 h p.i. and had cleared to 3.2±0.1% ID/g at 96 h p.i. This uptake was significantly lower than all other ligands (p<0.001) except $^{177}$Lu-PSMA-617.

A similar trend within the RPS series was observed for kidney uptake, with the lowest affinity ligand, $^{177}$Lu-RPS-067, distinguished by significantly lower uptake (54.9±13.2% ID/g) at 4 h p.i. than the other RPS ligands tested (p<0.004) (FIG. 8). Kidney uptake exceeded 100% ID/g at 4 h p.i. for all other ligands of the RPS series, while $^{177}$Lu-PSMA-617 was found to clear rapidly (14.1±3.1% ID/g at 4 h p.i.) in agreement with published reports [21]. Prolonged retention of $^{177}$Lu-RPS-068 (87.3±6.7% ID/g at 24 h p.i.) and $^{177}$Lu-RPS-063 (51.8±8.6% ID/g at 24 h p.i.) was evident, but $^{177}$Lu-RPS-066 (6.2±0.8% ID/g at 24 h p.i.) and $^{177}$Lu-RPS-067 (4.6±0.6% ID/g at 24 h p.i.) cleared significantly (p<0.001) and more rapidly. Uptake of these two ligands was significantly lower than the other RPS ligands (p<0.001) but not significantly different to each other (p<0.14).

In combination with persistent tumor accumulation, more rapid kidney clearance gave rise to tumor-to-kidney ratios of 1.92±0.30 and 1.25±0.20 for $^{177}$Lu-RPS-066 and $^{177}$Lu-RPS-067 at 24 h p.i. These ratios are significantly higher than the other RPS ligands (p<0.001), but reflect low and rapid kidney clearance rather than high and persistent tumor uptake. For the same reason, the tumor-to-kidney ratio of $^{177}$Lu-PSMA-617 is significantly higher than the other ligands at all time points studied (p<0.001). By 96 h, each member of the RPS series demonstrated a tumor-to-kidney ratio substantially in excess of 1 (range=1.56-3.32).

Figure 9:
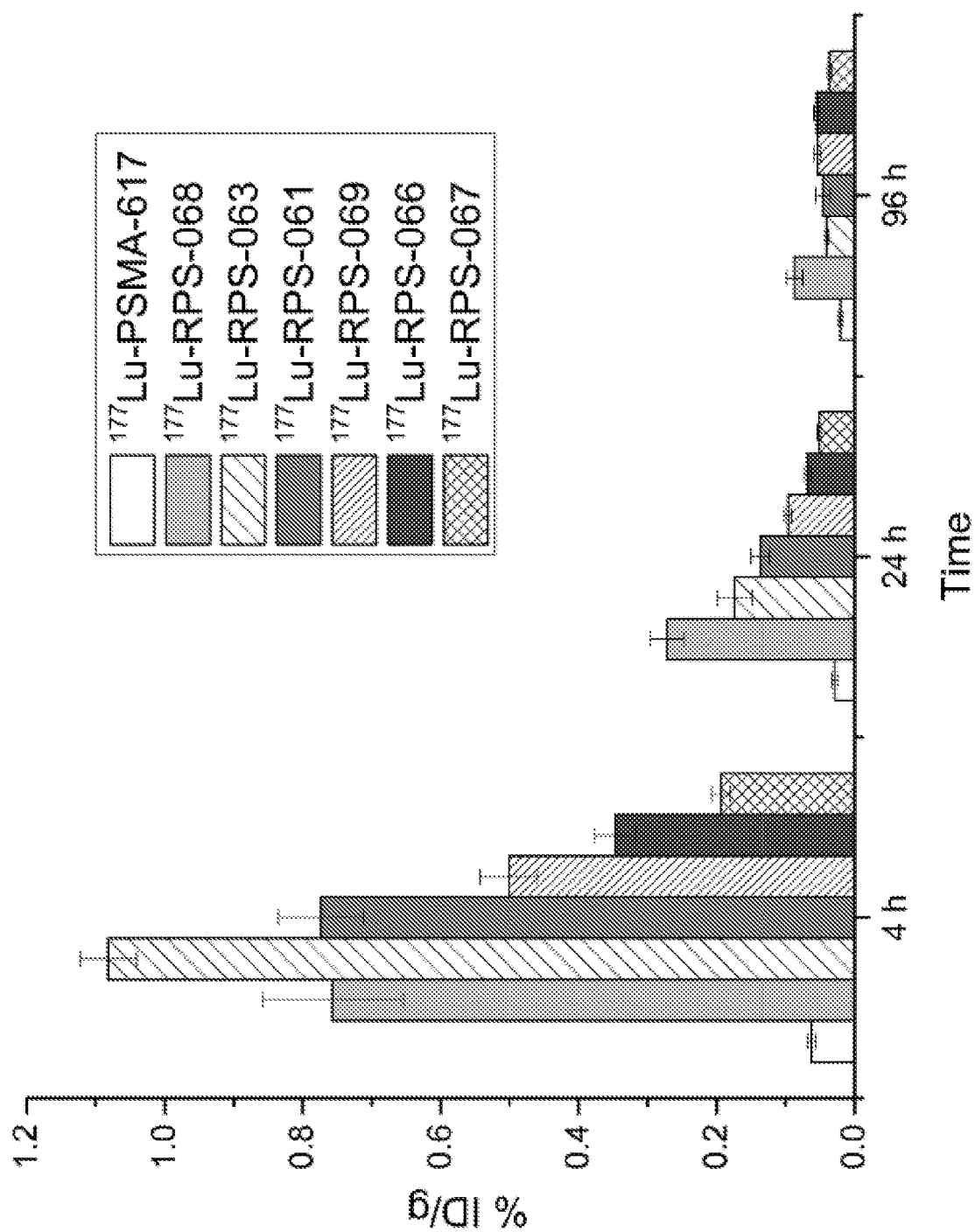
FIG. 9 provides a comparison of the blood pool activity of different $^{177}$Lu-labeled ligands at 4 h, 24 h and 96 h post injection. Errors are expressed as SEM. RPS ligands are displayed in order of increasing size.

Uptake in other tissues was negligible with the exception of the spleen, which showed modest, likely PSMA-mediated uptake at 4 h p.i. followed by clearance to background levels (FIG. 8). As expected, blood activity was significantly greater for all of the RPS series than for $^{177}$Lu-PSMA-617 (p<0.05). $^{177}$Lu-RPS-063, $^{177}$Lu-RPS-061 and $^{177}$Lu-RPS-068 showed the highest blood activity at 4 h p.i. (FIG. 9), while $^{177}$Lu-RPS-069, $^{177}$Lu-RPS-066 and $^{177}$Lu-RPS-067 showed lower blood retention at the same time point. By 24 h p.i., the blood activity was below 0.3% ID/g for all of the ligands, and by 96 h it had decreased to below 0.1% ID/g. Interestingly, although all of the RPS ligands contained the same albumin-binding group, $N^6$-(2-(4-iodophenyl)acetyl)-L-lysine, significant differences (p<0.001) were observed between the shorter PEG compounds $^{177}$Lu-RPS-068 and $^{177}$Lu-RPS-063 and the longer PEG compounds $^{177}$Lu-RPS-066 and $^{177}$Lu-RPS-067. This indicates that the linker influences binding to plasma proteins and/or clearance.

The inverse correlation between PEG length and affinity for PSMA is consistent with findings reported to date for PSMA constructs and other targeting ligands. Small PEG linkers such as PEG3 or PEG4 have been incorporated into small molecule drug conjugates that target PSMA [22,23], but constructs of this nature to date have shown low affinity and/or poor tumor uptake. One SAR study did establish that PEG2 and PEG4 linkers best retained PSMA affinity in a family of PSMA-targeting contrast agents, with PEG12 and PEG24 leading to large decreases in affinity [24]. These results were in agreement with the observation that a PEG12 linker decreased affinity relative to PEG8 in a small molecule GCPII ligand [25]. An SAR study of the influence of PEG linkers on $^{66}$Ga-labeled antagonists of bombesin found that affinity slightly weakened upon each incremental extension of the PEG linker [26]. This study also identified small differences in the biodistribution of the ligands.

Figure 10:
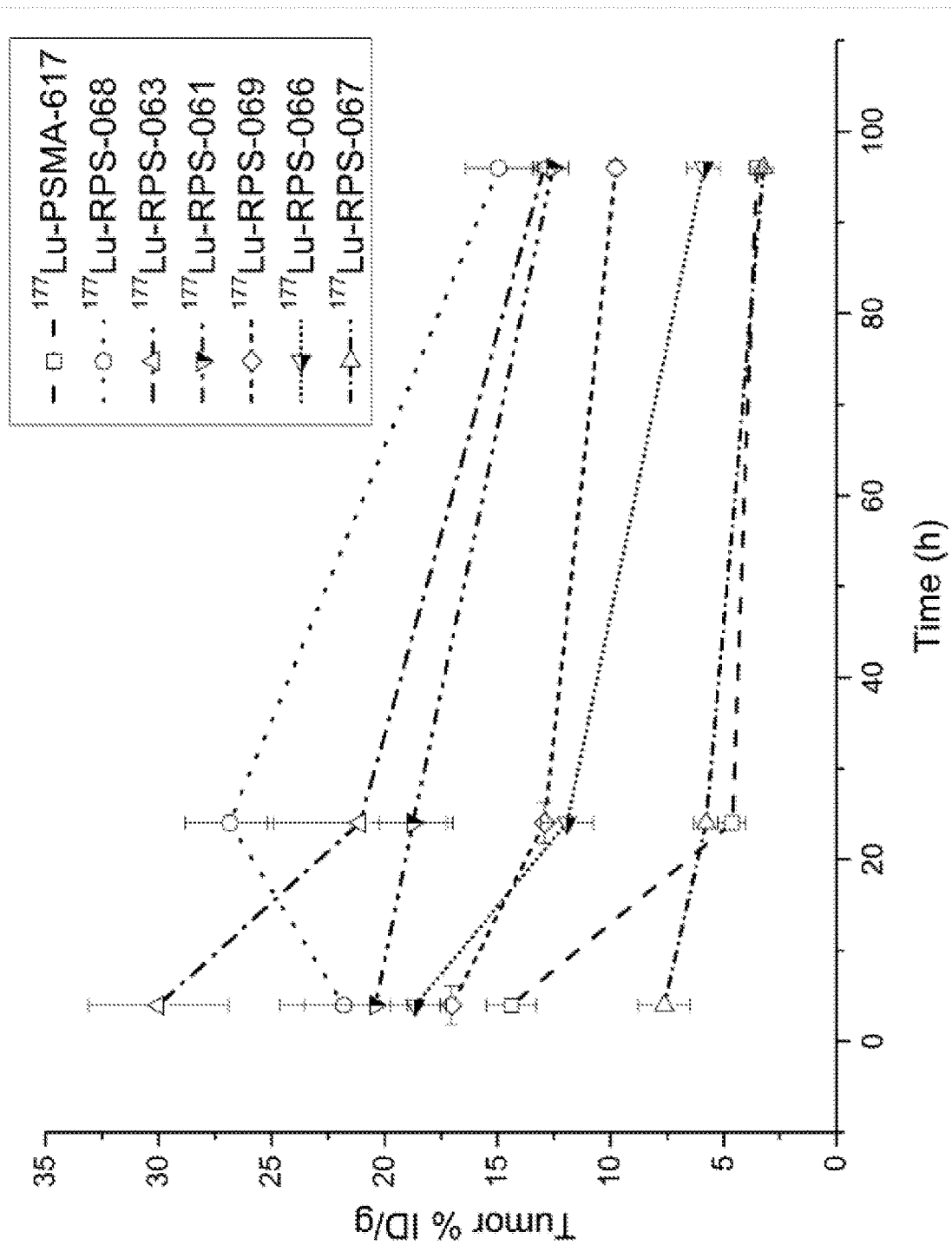
FIG. 10 provides time-activity curves (TAC) of tumor and kidney uptake of $^{177}$Lu-PSMA-617, $^{177}$Lu-RPS-061, $^{177}$Lu-RPS-063, $^{177}$Lu-RPS-066, $^{177}$Lu-RPS-067, $^{177}$Lu-RPS-068 and $^{177}$Lu-RPS-069 in male athymic nude mice bearing LNCaP xenograft tumors. Uptake is expressed as % ID/g.
Figure 11:
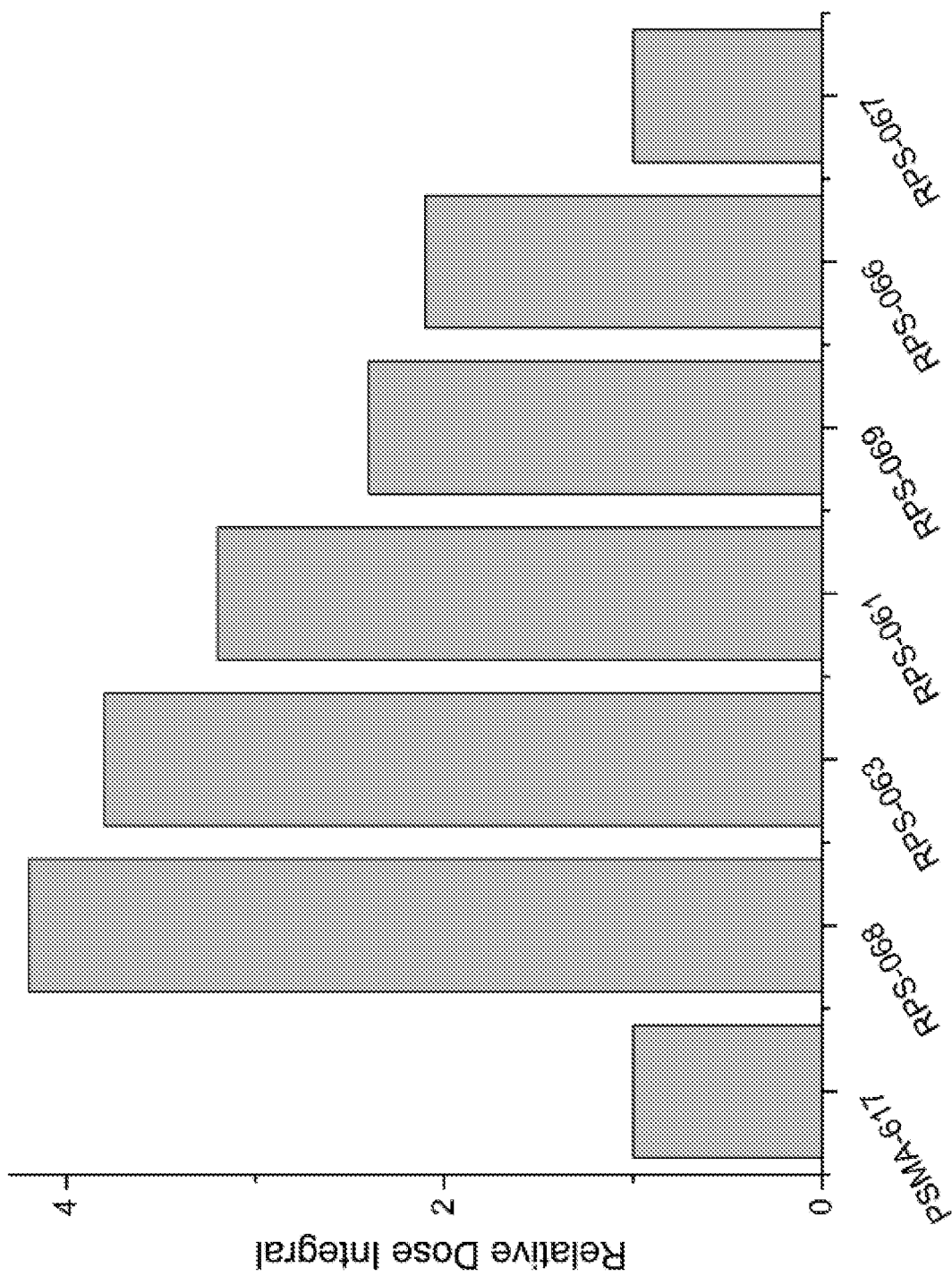
FIG. 11 provides a comparison of relative dose integral in the tumor of male LNCaP xenograft tumor-bearing mice injected with the corresponding $^{177}$Lu-labeled compounds and studied over 96 h. Values are normalized to $^{177}$Lu-PSMA-617.

The areas under the curve (AUC) of the time-activity curves (TACs) for tumor uptake suggest that the $^{177}$Lu-labeled RPS-061, -063, 066, -068 and -069 ligands deliver a significantly larger dose to the tumor than does $^{177}$Lu-PSMA-617 (FIG. 10). This is confirmed by a comparison of the dose integrals in the tumor. $^{177}$Lu-RPS-068 and $^{177}$Lu-RPS-063 are nearly four times higher than $^{177}$Lu-PSMA-617, while $^{177}$Lu-RPS-061, $^{177}$Lu-RPS-069 and $^{177}$Lu-RPS-066 are also at least two times higher (FIG. 11).

It is likely that the tumor uptake of the $^{177}$Lu-labeled RPS ligands is also higher than other $^{177}$Lu-labeled PSMA-targeting ligands reported to date, including $^{177}$Lu-PSMA I&T, with a reported uptake in LNCaP tumors of 7.96±1.76 at 1 h p.i. [27], and the recently reported $^{177}$Lu-CTT1403, which was reported to reach 46% ID/g at 72 h p.i. in PC3-PIP tumors [23]. PSMA expression is PC3-PIP tumors is higher than typically found in human prostate cancers, notably ten-fold greater than LNCaP cells [28], meaning that uptake of $^{177}$Lu-CTT1403 is likely to be considerably lower in LNCaP tumors. Uptake in LNCaP tumors for $^{177}$Lu-RPS-063 and $^{177}$Lu-RPS-068 is on a par with the uptake reported for $^{133}$I-MIP-1095 [29], the small molecule, to our knowledge, with the greatest uptake in LNCaP xenograft tumors reported to date. A comparison of the TACs for $^{177}$Lu-RPS-063, $^{177}$Lu-RPS-068 and $^{131}$I-MIP-1095 suggests a similar AUC for the 96 h period studied (FIG. 10).

It has previously been reported that prolonged blood retention leads to increased tumor accumulation with time [23,30], a consequence presumably of an increase in the number of times the ligand passes through the tumor bed. $^{177}$Lu-RPS-068 appears to increase from 4 h to 24 h, but this difference is not statistically significant (p=0.26). The phenomenon is not evident among the other trifunctional RPS ligand series after 4 h p.i. either, though it is possible that delayed blood clearance during the first 4 h may increase tumor uptake in this time interval. Nevertheless, clearance of the ligands from the tumor is slow, enabling the delivery of greater amounts of activity to the target tissue compared to $^{177}$Lu-PSMA-617. Further modification of albumin binding by substitution of the albumin binding group may be used to subtly modify blood clearance and reinforce the high and persistent tumor accumulation.

In spite of promising clinical outcomes using PSMA-targeted radioligand therapy for mCRPC, next generation ligands that (1) overcome resistance to β-particle radiation, (2) are appropriate for treating diffuse metastatic lesions (particularly in the bone) and (3) provide longer duration of progression free survival are essential to continued improvements in treatment. Although minimal toxicity is currently associated with a single administration of $^{177}$Lu-PSMA-617 or $^{131}$I-MIP-1095, the incidence of hematological toxicity and persistent xerostomia can increase upon subsequent therapy cycles [3] while biochemical response may decrease [3,5]. Alpha-particle mediated therapy has been proposed as a method of overcoming resistance to β-particles and reducing hematological toxicity [31]. Early preclinical studies with $^{213}$Bi-PSMA I&T have identified the formation of DNA double-strand breaks in tumors in vivo [32], while preliminary treatment of human patients with $^{225}$Ac-PSMA-617 or $^{213}$Bi-PSMA-617 have led to dramatic responses in refractory cancer [31,33]. Nevertheless, multiple therapy cycles were required for efficacy, leading to irreversible xerostomia and keratoconjunctivitis sicca [33].

These early findings have demonstrated the therapeutic potential for α-particle radiotherapy, but highlighted the need for radioligands with greater therapeutic index that can deliver a high dose to the tumor. Each of $^{177}$Lu-RPS-061, -063, -066, -068 and -069 shows significantly higher tumor uptake than $^{177}$Lu-PSMA-617 in LNCaP xenograft tumors, with the corresponding increase in AUC correlating to an increase in the dose of radioactivity delivered to the tumor. The tumor-to-kidney ratios of $^{177}$Lu-RPS-063, $^{177}$Lu-RPS-068 and $^{177}$Lu-RPS-061, the three ligands with highest tumor uptake, are 2.75±0.17, 1.56±0.23 and 3.64±0.29, respectively, at 96 h p.i. In contrast, $^{177}$Lu-CTT1403 never reaches 1.0 [23]. Although the tumor-to-kidney ratio of $^{177}$Lu-PSMA-617 at the same time point is 14.39±2.2, and the ratio of tumor dose integral to kidney dose integral over the 96 h is 1.95, these are driven by very low kidney uptake rather than high tumor uptake. It has been widely demonstrated that the expression of PSMA in the kidneys of nude mice is higher than expression levels in human kidneys [34,35,36], meaning that preclinical studies consistently overestimate the dose delivered to this organ. Several PSMA-targeted therapeutics including $^{131}$I-MIP-1095 (29), $^{177}$Lu-DKFZ-617 (21) and $^{177}$Lu-PSMA I&T (37) all show early kidney concentrations at or above 100% ID/g in nude mice, yet have been safely translated to the clinic with acceptable; albeit not identical kidney doses.

Furthermore, additional nephroprotection schemes, including pharmacological displacement with 2-PMPA, have been shown to reduce activity in the kidney still further [37,38]. Taken together, these observations illustrate that the trifunctional RPS ligands show both the high and persistent tumor uptake and broad therapeutic index that are desirable for α-particle radiotherapeutics.

SECTION 1.3 REFERENCES

[1] Nussbaum N, George D J, Abernethy A P, Dolan C M, Oestreicher N, Flanders S, Dorff T B. Patient experience in the treatment of metastatic castration-resistant prostate cancer: state of the science. *Prostate Cancer Prostatic Dis.* 2016; 19:111-21.

[2] Zechmann C M, Afshar-Oromieh A, Armor T, Stubbs J B, Mier W, Hadaschik B, Joyal J, Kopka K, Debus J, Babich J W, Haberkorn U. Radiation dosimetry and first therapy results with a $^{124}$I/$^{131}$I-labeled small molecule (MIP-1095) targeting PSMA for prostate cancer therapy. *Eur J Nucl Med Mol Imaging* 2014; 41:1280-92.

[3] Afshar-Oromieh A, Haberkorn U, Zechmann C, Armor T, Mier W, Spohn F, Debus N, Holland-Letz T, Babich J, Kratochwil C. Repeated PSMA-targeting radioligand therapy of metastatic prostate cancer with $^{131}$I-MIP-1095. *Eur J Nucl Med Mol Imaging* 2017; 44:950-9.

[4] Kratochwil C, Giesel F L, Stefanova M, Benešová M, Bronzel M, Afshar-Oromieh A, Mier W, Eder M, Kopka K, Haberkorn U. PSMA-Targeted Radionuclide Therapy of Metastatic Castration-Resistant Prostate Cancer with $^{177}$Lu-Labeled PSMA-617. *J Nucl Med.* 2016; 57:1170-6.

[5] Ahmadzadehfar H, Eppard E, Kürpig S, Fimmers R, Yordanova A, Schlenkhoff C D, Gärtner F, Rogenhofer S, Essler M. Therapeutic response and side effects of repeated radioligand therapy with $^{177}$Lu-PSMA-DKFZ-617 of castrate-resistant metastatic prostate cancer. *Oncotarget* 2016; 7:12477-88.

[6] Fendler W P, Reinhardt S, Ilhan H, Delker A, Böning G, Gildehaus F J, Stief C, Bartenstein P, Gratzke C, Lehner S, Rominger A. Preliminary experience with dosimetry, response and patient reported outcome after $^{177}$Lu-PSMA-617 therapy for metastatic castration-resistant prostate cancer. *Oncotarget* 2017; 8:3581-90.

[7] Rahbar K, Ahmadzadehfar H, Kratochwil C, Haberkorn U, Schäfers M, Essler M, Baum R P, Kulkarni H R, Schmidt M, Drzezga A, Bartenstein P, Pfestroff A, Luster M, Lutzen U, Marx M, Prasad V, Brenner W, Heinzel A, Mottaghy F M, Ruf J, Meyer P T, Heuschkel M, Eveslage M, Bögemann M, Fendler W P, Krause B J. German Multicenter Study Investigating $^{177}$Lu-PSMA-617 Radioligand Therapy in Advanced Prostate Cancer Patients. *J Nucl Med* 2017; 58:85-90.

[8] Rahbar K, Schmidt M, Heinzel A, Eppard E, Bode A, Yordanova A, Claesener M, Admadzadehfar H. Response and Tolerability of a Single Dose of $^{177}$Lu-PSMA-617 in Patients with Metastatic Castration-Resistant Prostate Cancer: A Multicenter Retrospective Analysis. *J Nucl Med.* 2016; 57:1334-8.

[9] Baum R P, Kulkarni H R, Schuchardt C, Singh A, Wirtz M, Wiessalla S, Schottelius M, Mueller D, Klette I, Wester H-J. Lutetium-177 PSMA Radioligand Therapy of Metastatic Castration-Resistant Prostate Cancer: Safety and Efficacy. *J Nucl Med.* 2016; 57:1006-13.

[10] Heck M M, Retz M, D'Alessandria C, Rauschner I, Scheidhauer K, Maurer T, Storz E, Janssen F, Schottelius M, Wester H-J, Gschwend J E, Schwaiger M, Tauber R, Eiber M. Systemic Radioligand Therapy with $^{177}$Lu Labeled Prostate Specific Membrane Antigen Ligand for Imaging and Therapy in Patients with Metastatic Castration Resistant Prostate Cancer. *J Urol.* 2016; 196:382-91.

[11] Yordanova A, Becker A, Eppard E, Kürpig S, Fisang C, Feldmann G, Essler M, Ahmadzadehfar H. The impact of repeated cycles of radioligand therapy using [$^{177}$Lu]Lu-PSMA-617 on renal function in patients with hormone refractory metastatic prostate cancer. *Eur J Nucl Med Mol Imaging* 2017; 44:1473-9.

[12] Bräuer A, Grubert L S, Roll W, Schrader A J, Schäfers M, Bögemann M, Rahbar K. $^{177}$Lu-PSMA-617 radioligand therapy and outcome in patients with metastasized castration-resistant prostate cancer. *Eur J Nucl Med Mol Imaging* 2017; 44:1663-70.

[13] Rathke H, Giesel F L, Fleschig P, Kopka K, Mier W, Hohenfellner M, Haberkorn U, Kratochwil C. Repeated Lu-177-PSMA-617 radioligand therapy using treatment activities up to 9.3 GBq. *J Nucl Med.* 2017; doi: 10.2967/jnumed.117.194209.

[14] Grimes J, Celler A. Comparison of internal dose estimates obtained using organ-level, voxel S value, and Monte Carlo techniques. *Med Phys.* 2014; 41:092501.

[15] Denis-Baceler A M, Chittenden S J, Murray I, Divoli A, McCready V R, Dearnaley D P, O'Sullivan J M, Johnson B, Flux G D. A radiobiological model of metastatic burden reduction for molecular radiotherapy: application to patients with bone metastases. *Phys Med Biol.* 2017; 62:2859-70.

[16] Delker A, Fendler W P, Kratochwil C, Brunegraf A, Gosewisch A, Gildehaus F J, Tritschler S, Stief C G, Kopka K, Haberkorn U, Bartenstein P, Boning G. Dosimetry for $^{177}$Lu-DKFZ-PSMA-617: a new radiopharmaceutical for the treatment of metastatic prostate cancer. *Eur J Nucl Med Mol Imaging* 2016; 43:42-51.

[17] Loke K S H, Padhy A K, Ng DCE, Goh A S W, Divgi C. Dosimetric Considerations in Radioimmunotherapy and Systemic Radionuclide Therapies: A Review. *World J Nucl Med.* 2011; 10:122-38.

[18] Kelly J M, Amor-Coarasa A, Nikolopoulou A, Wüstemann T, Barelli P, Kim D, Williams C., Jr, Zheng X, Bi C, Hu B, Warren J D, Hage D S, DiMagno S G, Babich J W. Dual-Target Binding Ligands with Modulated Pharmacokinetics for Endoradiotherapy of Prostate Cancer. *J Nucl Med* 2017; 58:1442-9.

[19] Kelly J, Amor-Coarasa A, Nikolopoulou A, Kim D, Williams C., Jr, Ponnala S, Babich J W. Synthesis and pre-clinical evaluation of a new class of high-affinity $^{18}$F-labeled PSMA ligands for detection of prostate cancer by PET imaging. *Eur J Nucl Med Mol Imaging* 2017; 44:647-61.

[20] Amor-Coarasa A, Milera A, Carvajal D, Gulec S, McGoron A J. Lyophilized Kit for the Preparation of the PET Perfusion Agent [$^{68}$Ga]-MAA. *Int J Mol Imaging* 2014; Article ID 269365: doi:10.1155/2014/269365

[21] Benešová M, Schäfer M, Bauder-Wüst U, Afshar-Oromieh A, Kratochwil C, Mier W, Haberkorn U, Kopka K, Eder M. Preclinical Evaluation of a Tailor-Made DOTA-Conjugated PSMA Inhibitor with Optimized Linker Moiety for Imaging and Endoradiotherapy of Prostate Cancer. *J Nucl Med.* 2015; 56:914-20.

[22] Kumar A, Mastren T, Wang B, Hsieh J-T, Hao G, Sun X. Design of a Small-Molecule Drug Conjugate for Prostate Cancer Targeted Theranostics. *Bioconjugate Chem.* 2016; 27:1681-9.

[23] Choy C J, Ling X, Geruntho J J, Beyer S K, Latoche J D, Langton-Webster B, Anderson C J, Berkman C E. $^{177}$Lu-Labeled Phosphoramidate-Based PSMA Inhibitors: The Effect of an Albumin Binder on Biodistribution and Therapeutic Efficacy in Prostate Tumor-Bearing Mice. *Theranostics* 2017; 7:1928-39.

[24] Bao K, Lee J H, Kang H, Park G K, El Fakhri G, Choi H S. PSMA-targeted contrast agents for intraoperative imaging of prostate cancer. *Chem Commun.* 2017; 53:1611-4.

[25] Tykvart J, Schimer J, Bařinková J, Pachl P, Poštová-Slavětinská L, Majer P, Konvalinka J, Šácha P. Rational design of urea-based glutamate carboxypeptidase II (GC-PII) inhibitors as versatile tools for specific drug targeting and delivery. *Bioorg Med Chem.* 2014; 22:4099-108.

[26] Varasteh Z, Rosenström U, Velikyan I, Mitran B, Altai M, Honarvar H, Rosestedt M, Lindeberg G, Sorensen J, Larhed M, Tolmachev V, Orlova A. The Effect of Mini-PEG-Based Spacer Length on Binding and Pharmacokinetic Properties of a $^{68}$Ga-Labeled NOTA-Conjugated Antagonist Analog of Bombesin. *Molecules* 2014; 19:10455-72.

[27] Weineisen M, Schottelius M, Simecek J, Baum R P, Yildiz A, Beykan S, Kulkarni H R, Lassmann M, Klette I, Eiber M, Schwaiger M, Wester H-J. $^{68}$Ga- and 17Lu-Labeled PSMA I&T: Optimization of a PSMA-Targeted Theranostic Concept and First Proof-of-Concept Human Studies. *J Nucl Med.* 2015; 56:1169-76.

[28] Kiess A P, Minn I, Chen Y, Hobbs R, Sgouros G, Mease R C, Pullambhatla M, Shen C J, Foss C A, Pomper M G. Auger Radiopharmaceutical Therapy Targeting Prostate-Specific Membrane Antigen. *J Nucl Med.* 2015; 56:1401-7.

[29] Hillier S M, Maresca K P, Femia F J, Marquis J C, Foss C A, Nguyen N, Zimmerman C N, Barrett J A, Eckelman W C, Pomper M G, Joyal J L, Babich J W. Preclinical Evaluation of Novel Glutamate-Urea-Lysine Analogs that Target Prostate Specific Membrane Antigen as Molecular Imaging Pharmaceuticals for Prostate Cancer. *Cancer Res.* 2009; 69:6932-40.

[30] Müller C, Struthers H, Winiger C, Zhernosekov K, Schibli R. DOTA Conjugate with an Albumin-Binding Entity Enables the First Folic Acid-Targeted $^{177}$Lu Radionuclide Tumor Therapy in Mice. *J Nucl Med.* 2013; 54:121-31.

[31] Sathekge M, Knoesen O, Meckel M, Modiselle M, Vorster M, Marx S. $^{213}$Bi-PSMA-617 targeted alpha-radionuclide therapy in metastatic castration-resistant prostate cancer. *Eur J Nucl Med Mol Imaging* 2017; 44:1099-1100.

[32] Nonnekens J, Chatalic K L S, Molkenboer-Kuenen J D M, Beerens C E M T, Bruchertseifer F, Morgenstern A, Veldhoven-Zweistra J, Schottelius M, Wester H-J, van Gent D C, van Weerden W M, Boerman O C, de Jong M, Heskamp S. $^{213}$Bi-Labeled Prostate-Specific Membrane Antigen-Targeting Agents Induce DNA Double-Strand Breaks in Prostate Cancer Xenografts. *Cancer Biother Radiopharm.* 2017; 32:67-73.

[33] Kratochwil C, Bruchertseifer F, Giesel F L, Weis M, Verburg F A, Mottaghy F, Kopka K, Apostolidis C, Haberkorn U, Morgenstern A. $^{225}$Ac-PSMA-617 for PSMA-Targeted α-Radiation Therapy of Metastatic Castration-Resistant Prostate Cancer. *J Nucl Med.* 2016; 57:1941-4.

[34] Kularatne S A, Wang K, Santhapuram H R, Low P S. Prostate-Specific Membrane Antigen Targeted Imaging and Therapy of Prostate Cancer Using a PSMA Inhibitor as a Homing Ligand. *Mol Pharm.* 2009; 6:780-9.

[35] Bacich D J, Pinto J T, Tong W P, Heston W D. Cloning, expression, genomic localization, and enzymatic activities of the mouse homolog of prostate-specific membrane antigen/NAALADase/folate hydrolase. *Mamm. Genome* 2001; 12:117-23.

[36] Schmittgen T D, Zakrajsek B A, Hill R E, Liu Q, Reeves J J, Axford P D, Singer M J, Reed M W. Expression Pattern of Mouse Homolog of Prostate-Specific Membrane Antigen (FOLHI) in the Transgenic Adenocarcinoma of the Mouse Prostate Model. *Prostate* 2003; 55:308-16.

[37] Chatalic K L S, Heskamp S, Konijnenberg M, Molkenboer-Kuenen J D M, Franssen G M, Clahsen-van Groningen M C, Schottelius M, Wester H-J, van Weerden W M, Boerman O C, de Jong M. Towards Personalized Treatment of Prostate Cancer: PSMA I&T, a Promising Prostate-Specific Membrane Antigen-Targeted Theranostic Agent. *Theranostics* 2016; 6:849-61.

[38] Kratochwil C, Giesel F L, Leotta K, Eder M, Hoppe-Tich T, Youssoufian H, Kopka K, Babich J W, Haberkorn U. PMPA for Nephroprotection in PSMA-Targeted Radiotherapy of Prostate Cancer. *J Nucl Med.* 2015; 56:293-8.

Section 1.4

Materials and Instrumentation. The synthesis of RPS-074 is described below. All solvents and reagents were purchased from commercial vendors and used without further purification. The intermediate di-tert-butyl (((S)-1-(tert-butoxy)-6-(3-(3-ethynylphenyl)ureido)-1-oxohexan-2-yl)carbamoyl)-L-glutamate (406) and macropa-NCS were synthesized as described above. Compounds were purified using silica chromatography on VWR® High Purity Silica Gel 60 Å, preparative TLC on silica-coated glass plates (Analtech), or flash chromatography using a CombiFlash Rf+(Teledyne Isco) system. Preparative HPLC was performed using an XBridge™ Prep C18 5 μm OBD™ 19×100 mm column (Waters) on a dual pump Agilent ProStar HPLC fitted with an Agilent ProStar 325 Dual Wavelength UV-Vis Detector. UV absorption was monitored at 220 nm and 280 nm. A binary solvent system was used, with solvent A comprising H₂O+0.01% TFA and solvent B consisting of 90% v/v MeCN/H₂O+0.01% TFA. Purification was achieved using the following gradient HPLC method: 0% B 0-1 min., 0-100% B 1-28 mins., 100-0% B 28-30 mins.

Final products were identified and characterized using thin layer chromatography, analytical HPLC and mass spectrometry. NMR spectroscopy was used to confirm the structure of compound 406 and macropa-NCS. NMR analyses were performed using a Bruker Avance III 500 MHz spectrometer. Spectra are reported in CDCl₃ or DMSO-d6. Analytical HPLC was performed using an XSelect™ CSH™ C18 5 μm 4.6×50 mm column (Waters). Mass determinations were performed by LCMS analysis using a Waters ACQUITY UPLC® coupled to a Waters SQ Detector 2. The purity of all compounds evaluated in the biological assay was >95% purity as judged by analytical HPLC.

Synthesis of RPS-074.

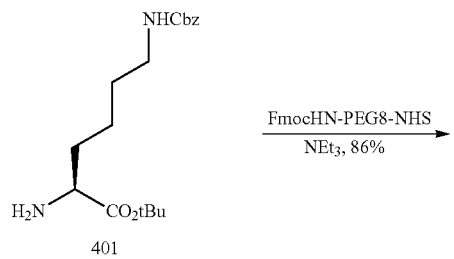

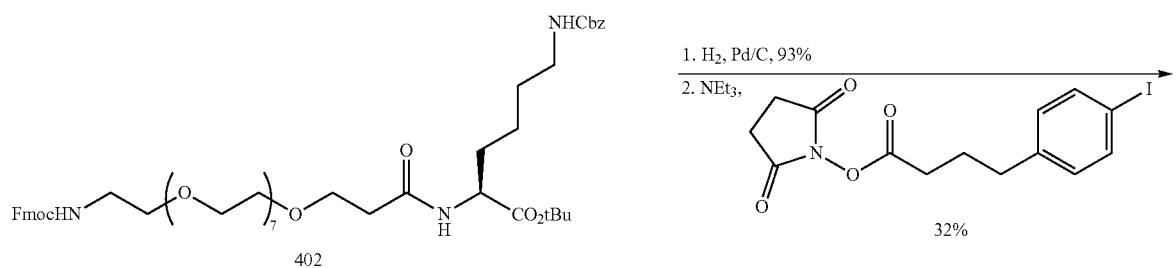

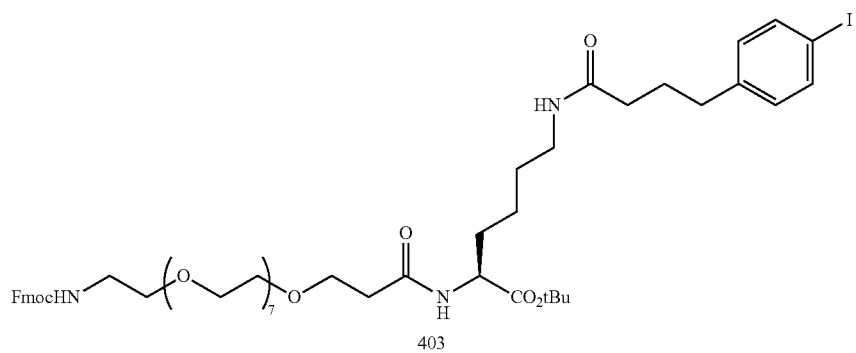

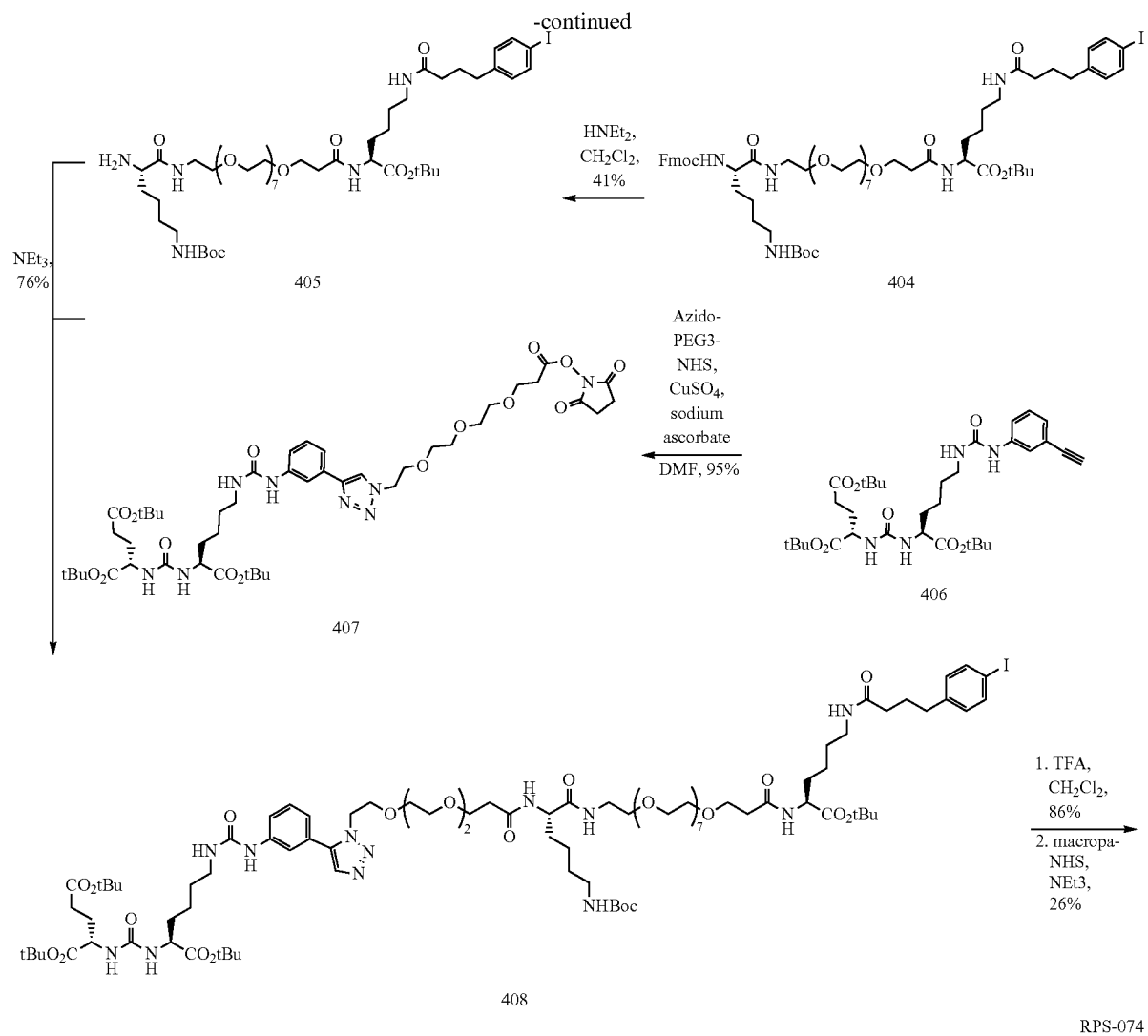

Preparation of tert-Butyl $N^2$-(1-(9H-fluoren-9-yl)-3-oxo-2,7,10,13,16,19,22,25,28-nonaoxa-4-azahentriacontan-31-oyl)-$N^6$-((benzyloxy)carbonyl)-L-lysinate (402). To a stirred mixture of Fmoc-N-amido-PEG-8-acid (663 mg, 1.0 mmol), L-$N^\varepsilon$-Z-Lys-OtBu hydrochloride (446 mg, 1.2 mmol) and HATU (456 mg, 1.2 mmol) in DMF (10 mL) was added DIPEA (260 mg, 2.0 mmol), and the reaction was stirred overnight at room temperature under $N_2$. The solvent was removed under reduced pressure and the crude residue was purified by flash chromatography (0-10N MeOH in $CH_2Cl_2$) to give compound 2 as a colorless oil (845 mg, 86%). Mass (ESI+): 983.0 [M+H]+. Calc. Mass: 981.5.

Preparation of tert-Butyl $N^2$-(1-(9H-fluoren-9-yl)-3-oxo-2,7,10,13,16,19,22,25,28-nonaoxa-4-azahentriacontan-31-oyl)-$N^6$-(4-(4-iodophenyl)butanoyl)-L-lysinate (403). Compound 402 (1.45 g, 1.48 mmol) was dissolved in MeOH (25 mL). 10% Palladium on charcoal (15 mg) was added, and the suspension was stirred in a three-neck flask at room temperature for 10 min. The flask was evacuated and then placed under an $H_2$ atmosphere. The suspension was then stirred at room temperature for 5 h before it was filtered through celite. The filter cake was washed with MeOH, and the combined filtrate was concentrated under reduced pressure to give the amine as a yellow oil (1.17 g, 93%) that was used without further purification. Mass (ESI+): 849.4 [M+H]+. Calc. Mass: 848.0. To a solution of the amine (865 mg, 1.01 mmol) and 2,5-dioxopyrrolidin-1-yl 4-(4-iodophenyl)butanoate (387 mg, 1.00 mmol) in $CH_2Cl_2$ (20 mL) was added TEA (167 µL, 1.20 mmol). The resulting solution was stirred at room temperature under Ar for 4 h. The solution was then washed successively with 1% v/v AcOH/$H_2O$ and brine. The organic layer was dried over $MgSO_4$, filtered and concentrated under reduced pressure to give a yellow oil. The crude product was purified by flash chromatography (0-30% MeOH in $CH_2Cl_2$) and compound 3 was isolated as a yellow oil (360 mg, 32%). Mass (ESI+): 1120.9 [M+H]+. Calc. Mass: 1119.5.

Preparation of tert-Butyl $N^2$—((S)-10-((((9H-fluoren-9-yl)methoxy)carbonyl)amino)-2,2-dimethyl-4,11-dioxo-3, 15,18,21,24,27,30,33,36-nonaoxa-5,12-diazanonatriacontan-39-oyl)-N⁶-(4-(4-iodophenyl)butanoyl)-L-lysinate (404). A solution of 403 (360 mg, 0.32 mmol) and diethylamine (0.67 mL, 6.48 mmol) in $CH_2Cl_2$ (2 mL) was stirred at room temperature for 7 h. The solution was concentrated under reduced pressure and the crude residue was purified by flash chromatography (0-30% MeOH in $CH_2Cl_2$). The fractions containing the product were combined and concentrated to give the amine as a yellow oil (96 mg, 33%). Mass (ESI+): 899.2 [M+H]⁺. Calc. Mass: 897.4. To a solution of the amine (96 mg, 107 μmol) and Fmoc-L-Lys(Boc)-OSu (62 mg, 110 μmol) in $CH_2Cl_2$ (5 mL) was added TEA (28 μL, 200 μmol). The mixture was stirred overnight at room temperature under Ar. The solvent was removed under reduced pressure and the crude product was purified by flash chromatography (0-30% MeOH in $CH_2Cl_2$). The desired product co-eluted with a minor impurity, therefore the mixture was purified a second time by prep TLC (10% v/v MeOH/$CH_2Cl_2$). Compound 404 was isolated as a colorless oil (78 mg, 51%). Mass (ESI+): 1349.0 [M+H]⁺. Calc. Mass: 1347.6.

Preparation of tert-Butyl N²—((S)-10-amino-2,2-dimethyl-4,11-dioxo-3,15,18,21,24,27,30,33,36-nonaoxa-5,12-diazanonatriacontan-39-oyl)-N⁶-(4-(4-iodophenyl)butanoyl)-L-lysinate (405). A solution of 404 (73 mg, 54 μmol) and diethylamine (0.5 mL, 4.83 mmol) in $CH_2Cl_2$ (2 mL) was stirred overnight at room temperature. The solvent was removed under reduced pressure and the crude product was dissolved in MeOH and purified by prep TLC (10% v/v MeOH in $CH_2Cl_2$). Amine 405 was isolated as a pale oil (25 mg, 41%). Mass (ESI+): 1127.7 [M+H]⁺. Calc. Mass: 1126.2.

Preparation of di-tert-butyl (((S)-1-(tert-butoxy)-6-(3-(3-(1-(2-(2-(2-(3-((2,5-dioxopyrrolidin-1-yl)oxy)-3-oxopropoxy)ethoxy)ethoxy)ethyl)-1H-1,2,3-triazol-4-yl)phenyl)ureido)-1-oxohexan-2-yl)carbamoyl)-L-glutamate (407). A solution of 0.5M $CuSO_4$ (100 μL) and 1.5M sodium ascorbate (100 μL) was mixed until the brown color was converted to orange. This mixture was then added to a solution of 406 (315 mg, 0.5 mmol) and azido-PEG₃-NHS (177 mg, 0.5 mmol) in DMF (2 mL). The mixture was stirred at room temperature for 2 h. It was then diluted with $CH_2Cl_2$ and washed with $H_2O$. The organic layer was dried over $MgSO_4$, filtered and concentrated under reduced pressure to give a pale oil. The crude product was purified by flash chromatography (0-30% MeOH in $CH_2Cl_2$) to give compound 407 as a clear oil (460 mg, 95%). Mass (ESI+): 975.9 [M+H]⁺. Calc. Mass: 974.5.

Preparation of di-tert-butyl (((S)-1-(tert-butoxy)-6-(3-(3-(1-((14S,45S)-45-(tert-butoxycarbonyl)-14-(4-((tert-butoxycarbonyl)amino)butyl)-54-(4-iodophenyl)-12,15,43,51-tetraoxo-3,6,9,19,22,25,28,31,34,37,40-undecaoxa-13,16,44,50-tetraazatetrapentacontyl)-1H-1,2,3-triazol-4-yl)phenyl)ureido)-1-oxohexan-2-yl)carbamoyl)-L-glutamate (408). To a solution of amine 405 (25 mg, 22 μmol) in $CH_2Cl_2$ (4 mL) was added a solution of ester 407 (24 mg, 25 μmol) and TEA (7 μL, 50 μmol) in $CH_2Cl_2$ (1 mL). The reaction was stirred for 5 h at room temperature under Ar. Then the reaction was concentrated under reduced pressure and the crude residue was dissolved in EtOAc (1 mL) and purified by prep TLC (90% EtOAc in hexanes) to give compound 408 as a pale oil (33 mg, 76%). Mass (ESI+): 994.3 [(M+2H)/2]⁺. Calc. Mass: 1986.2.

Preparation of (((S)-1-Carboxy-5-(3-(3-(1-((14S,45S)-45-carboxy-14-(4-(3-(2-carboxy-6-((16-((6-carboxypyridin-2-yl)methyl)-1,4,10,13-tetraoxa-7,16-diazacyclooctadecan-7-yl)methyl)pyridin-4-yl)thioureido)butyl)-54-(4-iodophenyl)-12,15,43,51-tetraoxo-3,6,9,19,22,25,28,31,34,37,40-undecaoxa-13,16,44,50-tetraazatetrapentacontyl)-1H-1,2,3-triazol-4-yl)phenyl)ureido)pentyl)carbamoyl)-L-glutamic acid (RPS-074).

Compound 408 (33 mg, 16 μmol) was dissolved in $CH_2Cl_2$ (2 mL). Then TFA (0.5 mL) was added and the reaction was stirred overnight at room temperature. The solvent was removed under N2 flow and the crude product was lyophilized to give a white residue (22 mg, 83%). Mass (ESI+): 832.0 [(M+2H)/2]⁺. Calc. Mass: 1661.8. To a solution of the free amine (13 mg, 7.8 μmol) and TEA (0.22 mL, 1.56 mmol) in DMF (1 mL) was added a solution of macropa-NHS (6 mg, 10 μmol) in DMF (1 mL). The resulting mixture was stirred for 90 min at room temperature. The reaction was concentrated under reduced pressure and the crude product was purified by prep HPLC. The peak corresponding to the desired product was collected and lyophilized to give RPS-074 as a white powder (4.5 mg, 26%). Mass (ESI+): 1126.6 [(M+2H)/2]⁺. Calc. Mass: 2251.3.

Synthesis of DOTA-Lys-IPBA

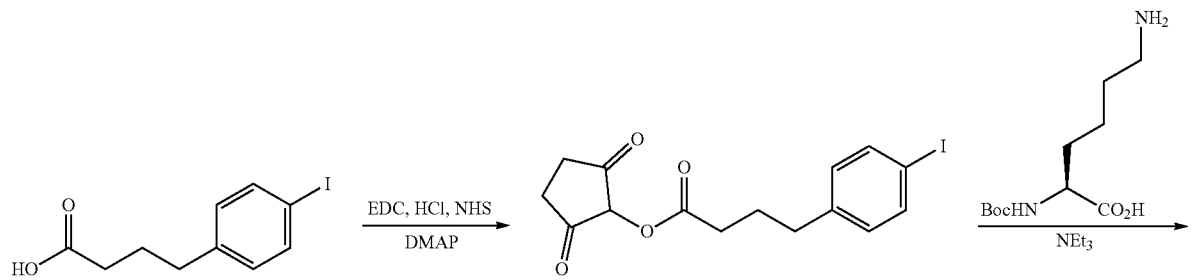

409

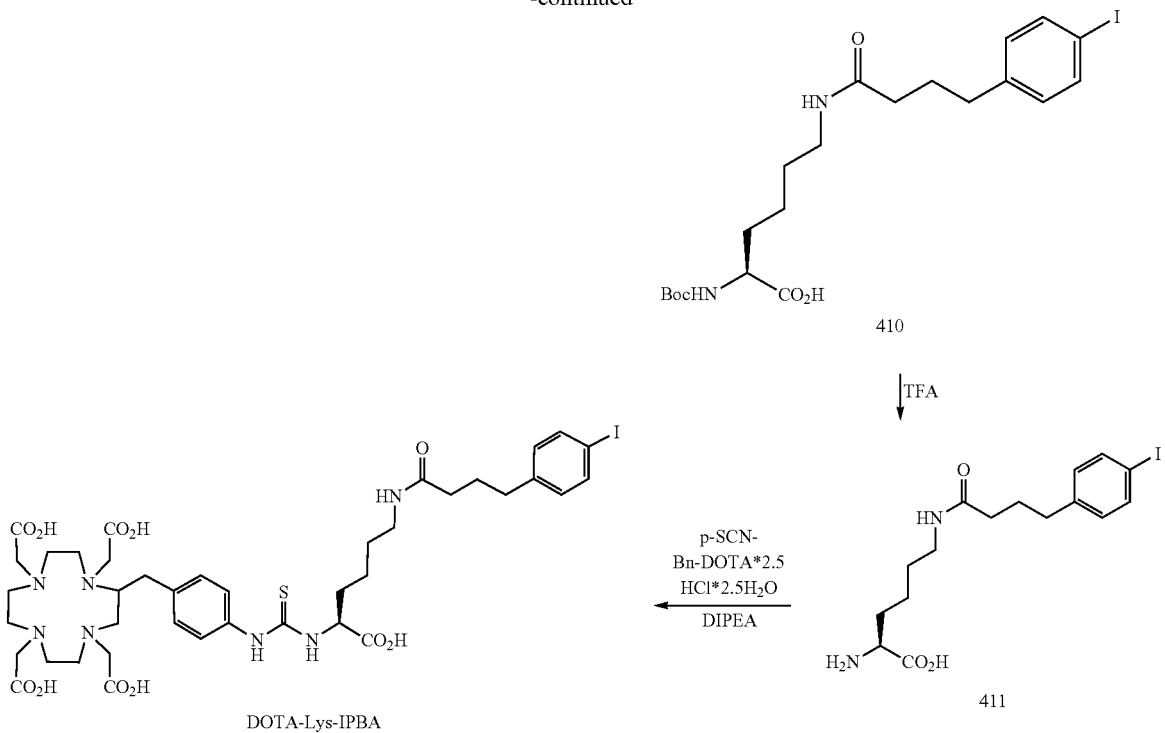

Preparation of 2,5-dioxopyrrolidin-1-yl 4-(4-iodophenyl)butanoate (409). A solution of 4-(4-iodophenyl)butanoic acid (1.16 g, 4.0 mmol), N-hydroxysuccinimide (483 mg, 4.2 mmol), EDC.HCl (768 mg, 4.0 mmol) and 4-DMAP (5.8 mg, 47 µmol) in $CH_2Cl_2$ (30 mL) was stirred for 20 h. Then the reaction mixture was washed successively with 1M HCl, saturated $NaHCO_3$ and brine. The organic layer was dried over $MgSO_4$, filtered and concentrated under reduced pressure to give NHS ester 409 as a white powder (1.29 g, 83%). $^1$H NMR ($CDCl_3$, 500 MHz): δ 7.61 (d, 2H, J=7.2 Hz). 6.95 (d, 2H, J=7.6 Hz), 2.83 (s, 4H), 2.67 (t, 2H, J=7.6 Hz), 2.59 (t, 2H, J=7.3 Hz), 2.03 (quint, 2H, J=7.3 Hz).

Preparation of $N^2$-(tert-butoxycarbonyl)-$N^6$-(4-(4-iodophenyl)butanoyl)-L-lysine (410). Boc-L-Lys-OH (871 mg, 3.53 mmol) was suspended in DMF (10 mL) and stirred at room temperature. To the stirred suspension was slowly added a solution of NHS ester 409 (1.29 g, 3.33 mmol) and $NEt_3$ (557 µL, 4.00 mmol) in DMF (5 mL). The resulting suspension was stirred overnight at room temperature. The reaction was quenched with 1M HCl (2 mL), and the solvent was removed under reduced pressure. The crude residue was dissolved in $CH_2Cl_2$ and washed successively with 1M HCl, saturated $NaHCO_3$ solution and brine. The organic fraction was dried over $MgSO_4$, filtered and concentrated under reduced pressure to give Boc-Lys-IPBA (410) as a clear foam (1.25 g, 72%). $^1$H NMR ($CDCl_3$, 500 MHz): δ 7.57 (d, 2H, J=7.7 Hz), 6.91 (d, 2H, J=7.8 Hz), 5.94 (br s, 1H), 5.32 (br s, 1H), 4.21 (m, 1H), 3.21 (m, 2H), 2.56 (t, 2H, J=7.6 Hz), 2.15 (t, 2H, J=7.1 Hz), 1.90 (quint, 2H, J=7.5 Hz), 1.88 (m, 1H), 1.69 (m, 1H), 1.51 (m, 2H), 1.42 (s, 9H), 1.41 (m, 2H). Mass (ESI+): 519.3 (M+H)*. Calc. Mass: 518.4.

Preparation of $N^6$-(4-(4-iodophenyl)butanoyl)-L-lysine (411). Boc-Lys-IPBA (518 mg, 1.0 mmol) was dissolved in 10 mL of a 20% v/v $TFA/CH_2Cl_2$ solution and stirred overnight at room temperature. The solvents were removed under a stream of N2 and Lys-IPBA (411) was isolated as a colorless oil (402 mg; 96%). $^1$H NMR (DMSO, 500 MHz): δ 7.75 (br s, 1H), 7.61 (d, 2H, J=7.8 Hz), 6.99 (d, 2H, J=7.8 Hz), 3.79 (m, 1H), 2.99 (m, 2H), 2.02 (t, 2H, J=7.3 Hz), 1.74 (quint, 2H, J=7.4 Hz), 1.37 (m, 4H), 1.24 (m, 2H). Mass (ESI+): 419.2 (M+H)*. Calc. Mass: 418.3.

Preparation of 2,2',2'',2'''-(2-(4-(3-((S)-1-carboxy-5-(4-(4-iodophenyl)butanamido)pentyl)thioureido)benzyl)-1,4,7,10-tetraazacyclododecane-1,4,7,10-tetrayl)tetraacetic acid (DOTA-Lys-IPBA). To a solution of Lys-IPBA (11 mg, 26 µmol) and DIPEA (17 µL, 100 µmol) in DMF (1 mL) was added a solution of p-SCN-Bn-DOTA.2.5Cl.2.5$H_2O$ (8 mg, 11.6 µmol) in $H_2O$ (1 mL). The reaction was stirred at room temperature for 4 h. The solvent was removed under reduced pressure and the crude residue was purified by prep HPLC. The peak corresponding to the product was collected and lyophilized to give DOTA-Lys-IPBA as a white powder (5 mg, 43%). $^1$H NMR (DMSO, 500 MHz): δ 9.72 (br s, 1H), 7.89 (d, 2H, J=7.6 Hz), 7.77 (m, 1H), 7.61 (d, 2H, J=7.1 Hz), 7.51 (d, 2H, J=7.8 Hz), 7.24 (m, 2H), 6.99 (d, 2H, J=7.8 Hz), 4.84 (m, 1H), 3.70-3.04 (m, 14H), 3.01 (m, 4H), 2.02 (t, 2H, J=7.1 Hz), 1.76 (m, 4H), 1.39 (m, 2H), 1.31 (m, 2H). Mass (ESI+): 971.0 (M+H)*. Calc. Mass: 969.9.

Radiochemistry. All reagents were purchased from Sigma Aldrich unless otherwise noted, and were reagent grade. Hydrochloric acid (HCl) was traceSELECT® (>99.999%) for trace analysis quality. Aluminum-backed silica thin layer chromatography (TLC) plates were purchased from Sigma Aldrich. Stock solutions of 0.05M HCl and 1M $NH_4OAc$ were prepared by dilution in Milli-Q® water.

$^{225}$Ac-RPS-074: To a solution of $^{225}$Ac(NO$_3$)$_3$ (Oak Ridge National Laboratory, USA) in 0.05M HCl (16.7-21.0 MBq in 950 µL) was added 20 µL of a 1 mg/mL solution of RPS-074 in DMSO. The pH was increased to 5-5.5 by addition of 90 µL 1M $NH_4OAc$. The reaction was gently shaken for 20 min at 25° C. on an Eppendorf Thermomixer® C (VWR). Then the reaction was diluted with $H_2O$ (9 mL)

and passed through a pre-activated Sep-Pak C18 Light cartridge (Waters). The reaction vial and cartridge were washed with $H_2O$ (5 mL) and the product was eluted with 500 μL of EtOH followed by 500 μL normal saline (0.9% NaCl in deionized $H_2O$; VWR). The eluate was diluted to 4 mL in normal saline to give a stock solution with a radioactivity concentration of 1.1-1.5 MBq/mL. An aliquot was removed from the final solution and spotted onto an aluminum-backed silica TLC plate to determine radiochemical impurity. An aliquot of the $^{225}Ac(NO_3)_3$ solution in 0.05M HCl was spotted in a parallel lane as a control. The plate was immediately run in a 10% v/v MeOH/10 mM EDTA mobile phase, and then allowed to stand for 8 h to enable radiochemical equilibrium to be reached. The plate was visualized on a Cyclone Plus Storage Phosphor System (Perkin Elmer) following a 3 min exposure on the phosphor screen. The radiochemical purity was expressed as a ratio of $^{225}Ac$-RPS-074 to total activity and was determined to be 98.1%. The plate was visualized again 16 h later to confirm purity.

$^{225}Ac$-DOTA-Lys-IPBA: To a solution of $^{225}Ac(NO_3)_3$ (Oak Ridge National Laboratory, USA) in 0.05M HCl (5.0 MBq in 900 μL) was added 30 μL of a 1 mg/mL solution of DOTA-Lys-IPBA in DMSO. The pH was increased to 5-5.5 by addition of 80 μL 1M $NH_4OAc$, and the reaction was heated for 25 min at 95° C. on an Eppendorf Thermomixer® C (VWR). Then the reaction mixture was diluted with $H_2O$ (9 mL) and passed through a pre-activated Sep-Pak C18 Light cartridge (Waters). The reaction vial and cartridge were washed with $H_2O$ (5 mL) and the product was eluted with 200 μL of a 50% v/v EtOH/saline solution followed by 800 μL normal saline (0.9% NaCl in deionized $H_2O$; VWR). Radiochemical purity (96%) was determined by radioTLC as described above.

Cell Culture. The PSMA expressing human prostate cancer cell line, LNCaP, was obtained from the American Type Culture Collection. Cell culture supplies were obtained from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 μg/mL gentamicin in a humidified incubator at 37° C./5% $CO_2$. Cells were removed from flasks for passage or for transfer to 12-well assay plates by incubating them with 0.25% trypsin/ethylenediaminetetraacetic acid (EDTA).

In vitro determination of ICs&. $IC_{50}$ values of the non-labeled, metal-free ligands were determined by screening in a multi-concentration competitive binding assay against $^{99m}Tc$-((7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid technetium tricarbonyl complex) ($^{99m}Tc$-MIP-1427), with $K_d$=0.64±0.46 nM [1] for binding to PSMA on LNCaP cells, according to previously described methods [2] with small modifications. Briefly, LNCaP cells were plated 72 h prior to the experiment to achieve a density of approximately $5\times10^5$ cells/well (in triplicate) in RPMI-1640 medium supplemented with 0.25% bovine serum albumin. The cells were incubated for 2 h with 1 nM $^{99m}Tc$-MIP-1427 in RPMI-1640 medium containing 0.00125% w/v bovine serum albumin [3] in the presence of 0.001-10,000 nM test compounds. Radioactive incubation media was then removed by pipette and the cells were washed twice using 1 mL ice-cold PBS 1× solution. Cells were harvested from the plates following treatment with 1 mL 1M NaOH and transferred to tubes for radioactive counting using a 2470 Wizard[2] Automatic Gamma Counter (Perkin Elmer). Standard solutions (10% of activity added to each well) were prepared to enable decay correction. Cell-specific activity was corrected for non-specific binding of $^{99m}Tc$-MIP-1427. $IC_{50}$ values were determined by fitting the data points to a sigmoidal Hills1 curve in Origin software.

Inoculation of mice with xenografts. All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Male BALB/c athymic nu/nu mice were purchased from the Jackson Laboratory. For inoculation in mice, LNCaP cells were suspended at $4\times10^7$ cells/mL in a 1:1 mixture of PBS:Matrigel (BD Biosciences). Each mouse was injected in the left flank with 0.25 mL of the cell suspension. Biodistributions were conducted when tumors were in the range 200-800 $mm^3$, while therapy studies were initiated when tumors were in the range 50-900 $mm^3$.

Biodistribution studies in LNCaP xenograft mice. LNCaP xenograft tumor-bearing mice (4 per time point per compound) were injected intravenously with a bolus injection of 105 kBq and 320 ng (142 pmol) of $^{225}Ac$-RPS-074. The mice were sacrificed at 4 h, 24 h, 7 d, 14 d and 21 d post injection. A blood sample was removed, and a full biodistribution study was conducted on the following organs (with contents): heart, lungs, liver, small intestine, large intestine, stomach, spleen, pancreas, kidneys, muscle, bone and tumor. Tissues were weighed and counted on a 2470 Wizard Automatic Gamma Counter (Perkin Elmer). Counts were corrected for decay and for activity injected, and tissue uptake was expressed as percent injected dose per gram (% ID/g). Standard error measurement was calculated for each data point.

Therapy study in LNCaP xenograft mice. LNCaP xenograft tumor-bearing mice were randomly assigned to 5 groups (7 mice per group). One group was injected intravenously with a bolus injection of 148 kBq and 93 ng (41 pmol) $^{225}Ac$-RPS-074. The second treatment group was injected with 74 kBq and 47 ng (21 pmol) $^{225}Ac$-RPS-074. The third treatment group was injected with 37 kBq and 23 ng (10 pmol) $^{225}Ac$-RPS-074. The fourth group was injected with the same volume of vehicle. The fifth group was injected with 133 kBq $^{225}Ac$-DOTA-Lys-IPBA. Tumor dimensions were measured and recorded three times weekly with digital calipers, and tumor volumes were calculated using the modified ellipsoid equation, $V=0.5*\text{length}*\text{width}*\text{width}$ [4]. Mice were sacrificed after tumors reached 2000 mm³ or if they showed any visible signs of distress, including loss of body weight, lack of appetite, excessive lethargy or formation of sores and rashes. Body weight was measured with a digital balance twice weekly, and mice were monitored for signs of distress. The mice were photographed weekly to visually confirm changes in tumor volume.

Imaging of Treated Mice by μPET/CT. $^{68}$Ga-PSMA-11 (also known as $^{68}$Ga-HBED-CC) was prepared as previously reported [5]. Eight mice were injected intravenously with 5.5 MBq $^{68}$Ga-PSMA-11, 75 days after injection of either 138 kBq or 74 kBq $^{225}$Ac-RPS-074. The mice were imaged using μPET/CT (Inveon™; Siemens Medical Solutions, Inc.) at 1 h post-injection following inhalation anesthetization with isoflurane. Total acquisition time was 30 min. A CT scan was obtained immediately before the acquisition for both anatomical co-registration and attenuation correction. Images were reconstructed using the Inveon™ software supplied by the vendor.

In Vitro and In Vivo Evaluation of RPS-074

Figure 12:
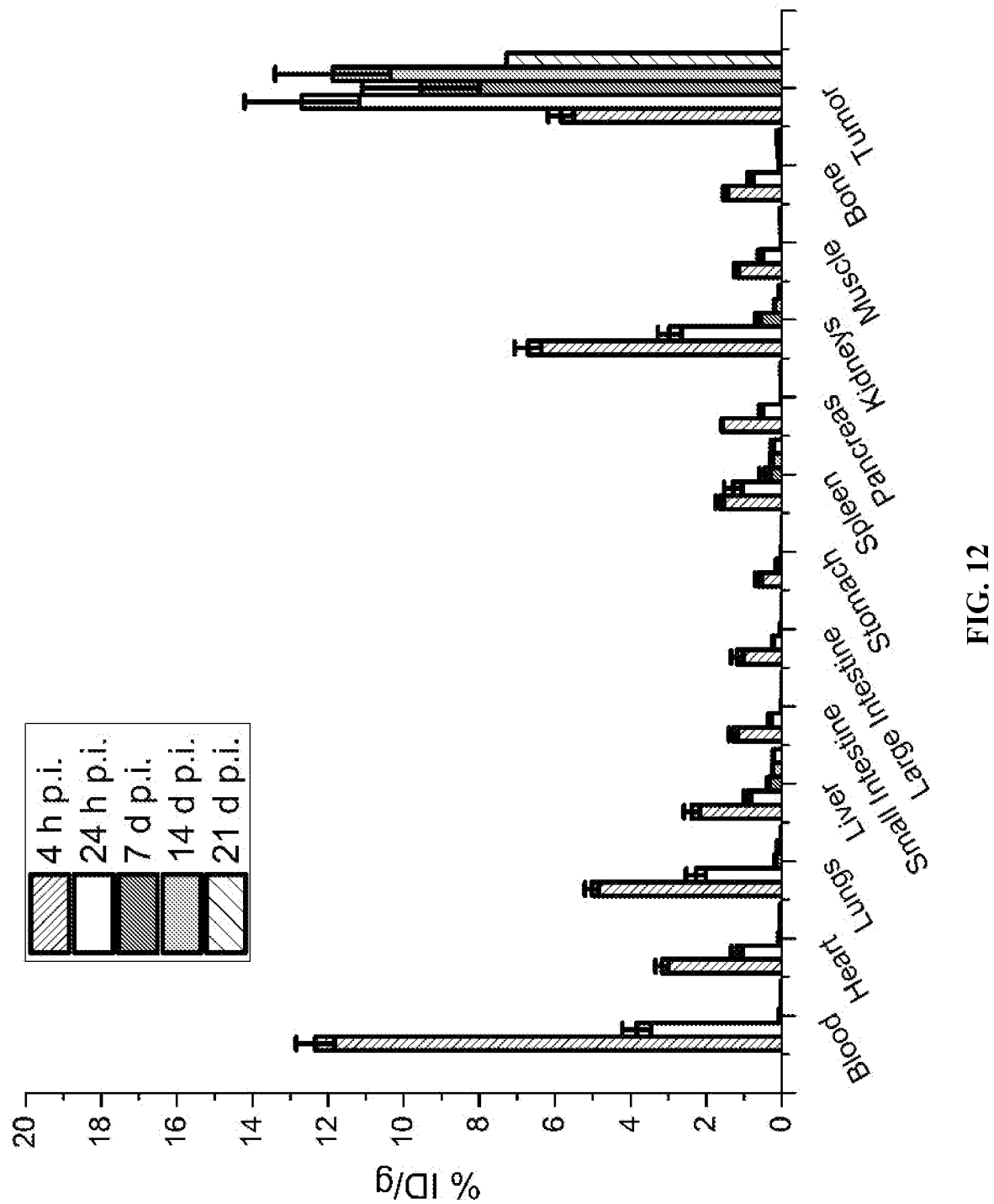
FIG. 12 shows the uptake of activity in blood, normal tissue and tumor in male BALB/C nu/nu mice bearing LNCaP xenograft tumors. Mice (n=4/time point) were injected intravenously with 105 kBq $^{225}$Ac-RPS-074 and sacrificed at 4 h, 24 h, 7 d, 14 d and 21 d p.i.

The $IC_{50}$ value of RPS-074 was determined in vitro using a multi-concentration competitive binding assay against $^{99m}$Tc-MIP-1427, which displays affinity for PSMA on LNCaP cells. It was demonstrated that the $IC_{50}$ of RPS-074 was 12.0±3.4 nM, a value that is consistent with the reported PSMA affinities of structurally analogous trifunctional ligands [6]. The biodistribution of RPS-074 was examined in vivo in LNCaP xenograft tumor-bearing mice. Mice were injected intravenously with a bolus injection of 105 kBq and 320 ng (142 pmol) of $^{225}$Ac-RPS-074. The mice were sacrificed at 4 h, 24 h, 7 d, 14 d and 21 d post injection. FIG. 12 demonstrates that uptake of $^{225}$Ac-RPS-074 was evident in the blood (12.3±0.5% ID/g), the lungs (5.0±0.2% ID/g), the kidneys (6.7±0.4% ID/g) and the tumor (5.8±0.3% ID/g) at 4 h post injection (p.i.). By 24 h p.i., the activity in non-target tissue, including kidneys (3.0±0.3% ID/g), cleared in concert with blood clearance, while activity in the tumor increased to 12.7 f 1.5% ID/g (FIG. 12). By 7 d p.i., activity in the tumor remained high (9.5±1.5% ID/g), while the activity in the blood and every other tissue was less than 1% ID/g (FIG. 12). Persistent tumor uptake (11.9±1.5% ID/g) was evident at 14 d p.i., with all other tissues becoming largely indistinguishable from background. By 21 d p.i., an anti-tumor effect was evident, with only 1 mouse still bearing a tumor. Notwithstanding the absence of tumors, activity in the non-target tissue remained indistinguishable from background.

$^{225}$Ac-RPS-074 showed excellent complex stability over 3 weeks even when tumors were absent. Biodistribution studies demonstrated that no accumulation of signal was evident in the liver or bone, two organs that typically take up free $^{225}$Ac$^{3+}$[7]. $^{225}$Ac-RPS-074 also demonstrated a favorable pharmacokinetic profile; the tumor-to-kidney and tumor-to-blood ratios rapidly favor the tumor. By 24 h p.i., the tumor-to-kidney ratio reached 4.3±0.7 while at 7 d and 14 d p.i. it is 15.0±2.9 and 62.2±9.5, respectively. The tumor-to-blood ratio at the same time points is 3.3±0.5, 137.5±30.4 and 995.8±139.7. Significant differences in the pharmacokinetic profile demonstrates that the dose absorbed by each tissue will be different.

Therapeutic Evaluation in LNCaP Xenograft Mice

Figure 13:
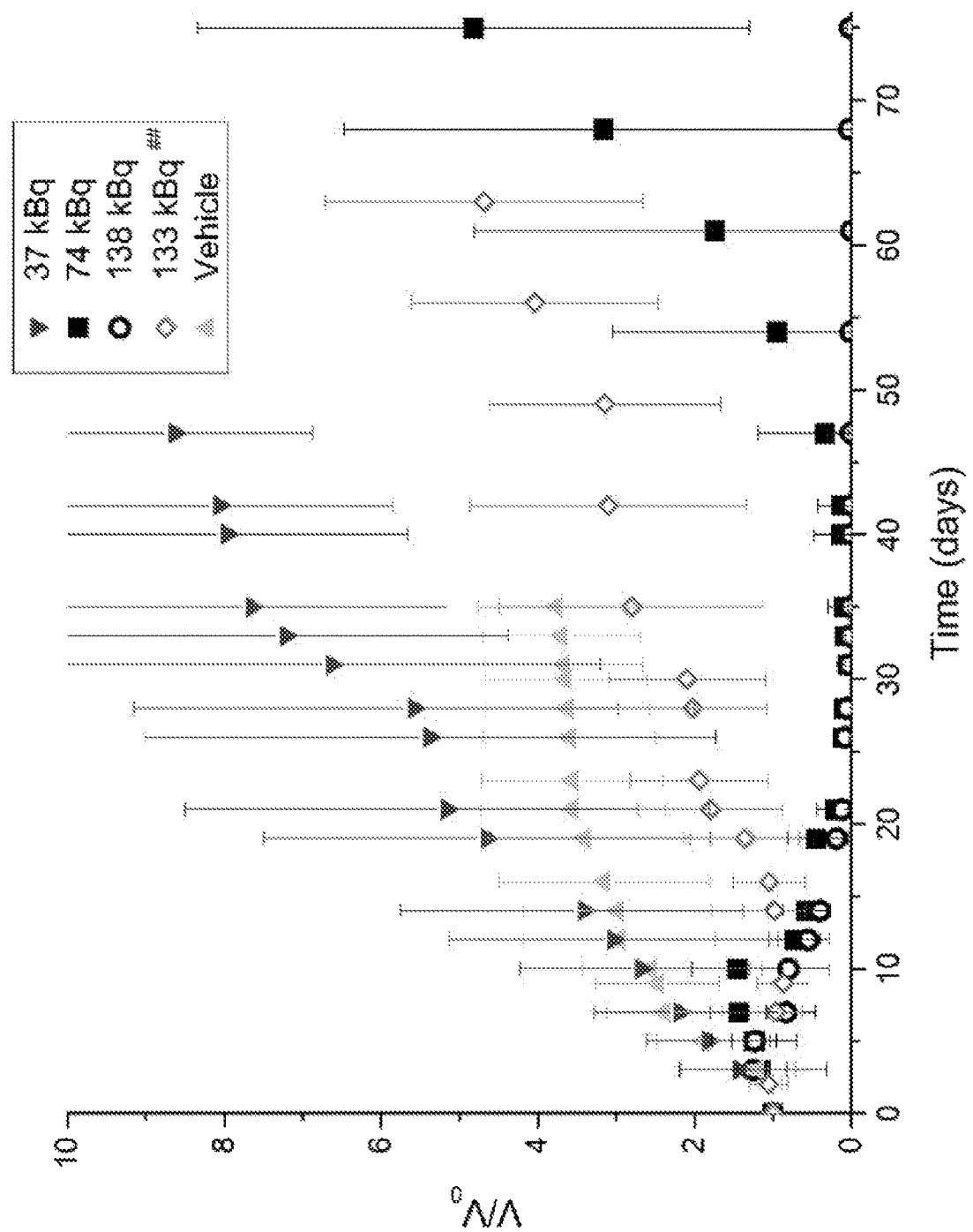
FIG. 13 plots the change in average tumor volumes of individual male BALB/C nu/nu mice bearing LNCaP xenograft tumors and treated with a) 138 kBq $^{225}$Ac-RPS-074; b) 74 kBq $^{225}$Ac-RPS-074; c) 37 kBq $^{225}$Ac-RPS-074; d) 133 kBq $^{225}$Ac-DOTA-Lys-IPBA; and e) vehicle.
Figure 14:
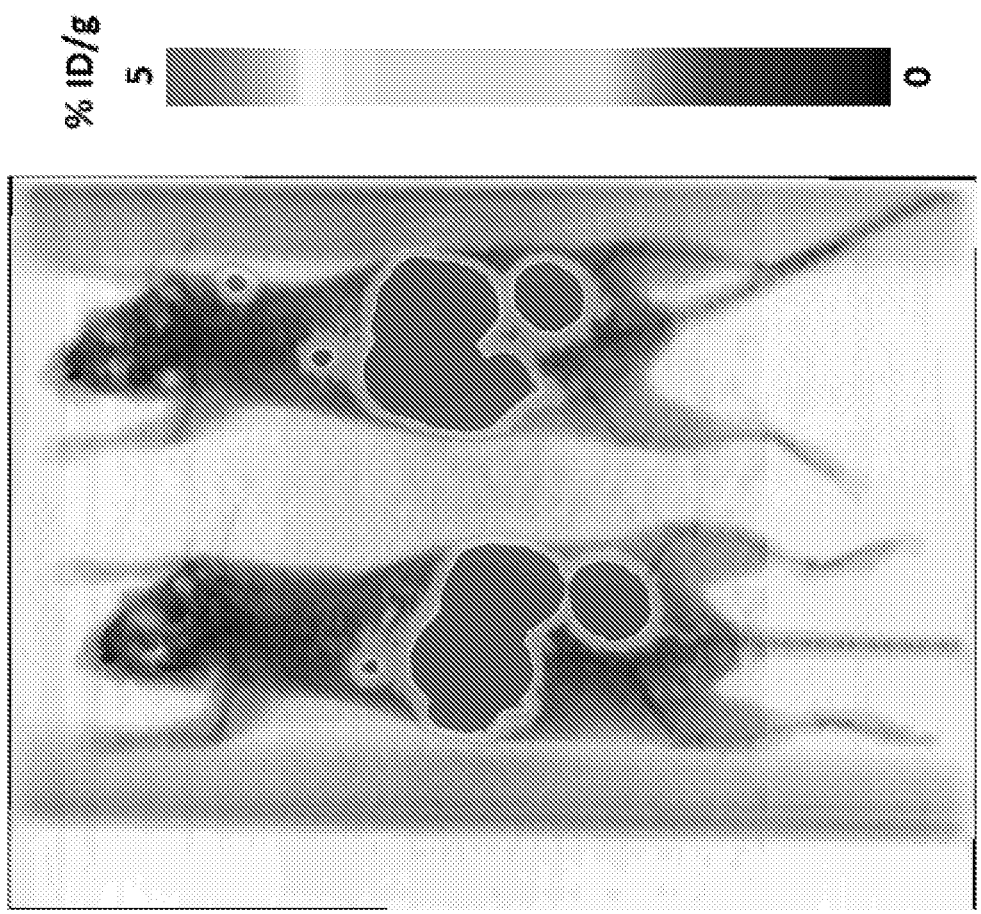
FIG. 14 provides $^{68}$Ga-PSMA-11 μPET/CT images of mice treated with 138 kBq $^{225}$Ac-RPS-074 (left) or 74 kBq $^{225}$Ac-RPS-074 (right). Images were acquired 60 min post injection and are corrected for decay and for activity injected.

LNCaP xenograft were randomly assigned to 5 groups and treated with a bolus injection of 148 kBq and 93 ng (41 pmol) $^{225}$Ac-RPS-074, 74 kBq and 47 ng (21 pmol) $^{225}$Ac-RPS-074, 37 kBq and 23 ng (10 pmol) $^{225}$Ac-RPS-074, 133 kBq $^{225}$Ac-DOTA-Lys-IPBA, or vehicle control. A significant antitumor effect was observed in the mice treated with 138 kBq and 74 kBq of $^{225}$Ac-RPS-074. In the 138 kBq treatment group, 6/7 (86%) of tumors were not detectable (<0.5 mm³) at 75 d post injection, while 1/7 (14%) of tumors were not detectable in the 74 kBq group. The distribution of initial tumor volumes was 100-624 mm³ and 64-455 mm³ for the two groups, respectively (FIG. 13). Tumor volume decreased in the 74 kBq group for as much as 42 d post injection before 6/7 (86%) of tumor volumes began to increase again. The absence of tumors was confirmed by μPET/CT imaging with $^{66}$Ga-PSMA-11 (FIG. 14) prior to the collection of samples for pathology. Those tumors that re-emerged in the 74 kBq treatment group were shown by imaging to express PSMA. Physiologic uptake was also evident in the kidneys and salivary glands.

FIG. 13 demonstrates that both the 37 kBq treatment group and the positive control group, which received 133 kBq $^{225}$Ac-DOTA-Lys-IPBA, showed an initial effect relative to the vehicle group, but tumor volumes increased from a starting volume of 99-331 mm³ and 233-859 mm³, respectively, to a final volume of greater than 2000 mm³. A clear dose-response was evident in this study. Up to 42 days p.i., the 74 kBq and 138 kBq treatment groups behaved similarly, but while the tumor volume of 5/7 (71%) of mice in the former group was measured to be less than 1 mm³, the tumors progressively returned. In contrast, the tumors of the mice in the 37 kBq treatment group appeared to grow at a similar rate to the untreated tumors.

Figure 15:
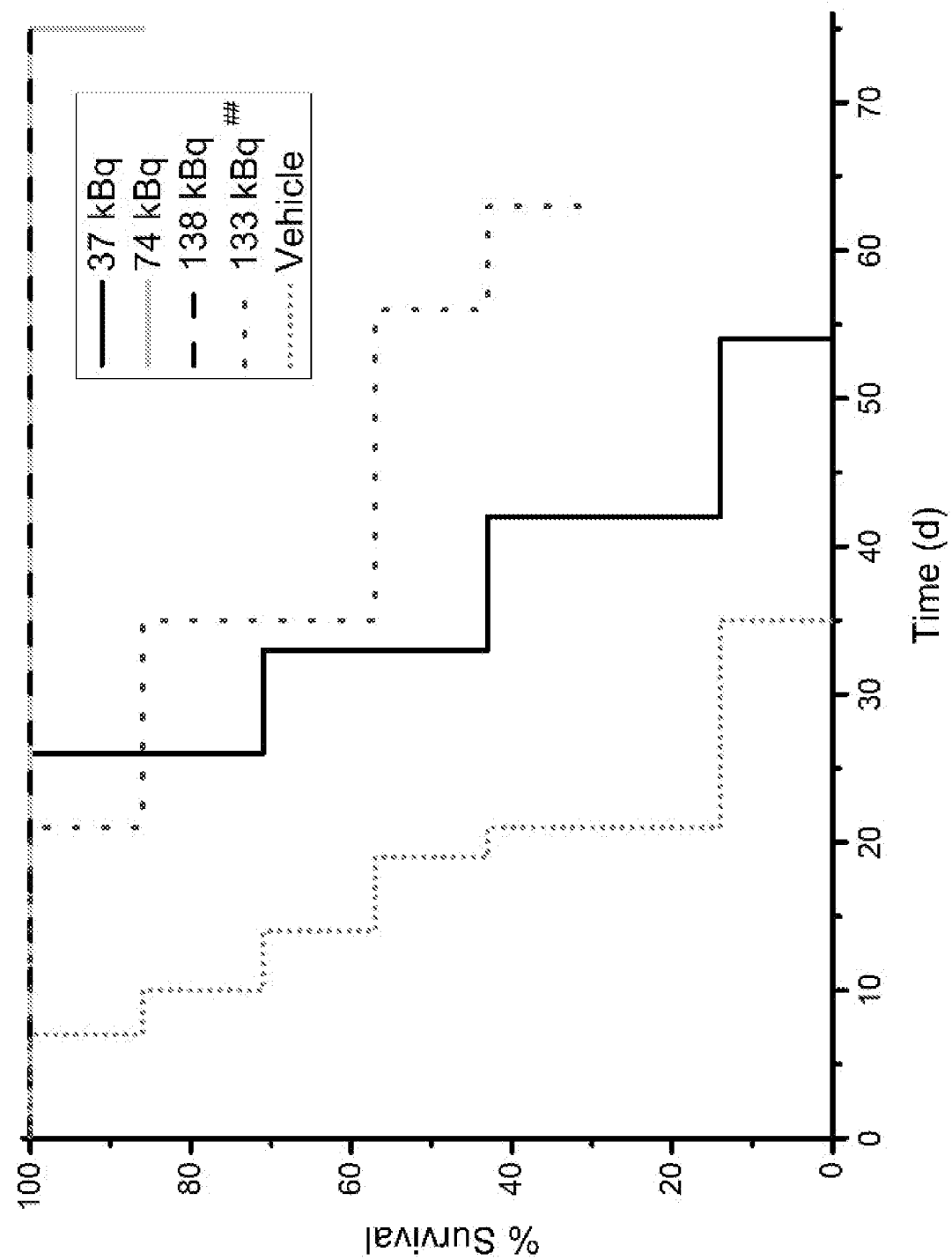
FIG. 15 plots a Kaplan-Meier curve illustrating the overall survival of the mice. ##=Activity of $^{225}$Ac-DOTA-Lys-IPBA administered. Mice were sacrificed when tumor volume exceeded 2000 mm$^3$.

Every mouse in the 138 kBq treatment group survived the 75 d study (FIG. 15). In contrast, in each of the other groups at least one mouse was sacrificed prior to the termination of the study due to excessive tumor growth. The survival curves for the 37 kBq group and the 133 kBq $^{225}$Ac-DOTA-Lys-IPBA positive control group are similar, with 100% of mice surviving the first 21 d. In contrast, only 1/7 (14%) of the untreated mice survived to this time point. No toxic effects were visible in any of the groups. The variation in body weight during the 75 day study was 92-106% of the original measurement. The remaining mice were sacrificed at 75 d post injection and the tumor (if present), kidneys, liver, parotid glands and sublingual glands were excised and examined for evidence of damage.

Further Exemplary Compounds of the Present Technology

The following compounds of the present technology were synthesized and characterized via similar protocols and methods as described above.

119 120
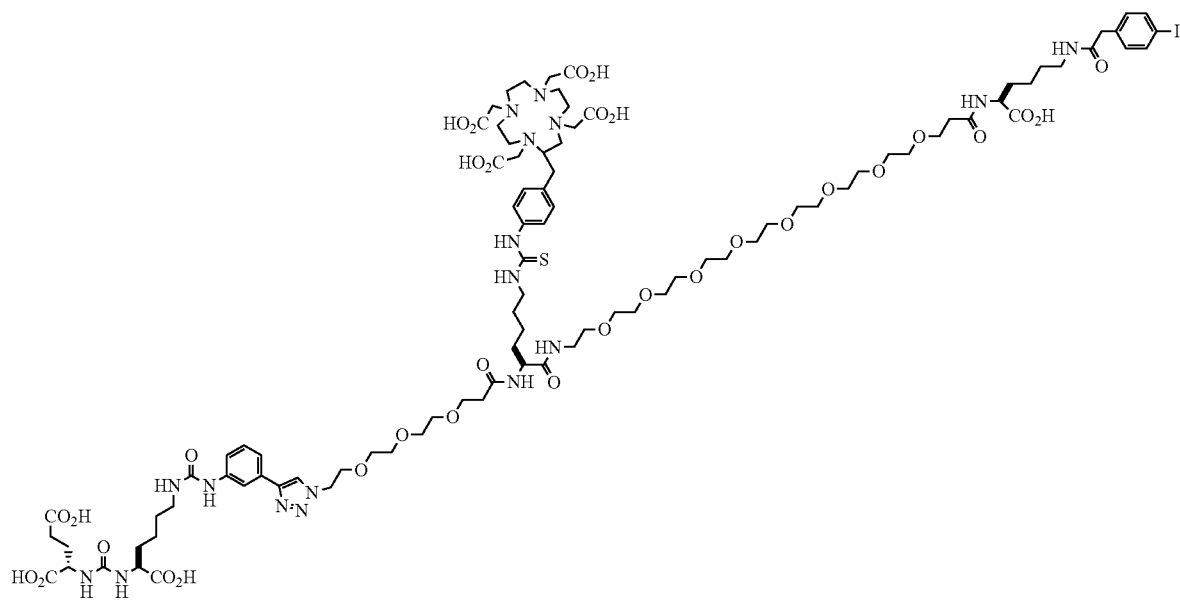
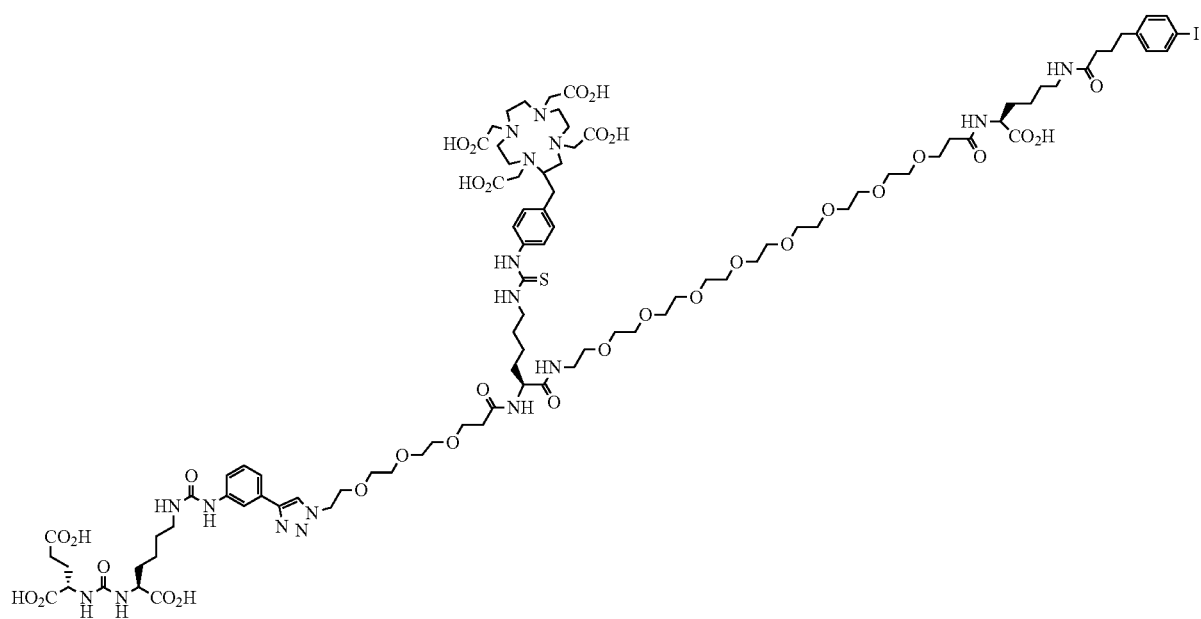

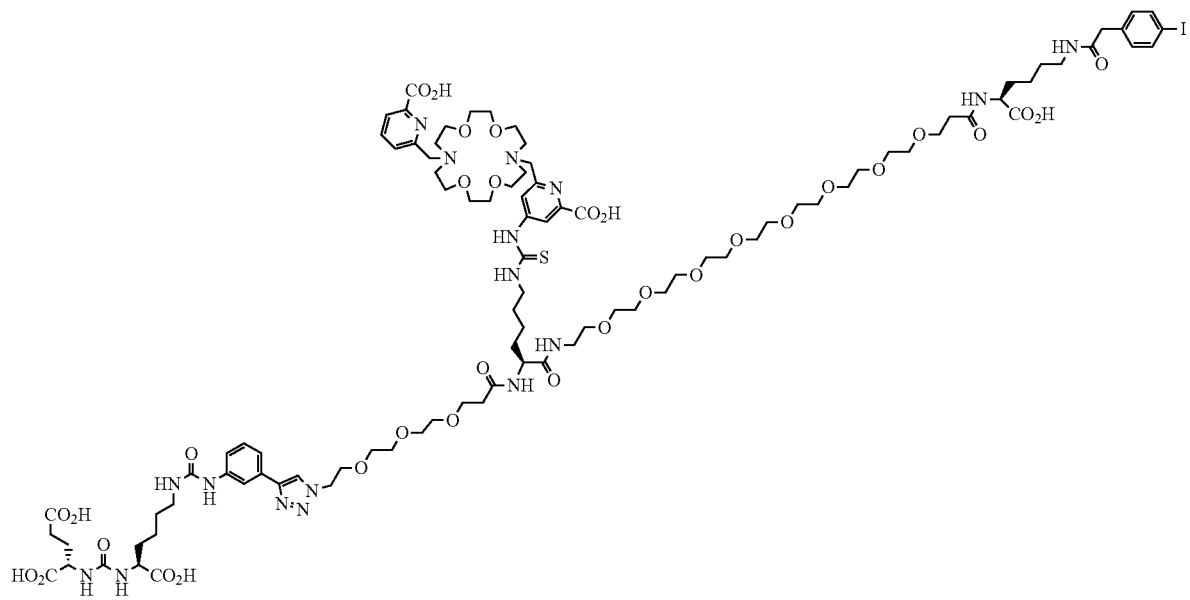
RPS-073
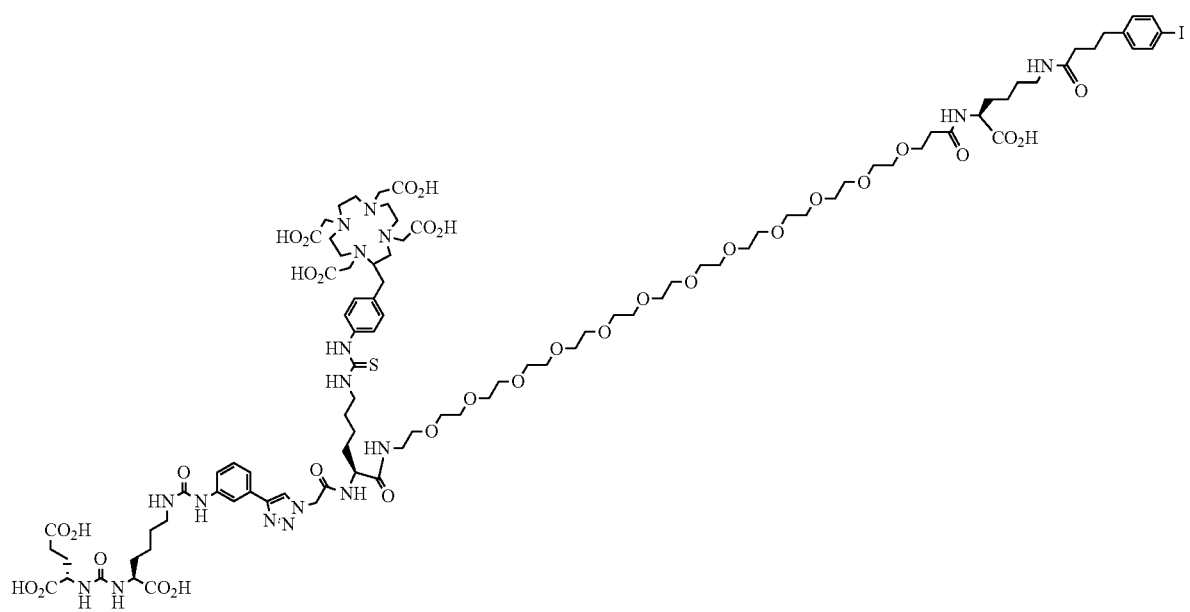
RPS-075

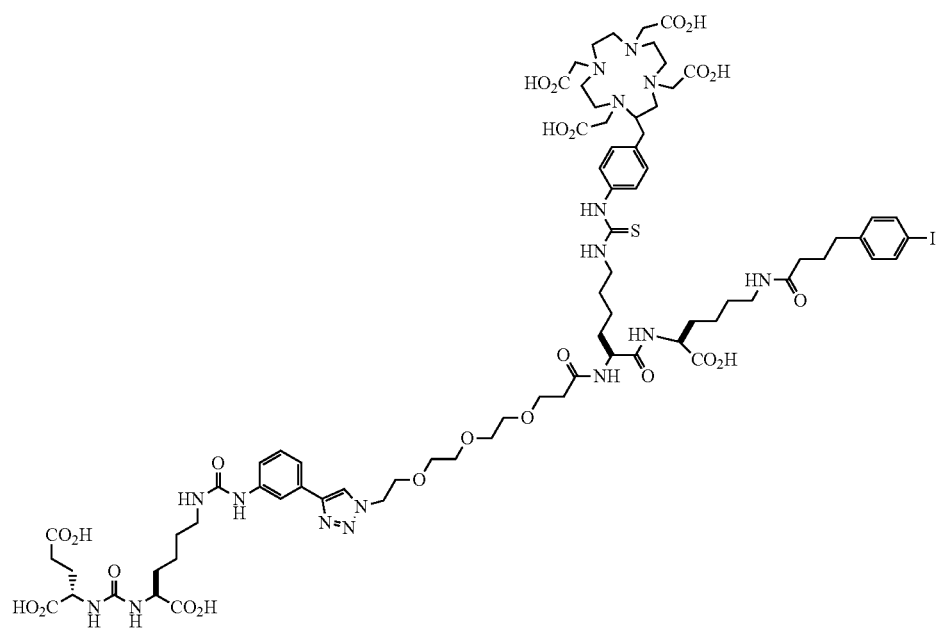
RPS-077
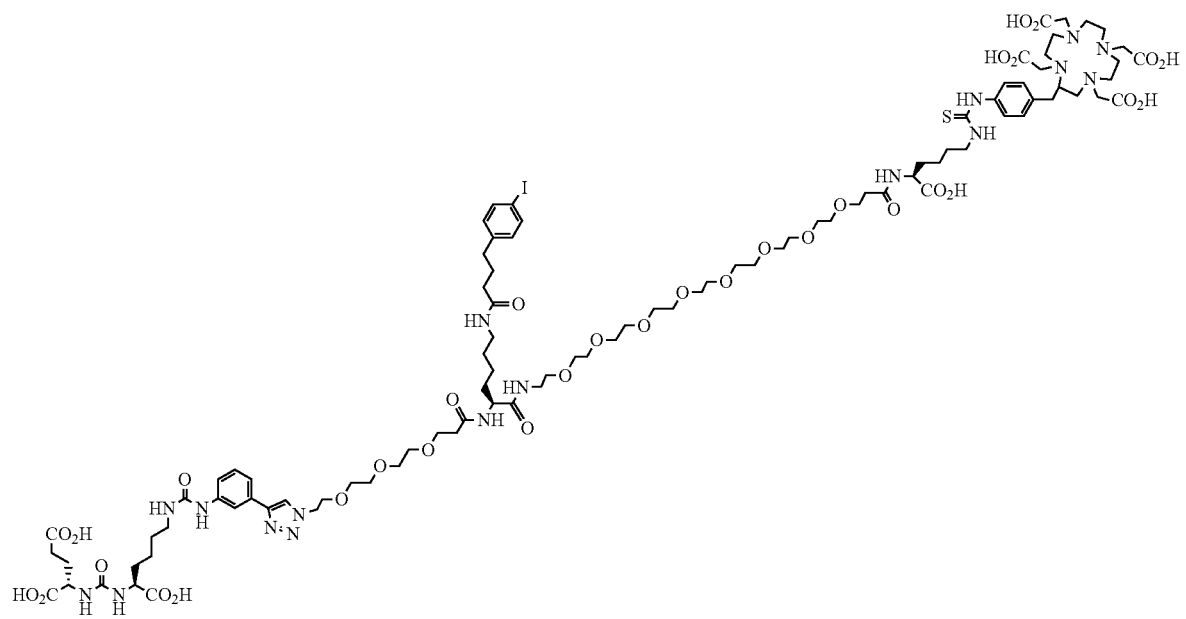
RPS-078

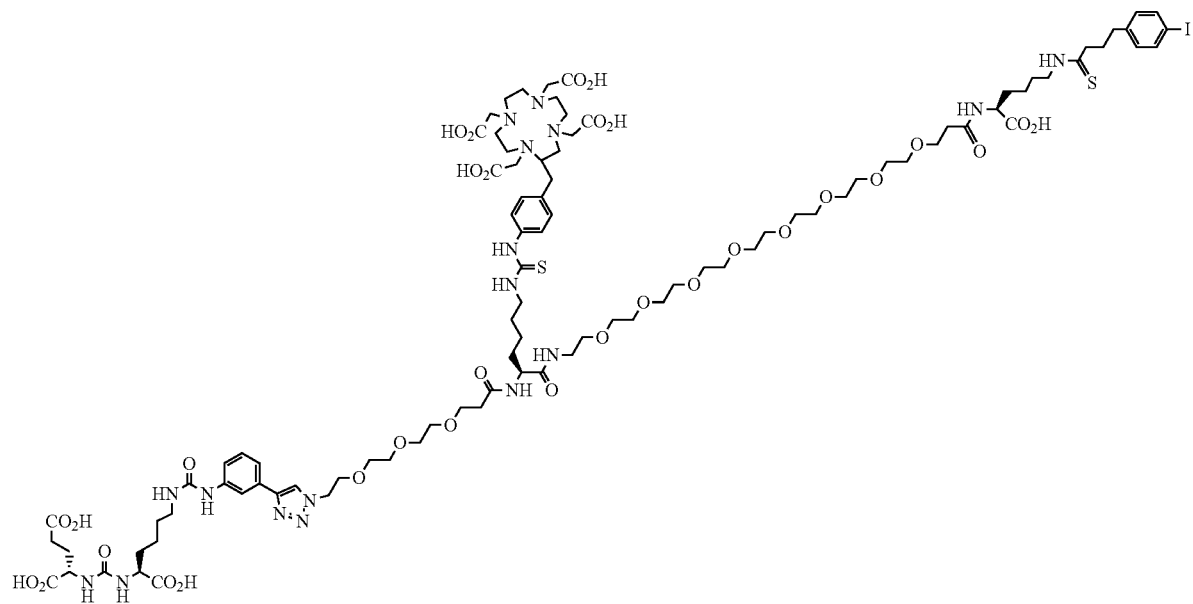
RPS-080
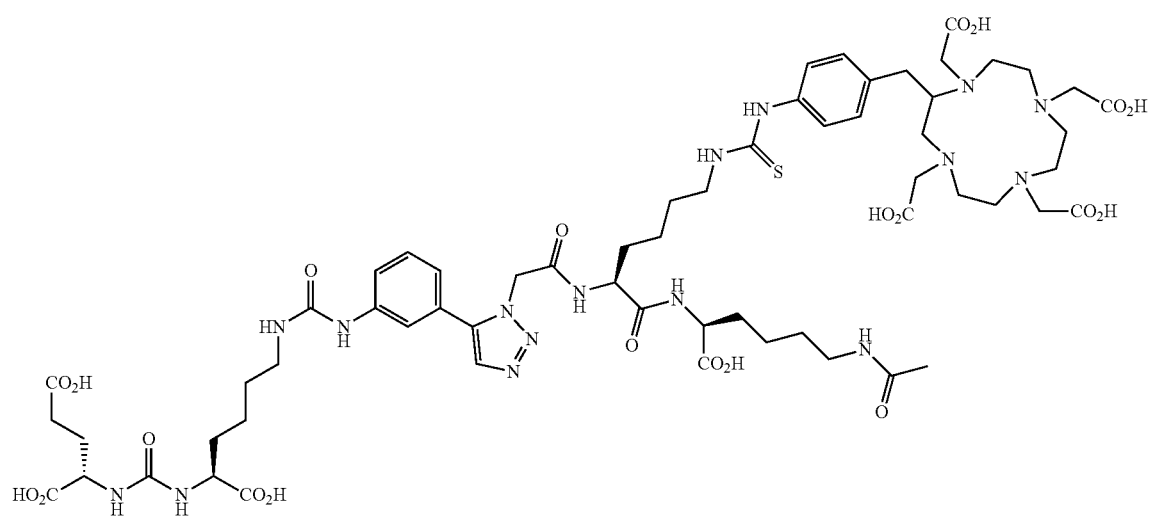
RPS-081

RPS-082

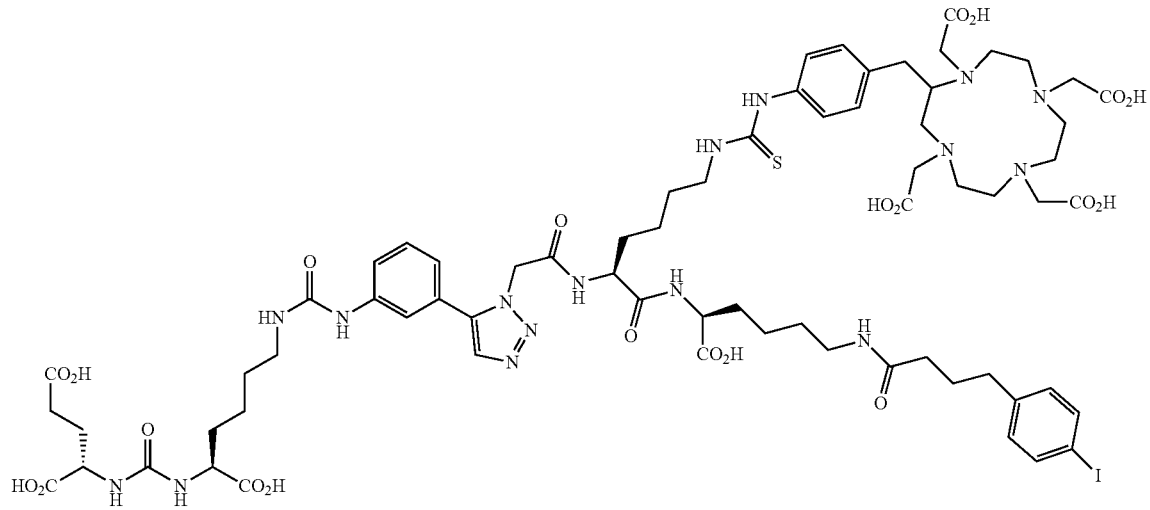

SECTION 1.4 REFERENCES

[1] Hillier S M, Maresca K P, Lu G, Merkin R D, Marquis J C, Zimmerman C N, Eckelman W C, Joyal J L, Babich J W. $^{99m}$Tc-Labeled Small-Molecule Inhibitors of Prostate-Specific Membrane Antigen for Molecular Imaging of Prostate Cancer. J Nucl Med. 2013; 54:1369-76.

[2] Kelly J M, Amor-Coarasa A, Nikolopoulou A, Wüstemann T, Barelli P, Kim D, Williams C. Jr, Zheng X, Bi C, Hu B, Warren J D, Hage D S, DiMagno S G, Babich J W. Dual-Target Binding Ligands with Modulated Pharmacokinetics for Endoradiotherapy of Prostate Cancer. J Nucl Med. 2017; 58:1442-1449.

[3] Benešová M, Umbricht C A, Schibli R, Müller C. Albumin-Binding PSMA Ligands: Optimization of the Tissue Distribution Profile. Mol Pharm. 2018; 15:934-946.

[4] Jensen M M, Jørgensen J T, Binderup T, Kjær A. Tumor volume in subcutaneous mouse xenografts measured by microCT is more accurate and reproducible than determined by $^{18}$F-FDG-microPET or external caliper. BMC Med Imaging 2008; 8:16.

[5] Amor-Coarasa A, Kelly J M, Gruca M, Nikolopoulou A, Vallabhajosula S, Babich J W. Continuation of comprehensive quality control of the itG $^{68}$Ge/$^{68}$Ga generator and production of $^{68}$Ga-DOTATOC and $^{68}$Ga-PSMA-HBED-CC for clinical research studies. Nucl Med Biol. 2017; 53:37-39.

[6] Kelly J, Amor-Coarasa A, Ponnala S, Nikolopoulou A, Williams C., Jr, Schlyer D, Zhao Y, Kim D, Babich J W. Trifunctional PSMA-Targeting Constructs for Prostate Cancer with Unprecedented Localization to LNCaP Tumors. Eur J Nucl Med Mol Imaging 2018; In press.

[7] Miederer M, Scheinberg D A, McDevitt M R. Realizing the potential of the Actinium-225 radionuclide generator in targeted alpha-particle therapy applications. Adv Drug Deliv Rev. 2008; 60:1371-1382.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A compound of Formula I

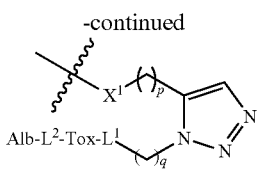

(I)

or a pharmaceutically acceptable salt and/or solvate thereof, wherein
  ABD is an antigen-binding domain;
  $W^1$ is —C(O)—, —(CH$_2$)$_n$—, or —(CH$_2$)$_o$—NH—C(O)—;
  one of $R^1$, $R^2$, and $R^3$ is

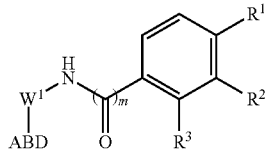 or

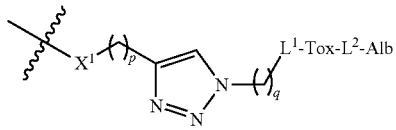

and the remaining two of $R^1$, $R^2$, and $R^3$ are each H;
  $X^1$ is absent, O, S, or NH;
  $L^1$ is absent, —C(O)—, —C(O)—NR$^4$—, —C(O)—NR$^5$—C$_1$-C$_{12}$ alkylene-, —C$_1$-C$_{12}$ alkylene-C(O)—, —C(O)—NR$^6$—C$_1$-C$_{12}$ alkylene-C(O)—, -arylene-, —O(CH$_2$CH$_2$O)$_r$—CH$_2$CH$_2$C(O)—, an amino acid, a peptide of 2, 3, 4, 5, 6, 7, 8, 9, or 10 amino acids, or a combination of any two or more thereof, where r is 0, 1, 2, 3, 4, 5, 6, 7, 8, or 9, and where $R^4$, RV, and $R^6$ are each independently H, alkyl, or aryl;
  Tox is a cytotoxin-containing and/or imaging agent-containing domain;
  $L^2$ is absent, —C(O)—, —(CH$_2$CH$_2$O)$_s$—CH$_2$CH$_2$C(O)—, a peptide of 2, 3, 4, 5, 6, 7, 8, 9, 10, 11, 12, 13, 14, 15, 16, 17, 18, 19, or 20 amino acids, or a combination of any two or more thereof, where s is 0, 1, 2, 3, 4, 5, 6, 7, 8, 9, 10, 11, 12, 13, 14, 15, 16, 17, 18, or 19;
  Alb is an albumin-binding moiety;
  m is 0 or 1;
  n is 1 or 2;
  o is 1 or 2;
  p is 0, 1, 2, or 3, provided that when p is 0 then $X^1$ is absent; and
  q is 1 or 2.

B. The compound of Paragraph A, wherein the compound of Formula I is of Formula II

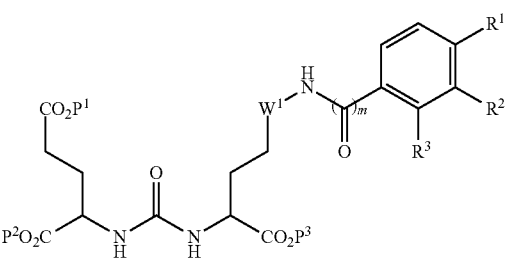

(II)

or a pharmaceutically acceptable salt and/or solvate thereof, wherein
  $P^1$, $P^2$, and $P^3$ are each independently H, methyl, benzyl, 4-methoxybenzyl, or tert-butyl;
  one of $R^1$, $R^2$, and $R^3$ is

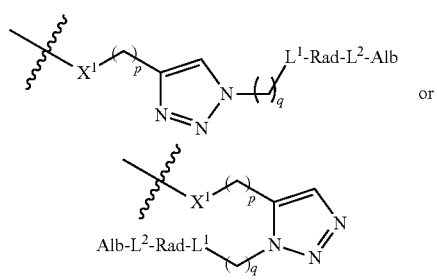 or and the remaining two of $R^1$, $R^2$, and $R^3$ are each H;
Rad is a moiety capable of including a metal ion, optionally further including a metal ion.

C. The compound of Paragraph B, wherein $P^1$, $P^2$, and $P^3$ are each independently H or tert-butyl.

D. The compound of Paragraph B or Paragraph C, wherein $P^1$, $P^2$, and $P^3$ are each independently H.

E. The compound of any one of Paragraphs A-D, wherein Tox of Formula I or Rad of Formula II comprises a metal ion.

F. The compound of any one of Paragraphs B-E, wherein Rad of Formula II comprises a chelator and a chelated metal ion.

G. The compound of any one of Paragraphs A-F, wherein the metal ion is a radionuclide that is $^{177}Lu^{3+}$, $^{175}Lu^{3+}$, $^{45}Sc^{3+}$, $^{66}Ga^{3+}$, $^{67}Ga^{3+}$, $^{68}Ga^{3+}$, $^{69}Ga^{3+}$, $^{71}Ga^{3+}$, $^{89}Y^{3+}$, $^{86}Y^{3+}$, $^{89}Zr^{4+}$, $^{90}Y^{3+}$, $^{99m}Tc^{+1}$, $^{111}In^{3+}$, $^{113}In^{3+}$, $^{115}In^{3+}$, $^{139}La^{3+}$, $^{136}Ce^{3+}$, $^{3}Ce^{3+}$, $^{10}Ce^{3+}$, $^{142}Ce^{3+}$, $^{151}Eu^{3+}$, $^{153}Eu^{3+}$, $^{152}Dy^{3+}$, $^{149}Tb^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, $^{160}Gd^{3+}$, $^{188}Re^{+1}$, $^{186}Re^{+1}$, $^{213}Bi^{3+}$, $^{211}At^{+}$, $^{217}At^{+}$, $^{227}Th^{4+}$, $^{226}Th^{4+}$, $^{225}Ac^{3+}$, $^{233}Ra^{2+}$, $^{152}Dy^{3+}$, $^{213}Bi^{3+}$, $^{212}Bi^{3+}$, $^{211}Bi^{3+}$, $^{212}Pb^{2+}$, $^{212}Pb^{4+}$, $^{255}Fm^{3+}$, or uranium-230.

H. The compound of any one of Paragraphs A-G, wherein the metal ion is an alpha-emitting radionuclide selected from $^{213}Bi^{3+}$, $^{211}At^{+}$, $^{225}Ac^{3+}$, $^{152}Dy^{3+}$, $^{212}Bi^{3+}$, $^{211}Bi^{3+}$, $^{217}At^{+}$, $^{227}Th^{4+}$, $^{226}Th^{4+}$, $^{233}Ra^{2+}$, $^{212}Pb^{2+}$, and $^{212}Pb^{4+}$.

I. The compound of any one of Paragraphs A-H, wherein the albumin-binding moiety is

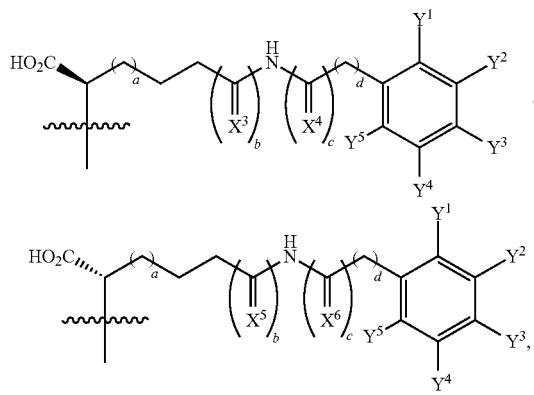

wherein
$Y^1$, $Y^2$, $Y^3$, $Y^4$, and $Y^5$ are independently at each occurrence H, halo, or alkyl;
$X^3$, $X^4$, $X^5$, and $X^6$ are each independently O or S
a is independently at each occurrence 0, 1, or 2;
b is independently at each occurrence 0 or 1;
c is independently at each occurrence 0 or 1; and
d is independently at each occurrence 0, 1, 2, 3, or 4, optionally wherein b and c cannot be the same value.

J. The compound of any one of Paragraphs A-I, wherein one of $R^1$, $R^2$, and $R^3$ is

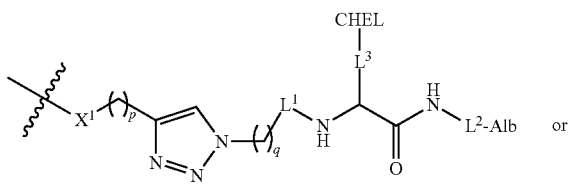

or

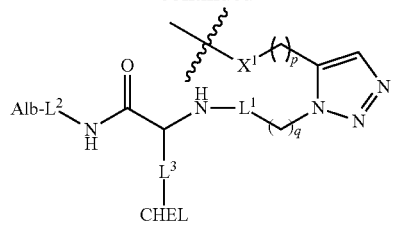

and the remaining two of $R^1$, $R^2$, and $R^3$ are each H;
$L^3$ is absent, —C(O)—, —$C_1$-$C_{12}$ alkylene-, —$C_1$-$C_{12}$ alkylene-C(O)—, —$C_1$-$C_{12}$ alkylene-$NR^{10}$—, or -arylene-;
$R^{10}$ is H, alkyl, or aryl; and
CHEL is a covalently conjugated chelator that optionally includes a chelated metal ion.

K. The compound of any one of Paragraphs A-J, wherein the compound of Formula I is a compound of Formula III (III)

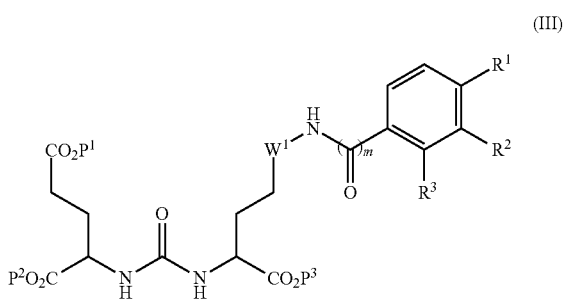

or a pharmaceutically acceptable salt and/or solvate thereof, wherein one of $R^1$, $R^2$, and $R^3$ is

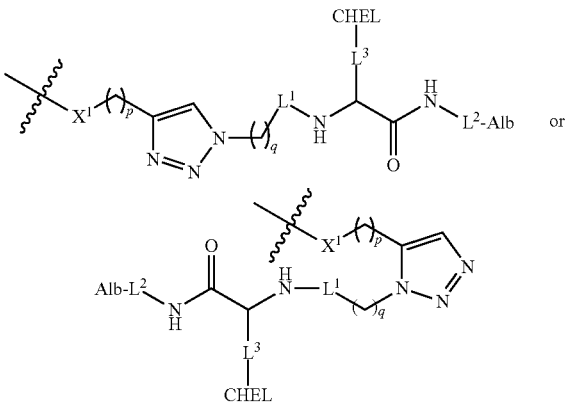

and the remaining two of $R^1$, $R^2$, and $R^3$ are each H;
$L^3$ is absent, —C(O)—, —$C_1$-$C_{12}$ alkylene-, —$C_1$-$C_{12}$ alkylene-C(O)—, —$C_1$-$C_{12}$ alkylene-$NR^{10}$—, or -arylene-;
$R^{10}$ is H, alkyl, or aryl; and
CHEL is a covalently conjugated chelator that optionally includes a chelated metal ion.

L. The compound of any one of Paragraphs A-K, wherein $L^1$ is —O($CH_2CH_2O$)$_r$—$CH_2CH_2C(O)$—, an amino acid, a peptide of 2, 3, 4, 5, 6, 7, 8, 9, or 10 amino acids, or a combination of any two or more thereof.

M. The compound of any one of Paragraphs A-L, wherein $L^1$ is —O(CH$_2$CH$_2$O)$_r$—CH$_2$CH$_2$C(O)—, glycine, a polyglycine composed of 2, 3, 4, 5, 6, 7, 8, 9, or 10 glycine residues, or a combination of any two or more thereof.

N. The compound of any one of Paragraphs A-M, wherein $L^2$ is —(CH$_2$CH$_2$O)$_s$—CH$_2$CH$_2$C(O)—, a peptide of 2, 3, 4, 5, 6, 7, 8, 9, 10, 11, 12, 13, 14, 15, 16, 17, 18, 19, or 20 amino acids, or a combination of any two or more thereof.

O. The compound of any one of Paragraphs A-N, wherein $L^2$ is —(CH$_2$CH$_2$O)$_s$—CH$_2$CH$_2$C(O)—, a polyglycine composed of 2, 3, 4, 5, 6, 7, 8, 9, 10, 11, 12, 13, 14, 15, 16, 17, 18, 19, or 20 amino acids, or a combination of any two or more thereof.

P. A composition comprising a pharmaceutically acceptable carrier and a composition of any one of Paragraphs A-O.

Q. A pharmaceutical composition, the composition comprising
an effective amount of the compound of any one of Paragraphs A-O for detecting a cancer and/or mammalian tissue overexpressing prostate specific membrane antigen ("PSMA"); and
a pharmaceutically acceptable carrier.

R. The pharmaceutical composition of Paragraph Q, wherein the cancer comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

S. The pharmaceutical composition of Paragraph Q or Paragraph R, wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

T. The pharmaceutical composition of any one of Paragraphs Q-S, wherein the pharmaceutical composition is formulated for intravenous administration, optionally comprising sterilized water, Ringer's solution, or an isotonic aqueous saline solution.

U. The pharmaceutical composition of any one of Paragraphs Q-T, wherein the effective amount of the compound is from about 0.01 µg to about 10 mg of the compound per gram of the pharmaceutical composition.

V. The pharmaceutical composition of any one of Paragraphs Q-U, wherein the pharmaceutical composition is provided in an injectable dosage form.

W. A pharmaceutical composition comprising
an effective amount of the compound of any one of Paragraphs A-O for treating a cancer and/or mammalian tissue overexpressing prostate specific membrane antigen ("PSMA"); and
a pharmaceutically acceptable carrier.

X. The pharmaceutical composition of Paragraph W, wherein the cancer comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

Y. The pharmaceutical composition of Paragraph W or Paragraph X, wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

Z. The pharmaceutical composition of any one of Paragraphs W-Y, wherein the pharmaceutical composition is formulated for intravenous administration, optionally comprising sterilized water, Ringer's solution, or an isotonic aqueous saline solution.

AA. The pharmaceutical composition of any one of Paragraphs W-Z, wherein the effective amount of the compound is from about 0.01 µg to about 10 mg of the compound per gram of the pharmaceutical composition.

AB. The pharmaceutical composition of any one of Paragraphs W-AA, wherein the pharmaceutical composition is provided in an injectable dosage form.

AC. The pharmaceutical composition of any one of Paragraphs W-AB, wherein the effective amount of the compound for treating a cancer and/or mammalian tissue overexpressing PSMA is also an effective amount of the compound for imaging a cancer and/or mammalian tissue overexpressing PSMA.

AD. A method comprising
administering to a subject an effective amount of a compound of any one of Paragraphs A-O for imaging a cancer and/or mammalian tissue overexpressing prostate specific membrane antigen ("PSMA"); and
subsequent to the administering, detecting radiation from the compound.

AE. The method of Paragraph AD, wherein subsequent to the administering, the method comprises detecting one or more of positron emission, gamma rays from positron emission and annihilation, and Cerenkov radiation due to positron emission.

AF. The method of Paragraph AD or Paragraph AE, wherein the cancer comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

AG. The method of any one of Paragraphs AD-AF, wherein the subject is suspected of suffering from a mammalian tissue overexpressing PSMA, optionally wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

AH. The method of any one of Paragraphs AD-AG, wherein administering the compound comprises parenteral administration.

AI. The method of any one of Paragraphs AD-AH, wherein administering the compound comprises intravenous administration.

AJ. The method of any one of Paragraphs AD-AI, wherein the effective amount of the compound is from about 0.1 µg to about 50 µg per kilogram of subject mass.

AK. A method comprising
administering to a subject an effective amount of a compound of any one of Paragraphs A-O for treating a cancer and/or a mammalian tissue overexpressing prostate specific membrane antigen ("PSMA").

AL. The method of Paragraph AK, wherein the cancer comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

AM. The method of Paragraph AK or Paragraph AL, wherein the subject is suspected of suffering from a mammalian tissue overexpressing PSMA, optionally wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

AN. The method of any one of Paragraphs AK-AM, wherein administering the compound comprises parenteral administration.

AO. The method of any one of Paragraphs AK-AN, wherein administering the compound comprises intravenous administration.

AP. The method of any one of Paragraphs AK-AO, wherein the effective amount of the compound for treating the cancer and/or the mammalian tissue overexpressing PSMA is from about 0.1 µg to about 50 µg per kilogram of subject mass.

AQ. The method of any one of Paragraphs AK-AP, wherein the effective amount of the compound is also an effective amount of the compound for imaging the cancer and/or the mammalian tissue overexpressing PSMA.

AR. The method of any one of Paragraphs AK-AQ, wherein the method further comprises, subsequent to the administering, detecting radiation from the compound.

AS. The method of any one of Paragraphs AK-AR, wherein the method further comprises, subsequent to the administering, detecting one or more of positron emission, gamma rays from positron emission and annihilation, and Cerenkov radiation due to positron emission.

AT. A method of achieving an in vivo tissue distribution of a radiotherapeutic in a mammalian subject in which a ratio of tumor activity to kidney activity of 1 or greater is observed within about 4 hours to about 24 hours of administration of the radiotherapeutic to the mammalian subject, wherein
the method comprises administering to the mammalian subject the radiotherapeutic; and
the radiotherapeutic comprises a first moiety that targets prostate specific membrane antigen ("PSMA"), a second moiety that bears a radionuclide, and a third moiety that has an affinity for serum albumin, the first moiety being separated from the second moiety by a first covalent linker and the third moiety being separated from the second moiety by a second covalent linker,
wherein the separation between the first and second moieties (on the basis of a contiguous atom count associated with the first covalent linker) is from about 8 atoms to about 40 atoms, and the separation between the third moiety and the first and second moieties (on the basis of a contiguous atom count associated with the second covalent linker) is from about 10 atoms to about 100 atoms.

AU. The method of Paragraph AT, wherein the method further comprises obtaining an image of the mammalian subject about 4 hours to about 24 hours after administration of the radiotherapeutic.

AV. The method of Paragraph AT or Paragraph AU, wherein the ratio of tumor activity to kidney activity of 1 or greater persists up to about 24 hours after administration of the radiotherapeutic.

AW. The method of any one of Paragraphs AT-AV, wherein in substantially no radionuclide activity is observed in salivary glands of the mammalian subject about 24 hours to about 48 hours after administration of the radiotherapeutic.

AX. The method of any one of Paragraphs AT-AW, wherein the contiguous atom count associated with the first covalent linker ranges from about 10 atoms to about 30 atoms.

AY. The method of any one of Paragraphs AT-AX, wherein the contiguous atom count associated with the second covalent linker ranges from about 15 atoms to about 40 atoms.

AZ. The method of any one of Paragraphs AT-AY, wherein the administration comprises intravenous administration.

BA. The method of any one of Paragraphs AT-AZ, wherein the radiotherapeutic is a compound of any one of Paragraphs A-O.

Other embodiments are set forth in the following claims, along with the full scope of equivalents to which such claims are entitled.

What is claimed is:
1. A compound of Formula I

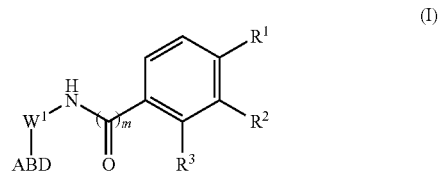

or a pharmaceutically acceptable salt and/or solvate thereof, wherein
ABD is an antigen-binding domain;
$W^1$ is —C(O)—, —(CH$_2$)$_n$—, or —(CH$_2$)$_o$—NH—C(O)—;
one of $R^1$, $R^2$, and $R^3$ is

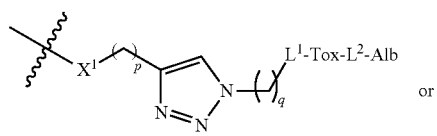

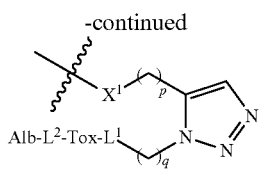

and the remaining two of $R^1$, $R^2$, and $R^3$ are each H;

$X^1$ is absent, O, S, or NH;

$L^1$ is absent, —C(O)—, —C(O)—$NR^4$—, —C(O)—$NR^5$—$C_1$-$C_{12}$ alkylene-, —$C_1$-$C_{12}$ alkylene-C(O)—, —C(O)—$NR^6$—$C_1$-$C_{12}$ alkylene-C(O)—, -arylene-, —O($CH_2CH_2O)_r$—$CH_2CH_2C$(O)—, an amino acid, a peptide of 2, 3, 4, 5, 6, 7, 8, 9, or 10 amino acids, or a combination of any two or more thereof, where r is 0, 1, 2, 3, 4, 5, 6, 7, 8, or 9, and where $R^4$, $R^5$, and $R^6$ are each independently H, alkyl, or aryl;

Tox is a cytotoxin-containing and/or imaging agent-containing domain;

$L^2$ is absent, —C(O)—, —$(CH_2CH_2O)_s$—$CH_2CH_2C$(O)—, a peptide of 2, 3, 4, 5, 6, 7, 8, 9, 10, 11, 12, 13, 14, 15, 16, 17, 18, 19, or 20 amino acids, or a combination of any two or more thereof, where s is 0, 1, 2, 3, 4, 5, 6, 7, 8, 9, 10, 11, 12, 13, 14, 15, 16, 17, 18, or 19;

Alb is an albumin-binding moiety;

m is 0 or 1;

n is 1 or 2;

o is 1 or 2;

p is 0, 1, 2, or 3, provided that when p is 0 then $X^1$ is absent; and q is 1 or 2.

2. The compound of claim 1, wherein the compound of Formula I is of Formula II

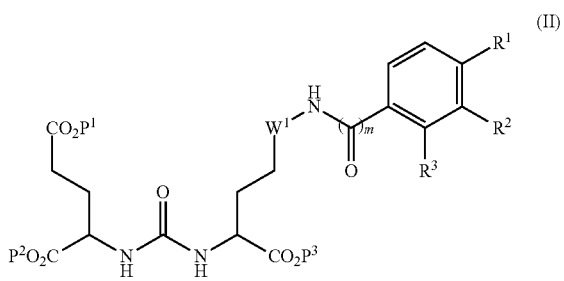

or a pharmaceutically acceptable salt and/or solvate thereof, wherein $P^1$, $P^2$, and $P^3$ are each independently H, methyl, benzyl, 4-methoxybenzyl, or tert-butyl; one of $R^1$, $R^2$, and $R^3$ is

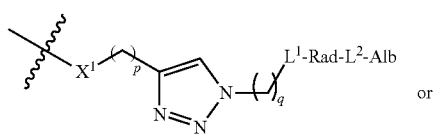

or

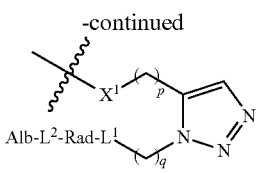

and the remaining two of $R^1$, $R^2$, and $R^3$ are each H;

Rad is a moiety capable of including a metal ion, optionally further including a metal ion.

3. The compound of claim 2, wherein $P^1$, $P^2$, and $P^3$ are each independently H or tert-butyl.

4. The compound of claim 2, wherein $P^1$, $P^2$, and $P^3$ are each independently H.

5. The compound of claim 2, wherein Rad comprises a chelator that chelates the metal ion.

6. The compound of claim 5, wherein the metal ion is a radionuclide that is $^{177}Lu^{3+}$, $^{175}Lu^{3+}$, $^{45}Sc^{3+}$, $^{66}Ga^{3+}$, $^{67}Ga^{3+}$, $^{68}Ga^{3+}$, $^{69}Ga^{3+}$, $^{71}Ga^{3+}$, $^{89}Y^{3+}$, $^{86}Y^{3+}$, $^{89}Zr^{1+}$, $^{90}Y^{3+}$, $^{99m}Tc^{+1}$, $^{111}In^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{152}Dy^{3+}$, $^{149}Tb^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, $^{160}Gd^{3+}$, $^{188}Re^{+1}$, $^{186}Re^{+1}$, $^{213}Bi^{3+}$, $^{211}At^{+}$, $^{217}At^{+}$, $^{227}Th^{4+}$, $^{226}Th^{4+}$, $^{225}Ac^{3+}$, $^{223}Ra^{2+}$, $^{152}Dy^{3+}$, $^{213}Bi^{3+}$, $^{212}Bi^{3+}$, $^{211}Bi^{3+}$, $^{212}Pb^{2+}$, $^{212}Pb^{4+}$, $^{255}Fm^{3+}$, or uranium-230.

7. The compound of claim 5, wherein the metal ion is an alpha-emitting radionuclide selected from $^{213}Bi^{3+}$, $^{211}At^{+}$, $^{225}Ac^{3+}$, $^{152}Dy^{3+}$, $^{212}Bi^{3+}$, $^{211}Bi^{3+}$, $^{217}At^{+}$, $^{227}Th^{4+}$, $^{226}Th^{4+}$, $^{233}Ra^{2+}$, $^{212}Pb^{2+}$, and $^{212}Pb^{4+}$.

8. A pharmaceutical composition, the composition comprising an effective amount of the compound of claim 1, for detecting mammalian tissue overexpressing prostate specific membrane antigen ("PSMA"), and a pharmaceutically acceptable carrier.

9. The pharmaceutical composition of claim 8, wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

10. A method comprising
administering to a subject an effective amount of a compound of claim 1, for imaging a cancer; and
subsequent to the administering, detecting one or more of positron emission, gamma rays from positron emission and annihilation, and Cerenkov radiation due to positron emission.

11. The method of claim 10, wherein the cancer comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

12. The method of claim 10, wherein the subject is suspected of suffering from a mammalian tissue overexpressing prostate specific membrane antigen ("PSMA").

13. The method of claim 12, wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

14. The method of claim 10, wherein administering the compound comprises parenteral administration.

15. A pharmaceutical composition comprising an effective amount of the compound of claim 1, for treating mammalian tissue overexpressing prostate specific membrane antigen ("PSMA"), and a pharmaceutically acceptable carrier.

16. The pharmaceutical composition of claim 15, wherein the mammalian tissue comprises one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary, gastric adenocarcinoma, a primary colorectal adenocarcinoma, a renal cell carcinoma, and a prostate cancer.

17. A method comprising
  administering to a subject an effective amount of a compound of claim 1, for treating a cancer.

18. The method of claim 17, wherein the cancer comprises one or more of glioma, cervical carcinoma, vulvar carcinoma, endometrial carcinoma, primary ovarian carcinoma, metastatic ovarian carcinoma, non-small cell lung cancer, small cell lung cancer, bladder cancer, colon cancer, primary, gastric adenocarcinoma, primary colorectal adenocarcinoma, renal cell carcinoma, and prostate cancer.

19. The method of claim 17, wherein administering the compound comprises parenteral administration.

\* \* \* \* \*